(12) United States Patent
Agnihotri et al.

(10) Patent No.: US 11,173,160 B2
(45) Date of Patent: Nov. 16, 2021

(54) USE OF TG02 FOR TREATING GLIOMAS IN PEDIATRIC SUBJECTS

(71) Applicants: UNIVERSITY OF PITTSBURGH—OF THE COMMONWEALTH SYSTEM OF HIGHER EDUCATION, Pittsburgh, PA (US); ADASTRA PHARMACEUTICALS, INC., Princeton, NJ (US)

(72) Inventors: Sameer Agnihotri, Pittsburgh, PA (US); Alberto Broniscer, Pittsburgh, PA (US); Ian F. Pollack, Pittsburgh, PA (US); Thomas M. Estok, Lakewood Ranch, FL (US)

(73) Assignees: UNIVERSITY OF PITTSBURGH—OF THE COMMONWEALTH SYSTEM OF HIGHER EDUCATION, Pittsburgh, PA (US); ADASTRA PHARMACEUTICALS, INC., Princeton, NJ (US)

(*) Notice: Subject to any disclaimer, the term of this patent is extended or adjusted under 35 U.S.C. 154(b) by 0 days.

(21) Appl. No.: 16/991,863

(22) Filed: Aug. 12, 2020

(65) Prior Publication Data

US 2020/0368242 A1 Nov. 26, 2020

Related U.S. Application Data

(63) Continuation of application No. PCT/US2020/029400, filed on Apr. 22, 2020.

(60) Provisional application No. 62/837,049, filed on Apr. 22, 2019, provisional application No. 62/907,019, filed on Sep. 27, 2019.

(51) Int. Cl.
| | |
|---|---|
| A61K 31/519 | (2006.01) |
| A61P 35/00 | (2006.01) |
| A61K 31/395 | (2006.01) |
| A61N 5/10 | (2006.01) |
| C07C 309/24 | (2006.01) |
| C07C 69/76 | (2006.01) |
| C07D 239/00 | (2006.01) |
| C07D 239/70 | (2006.01) |
| C07D 471/00 | (2006.01) |
| C07D 471/04 | (2006.01) |
| C07D 487/00 | (2006.01) |
| C07D 487/04 | (2006.01) |
| C07D 471/22 | (2006.01) |

(52) U.S. Cl.
CPC .......... *A61K 31/519* (2013.01); *A61K 31/395* (2013.01); *A61P 35/00* (2018.01); *A61N 5/10* (2013.01); *C07B 2200/13* (2013.01); *C07C 69/76* (2013.01); *C07C 309/24* (2013.01); *C07D 239/00* (2013.01); *C07D 239/70* (2013.01); *C07D 471/00* (2013.01); *C07D 471/04* (2013.01); *C07D 471/22* (2013.01); *C07D 487/00* (2013.01); *C07D 487/04* (2013.01)

(58) Field of Classification Search
CPC ..... A61K 31/395; A61K 31/519; A61P 35/00; A61N 5/10
See application file for complete search history.

(56) References Cited

U.S. PATENT DOCUMENTS

| | | |
|---|---|---|
| 8,143,255 B2 | 3/2012 | Blanchard et al. |
| 8,415,338 B2 | 4/2013 | Blanchard et al. |
| 9,120,815 B2 | 9/2015 | Mansfield et al. |
| 2011/0251216 A1 | 10/2011 | Chinnaiyan et al. |
| 2012/0071418 A1 | 3/2012 | Copeland et al. |
| 2014/0128393 A1 | 5/2014 | Knutson et al. |
| 2014/0275081 A1 | 9/2014 | Kuntz et al. |
| 2019/0055263 A1 | 2/2019 | Mansfield et al. |

FOREIGN PATENT DOCUMENTS

| | | |
|---|---|---|
| WO | WO 2003/070887 A2 | 8/2003 |
| WO | WO 2013/049770 A2 | 4/2013 |
| WO | WO 2013/138361 A1 | 9/2013 |
| WO | WO 2017/165732 A1 | 9/2017 |

OTHER PUBLICATIONS

Burrows, F., et al. "TG02: A novel, multi-kinase inhibitor with potent activity against solid tumors." Journal of Clinical Oncology 28.15_suppl (2010): e13549-e 13549.*
Remington's Pharmaceutical Sciences (Sixteenth Edition; 1980, p. 420-425).*
Berge et al. ("Pharmaceutical Salts", Journal of Pharmaceutical Sciences, 66(1); 1977:1-19).*
Amanchy et al., "A curated compendium of phosphorylation motifs," Nature Biotechnology 25:285-6 (2007).
Agnihotri et al., "A GATA4-regulated tumor suppressor network represses formation of malignant human astrocytomas," J. Exp. Med. 208:689-702 (2011).

(Continued)

*Primary Examiner* — Anna Pagonakis
(74) *Attorney, Agent, or Firm* — Baker Botts L.L.P.

(57) ABSTRACT

The present disclosure relates to uses of TG02, for treating a glioma in a pediatric human subject. In certain embodiments, the glioma can be a pediatric high-grade glioma (PHGG), e.g., a diffuse intrinsic pontine glioma (DIPG), and/or a H3.3-mutated glioma (e.g., a H3K27M-mutated glioma). The present disclosure further provides pharmaceutical compositions and kits that include an ERK5 inhibitor.

Figures 1D, 1E, 1F, 1G:
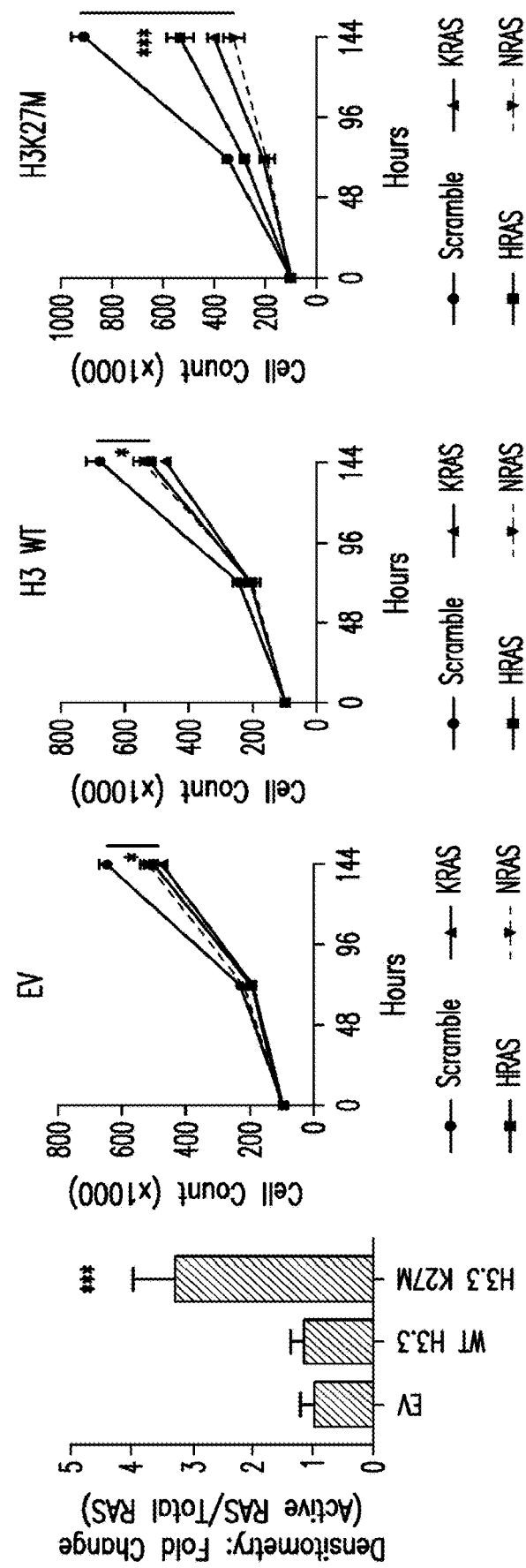
Figure 1J:
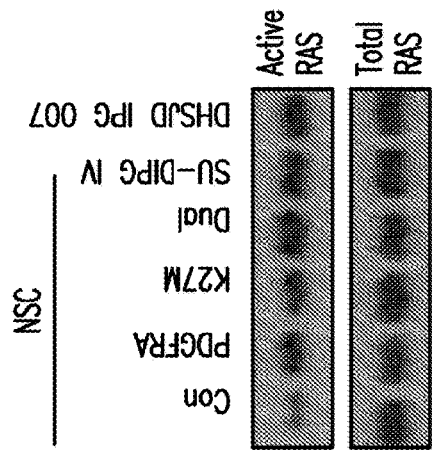

9 Claims, 77 Drawing Sheets
Specification includes a Sequence Listing.

(56) References Cited

OTHER PUBLICATIONS

Bender et al., International Cancer Genome Consortium PedBrain Tumor Project, "Recurrent MET fusion genes represent a drug target in pediatric glioblastoma," Nat Med. 22:1314-1320 (2016).
Berchtold et al., "Gene expression changes in the course of normal brain aging are secually dimorphic," Proceedings of the National Academy of Sciences of the United States of America 105:15605-15610 (2008).
Berlow et al., "IL-13 receptors as possible therapeutic targets in diffuse intrinsic pontine glioma," PLoS One 13:e0193565 15 (2018).
Biter et al., "Targeting EZH2 methvltransferase activity in ARID1A mutated cancer cells is synthetic lethal," Nature Med. 21, 231-238 (2015).
Broniscer et al., "Young Age May Predict a Better Outcome for Children with Diffuse Pontine Glioma," Cancer, 113 3 566-572 (2008).
Cancer Genome Atlas Research Network, "Comprehensive, Integrative Genomic Analysis of Diffuse Lower-Grade Gliomas," The New England Journal of Medicine 372(26):2481-2498 (2015).
English et al., "Identification of substrates and regulators of the mitogen-activated protein kinase ERK5 using chimeric protein kinases," J Biol Chern 273:3854-3860 (1998).
Fangusaro, "Pediatric High-Grade Gliomas and Diffuse Intrinsic Pontine Gliomas," Journal of Child Neurology 24:1409-1417 (2009).
Filbin et al., "Developmental and oncogenic programs in H3K27M gliomas dissected by single-cell RNA-seq," Science 360, 331-335 (2018).
Garapaty-Rao et al., "Identification of EZH2 and EZH1 Small Molecule Inhibitors with Selective Impact on Diffuse Large B Cell Lymphoma Cell Growth," Chemistry and Biology, 20, 1329-1339 (2013).
Geoerger et al., A Phase I Study of the CDK4/6 Inhibitor Ribociclib (LEE011) in Pediatric Patients with Malignant Rhabdoid Tumors, Neuroblastoma, and Other Solid Tumors, Clin Cancer Res 23:2433-2441 (2017).
Grasso et al., "Functionally defined therapeutic targets in diffuse intrinsic pontine glioma," Nature Medicine 21, 555-559 (2015).
Grimaldi et al., "MEK Inhibitors in the Treatment of Metastatic Melanoma and Solid Tumors, " Am J Clin Dermatol 18:745-754 (2017).
Gupta et al., "Stochastic State Transitions Give Rise to Phenotypic Equilibrium in Populations of Cancer Cells," Cell 146:633-644 (2011).
Harutyunyan et al., "H3K27M induces defective chromatin spread of PRC2-mediated repressive H3K27me2/me3 and is essential for glioma tumor genesis," Nature Communications 10:1262 (2019).
Hashizume et al., "Pharmacologic inhibition of histone demethylation as a therapy for pediatric brainstem glioma," Nature Medicine 20:1394-1396 (2014).
Hayashi et al., "Targeted deletion of BMK1/ERK5 in adult mice perturbs vascular integrity and leads to endothelial failure," The Journal of Clinical Investigation 113:1138-48 (2004).
He et al., "Cdk7 Is Required for Activity-Dependent Neuronal Gene Expression, Long-Lasting Synaptic Plasticity and Long-Term Memory," Frontiers in Molecular Neuroscience, https://doi.org/10.3389/fnmol.2017.00365 (2017).
Hoffman et al., "Clinical, Radiologic, Pathologic, and Molecular Characteristics of Long-Term Survivors of Diffuse Intrinsic Pontine Glioma (DIPG): A Collaborative Report from the International and European Society for Pediatric Oncology DIPG Registries," Journal of Clinical Oncology 36(19):1963-1972 (2018).
Hoang et al., "MFK5-ERK5 Signaling in Cancer: Implications for Targeted Therapy," Cancer Lett 392:51-59 (2017).
International Search Report dated Jul. 27, 2020 in International Application No. PCT/US2020/029400.
Jones et al., "Pediatric high-grade glioma: biologically and clinically in need of new thinking," Neuro-Oncology 19(2): 153-161 (2017).
Jones et al., "Unique genetic and epigenetic mechanisms driving paediatric diffuse highgrade glioma," Nature Reviews Cancer 14,10 (2014): 10.1038/nrc3811. doi:10.1038/nrc3811.
Klein et al., "CDK4/6 Inhibitors: The Mechanism of Action May Not Be as Simple as Once Thought," Cancer Cell 34:9-20 (2018).
Khuong-Quang et al., "K27M mutation in histone H3.3 defines clinically and biologically distinct subgroups of pediatric diffuse intrinsic pontine gliomas," Acta Neuropathol 124:439-447 (2012).
Larson et al., "Histone H3.3 K27M Accelerates Spontaneous Brainstem Glioma and Drives Restricted Changes in Bivalent Gene Expression," Cancer Cell 35:140-55 e7 (2019).
Lewis et al., "Inhibition of PRC2 Activity by a Gain-of-Function H3 Mutation Found in Pediatric Glioblastoma," Science 340(6134): 857-861 (2013).
Mackay et al., "Integrated Molecular Meta-Analysis of 1,000 Pediatric High-Grade and Diffuse Intrinsic Pontine Glioma," Cancer Cell 32(4):520-537 e5 (2017).
Malumbres et al., "Cell cycle, CDKs and cancer: a changing paradigm," Nat Rev Cancer 9:153-166 (2009).
Mohammad et al., "EZH2 is a potential therapeutic target for H3K27M-mutant pediatric gliomas," Nature Medicine 23:483-492 (2017).
Nagaraja et al., "Transcriptional Dependencies in Diffuse Intrinsic Pontine Glioma," Cancer Cell 31, 63 5-652 (2017).
Ostrom et al., "CBTRUS Statistical Report: Primary Brain and Central Nervous System Tumors Diagnosed in the United States in 2008-2012," Neuro-Oncology 17 Suppl 4:iv1-iv62 (2015).
Paugh et al., "Novel Oncogenic PDGFRA Mutations in Pediatric High-Grade Gliomas," Journal of clinical oncology : official journal of the American Society of Clinical Oncology 28:3061-3098 (2010).
Pavan et al., "A kinome-wide high-content siRNA screen identifies MEK5-ERK5 signaling as critical for breast cancer cell EMT and metastasis," Oncogene 37:4197-4213 (2018).
Piunti et al., "Therapeutic targeting of polycomb and BET bromodomain proteins in diffuse intrinsic pontine gliomas," Nature Medicine 23(4):493-500 (2017).
Sharifnia et al., "Small-molecule targeting of brachyury transcription factor addiction in chordoma," Nat Med. 25:292-300 (2019).
Silveira et al., "H3.3 K27M depletion increases diferentiation and extends latency of difuse intrinsic pontine glioma growth in vivo," Acta Neuropathologica 137:637-655 (2019).
Smith et al., "The E3 ubiquitin ligases RNF126 and Rabring7 regulate endosomal sorting of the epidermal growth factor receptor," Journal of Cell Science 126:1366-1380 (2013).
Song et al., "Stat3 upregulates MEK5 expression in human breast cancer cells," Oncogene 23:8301-83099 (2004).
Sturm et al., "Hotspot Mutations in H3F3A and IDH1 Define Distinct Epigenetic and Biological Subgroups of Glioblastoma," Cancer Cell 22, 425-437 (2012).
Schwartzentruber et al., "Driver mutations in histone H3.3 and chromatin remodelling genes in paediatric glioblastoma," Nature 482:226-231 (2012).
Tischmeyer et al., "Activation of immediate early genes and memory formation," Cell Mol Life Sci 55:564-574 (1999).
Townson et al., "Spotlight on Cancer Cell Dormancy Dormancy of Solitary Metastatic Cells," Cell cycle, 5:16, 1744-1750 (2006).
Tusa et al., "ERK5 is activated by oncogenic BRAF and promotes melanoma growth," Oncogene 3 7:2601-2614 (2018).
Umapathy et al., "The kinase ALK stimulates the kinase ERK5 to promote the expression of the oncogene MYCN in neuroblastoma," Science Signaling 7:ra102 (2014).
Vaseva et al., "KRAS Suppression-Induced Degradation of MYC is Antagonized by a MEK5-ERK5 Compensatory Mechanism," Cancer Cell 34:807-822 e7 (2018).
Vinci et al., "Functional diversity and co-operativity between subclonal populations of paediatric glioblastoma and diffuse intrinsic pontine glioma cells," Nat Med 24(8): 1204-1215(2018).
Wander et al., "Blocking the Cycle: Cyclin-Dependent Kinase 4/6 Inhibitors in Metastatic, Hormone Receptor-Positive Breast Cancer," J Clin Oncol 3 5:2866-2870 (2017).
Wang et al., "The ERK5-MEF2C transcription factor pathway contributes to anti-apoptotic effect of cerebral ischemia preconditioning in the hippocampal CA1 region of rats," Brain Res. 1255:32-41 (2009).

(56) References Cited

OTHER PUBLICATIONS

Warren, "Diffuse intrinsic pontine glioma: poised for progress," frontiers in oncology 2:205 (2012).
Yeh et al., "Mechanisms of Cancer Cell Dormancy—Another Hallmark of Cancer?," Cancer Res 75:5014-5022 (2015).
Zhang et al., "Targeting CDK9 Reactivates Epigenetically Silenced Genes in Cancer," Cell 175, 1244-1258 (2018).
Alberto Broniscer, Presentation at the Pediatric Brain Tumor Consortium on Oct. 29, 2018.
Koncar et al., "DIPG-11. Activation of Ras Signaling and Distinct Mitogen-Activated Protein Kinases (MAPKS) Provides Unique Therapeutic Vulnerabilities in Mutant Histone DIPG," Neuro-Oncology, vol. 21, Issue Supplement_2, Apr. 2019, p. ii70.
Koncar et al., "Identification of Novel RAS Signaling Therapeutic Vulnerabilities in Diffuse Intrinsic Pontine Gliomas" Cancer Res. 79(16):4026-4041 (2019).
Parrott et al., "Abstract P08.32 TG02, An Oral CDK Inhibitor, Demonstrates Activity in Glioma Models: EORTC Brain Tumor Group Conducts Phase IB Study (STEAM / EORTC 1608)," Neuro-Oncology, p. 48 (Oct. 2016).
Pelton et al., "EXTH-63 Preclinical Efficacy of a CDK Inhibitor (Tg02) In Glioblastoma," Neuro-Oncology, p. 73 (Nov. 2016).
Presentation at the Pediatric Brain Tumor Consortium on Apr. 8, 2019.
Wadhwa et al., "PDTM-41. TG02, A Novel Multikinase Inhibitor, is Effective in Pediatric Brain Tumors, With Selective Potency In Those With MYC Expression," Neuro-Oncology, p. 98-99 (Nov. 2017).

\* cited by examiner

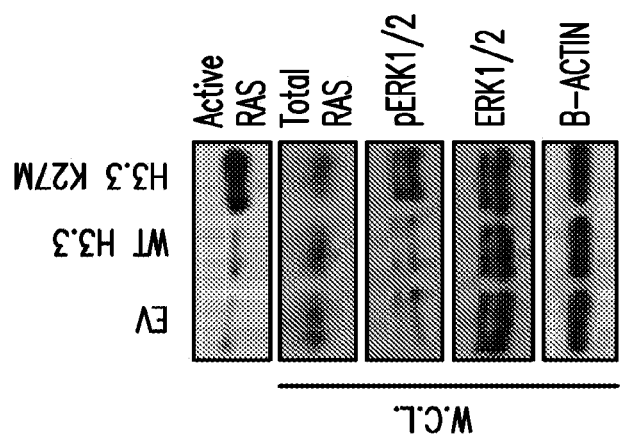
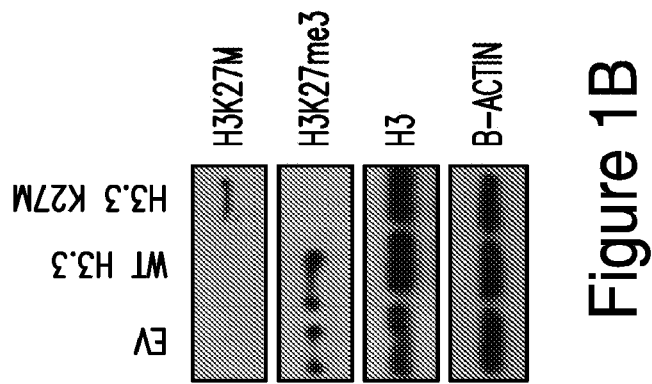
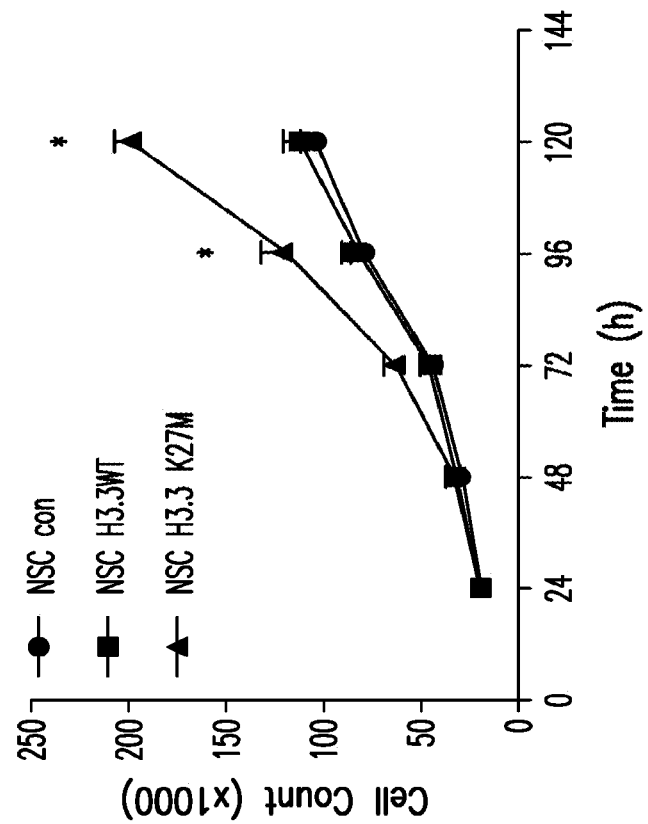
Figure 1A
Figure 1B
Figure 1C

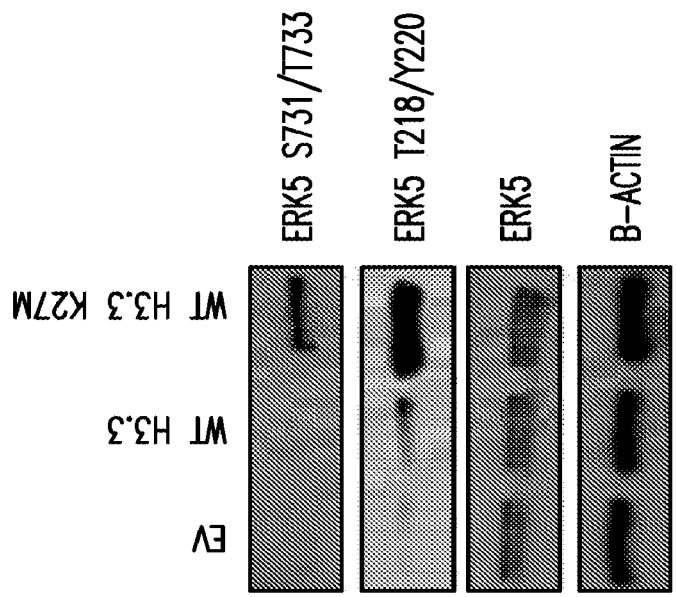
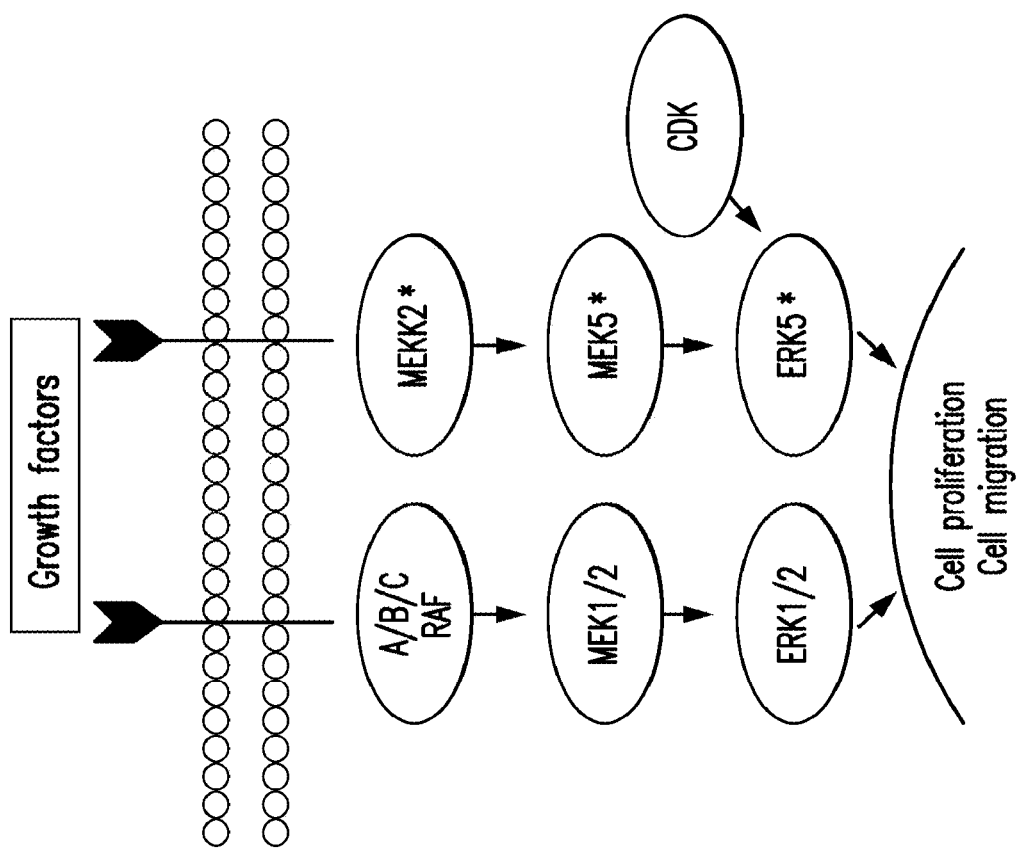
Figure 3B
Figure 3A

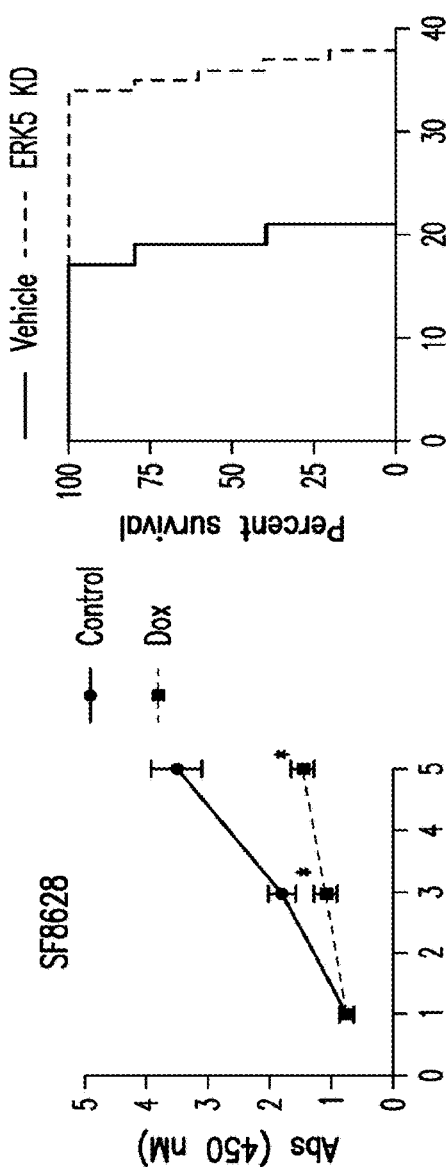
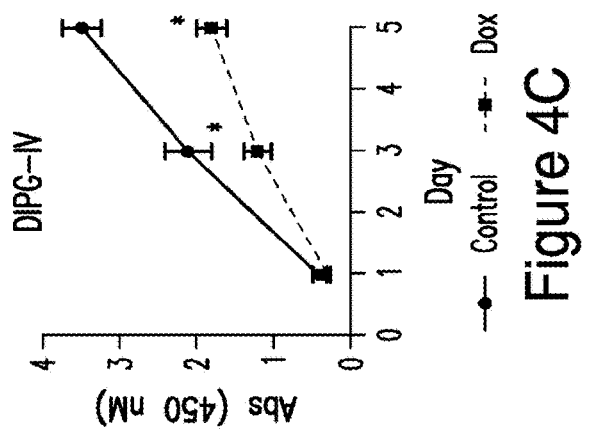
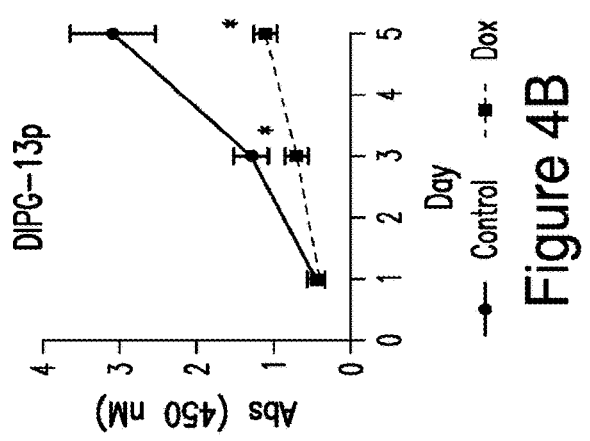
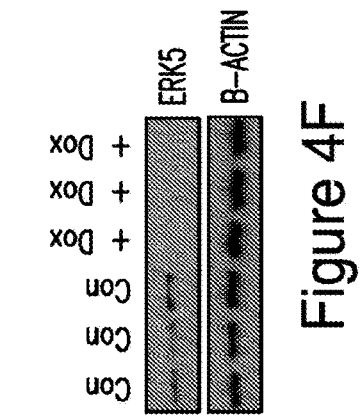
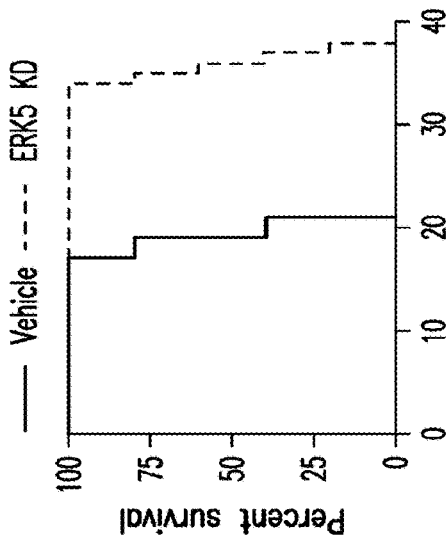
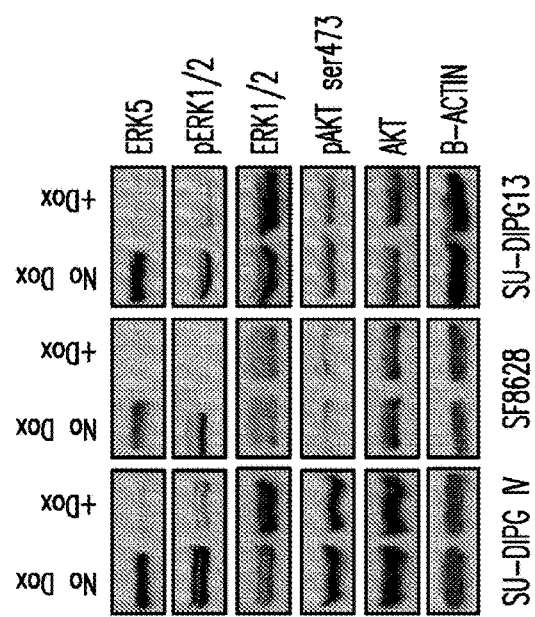
Figure 4A
Figure 4B
Figure 4C
Figure 4D
Figure 4E
Figure 4F

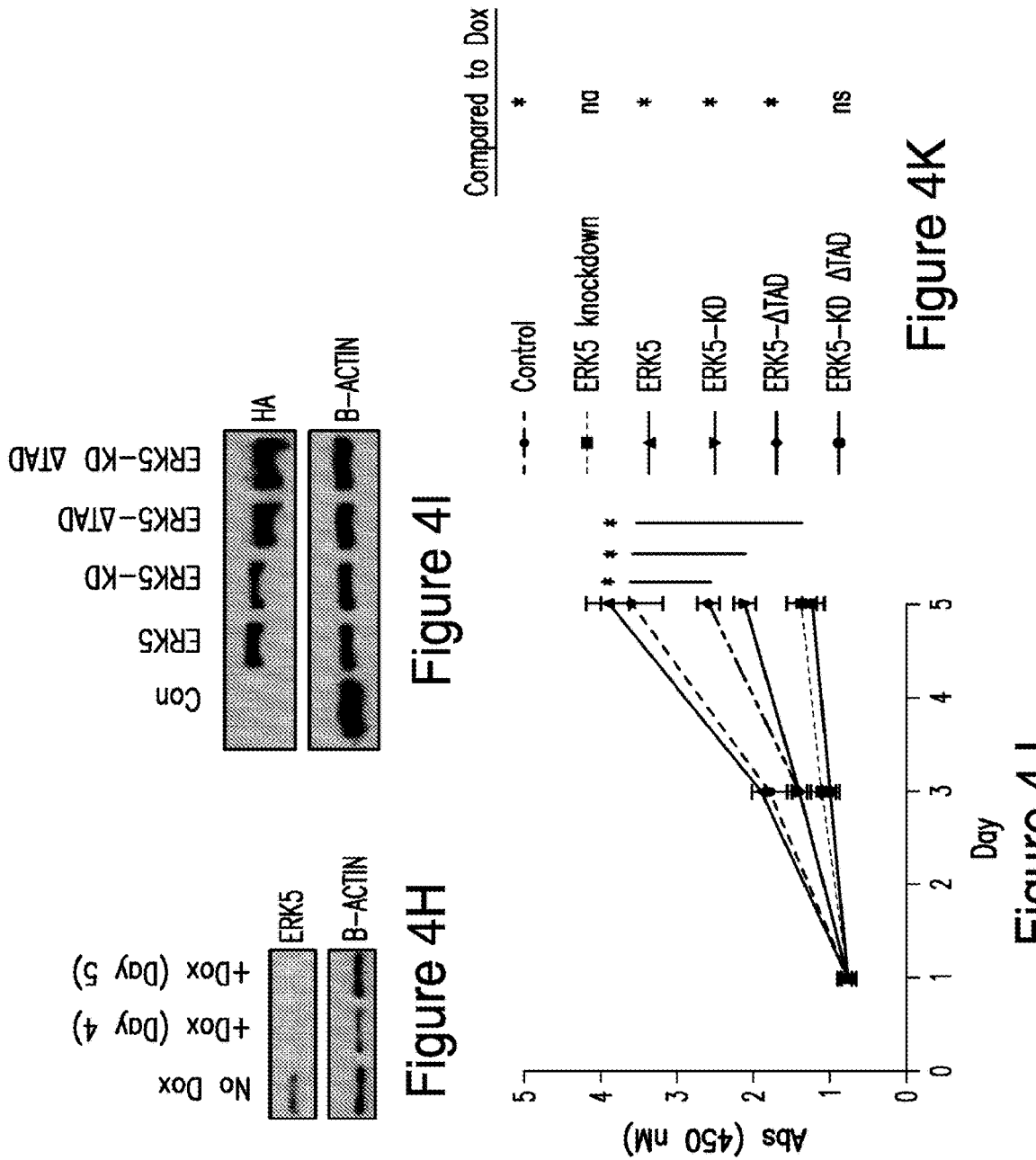

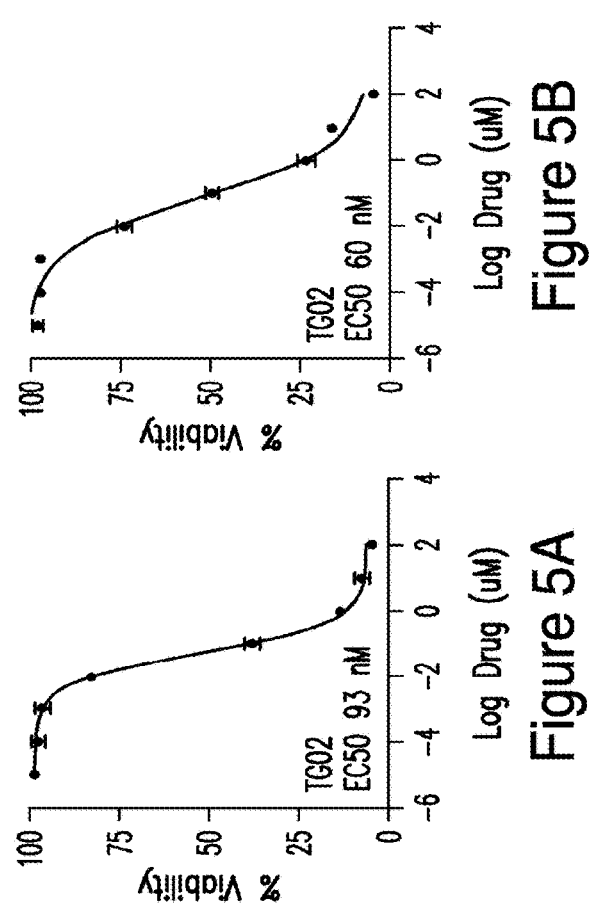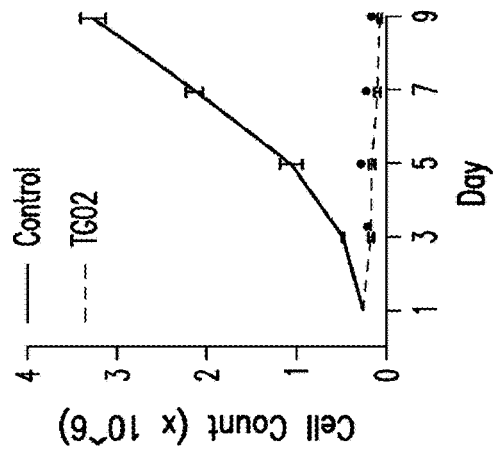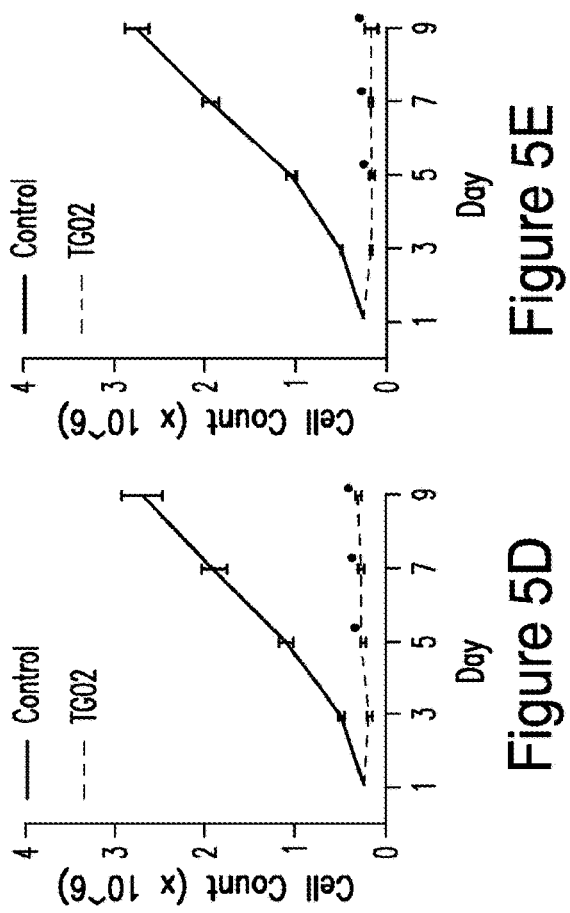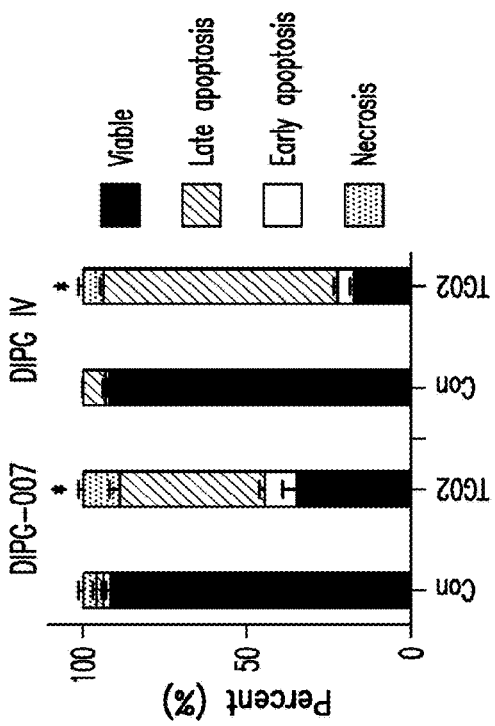

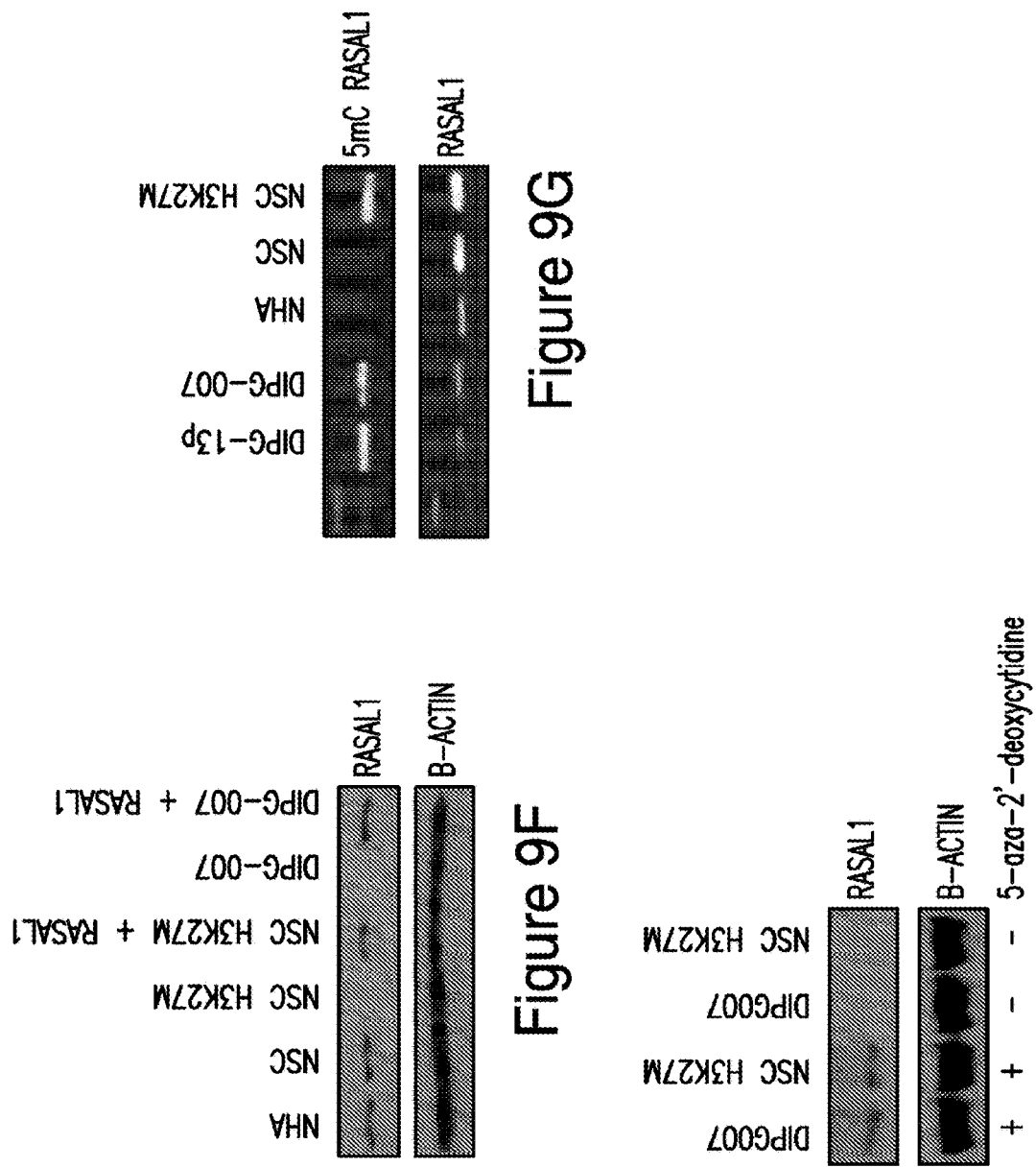

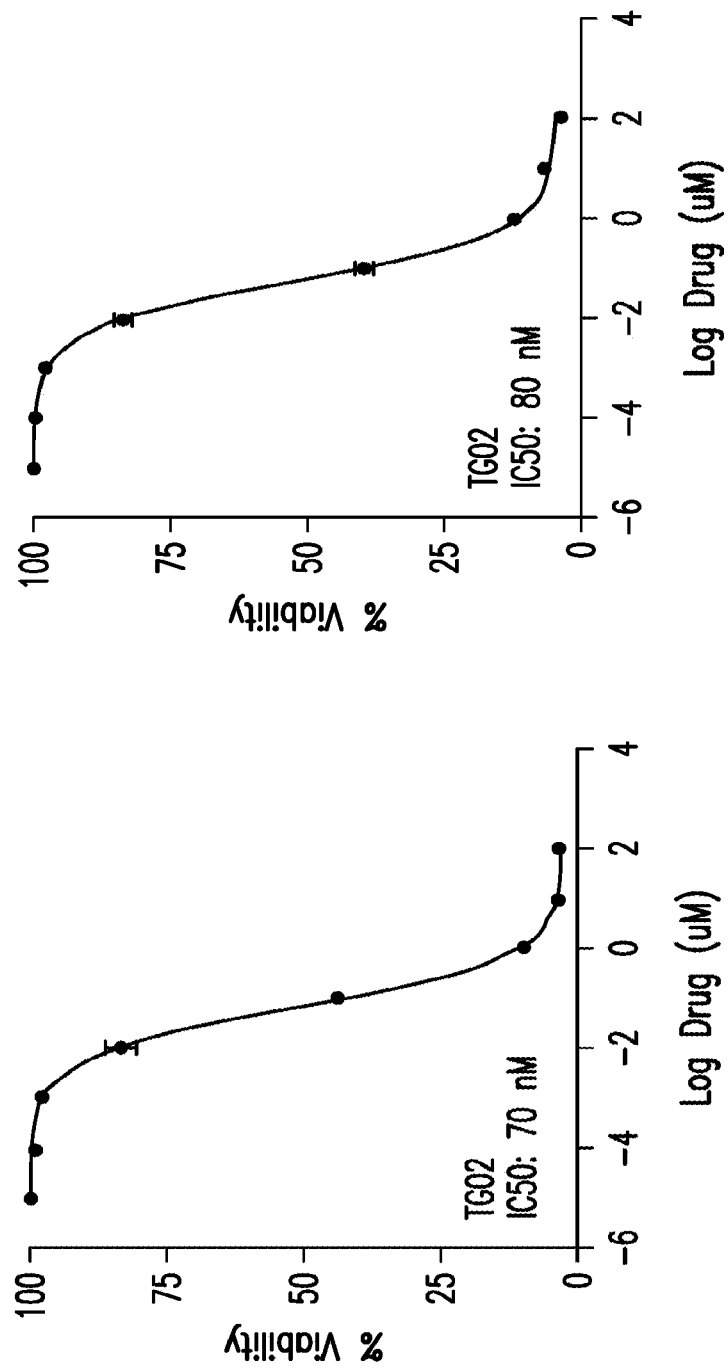

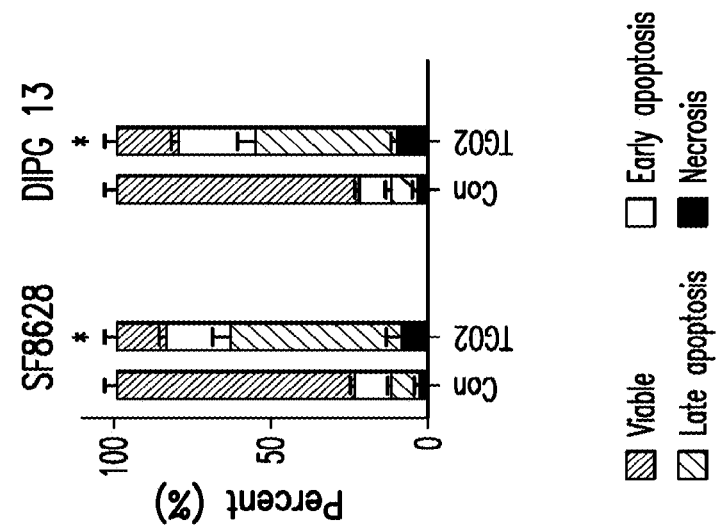
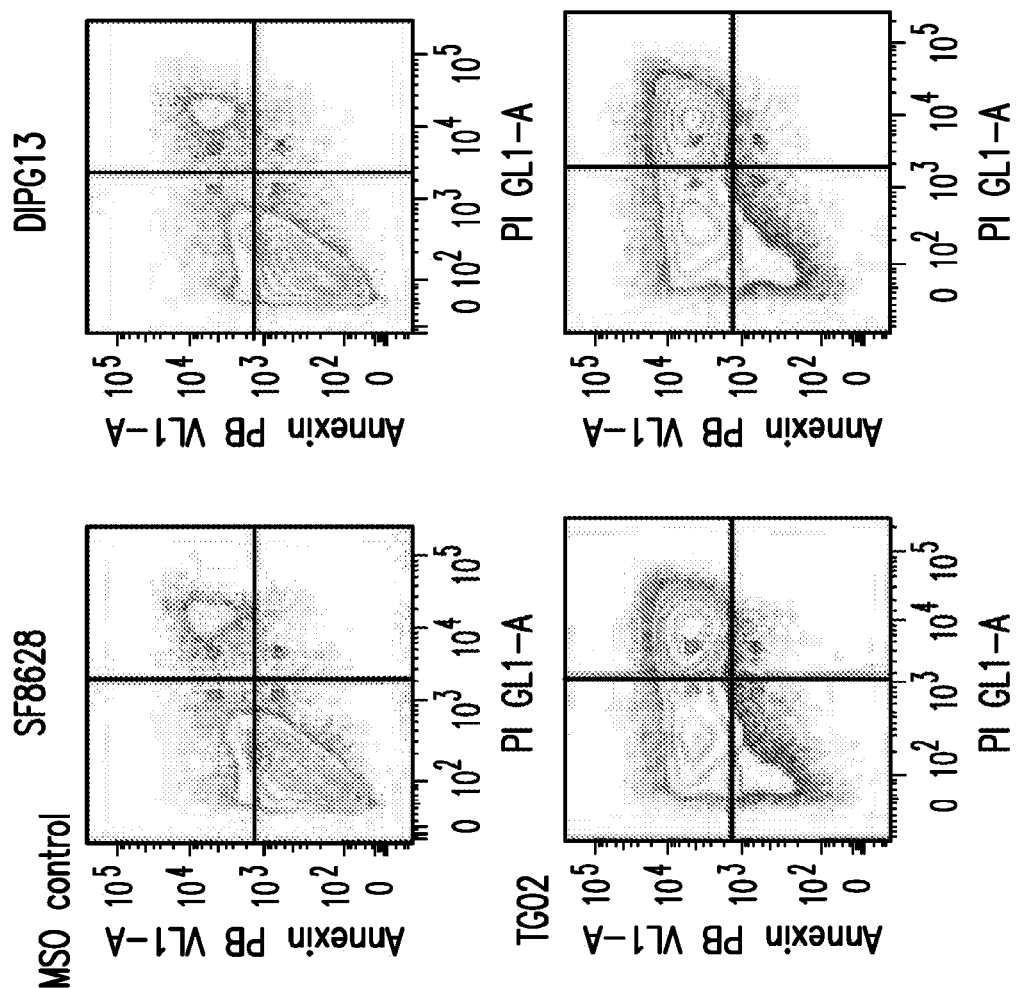
Figure 12C
Figure 12D
Figure 12E

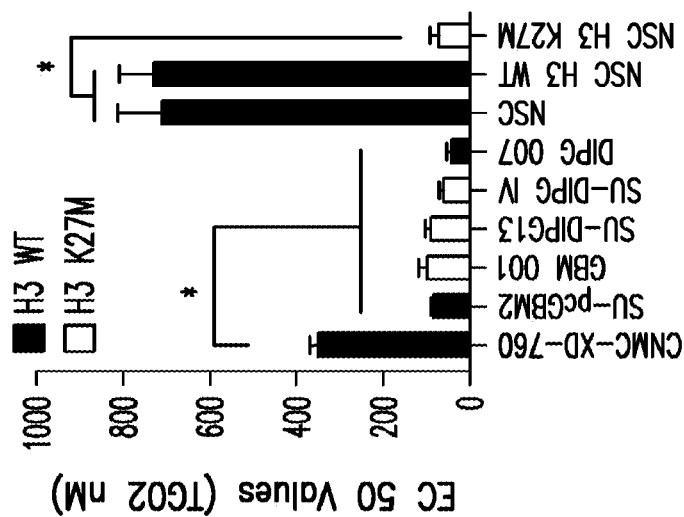
Figure 12I
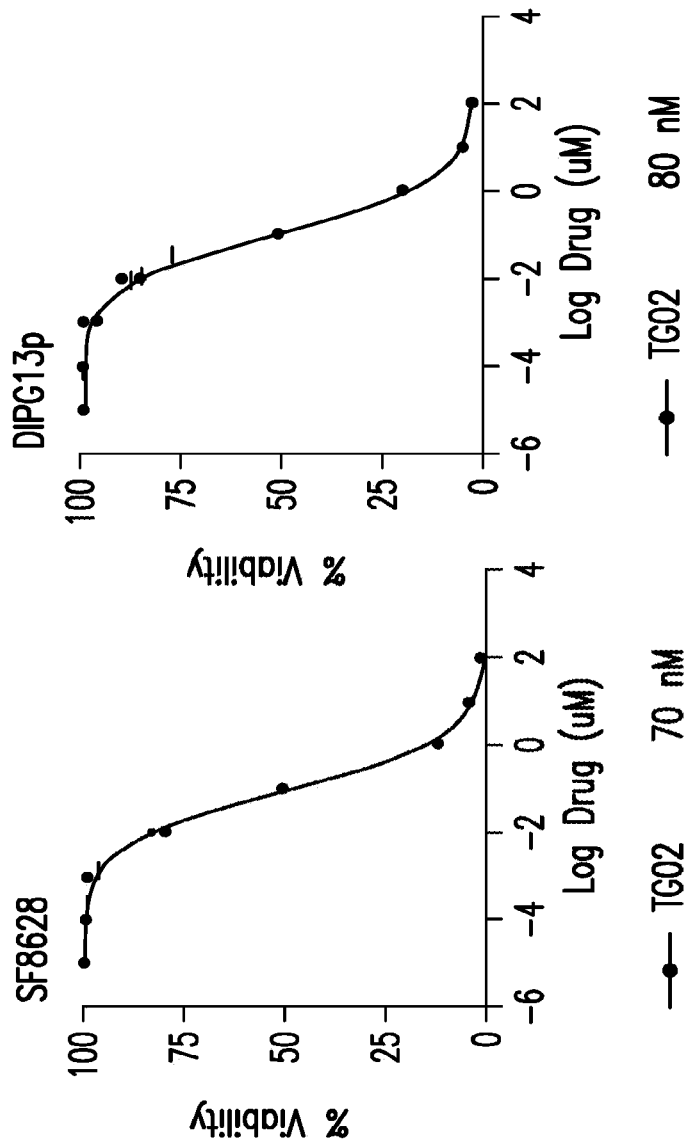
Figure 12H
Figure 12G

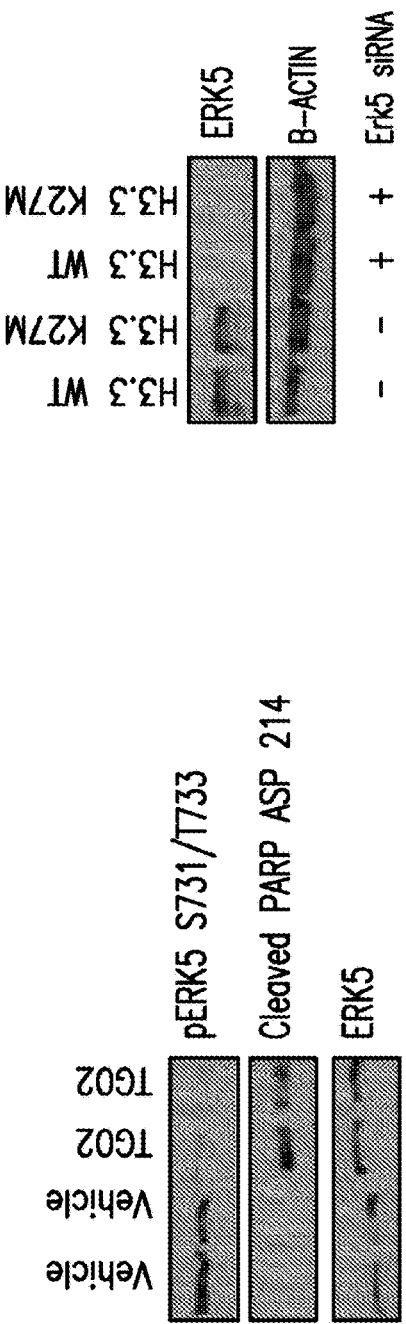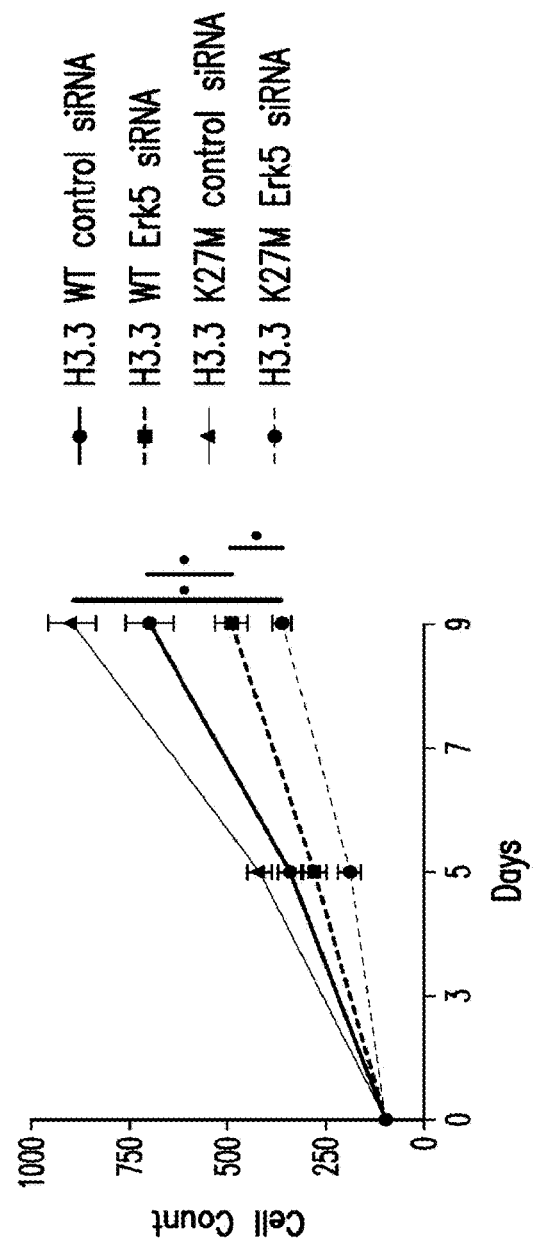

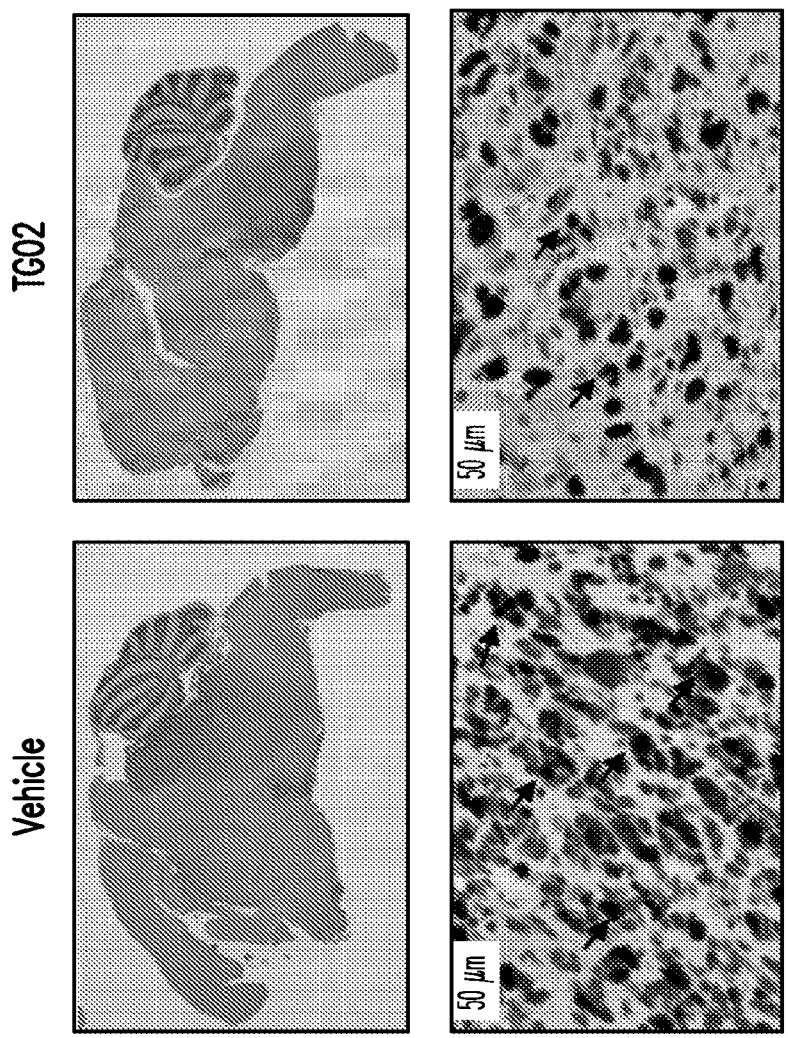
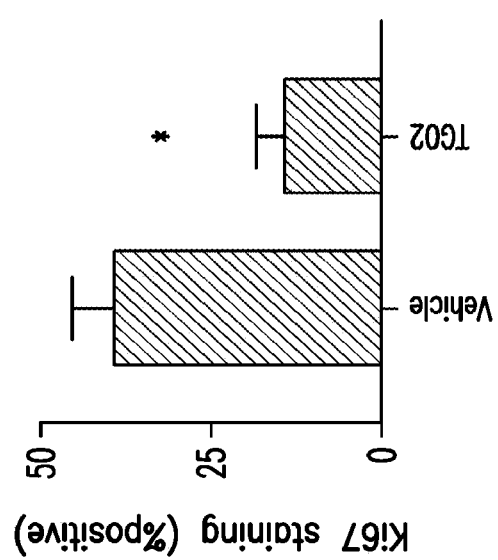
Figure 26A
Figure 26B

| NSCK27M-NSCA2:E35A1A2:A2:E237 ||||
| --- | --- | --- | --- | --- |
| Gene | Z-Score 1 | Z-Score 2 | Z-Score 3 | Average Viability Difference( % ) (NSCK27M/Control siRNA)/ (NSC/Control siRNA) (n=3) |
| LIN28B | -2.9425488 | -2.8580218 | -3.2609782 | -57.23 |
| HSPB2 | -3.4728039 | -2.4544055 | -2.92375 | -55.93 |
| MAP3K2 | -3.0368164 | -2.8118942 | -2.6151004 | -53.73 |
| JUN | -2.8718482 | -2.9329791 | -2.49507 | -52.80 |
| AURKB | -3.0780585 | -2.3967461 | -2.815151 | -52.73 |
| HSPA4 | -2.2885676 | -2.8118942 | -3.0837905 | -52.23 |
| LAMTOR3 | -2.9484406 | -2.5351288 | -2.7008364 | -52.13 |
| ZAK | -3.172326 | -2.7484688 | -2.2321463 | -51.90 |
| KRAS | -2.6656378 | -3.0021705 | -2.4436284 | -51.73 |
| MAPK7 | -2.5006696 | -2.9041494 | -2.6265319 | -51.30 |
| MAP2K5 | -2.7775806 | -2.8061283 | -2.409334 | -51.03 |
| FOXM1 | -2.9837909 | -2.8234261 | -2.1349788 | -50.70 |
| MAP2K3 | -2.6067206 | -2.1488104 | -3.0152017 | -49.80 |
| MAP3K14 | -2.36516 | -2.5927883 | -2.7236993 | -49.30 |
| MAP3K7 | -2.6420709 | -2.1488104 | -2.8665926 | -49.13 |
| LIN28A | -2.1177076 | -2.8291921 | -2.6608263 | -48.90 |
| GADD45B | -2.3357013 | -2.8753196 | -2.3921868 | -48.83 |
| HSP90AB1 | -2.577262 | -2.2583633 | -2.7236993 | -48.57 |
| AKT2 | -2.5949372 | -2.3794482 | -2.5750903 | -48.50 |
| PDGFRA | -2.6185041 | -2.4717034 | -2.4150497 | -48.23 |
| MAP3K13 | -2.3828351 | -2.3102569 | -2.8037196 | -48.23 |
| MYC | -2.4829944 | -2.408278 | -2.5179329 | -47.70 |
| NRAS | -2.2237586 | -2.8464899 | -2.2550092 | -47.23 |
| HSP90AA1 | -2.4299689 | -2.2583633 | -2.3921868 | -45.80 |
| PAK2 | -2.3298096 | -2.0392574 | -2.4321969 | -44.20 |
| AURKA | -2.1471662 | -2.1545763 | -2.2321463 | -42.67 |
| MAP3K1 | -1.575669 | -1.9354703 | -1.5576898 | -34.23 |
| MAPKAPK3 | -1.2987581 | -1.7163643 | -1.4262279 | -30.63 |
| EGFR | -1.0630891 | -1.4395989 | -1.1518728 | -26.10 |
| MAP2K4 | -0.2205727 | -0.5458772 | -2.4607756 | -23.80 |
| HSPA6 | -0.5681844 | -0.9610253 | -1.6662887 | -23.53 |
| MAPKAPK5 | -0.0673879 | -0.5747069 | -0.7974973 | -13.40 |
| SOS1 | -0.6742354 | -0.3152393 | -0.2545027 | -12.17 |
| RAC1 | -0.1321969 | -0.3383031 | -0.3745331 | -9.93 |
| SOS2 | -0.2794899 | -0.1941544 | -0.3459544 | -9.77 |
| DUSP6 | -1.4048091 | 0.60731219 | -0.0201576 | -9.60 |

Figure 32

| | | | | |
|---|---|---|---|---|
| FYN | -0.3148403 | 0.13450456 | -0.4374061 | -8.60 |
| FGF1 | 0.2095231 | -0.6611961 | -0.1459037 | -8.53 |
| CHP1 | 0.07401346 | -0.5574091 | -0.077315 | -8.30 |
| RELA | -0.255923 | -0.3901966 | 0.1055885 | -8.13 |
| CACNG5 | 0.1093638 | -0.3152393 | -0.3059443 | -8.03 |
| HSPA1A | -0.0614962 | -0.5862388 | 0.13416717 | -8.00 |
| NFATC2 | -0.2382479 | -0.8168767 | 0.56856288 | -7.80 |
| CACNA1G | -0.4562416 | 0.56118462 | -0.5802995 | -7.77 |
| NFKB2 | 0.32735756 | -0.3959625 | -0.31166 | -7.30 |
| PLA2G1B | 0.05044657 | -0.3901966 | -0.0430206 | -7.27 |
| PPP3CB | -0.2912734 | 0.26712133 | -0.3573859 | -7.23 |
| DUSP10 | -0.3973244 | -0.2691117 | 0.27706049 | -7.23 |
| CHP2 | 0.68675268 | -0.4074944 | -0.6260253 | -7.17 |
| HSPB1 | -0.2028975 | -0.5055155 | 0.36279649 | -7.00 |
| MAPK1 | 0.49232581 | -0.1653247 | -0.6431725 | -6.97 |
| TAOK2 | 0.63961889 | -0.4824517 | -0.4659848 | -6.93 |
| TNFRSF1A | -0.5033754 | 0.02495157 | 0.15131437 | -6.87 |
| HSPA8 | -0.2912734 | -0.1191971 | 0.08844131 | -6.87 |
| TAB2 | 0.42162513 | -0.2518139 | -0.4659848 | -6.83 |
| MAP2K6 | 0.72799474 | -0.3613669 | -0.6260253 | -6.67 |
| CACNG1 | -0.1734389 | -0.4824517 | 0.40280662 | -6.47 |
| RPS6KA5 | 0.87528782 | -0.3325371 | -0.7517714 | -6.40 |
| CACNA1E | -0.4208913 | -0.6900258 | 0.88292819 | -6.27 |
| PLA2G2D | -0.4739168 | -0.344069 | 0.64858314 | -5.93 |
| MAPK8 | 0.02687968 | 0.38820622 | -0.5631523 | -5.93 |
| MAX | 0.2861155 | -0.3210052 | -0.0944621 | -5.83 |
| PLA2G12A | -0.0084707 | -0.0788355 | -0.0487363 | -5.83 |
| ATF2 | 1.08738986 | 0.07684509 | -1.2090301 | -5.50 |
| PPP3R1 | -0.3148403 | -0.1364949 | 0.38565942 | -5.37 |
| MAP3K8 | -0.1911141 | 0.11144077 | 0.02556824 | -5.33 |
| MAP3K3 | -0.6801271 | 0.82641817 | -0.1973453 | -5.27 |
| PPP3R2 | -0.597643 | 0.11720672 | 0.42566955 | -5.27 |
| PLA2G3 | -0.4857002 | 0.67650355 | -0.225924 | -5.20 |
| CDC42 | 0.19773965 | -0.6554301 | 0.43710102 | -5.17 |
| TGFBR1 | 0.07401346 | 0.00765373 | -0.0487363 | -4.87 |
| PDGFRB | -0.3678658 | 0.61307814 | -0.2144925 | -4.83 |
| PLA2G2C | 0.616052 | -0.2056863 | -0.3459544 | -4.77 |
| ARAF | -0.2735982 | 0.16910024 | 0.17989303 | -4.57 |
| MECOM | -0.7743947 | 0.66497166 | 0.17989303 | -4.53 |
| PLA2G6 | -0.638885 | -0.234516 | 0.94580125 | -4.50 |
| SRF | 0.23308999 | -0.2172182 | 0.08844131 | -4.47 |
| STK4 | -0.0614962 | 0.45163163 | -0.2773656 | -4.40 |
| PDGFA | 0.42162513 | 0.03648346 | -0.31166 | -4.27 |

Figure 32 continued

| | | | | |
|---|---|---|---|---|
| PRKCA | 0.10347208 | −0.3094733 | 0.36279649 | −4.13 |
| PLA2G12B | −0.2794899 | 0.14603645 | 0.31135489 | −3.97 |
| IL1R1 | −0.1852224 | −0.124963 | 0.48854261 | −3.97 |
| DUSP14 | 0.40394996 | −0.4305582 | 0.2427661 | −3.83 |
| JMJD7−PLA2G4B | 0.64551062 | 0.0537813 | −0.4545533 | −3.73 |
| RHEB | −0.0202541 | 0.2382916 | 0.02556824 | −3.63 |
| FGF20 | 0.1093638 | 0.44009974 | −0.2887971 | −3.57 |
| CACNB4 | −0.3089485 | 0.34207864 | 0.23133463 | −3.47 |
| IKBKG | 0.62783545 | 0.04224941 | −0.3745331 | −3.43 |
| TNF | 0.616052 | 0.03648346 | −0.3573859 | −3.43 |
| MAPK3 | 0.48054237 | −0.0903674 | −0.0887464 | −3.37 |
| RASGRP2 | 0.45697547 | 0.10567482 | −0.2487869 | −3.30 |
| MAPK13 | −0.1793306 | 1.20697065 | −0.6888984 | −3.10 |
| RAC3 | 0.3627079 | −0.1826225 | 0.17989303 | −3.00 |
| PRKCG | −0.597643 | 0.61307814 | 0.32850209 | −2.97 |
| PLA2G2A | 0.05633829 | 0.14027051 | 0.16846157 | −2.93 |
| RPS6KA2 | −0.6683437 | 1.05129009 | −0.0258734 | −2.90 |
| CACNA1D | 0.05633829 | 0.04801536 | 0.27134476 | −2.87 |
| FGF6 | −0.0556044 | −0.130729 | 0.56284714 | −2.83 |
| CRK | −0.1675472 | 0.69380139 | −0.1459037 | −2.83 |
| HSPA2 | −0.4326747 | 0.9417371 | −0.1344723 | −2.83 |
| MAP4K4 | −0.149872 | 0.68803545 | −0.1516195 | −2.80 |
| FGF3 | −0.3619741 | 0.78605654 | −0.0315891 | −2.73 |
| RPS6KA6 | −0.0556044 | −0.1710906 | 0.62572021 | −2.70 |
| MAPK11 | 0.16828103 | 0.16910024 | 0.07129411 | −2.70 |
| TSC1 | 0.23308999 | −0.0615376 | 0.24848183 | −2.63 |
| FOS | 0.40394996 | −0.1018993 | 0.13416717 | −2.57 |
| JUND | 0.60426855 | 0.4228019 | −0.5745837 | −2.53 |
| CHUK | 0.51000098 | −0.4420901 | 0.38565942 | −2.47 |
| IL1R2 | 0.14471414 | 0.39397216 | −0.0887464 | −2.47 |
| RASAL2 | −0.0202541 | 0.38244027 | 0.08272557 | −2.47 |
| IL1B | −0.5033754 | 0.3247808 | 0.61428874 | −2.43 |
| PIK3CA | 0.35681618 | 0.1518024 | −0.0430206 | −2.40 |
| TAB1 | −0.2735982 | 0.11144077 | 0.60857301 | −2.40 |
| PIK3R1 | −0.0320376 | 0.01341968 | 0.47711115 | −2.37 |
| CD14 | 0.39216652 | −0.6957918 | 0.78576073 | −2.27 |
| HRAS | −0.2618148 | 0.12297266 | 0.62000447 | −2.20 |
| PRKCB | 0.42751686 | −0.0903674 | 0.17989303 | −2.10 |
| CRKL | −0.5446175 | 0.46316352 | 0.57999434 | −2.07 |
| PTPN5 | 1.28181673 | −0.1883885 | −0.5345736 | −2.00 |
| PPP3CC | 0.29200722 | −0.0500057 | 0.29420769 | −1.97 |
| RAC2 | 0.52767615 | −0.1768566 | 0.20275597 | −1.90 |
| RPS6KA4 | −0.4798085 | 0.16333429 | 0.86006526 | −1.80 |

Figure 32 continued

| | | | | |
|---|---|---|---|---|
| PPP5C | −0.2912734 | 0.87254574 | −0.0201576 | −1.77 |
| CACNA2D1 | 0.49821754 | −0.4420901 | 0.51712128 | −1.77 |
| FGF17 | 0.62783545 | 0.18639808 | −0.225924 | −1.73 |
| NTRK2 | 0.35681618 | −0.1595587 | 0.37994369 | −1.73 |
| NGF | −0.2500313 | 0.71686518 | 0.11130424 | −1.67 |
| PLA2G4B | 1.14041537 | −0.6957918 | 0.16846157 | −1.63 |
| CACNA1H | 0.39216652 | −0.0615376 | 0.26562903 | −1.63 |
| DDIT3 | 0.72799474 | −0.3267712 | 0.20275597 | −1.63 |
| CACNG6 | 0.44519203 | −0.2691117 | 0.42566955 | −1.60 |
| RASA3 | 0.32735756 | 0.37667432 | −0.077315 | −1.47 |
| EGF | 1.1227402 | −0.2172182 | −0.2373555 | −1.33 |
| HSPA1L | 0.87528782 | −0.4074944 | 0.1913245 | −1.33 |
| FGF16 | −0.5269423 | 0.61884408 | 0.54569994 | −1.27 |
| DUSP1 | 0.15060586 | 0.09990888 | 0.42566955 | −1.13 |
| BRAF | −0.7390443 | 0.33631269 | 1.05440018 | −1.13 |
| PLA2G4A | 0.07401346 | 0.39973811 | 0.20275597 | −1.13 |
| TSC2 | 0.33914101 | 0.55541867 | −0.1973453 | −1.07 |
| PDGFB | 0.42751686 | 0.09990888 | 0.1741773 | −1.03 |
| IL1A | −0.2794899 | 0.38820622 | 0.59142581 | −0.93 |
| INPP5A | 0.35092445 | −0.0500057 | 0.41423809 | −0.93 |
| RRAS2 | 0.25076516 | −0.021176 | 0.49425835 | −0.87 |
| MAP3K4 | 0.83404576 | −0.2691117 | 0.18560877 | −0.80 |
| FGF8 | 0.27433205 | 0.40550406 | 0.07129411 | −0.73 |
| INPP5B | 0.39216652 | 0.0653132 | 0.31135489 | −0.63 |
| TGFB2 | 0.98723056 | −0.1826225 | −0.0201576 | −0.63 |
| FGFR4 | −0.2382479 | −0.1826225 | 1.17443057 | −0.60 |
| FASLG | −0.3384072 | 1.08588577 | 0.01413678 | −0.60 |
| FGF10 | 0.39216652 | 0.20369592 | 0.1913245 | −0.53 |
| FGF21 | 0.43340858 | 0.11720672 | 0.24848183 | −0.47 |
| FGF7 | −0.2205727 | 0.62461003 | 0.39709089 | −0.37 |
| PLA2G10 | 0.26254861 | 0.33631269 | 0.21418743 | −0.37 |
| CACNG2 | 0.32735756 | 0.68803545 | −0.1916296 | −0.33 |
| TRAF6 | 0.12703897 | 0.7687587 | −0.0715992 | −0.30 |
| FGF11 | −0.0614962 | 0.31901485 | 0.56284714 | −0.27 |
| PLK1 | 0.616052 | −0.0038782 | 0.23133463 | −0.23 |
| RASGRP3 | −0.0614962 | −0.240282 | 1.13442044 | −0.17 |
| FGFR2 | −0.0732796 | 0.63614193 | 0.28277623 | −0.13 |
| TGFBR2 | 0.04455485 | −0.0038782 | 0.81433939 | −0.07 |
| PRKACG | 0.25665688 | −0.1595587 | 0.7628978 | −0.07 |
| CACNB1 | 0.61016028 | 0.22675971 | 0.04271544 | −0.03 |
| CACNA2D4 | 0.45108375 | 0.61307814 | −0.1744824 | 0.03 |
| NTF4 | 0.3627079 | −0.1537928 | 0.67144607 | 0.03 |
| TAOK1 | −0.5387258 | 0.88984358 | 0.52283701 | 0.10 |

Figure 32 continued

| | | | | |
|---|---|---|---|---|
| PLA2G5 | −0.5740761 | 0.63614193 | 0.80862366 | 0.10 |
| CACNA1S | 0.32735756 | −0.1191971 | 0.70574047 | 0.23 |
| MAPK8IP2 | 0.60426855 | 0.12873861 | 0.20275597 | 0.30 |
| RAPGEF2 | 0.38038307 | 0.24982349 | 0.30563916 | 0.33 |
| MAP2K7 | 0.04455485 | 0.91290737 | −0.0258734 | 0.33 |
| RAF1 | 0.05044657 | 0.73416302 | 0.15131437 | 0.37 |
| CACNA1I | 0.53356788 | 0.29018512 | 0.1227357 | 0.37 |
| RASGRF1 | 0.12114725 | 0.5842484 | 0.2427661 | 0.43 |
| RASA1 | 0.67496923 | −0.5170474 | 0.81433939 | 0.53 |
| RASGRF2 | 0.0327714 | 0.45163163 | 0.48282688 | 0.57 |
| MAPK10 | 0.75745336 | 0.67650355 | −0.4145432 | 0.73 |
| MKNK1 | 0.32146584 | 0.33054675 | 0.35136502 | 0.73 |
| DUSP7 | −0.4680251 | 0.89560953 | 0.56284714 | 0.77 |
| RPS6KA1 | 1.08738986 | −0.0442398 | −0.0144419 | 0.77 |
| FGFR3 | 0.30379067 | 0.64190787 | 0.06557837 | 0.77 |
| RBL2 | 1.07560641 | 0.5957803 | −0.631741 | 0.80 |
| FLNC | −0.0791713 | 0.71109923 | 0.37994369 | 0.83 |
| CACNA2D3 | 0.5394596 | 0.07107914 | 0.42566955 | 0.90 |
| CACNG7 | 0.63372717 | 0.28441917 | 0.1227357 | 0.90 |
| FGF4 | 0.68086096 | −0.6150685 | 0.98009565 | 0.97 |
| FLNA | 0.7692368 | −0.021176 | 0.32278636 | 1.07 |
| STMN1 | 0.15649759 | 0.60154624 | 0.31135489 | 1.13 |
| PRKACA | 0.4393003 | 0.59001435 | 0.06557837 | 1.23 |
| AKTIP | 0.05044657 | −0.3037074 | 1.35733403 | 1.40 |
| TP53 | −0.0261458 | 0.23252565 | 0.90007539 | 1.40 |
| MKNK2 | −0.3678658 | 0.96480089 | 0.50568981 | 1.40 |
| CASP3 | 0.6926444 | 1.04552414 | −0.5974467 | 1.43 |
| FGF22 | 0.02098795 | 0.42856784 | 0.67144607 | 1.47 |
| RASA4 | 0.1859562 | 0.63614193 | 0.31135489 | 1.50 |
| INPP4B | 0.49821754 | −0.0557717 | 0.71717193 | 1.63 |
| MOS | 0.1859562 | 0.01341968 | 0.95151699 | 1.63 |
| PLA2G2E | −0.0673879 | 1.2127366 | 0.01985251 | 1.70 |
| NTRK1 | −0.0497127 | 0.97056684 | 0.2427661 | 1.70 |
| HSPA1B | 0.29789895 | 0.71109923 | 0.16846157 | 1.73 |
| MEF2C | −0.043821 | 0.50352515 | 0.71717193 | 1.80 |
| AKT1 | 0.39216652 | 0.18063213 | 0.62572021 | 1.87 |
| ATF4 | 0.60426855 | −0.1191971 | 0.72288767 | 1.90 |
| PPM1A | 1.08149814 | 0.2382916 | −0.0944621 | 1.90 |
| RASGRP4 | 0.15649759 | 0.2382916 | 0.80290793 | 1.90 |
| MAPK14 | 0.16828103 | 1.1262474 | −0.0887464 | 1.90 |
| MAP4K1 | 0.22130654 | 0.34784459 | 0.63143594 | 1.90 |
| GADD45G | 0.1859562 | 0.20369592 | 0.83720233 | 2.07 |
| CACNA1A | 0.52178443 | −0.0384738 | 0.75718206 | 2.10 |

Figure 32 continued

| | | | | |
|---|---|---|---|---|
| FGF14 | 0.34503273 | 0.07107914 | 0.82005513 | 2.10 |
| IKBKB | -0.2912734 | 0.67650355 | 0.84863379 | 2.17 |
| NFATC4 | 0.45697547 | -0.5112815 | 1.30589243 | 2.20 |
| TAOK3 | 0.44519203 | 0.44586568 | 0.38565942 | 2.30 |
| MAP2K1 | 0.46875892 | 0.03648346 | 0.7971922 | 2.47 |
| DUSP5 | 0.69853613 | 0.13450456 | 0.47711115 | 2.47 |
| RAP1A | 0.40984169 | 0.17486619 | 0.71717193 | 2.47 |
| BDNF | 0.06812174 | 0.64767382 | 0.57999434 | 2.47 |
| RASA2 | 0.1329307 | 0.27865323 | 0.88864392 | 2.50 |
| INPP4A | 0.52178443 | 0.48622731 | 0.32850209 | 2.63 |
| CACNG4 | 0.39216652 | 0.60154624 | 0.34564929 | 2.67 |
| NTF3 | 0.09168863 | 0.65343977 | 0.59714154 | 2.73 |
| PPP3CA | 1.07560641 | 0.10567482 | 0.21418743 | 2.90 |
| MAP3K5 | -0.3325154 | 0.89560953 | 0.81433939 | 3.00 |
| SYNGAP | 0.53356788 | 0.78605654 | 0.08844131 | 3.03 |
| FGF23 | 0.2861155 | 1.23003444 | -0.1116093 | 3.03 |
| FLNB | 0.4393003 | 0.18063213 | 0.81433939 | 3.23 |
| CACNA1C | -0.0791713 | 0.84371601 | 0.6600146 | 3.23 |
| FGF19 | 1.14630709 | 0.28441917 | 0.03699971 | 3.30 |
| PPM1B | 0.60426855 | -0.0730695 | 0.94008552 | 3.43 |
| FGFR1 | 1.25824983 | 0.05954725 | 0.19704023 | 3.57 |
| MRAS | 0.50410926 | 0.84371601 | 0.17989303 | 3.73 |
| STK3 | 0.43340858 | 0.60154624 | 0.49425835 | 3.77 |
| GRB2 | 0.98133884 | 0.18063213 | 0.39137515 | 3.83 |
| NFKB1 | 0.616052 | 0.86101385 | 0.07700984 | 3.87 |
| FGF5 | 0.39805824 | 0.57271651 | 0.61428874 | 4.10 |
| CACNA2D2 | 0.43340858 | 0.48046136 | 0.694309 | 4.23 |
| PLA2G4E | 0.73388647 | -0.026942 | 0.90579112 | 4.23 |
| MAP3K11 | 0.7162113 | 0.12873861 | 0.81433939 | 4.50 |
| MAPK9 | 0.34503273 | 0.9417371 | 0.39137515 | 4.63 |
| MAP4K3 | 0.25665688 | 0.69380139 | 0.7286034 | 4.67 |
| FGF2 | 0.64551062 | 1.09741766 | -0.0430206 | 4.70 |
| CACNA1B | 0.07401346 | 0.79182249 | 0.83720233 | 4.83 |
| ECSIT | 0.54535132 | 0.48622731 | 0.694309 | 4.90 |
| CACNA1F | 0.78691197 | 0.87254574 | 0.08272557 | 4.93 |
| TGFB3 | 0.07401346 | 0.9417371 | 0.70574047 | 4.93 |
| RRAS | 1.4526767 | 0.05954725 | 0.25419756 | 5.00 |
| NR4A1 | 0.12114725 | 1.0282263 | 0.58571008 | 5.00 |
| PRKX | 0.56302649 | 0.51505704 | 0.67144607 | 5.03 |
| PLA2G2F | 0.1329307 | 1.09741766 | 0.53426848 | 5.17 |
| DUSP2 | 0.66318579 | 0.75722681 | 0.36279649 | 5.20 |
| DUSP16 | 1.14630709 | 0.19792997 | 0.45996395 | 5.27 |
| FAS | 0.78102025 | 0.31901485 | 0.70574047 | 5.33 |

Figure 32 continued

| | | | | |
|---|---|---|---|---|
| DUSP9 | 1.07560641 | 0.05954725 | 0.7114562 | 5.53 |
| GNA12 | 0.2095231 | 1.13201334 | 0.48854261 | 5.53 |
| DUSP8 | 0.78102025 | 0.39397216 | 0.67144607 | 5.57 |
| CACNG8 | 0.68086096 | 1.15507713 | 0.01985251 | 5.60 |
| MAP4K2 | 0.39805824 | 0.30748296 | 1.14585191 | 5.67 |
| MAPK8IP3 | 0.91063816 | 0.57848246 | 0.39137515 | 5.73 |
| MAPK12 | 0.42751686 | 0.99363062 | 0.45996395 | 5.80 |
| NLK | 1.16987398 | 0.27865323 | 0.52855275 | 6.27 |
| RASGRP1 | 1.05793124 | 0.71109923 | 0.2256189 | 6.37 |
| RAP1B | 1.01079746 | 0.52658894 | 0.46567968 | 6.43 |
| CDC25B | 1.15219882 | 0.34207864 | 0.51712128 | 6.47 |
| MAPK8IP1 | 0.99312229 | 0.46892947 | 0.56856288 | 6.60 |
| DUSP4 | 0.23308999 | 1.17237497 | 0.62572021 | 6.70 |
| MAP3K12 | 1.14041537 | 0.52658894 | 0.41995382 | 6.90 |
| RELB | 0.96955539 | 0.54388678 | 0.57999434 | 6.97 |
| TRAF2 | 0.16238931 | 0.81488627 | 1.16299911 | 7.37 |
| FGF9 | 0.87528782 | 0.4977592 | 0.7971922 | 7.43 |
| MAP2K2 | 0.68086096 | 1.09741766 | 0.39709089 | 7.47 |
| MAP3K6 | 0.68086096 | 0.44009974 | 1.06583165 | 7.57 |
| MAPKAPK2 | 0.27433205 | 0.57848246 | 1.32303963 | 7.57 |
| TGFB1 | 0.75745336 | 0.69956734 | 0.79147646 | 7.90 |
| FGF13 | 1.1227402 | 0.48046136 | 0.7286034 | 8.33 |
| PRKACB | 1.24646639 | 0.93597116 | 0.2256189 | 8.73 |
| PTPN7 | 0.98723056 | 0.59001435 | 0.85434953 | 8.93 |
| ELK1 | 0.68086096 | 0.93597116 | 1.01439005 | 10.13 |
| CACNB2 | 1.25235811 | 1.04552414 | 0.36851222 | 10.23 |
| FGF18 | 1.47035187 | 1.31652364 | −0.1116093 | 10.23 |
| CACNB3 | 0.85172093 | 1.25309823 | 0.68287754 | 11.00 |
| FRK | 2.60745445 | 2.59079787 | 2.46047049 | 39.03 |
| MAPT | 2.39535242 | 3.0636055 | 2.46047049 | 40.57 |
| ARRB1 | 2.63102135 | 2.89639305 | 2.43189183 | 40.77 |
| ARRB2 | 2.61334618 | 2.91945684 | 2.47190196 | 41.03 |
| PTEN | 2.81955649 | 2.56196814 | 2.71767848 | 41.57 |
| FGF12 | 2.83133994 | 2.53890435 | 2.75768861 | 41.73 |
| NF1 | 2.99041647 | 2.65422329 | 2.50048062 | 41.80 |
| RPS6KA3 | 2.872582 | 2.45241515 | 2.96345499 | 42.67 |
| RASAL1 | 2.79009788 | 2.44088326 | 3.28925177 | 44.03 |
| AKT3 | 2.83133994 | 2.88486115 | 2.96917073 | 44.97 |
| DUSP3 | 2.872582 | 2.99441414 | 3.26638884 | 47.57 |
| DAXX | 2.40713586 | 3.62290234 | 3.11206405 | 47.67 |
| DAB2IP | 2.83133994 | 3.40379636 | 2.97488646 | 48.00 |
| FOXO3A | 2.40713586 | 3.64020018 | 3.42642937 | 49.60 |
| RBL1 | 3.08468404 | 3.29424337 | 3.83224641 | 53.80 |

Figure 32 continued

| DIPG007 | | | | |
|---|---|---|---|---|
| Gene | Z-Score1 | Z-Score2 | Z-Score3 | Average Viability Difference (%) Relative to Control siRNA (n=3) |
| AKT1 | 0.87204366 | 0.35343987 | 0.09635008 | -9.83 |
| AKT2 | -2.2053252 | -2.3871659 | -2.7316893 | -65.20 |
| AKT3 | 0.59038653 | -0.3282828 | -0.4569997 | -20.66 |
| AKTIP | 0.44871088 | -0.3368547 | 0.69025368 | 1.80 |
| ARAF | -0.3326759 | 0.24326502 | -0.0416554 | -12.53 |
| ARRB1 | 0.37967312 | 0.69077157 | 0.23026952 | -7.20 |
| ARRB2 | 1.014937 | 0.87451398 | 1.02954691 | 8.44 |
| ATF2 | 0.49106533 | -0.2338904 | -1.5918929 | -42.88 |
| ATF4 | 0.46734684 | 0.36665077 | 0.18951143 | -8.00 |
| AURKA | -2.2756336 | -2.7052359 | -2.1011137 | -52.85 |
| AURKB | -3.0613087 | -2.8344203 | -2.7302592 | -65.17 |
| BDNF | 0.61114021 | 0.19531249 | 0.12015117 | -9.36 |
| BRAF | -0.3083221 | 0.23040709 | 0.48881269 | -2.14 |
| CACNA1A | -0.0248119 | 0.06280013 | 0.28267278 | -6.18 |
| CACNA1B | 0.34711313 | 0.35343987 | 0.07719684 | -10.20 |
| CACNA1C | -0.2375372 | 0.47924594 | -0.0483973 | -12.66 |
| CACNA1D | 0.71252619 | 0.28456168 | 0.2360921 | -7.09 |
| CACNA1E | -0.2766092 | -0.1945603 | 0.24937168 | -6.83 |
| CACNA1F | 0.61738749 | 0.6358102 | 0.73101177 | 2.60 |
| CACNA1G | -0.0221648 | -0.2647495 | -0.278798 | -17.17 |
| CACNA1H | 0.07662699 | 0.22647407 | 0.75537469 | 3.08 |
| CACNA1I | 0.53278447 | 0.14448583 | 0.46746322 | -2.56 |
| CACNA1S | 0.58630991 | 0.28234306 | 0.45602235 | -2.78 |
| CACNA2D1 | -0.0063877 | -0.0595267 | 0.2354792 | -7.10 |
| CACNA2D2 | 0.17001856 | 0.24916455 | 0.47405193 | -2.43 |
| CACNA2D3 | 0.2865992 | 0.05695103 | 0.89649575 | 5.84 |
| CACNA2D4 | 0.62157 | 0.61059857 | -0.2543329 | -16.69 |
| CACNB1 | 0.57455655 | -0.2161414 | -0.0702576 | -13.09 |
| CACNB2 | 0.81422982 | 0.6301628 | -0.1269001 | -14.20 |
| CACNB3 | 0.56867987 | 0.73882495 | 0.79924837 | 3.94 |
| CACNB4 | -0.1128033 | -0.235504 | 0.13087698 | -9.15 |
| CACNG1 | -0.3840307 | -0.1905768 | 0.20391466 | -7.72 |
| CACNG2 | -0.2766092 | 0.51766847 | 0.23384479 | -7.13 |
| CACNG4 | 0.67176003 | 0.51681128 | -0.0453839 | -12.60 |
| CACNG5 | 0.01764841 | -0.4484919 | -0.2000399 | -15.63 |
| CACNG6 | 0.14243522 | -0.2076703 | 0.57610038 | -0.43 |
| CACNG7 | 0.13062892 | 0.12754361 | 0.12015117 | -9.36 |

Figure 32 continued

| | | | | |
|---|---|---|---|---|
| CACNG8 | 0.62172883 | 0.65759306 | 0.68734239 | 1.75 |
| CASP3 | 0.68086623 | 0.78314701 | −0.3630212 | −18.82 |
| CD14 | −0.0586955 | −0.3587889 | 0.24835018 | −6.85 |
| CDC25B | 0.67986032 | 0.30120136 | 0.27404105 | −6.35 |
| CDC42 | −0.2677147 | −0.0989073 | 0.12816999 | −9.20 |
| CHP1 | −0.5616546 | −0.0245834 | 0.38344435 | −4.21 |
| CHP2 | 0.17875417 | −0.1302202 | −0.2499405 | −16.61 |
| CHUK | 0.66291853 | −0.31961 | 0.49228581 | −2.07 |
| CRK | −0.0182999 | 0.3294384 | 0.34820239 | −4.90 |
| CRKL | −0.3228814 | 0.33543876 | 0.12536085 | −9.26 |
| DAB2IP | 0.94960525 | 0.89932223 | 0.95329148 | 6.95 |
| DAXX | 1.01297811 | 0.9818147 | 0.23864587 | −7.04 |
| DDIT3 | 0.46734684 | 0.04742103 | 0.06958662 | −10.35 |
| DUSP1 | 0.21020235 | −0.1790299 | 0.17960282 | −8.20 |
| DUSP10 | −0.2858213 | 0.22657492 | −0.0657629 | −13.00 |
| DUSP14 | −0.1063443 | −0.1807443 | 0.33109216 | −5.23 |
| DUSP16 | 0.64497083 | 0.38732431 | 0.43405997 | −3.21 |
| DUSP2 | 0.43637514 | 0.75546463 | −0.2459566 | −16.53 |
| DUSP3 | 2.7500402 | 3.29009129 | 3.0422713 | 47.85 |
| DUSP4 | −0.1889354 | 0.71946241 | 0.47154924 | −2.48 |
| DUSP5 | 0.42732188 | 0.58679878 | 0.63907623 | 0.80 |
| DUSP6 | −1.7444028 | −1.0231155 | −2.1853879 | −54.50 |
| DUSP7 | −0.2344665 | 0.33765739 | 0.25294695 | −6.76 |
| DUSP8 | 0.38173789 | 0.61735528 | 0.08828018 | −9.98 |
| DUSP9 | 0.83223047 | 0.01953696 | 0.34304379 | −5.00 |
| ECSIT | 0.48052966 | 0.49316276 | 0.27603299 | −6.31 |
| EGF | 0.4263689 | −0.1265897 | −0.3442255 | −18.45 |
| EGFR | −2.1923012 | −2.4115203 | −2.3637429 | −57.99 |
| ELK1 | −0.1188918 | 0.63460004 | 0.37767284 | −4.32 |
| FAS | 0.2392681 | 0.4780862 | 0.54714069 | −1.00 |
| FASLG | −0.1925885 | 0.70342781 | 0.36939864 | −4.48 |
| FGF1 | 0.22084391 | −0.327476 | 0.05620489 | −10.61 |
| FGF10 | 0.53532574 | 0.58745428 | 0.11381783 | −9.48 |
| FGF11 | 0.08636851 | −0.3424013 | 0.07903555 | −10.17 |
| FGF12 | 0.61114021 | 0.32994263 | 1.11377008 | 10.09 |
| FGF13 | 0.23037366 | 0.43048663 | 0.67482894 | 1.50 |
| FGF14 | −0.4065315 | 0.33765739 | 0.73744726 | 2.73 |
| FGF16 | −0.3069455 | 0.09431467 | 0.46174278 | −2.67 |
| FGF17 | 0.4912771 | 0.3701804 | −0.1745533 | −15.13 |
| FGF18 | 0.58630991 | 0.64609655 | 0.45081267 | −2.89 |
| FGF19 | 0.52166643 | −0.0034561 | 0.5655278 | −0.64 |
| FGF2 | 0.55650297 | 0.46739647 | 0.02484466 | −11.23 |
| FGF20 | −0.1746408 | 0.60011052 | 0.24824803 | −6.85 |

Figure 32 continued

| | | | | |
|---|---|---|---|---|
| FGF21 | 0.65974195 | −0.0055738 | −0.5203331 | −21.90 |
| FGF22 | 0.43843992 | −0.1763575 | 0.18900068 | −8.01 |
| FGF23 | 0.47099991 | 0.67483782 | 0.35489325 | −4.76 |
| FGF3 | −0.3884249 | 0.46184991 | 0.25498997 | −6.72 |
| FGF4 | 1.00863677 | −0.4366928 | 0.4945842 | −2.03 |
| FGF5 | 0.8575902 | 0.87784191 | 0.04318069 | −10.87 |
| FGF6 | −0.1230743 | 0.04752188 | 0.38778575 | −4.12 |
| FGF7 | 0.06307356 | 0.24341629 | −0.0218382 | −12.14 |
| FGF8 | 0.71882641 | 0.36125548 | 0.4253261 | −3.39 |
| FGF9 | 0.08478022 | 0.58135307 | 0.62743106 | 0.57 |
| FGFR1 | 0.73989776 | −0.1419184 | 0.11453289 | −9.47 |
| FGFR2 | 0.24816253 | 0.4839353 | −0.1217415 | −14.10 |
| FGFR3 | 0.79855868 | 0.44944579 | −0.2274163 | −16.17 |
| FGFR4 | 0.11760492 | −0.0635102 | 0.89036671 | 5.72 |
| FLNA | 0.64698267 | 0.54514916 | 0.21178026 | −7.57 |
| FLNB | 0.09801599 | −0.1866942 | 0.10707589 | −9.62 |
| FLNC | −0.1267803 | 0.42020029 | 0.37292284 | −4.41 |
| FOS | 0.03993744 | 0.10485314 | 0.16611894 | −8.46 |
| FOXM1 | −3.2018196 | −2.9076853 | −2.3782483 | −58.28 |
| FOXO3A | 2.82119568 | 3.32377403 | 3.27456176 | 52.40 |
| FRK | 3.54651572 | 3.30905044 | 3.17557783 | 50.46 |
| FYN | 0.04613178 | −0.2647495 | −0.0666823 | −13.02 |
| GADD45B | −1.422509 | −0.5420775 | −0.4804944 | −21.12 |
| GADD45G | 0.3660138 | 0.06582552 | 0.42599007 | −3.37 |
| GNA12 | 0.03871975 | 0.52165191 | 0.94261674 | 6.74 |
| GRB2 | 0.38179084 | 0.16742842 | −0.2355372 | −16.32 |
| HRAS | −0.0131115 | 0.06431283 | 0.59617298 | −0.04 |
| HSP90AA1 | −2.6031394 | −2.4001751 | −2.3161407 | −57.06 |
| HSP90AB1 | −2.178536 | −2.263528 | −2.11899 | −53.20 |
| HSPA1A | 0.03014297 | −0.3066008 | 0.16754905 | −8.43 |
| HSPA1B | −0.2520436 | 0.37920617 | −0.4346287 | −20.22 |
| HSPA1L | 0.88236755 | −0.2092839 | 0.53539337 | −1.23 |
| HSPA2 | −0.4438563 | 0.57711751 | −0.3801314 | −19.16 |
| HSPA4 | −2.10971 | −2.4047132 | −2.0781298 | −52.40 |
| HSPA6 | −1.0267595 | −1.3585311 | −1.2435594 | −36.06 |
| HSPA8 | 0.21131416 | 0.17978212 | −0.1518759 | −14.69 |
| HSPB1 | 0.15440036 | 0.09123885 | 0.5148611 | −1.63 |
| HSPB2 | −2.5544318 | −2.0618349 | −2.3181837 | −57.10 |
| IKBKB | 0.45824063 | 0.36765924 | 0.45443902 | −2.82 |
| IKBKG | 0.53929647 | 0.10349171 | −0.2332899 | −16.28 |
| IL1A | −0.0158116 | 0.08468383 | 0.89649575 | 5.84 |
| IL1B | −0.2322429 | 0.65819813 | 0.93046082 | 6.51 |
| IL1R1 | −0.5048997 | 0.13117409 | 0.57186113 | −0.52 |

Figure 32 continued

| | | | | |
|---|---|---|---|---|
| IL1R2 | −0.3007512 | 0.55125037 | 0.26372384 | −6.55 |
| INPP4A | 0.17213628 | 0.69631813 | 0.61456009 | 0.32 |
| INPP4B | 0.28861104 | 0.71346204 | 0.38165671 | −4.24 |
| INPP5A | 0.47973552 | 0.57933614 | 0.43477503 | −3.20 |
| INPP5B | 0.62003465 | 0.41344357 | 0.02617262 | −11.20 |
| JMJD7-PLA2G4B | 0.28072252 | −0.0630564 | −0.1446232 | −14.54 |
| JUN | −1.5883266 | −1.1849238 | 0.22357866 | −7.34 |
| JUND | 0.55067923 | 0.10374383 | −0.4304406 | −20.14 |
| KRAS | −2.8055937 | −2.6007588 | −2.2440224 | −55.65 |
| LAMTOR3 | −2.7222613 | −2.7586845 | −2.6747404 | −64.08 |
| LIN28A | −2.4616755 | −2.3879222 | −2.3586353 | −57.89 |
| LIN28B | −2.7225789 | −3.1711469 | −3.0384476 | −71.20 |
| MAP2K1 | 0.57979792 | 0.27740158 | 0.37915402 | −4.29 |
| MAP2K2 | 0.36431963 | 0.48514546 | 0.3111728 | −5.62 |
| MAP2K3 | −2.4060853 | −2.7752234 | −2.6129903 | −62.87 |
| MAP2K4 | −0.3840307 | −0.2223939 | −2.5339768 | −61.33 |
| MAP2K5 | −2.3045405 | −2.2262148 | −2.3151703 | −57.04 |
| MAP2K6 | 0.1613359 | −0.0725864 | −0.3963223 | −19.47 |
| MAP2K7 | 0.17700705 | 0.5387454 | 0.47972129 | −2.32 |
| MAP3K1 | −1.5715966 | −1.6626843 | −1.941248 | −49.72 |
| MAP3K11 | 0.23370907 | 0.37744135 | 0.00778551 | −11.56 |
| MAP3K12 | 0.90095057 | −0.0050696 | 0.87810864 | 5.48 |
| MAP3K13 | 0.00060074 | −0.5420775 | −1.0265915 | −31.81 |
| MAP3K14 | −2.0292365 | −2.4979962 | −2.0188824 | −51.24 |
| MAP3K2 | −2.7895519 | −2.2922693 | −2.3722724 | −58.16 |
| MAP3K3 | −0.188406 | 0.29046121 | 0.37552768 | −4.36 |
| MAP3K4 | 0.62321123 | −0.365596 | 0.02698982 | −11.18 |
| MAP3K5 | 0.12660525 | 0.47289261 | 0.65705474 | 1.15 |
| MAP3K6 | 0.57979792 | −0.1419184 | 0.77697954 | 3.50 |
| MAP3K7 | −2.2044781 | −2.6064567 | −3.1592918 | −73.57 |
| MAP3K8 | 0.25790406 | −0.0576106 | −0.3236932 | −18.05 |
| MAP4K1 | 0.66916582 | 0.7014613 | 0.4513745 | −2.87 |
| MAP4K2 | 0.32789479 | 0.28743581 | 0.62620525 | 0.55 |
| MAP4K3 | −0.0624015 | 0.09577695 | 0.10554364 | −9.65 |
| MAP4K4 | 0.27532233 | 0.09789473 | 0.159377 | −8.59 |
| MAPK1 | 1.00863677 | 0.03718511 | −0.4248223 | −20.03 |
| MAPK10 | 0.54485549 | 0.73146315 | −0.3249701 | −18.08 |
| MAPK11 | 0.29443477 | 0.21790212 | 0.21576413 | −7.49 |
| MAPK12 | 0.22195571 | 0.34143913 | 0.10125331 | −9.73 |
| MAPK13 | −0.2423021 | 0.64609655 | −0.4387148 | −20.30 |
| MAPK14 | −0.1349335 | 0.80961922 | 0.36674272 | −4.53 |
| MAPK3 | 0.20665517 | −0.0358278 | −0.183134 | −15.30 |
| MAPK7 | −2.7572037 | −2.5287544 | −2.8599905 | −67.71 |

Figure 32 continued

| | | | | |
|---|---|---|---|---|
| MAPK8 | 0.05216729 | −0.2994911 | −0.2215426 | −16.05 |
| MAPK8IP1 | 0.65693597 | −0.1210431 | 0.27184482 | −6.39 |
| MAPK8IP2 | 0.73672117 | −0.1449942 | 0.22460016 | −7.31 |
| MAPK8IP3 | 0.37268463 | 0.24245825 | 0.26995503 | −6.43 |
| MAPK9 | 0.4049799 | 0.45610166 | 0.14584205 | −8.86 |
| MAPKAPK2 | −0.327011 | 0.6009173 | 0.84858711 | 4.90 |
| MAPKAPK3 | −1.7788158 | −1.7300498 | −1.7780624 | −46.53 |
| MAPKAPK5 | −0.1306451 | −0.2703464 | −0.260513 | −16.81 |
| MAPT | 0.84483092 | 1.49951044 | 0.78525374 | 3.66 |
| MAX | −0.1423455 | 0.12300552 | −0.4046986 | −19.64 |
| MECOM | −0.2143481 | 0.39629966 | 0.20677488 | −7.66 |
| MEF2C | −0.3566591 | 0.18401768 | 0.84536937 | 4.84 |
| MKNK1 | 0.3159826 | 0.84264647 | 0.63907623 | 0.80 |
| MKNK2 | −0.0682252 | 0.6403483 | 0.41955459 | −3.50 |
| MOS | −2.1711239 | −2.1392346 | −2.9590766 | −69.65 |
| MRAS | −0.1892531 | 0.36211268 | 0.58943104 | −0.17 |
| MYC | −2.3114231 | −2.7147154 | −2.2154202 | −55.09 |
| NF1 | 3.48001923 | 3.10846666 | 3.03951323 | 47.80 |
| NFATC2 | 0.12395809 | −0.5309843 | −0.1665856 | −14.97 |
| NFATC4 | 0.03390193 | −0.2621274 | 0.83306022 | 4.60 |
| NFKB1 | 0.61601097 | 0.26751862 | −0.08415 | −13.36 |
| NFKB2 | −0.1046501 | 0.0022922 | −0.1096877 | −13.86 |
| NGF | −0.0708724 | 0.66979549 | −0.3734405 | −19.02 |
| NLK | 0.92350432 | 0.38485357 | 0.17326948 | −8.32 |
| NR4A1 | 0.24546244 | 0.52326546 | 0.5330439 | −1.28 |
| NRAS | −3.01636 | −3.2211668 | −2.8859367 | −68.22 |
| NTF3 | −0.013588 | 0.61735528 | 0.45392826 | −2.83 |
| NTF4 | 0.72062648 | −0.0438955 | 0.31566742 | −5.53 |
| NTRK1 | −0.0498011 | 0.61851502 | 0.07847373 | −10.18 |
| NTRK2 | −0.0248649 | 0.12527456 | 0.27194697 | −6.39 |
| PAK2 | −2.2366675 | −2.074945 | −2.1608718 | −54.02 |
| PDGFA | 0.22402049 | 0.42544431 | −0.1846662 | −15.33 |
| PDGFB | 0.10807517 | 0.30120136 | −0.0483973 | −12.66 |
| PDGFRA | −2.2610742 | −2.0346063 | −2.0684255 | −52.21 |
| PDGFRB | −0.3159988 | −0.1265897 | −0.1883436 | −15.40 |
| PIK3CA | 0.14142931 | 0.37865151 | 0.57778587 | −0.40 |
| PIK3R1 | 0.18431319 | 0.32419438 | 0.19625337 | −7.87 |
| PLA2G10 | 0.07027382 | 0.45302584 | 0.09057857 | −9.94 |
| PLA2G12A | 0.21422602 | 0.36110421 | −0.3054082 | −17.69 |
| PLA2G12B | −0.1002029 | −0.1887112 | 0.27102761 | −6.41 |
| PLA2G1B | 0.37374349 | 0.01257855 | 0.08746298 | −10.00 |
| PLA2G2A | 0.00451853 | 0.68572924 | −0.0758758 | −13.20 |
| PLA2G2C | 0.7571572 | 0.10167647 | −0.4753868 | −21.02 |

Figure 32 continued

| | | | | |
|---|---|---|---|---|
| PLA2G2D | −0.2016418 | 0.00894807 | 0.10135546 | −9.73 |
| PLA2G2E | 0.22619116 | 0.74129569 | −0.0894619 | −13.46 |
| PLA2G2F | 0.33985993 | 0.6503321 | 0.3448825 | −4.96 |
| PLA2G3 | −0.4159553 | 0.85147054 | −0.3170534 | −17.92 |
| PLA2G4A | −0.2858213 | −0.0317939 | 0.67585045 | 1.52 |
| PLA2G4B | 0.50483053 | −0.103395 | 0.49902775 | −1.94 |
| PLA2G4E | 0.61114021 | −0.4921584 | 0.16790658 | −8.42 |
| PLA2G5 | 0.03840209 | 0.40466992 | 0.44458148 | −3.01 |
| PLA2G6 | −0.4510036 | −0.1651635 | 0.57140146 | −0.53 |
| PLK1 | −2.831324 | −2.649266 | −2.8087109 | −66.70 |
| PPM1A | 0.92043362 | 0.09890319 | 0.08976137 | −9.96 |
| PPM1B | 0.76128676 | −0.0814104 | 0.88183714 | 5.55 |
| PPP3CA | 0.84483092 | 0.05311886 | 0.38421048 | −4.19 |
| PPP3CB | 0.01436594 | 0.04252997 | 0.08235545 | −10.10 |
| PPP3CC | 0.28225787 | 0.0031494 | 0.71354402 | 2.26 |
| PPP3R1 | −0.0186705 | 0.02594072 | 0.2011566 | −7.77 |
| PPP3R2 | −0.4949993 | 0.61745613 | −0.0602468 | −12.89 |
| PPP5C | −0.0660016 | 0.05695103 | 0.13138774 | −9.14 |
| PRKACA | −0.0616603 | 0.44995002 | 0.20759209 | −7.65 |
| PRKACB | 0.71077907 | 0.52326546 | 0.35714057 | −4.72 |
| PRKACG | −0.1722054 | 0.01232643 | 0.48676968 | −2.18 |
| PRKCA | 0.2621395 | 0.15053662 | 0.48917022 | −2.14 |
| PRKCB | −0.3062573 | 0.59950545 | 0.2360921 | −7.09 |
| PRKCG | −0.2883096 | −0.0609386 | −0.0453328 | −12.60 |
| PRKX | 0.04888482 | −0.0252389 | 0.63013805 | 0.62 |
| PTEN | 1.1229938 | 1.28737973 | 1.12950127 | 10.40 |
| PTPN5 | 0.59208071 | −0.4785946 | −0.5237551 | −21.97 |
| PTPN7 | 0.47370001 | 0.49754959 | 0.70772143 | 2.14 |
| RAC1 | 0.00690097 | 0.14942731 | −0.0981957 | −13.64 |
| RAC2 | −0.1711466 | 0.33327056 | 0.79122955 | 3.78 |
| RAC3 | 0.62554073 | 0.21497757 | 0.5231353 | −1.47 |
| RAF1 | 0.32376523 | 0.67816575 | −0.326247 | −18.10 |
| RAP1A | 0.49831853 | −0.3956987 | 0.61353858 | 0.30 |
| RAP1B | 0.82757148 | 0.77497844 | 0.85098765 | 4.95 |
| RAPGEF2 | 0.01680132 | 0.34501919 | 0.1426243 | −8.92 |
| RASA1 | 0.67488367 | 0.08942362 | 0.95778611 | 7.04 |
| RASA2 | 0.6036223 | −0.0880159 | 0.34896852 | −4.88 |
| RASA3 | 0.84980757 | 1.00894242 | 1.09875394 | 9.80 |
| RASA4 | 0.60626945 | 0.36856686 | 0.261119 | −6.60 |
| RASAL1 | 0.40826237 | −0.0075908 | 0.2309335 | −7.19 |
| RASAL2 | 0.28331673 | 0.97868846 | 0.64929129 | 1.00 |
| RASGRF1 | −0.0370947 | 0.1914299 | −0.3162362 | −17.90 |
| RASGRF2 | 0.2071846 | 0.09426425 | 0.47359225 | −2.44 |

Figure 32 continued

| | | | | |
|---|---|---|---|---|
| RASGRP1 | 0.63231744 | 0.06542214 | 0.33630185 | −5.13 |
| RASGRP2 | 0.80851197 | −0.4533325 | −0.1331823 | −14.32 |
| RASGRP3 | 0.29443477 | 0.27543507 | 0.89399306 | 5.79 |
| RASGRP4 | 0.5501498 | −0.3073067 | 0.79924837 | 3.94 |
| RBL1 | 2.07379838 | 2.28636562 | 2.20427883 | 31.45 |
| RBL2 | 0.55650297 | −0.2259235 | −0.2685319 | −16.97 |
| RELA | −0.518506 | −0.1568436 | −0.2506555 | −16.62 |
| RELB | 0.28374027 | 0.79393759 | 0.12822107 | −9.20 |
| RHEB | −3.0679795 | −3.387967 | −2.6808183 | −64.20 |
| RPS6KA1 | 0.81804173 | −0.2715062 | −0.2506555 | −16.62 |
| RPS6KA2 | −0.3922368 | 0.78808849 | −0.0702576 | −13.09 |
| RPS6KA3 | 2.10413476 | 2.67492736 | 2.22021432 | 31.76 |
| RPS6KA4 | −0.040589 | 0.23797058 | 0.62620525 | 0.55 |
| RPS6KA5 | 0.32773596 | −0.2718087 | −0.5034783 | −21.57 |
| RPS6KA6 | −0.1385336 | −0.00154 | 0.34820239 | −4.90 |
| RRAS | 0.91333925 | −0.1419184 | 0.25795233 | −6.66 |
| RRAS2 | 0.0406257 | −0.1225054 | 0.04701134 | −10.79 |
| SOS1 | −0.3387643 | −0.293995 | −0.5350939 | −22.19 |
| SOS2 | −0.4811812 | −0.0617454 | 0.04394682 | −10.85 |
| SRF | 0.55311461 | 0.21790212 | 0.81681828 | 4.28 |
| STK3 | 0.59208071 | 0.64145761 | 0.2443663 | −6.93 |
| STK4 | −0.3823894 | 0.29938612 | −0.145185 | −14.56 |
| STMN1 | −0.207042 | 0.60711936 | 0.07903555 | −10.17 |
| SYNGAP | 0.53214915 | 0.59042926 | 0.96085063 | 7.10 |
| TAB1 | −0.5208885 | −0.1302202 | −0.2057092 | −15.74 |
| TAB2 | 0.23370907 | −0.4710815 | −0.3155211 | −17.89 |
| TAOK1 | −0.3884249 | 0.4856497 | 0.60000362 | 0.03 |
| TAOK2 | 0.79442912 | −0.1661215 | 0.05523446 | −10.63 |
| TAOK3 | 0.5726506 | −0.3923203 | 0.59709233 | −0.02 |
| TGFB1 | 0.01039521 | 0.27140121 | 0.70756821 | 2.14 |
| TGFB2 | 0.82979509 | 0.24371883 | 0.63264074 | 0.67 |
| TGFB3 | −0.2202248 | 0.68946056 | 0.24937168 | −6.83 |
| TGFBR1 | −0.2464316 | −0.3016593 | −0.0845586 | −13.37 |
| TGFBR2 | 0.28119901 | −0.1539695 | 0.51036647 | −1.72 |
| TNF | 0.35971358 | −0.0418786 | −0.1947791 | −15.53 |
| TNFRSF1A | −0.1762291 | 0.33095109 | 0.36521047 | −4.56 |
| TP53 | 0.00801277 | 0.90809588 | 0.78147417 | 3.59 |
| TRAF2 | 0.46734684 | 0.7950469 | 0.47726968 | −2.37 |
| TRAF6 | 0.29199939 | 0.16309202 | −0.0167306 | −12.04 |
| TSC1 | 0.27008096 | 0.41041817 | 0.21755177 | −7.45 |
| TSC2 | 0.64968277 | 0.51025625 | 0.91488286 | 6.20 |
| ZAK | −2.8403243 | −2.4248825 | −2.3181837 | −57.10 |

Figure 32 continued

USE OF TG02 FOR TREATING GLIOMAS IN PEDIATRIC SUBJECTS

CROSS-REFERENCE TO RELATED APPLICATIONS

This application is a continuation of International Patent Application No. PCT/US2020/029400, filed Apr. 22, 2020, which claims priority to U.S. Provisional Patent Application Ser. No. 62/837,049, filed on Apr. 22, 2019 and U.S. Provisional Patent Application Ser. No. 62/907,019, filed on Sep. 27, 2019, the contents of which are hereby incorporated by reference herein in their entireties.

SEQUENCE LISTING

The instant application contains a Sequence Listing which has been submitted via EFS-Web and is hereby incorporated by reference in its entirety. Said ASCII copy, created on Aug. 12, 2020, is named 072396_0839_SL.txt and is 11,677 bytes in size.

1. INTRODUCTION

The present disclosure relates to uses of TG02 for treating a glioma in a pediatric human subject. The present disclosure further provides pharmaceutical compositions and kits that include TG02.

2. BACKGROUND

Primary brain and CNS tumors are a leading cause of cancer-related mortality in children ages 0-14. Many deaths are due to pediatric high-grade gliomas (PHGG), which are a commonly diagnosed type of malignant brain tumor in children (Ostrom et al., Neuro-oncology 2015; 17 Suppl 4:iv1-iv62). PHGGs can be largely incurable with a poor median survival post diagnosis of 9-15 months (Ostrom et al., Neuro-oncology 2015; 17 Suppl 4:iv1-iv62; Cancer Genome Atlas Research Network et al., The New England journal of medicine 2015; 372(26):2481-98). A particularly aggressive type of PHGG that originates primarily in the midline and pons is known as diffuse intrinsic pontine glioma (DIPG). Presenting nearly exclusively in children, DIPG has a two-year survival rate post diagnosis of only 10% and a median survival time of 9-12 months (Jones et al., Neuro-oncology 2017; 19(2):153-61). This poor prognosis is partly due to the tumor's anatomical location, preventing surgical excision, and narrowing therapeutic options to blood-brain barrier penetrating agents (Hoffman et al., Journal of clinical oncology 2018; 36(19):1963-72). Furthermore, radiation therapy may provide only temporary benefits while chemotherapy and targeted therapeutics in clinical trials can be relatively ineffective in treating DIPG (Warren et al., Frontiers in oncology 2012; 2:205).

As molecular profiling techniques have progressed, the understanding of cancer biology is shifting from a histopathological perspective to one informed by the genomics and epigenetics modulating disease pathogenesis. This reevaluation of tumor biology has revealed certain differences between PHGGs and their corresponding adult tumors, as well as the molecular heterogeneity amongst PHGGs (Mackay et al., Cancer cell 2017; 32(4):520-37 e5). It has also indicated certain shortcomings associated with traditional treatment of PHGG, which help explain the ineffectiveness of treatments used in previous clinical trials (Mackay et al., Cancer cell 2017; 32(4):520-37 e5; Filbin et al., Science 2018; 360(6386):331-35; Jones et al., Nature reviews Cancer 2014; 14(10)).

The discovery of novel DIPG-associated hotspot mutations (K27M) in the genes encoding histone H3.3 and H3.1 have increased the understanding that pediatric and adult HGGs possess distinct genetic as well as epigenetic characteristics (Sturm et al., Cancer cell 2012; 22(4):425-37). Amongst PHGGs, those with K27M or G34R H3 mutations exist as distinct tumor subtypes with certain clinical, biological, and pathological features (Sturm et al., Cancer cell 2012; 22(4):425-37; Mackay et al., Cancer cell 2017; 32(4): 520-37 e5). H3K27M mutations in DIPG can lead to an altered epigenetic state characterized by a global reduction of histone trimethylation (H3K27Me3), as the mutant histone can suppress the Polycomb repressive complex 2 (PRC2) through interaction with the EZH2 subunit of PRC2 (Lewis et al., Science 2013; 340(6134):857-61). Decreased H3K27Me3 can result in the transcriptional activation of several oncogenic proteins. The discovery of H3K27M mutation effects has fostered interest in using epigenetic-based therapies to counteract the transcriptional dependencies resulting from the H3K27M mutation (Grasso et al., Nature medicine 2015; 21(6):555-9; Piunti et al., Nature medicine 2017; 23(4):493-500; Nagaraja et al., Cancer cell 2017; 31(5):635-52 e6b; Bitler et al., Nature medicine 2015; 21(3):231-8). Moreover, H3K27M mutations may not be only required for tumor initiation but also required for tumor maintenance (Silveira et al., Acta neuropathologica 2019; Larson et al., Cancer cell 2019; 35:140-55 e7).

Therefore, there remains a need in the art for improved techniques to treat pediatric gliomas.

3. SUMMARY

The present disclosure provides uses of TG02 for treating a pediatric glioma. In one aspect, the present disclosure provides methods for treating a glioma in a pediatric subject. In certain embodiments, the methods include administering to the subject a therapeutically effective amount of an ERK5 inhibitor, wherein the ERK inhibitor consists of (16E)-14-methyl-20-oxa-5,7,14,26-tetraazatetracyclo[19.3.1.1(2,6).1(8,12)]-heptacosa-1(25),2(26),3,5,8(27),9,11,16,21,23-decaene (TG02), or a pharmaceutically acceptable salt thereof. In certain embodiments, the TG02 is a citric salt of TG02. In certain embodiments, the citric salt of TG02 has a powder x-ray diffraction pattern with peaks at 15.2, 15.5, 21.7, 22.1, 23.0, 26.2, and 29.9 degrees 2θ. In certain embodiments, the citric salt of TG02 has a powder x-ray diffraction pattern with peaks at 15.0, 18.4, 19.2, 19.8 and 21.5 degrees 2θ.

In certain embodiments, the glioma is a pediatric high-grade glioma (PHGG). In certain embodiments, the glioma is a diffuse intrinsic pontine glioma (DIPG). In certain embodiments, the glioma is a H3-mutant glioma. In certain embodiments, the glioma is a H3.3-mutant glioma. In certain embodiments, the glioma is a H3K27M-mutant glioma. In certain embodiments, the glioma is a H3K27M-mutant DIPG. In certain embodiments, the glioma is a H3.3-mutant non-DIPG high grade glioma.

In certain embodiments, the pediatric human subject is between about 4 years old and about 11 years old. In certain embodiments, the TG02 is administered orally. In certain embodiments, TG02 is administered in an amount between about 20 mg/m$^2$ and about 200 mg/m$^2$ per day. In certain embodiments, the TG02 is administered in an amount of about 35 mg/m$^2$ per day, about 50 mg/m$^2$ per day, about 65 mg/m$^2$ per day, or about 85 mg/m$^2$ per day. In certain embodiments, the pediatric human subject has a body surface area of at least 50 m². In certain embodiments, (a) the pediatric human subject has a body surface area of at least about 55 m², and the TG02 is administered in an amount of about 35 mg/m² per day or about 50 mg/m² per day, or (b) the pediatric human subject has a body surface area of at least about 50 m², and the TG02 is administered in an amount of about 65 mg/m² per day or about 85 mg/m² per day. In certain embodiments, the TG02 is administered in an amount of between about 20 mg and about 100 mg per day. In certain embodiments, the TG02 is administered in an amount of between about 0.4 mg/kg and about 6.6 mg/kg per day.

In certain embodiments, the TG02 is administered twice per week. In certain embodiments, the TG02 is administered once per day. In certain embodiments, the TG02 is administered cyclically. In certain embodiments, the number of cycles is from one to twenty-four cycles. In certain embodiments, the duration of each cycle is 28 days. In certain embodiments, the TG02 is administered intermittently.

In certain embodiments, the TG02 is administered in combination with a radiation. In certain embodiments, the radiation is administered to the pediatric human subject in fractionated doses. In certain embodiments, a total dose of between about 54 Gy and about 60 Gy of the radiation is administered to the pediatric human subject over a period of between about 1 week and about 8 weeks. In certain embodiments, a total dose of about 54 Gy of the radiation is administered to the pediatric human subject in fractionated doses over a period of about 6 weeks.

In certain embodiments, the TG02 is administered once per week during and/or after the administration of the radiation. In certain embodiments, the TG02 is administered for about 3 weeks or about 4 weeks after the administration of the radiation. In certain embodiments, the TG02 is administered twice per week for about 3 weeks or about 4 weeks after the administration of the radiation. In certain embodiments, the TG02 is administered on the same day as the radiation, and the TG02 is administered between about 1 hour and about 8 hours prior to the administration of the radiation. In certain embodiments, the TG02 is administered about 1 hour prior to the administration of the radiation. In certain embodiments, the TG02 is administered about 2 hours prior to the administration of the radiation. In certain embodiments, the TG02 is administered about 3 hours prior to the administration of the radiation. In certain embodiments, the TG02 is administered about 4 hours prior to the administration of the radiation. In certain embodiments, the TG02 is administered about 5 hours prior to the administration of the radiation. In certain embodiments, the TG02 is administered about 6 hours prior to the administration of the radiation. In certain embodiments, the TG02 is administered about 7 hours prior to the administration of the radiation. In certain embodiments, the TG02 is administered about 8 hours prior to the administration of the radiation.

In certain embodiments, the glioma is a newly diagnosed glioma, a refractory glioma, a relapsed glioma, or a relapsed and refractory glioma.

In another aspect, the present disclosure provides an ERK inhibitor for use in treating a glioma in a pediatric human subject, wherein the ERK inhibitor consists of (16E)-14-methyl-20-oxa-5,7,14,26-tetraazatetracyclo[19.3.1.1(2,6).1(8,12)]-heptacosa-1(25),2(26),3,5,8(27),9,11,16,21,23-decaene (TG02), or a pharmaceutically acceptable salt thereof.

In certain embodiments, the TG02 is a citric salt of TG02. In certain embodiments, the citric salt of TG02 has a powder x-ray diffraction pattern with peaks at 15.2, 15.5, 21.7, 22.1, 23.0, 26.2, and 29.9 degrees 2θ. In certain embodiments, the citric salt of TG02 has a powder x-ray diffraction pattern with peaks at 15.0, 18.4, 19.2, 19.8 and 21.5 degrees 2θ.

In certain embodiments, the glioma is a pediatric high-grade glioma (PHGG). In certain embodiments, the glioma is a diffuse intrinsic pontine glioma (DIPG). In certain embodiments, the glioma is a H3-mutant glioma. In certain embodiments, the glioma is a H3.3-mutant glioma. In certain embodiments, the glioma is a H3K27M-mutant glioma. In certain embodiments, the glioma is a H3K27M-mutant DIPG. In certain embodiments, the glioma is a H3.3-mutant non-DIPG high grade glioma.

In certain embodiments, the pediatric human subject is between about 4 years old and about 11 years old. In certain embodiments, the TG02 is administered orally. In certain embodiments, TG02 is administered in an amount between about 20 mg/m² and about 200 mg/m² per day. In certain embodiments, TG02 is administered in an amount of about 35 mg/m² per day, about 50 mg/m² per day, about 65 mg/m² per day, or about 85 mg/m² per day. In certain embodiments, the pediatric human subject has a body surface area of at least 50 m². In certain embodiments, (a) the pediatric human subject has a body surface area of at least about 55 m², and the TG02 is administered in an amount of about 35 mg/m² per day or about 50 mg/m² per day, or (b) the pediatric human subject has a body surface area of at least about 50 m², and the TG02 is administered in an amount of about 65 mg/m² per day or about 85 mg/m² per day. In certain embodiments, the TG02 is administered in an amount of between about 20 mg and about 100 mg per day. In certain embodiments, the TG02 is administered in an amount of between about 0.4 mg/kg and about 6.6 mg/kg per day.

In certain embodiments, the TG02 is administered twice per week. In certain embodiments, the TG02 is administered once per day. In certain embodiments, the TG02 is administered cyclically. In certain embodiments, the number of cycles is from one to twenty-four cycles. In certain embodiments, the duration of each cycle is 28 days. In certain embodiments, the TG02 is administered intermittently.

In certain embodiments, the TG02 is administered in combination with a radiation. In certain embodiments, the radiation is administered to the pediatric human subject in fractionated doses. In certain embodiments, a total dose of between about 54 Gy and about 60 Gy of the radiation is administered to the pediatric human subject over a period of between about 1 week and about 8 weeks. In certain embodiments, a total dose of about 54 Gy of the radiation is administered to the pediatric human subject in fractionated doses over a period of about 6 weeks.

In certain embodiments, the TG02 is administered once per week during and/or after the administration of the radiation. In certain embodiments, the TG02 is administered for about 3 weeks or about 4 weeks after the administration of the radiation.

In certain embodiments, the TG02 is administered twice per week for about 3 weeks or about 4 weeks after the administration of the radiation. In certain embodiments, the TG02 is administered on the same day as the radiation, and the TG02 is administered between about 1 hour and about 8 hours prior to the administration of the radiation.

In certain embodiments, the glioma is a newly diagnosed glioma, a refractory glioma, a relapsed glioma, or a relapsed and refractory glioma.

In another aspect, the present disclosure provides use of an ERK inhibitor for the preparation of a medicament for use in a method of disclosed herein, wherein the ERK inhibitor consists of (16E)-14-methyl-20-oxa-5,7,14,26-tetraazatetracyclo[19.3.1.1(2,6).1(8,12)]-heptacosa-1(25),2(26),3,5,8 (27),9,11,16,21,23-decaene (TG02), or a pharmaceutically acceptable salt thereof.

In another aspect, the present disclosure provides a kit for treating a glioma in a pediatric human subject, consisting of an ERK inhibitor and instructions for using the ERK5 inhibitor in treating the glioma in a pediatric human subject, wherein the ERK inhibitor consists of (16E)-14-methyl-20-oxa-5,7,14,26-tetraazatetracyclo[19.3.1.1(2,6).1(8,12)]-heptacosa-1(25),2(26),3,5,8(27),9,11,16,21,23-decaene (TG02), or a pharmaceutically acceptable salt thereof.

In certain embodiments, the TG02 is a citric salt of TG02.

In certain embodiments, the TG02 has a powder x-ray diffraction pattern with peaks at 15.2, 15.5, 21.7, 22.1, 23.0, 26.2, and 29.9 degrees 2θ.

In certain embodiments, the TG02 has a powder x-ray diffraction pattern with peaks at 15.0, 18.4, 19.2, 19.8 and 21.5 degrees 2θ.

In certain embodiments, the glioma is a pediatric high-grade glioma (PHGG).

In certain embodiments, the glioma is a diffuse intrinsic pontine glioma (DIPG).

In certain embodiments, the glioma is a H3-mutant glioma.

In certain embodiments, the glioma is a H3K27M-mutant glioma.

In certain embodiments, the glioma is a H3K27M-mutant DIPG.

In certain embodiments, the glioma is a H3.3-mutant non-DIPG high grade glioma.

In certain embodiments, the pediatric human subject is between about 4 years old and about 11 years old.

In certain embodiments, the instructions comprise that the TG02 is administered orally.

In certain embodiments, the instructions comprise that the TG02 is administered in an amount between about 20 mg/m$^2$ and about 200 mg/m$^2$ per day.

In certain embodiments, the instructions comprise that the TG02 is administered in an amount of about 35 mg/m$^2$ per day, about 50 mg/m$^2$ per day, about 65 mg/m$^2$ per day, or about 85 mg/m$^2$ per day.

In certain embodiments, the pediatric human subject has a body surface area of at least about 50 m$^2$.

In certain embodiments, (a) the pediatric human subject has a body surface area of at least about 55 m$^2$, and the TG02 is administered in an amount of about 35 mg/m$^2$ per day or about 50 mg/m$^2$ per day, or (b) the pediatric human subject has a body surface area of at least about 50 m$^2$, and the TG02 is administered in an amount of about 65 mg/m$^2$ per day or about 85 mg/m$^2$ per day.

In certain embodiments, the instructions comprise that the TG02 is administered in an amount of between about 20 mg and about 100 mg per day.

In certain embodiments, the instructions comprise that the TG02 is administered in an amount of between about 0.4 mg/kg and about 6.6 mg/kg per day.

In certain embodiments, the instructions comprise that the TG02 is administered twice per week.

In certain embodiments, the instructions comprise that the TG02 is administered once per day.

In certain embodiments, the instructions comprise that the TG02 is administered cyclically.

In certain embodiments, the instructions comprise that the number of cycles is from one to twenty-four cycles.

In certain embodiments, the instructions comprise that the duration of each cycle is 28 days.

In certain embodiments, the instructions comprise that the TG02 is administered intermittently.

In certain embodiments, the instructions comprise that the TG02 is administered in combination with a radiation.

In certain embodiments, the instructions comprise that the radiation is administered to the pediatric human subject in fractionated doses.

In certain embodiments, the instructions comprise that a total dose of between about 54 Gy and about 60 Gy of the radiation is administered to the pediatric human subject over a period of between about 1 week and about 8 weeks.

In certain embodiments, the instructions comprise that a total dose of about 54 Gy of the radiation is administered to the pediatric human subject in fractionated doses over a period of about 6 weeks.

In certain embodiments, the instructions comprise that the TG02 is administered once per week during and/or after the administration of the radiation.

In certain embodiments, the instructions comprise that the TG02 is administered for about 3 weeks or about 4 weeks after the administration of the radiation.

In certain embodiments, the instructions comprise that the TG02 is administered twice per week for about 3 weeks or about 4 weeks after the administration of the radiation.

In certain embodiments, the instructions comprise that the TG02 is administered on the same day as the radiation, the TG02 is administered between about 1 hour and about 8 hours prior to the administration of the radiation.

In certain embodiments, the glioma is a newly diagnosed glioma, a refractory glioma, a relapsed glioma, or a relapsed and refractory glioma.

4. BRIEF DESCRIPTION OF THE DRAWINGS

Figure 1I:
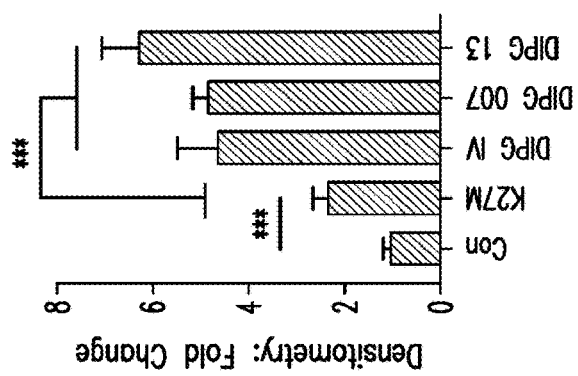
Figure 1H:
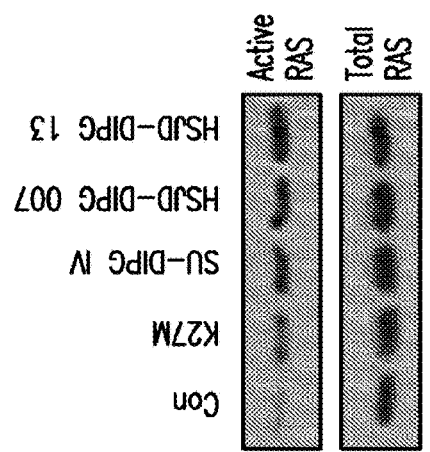
Figure 1K:
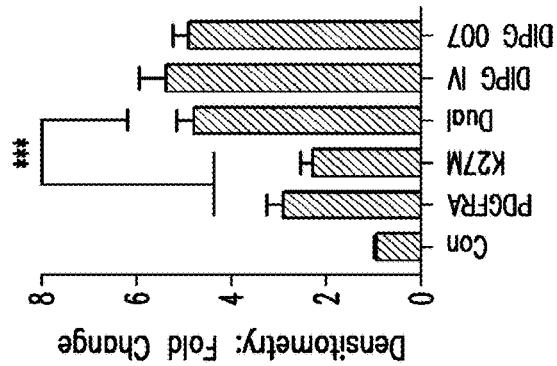
Figure 1L:
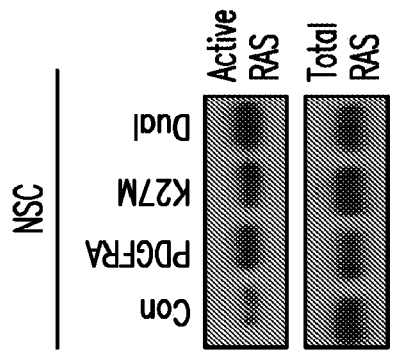
Figure 1M:
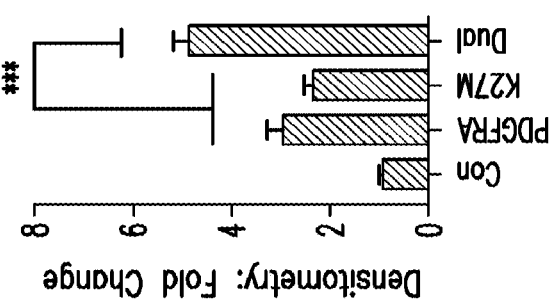
Figure 1N:
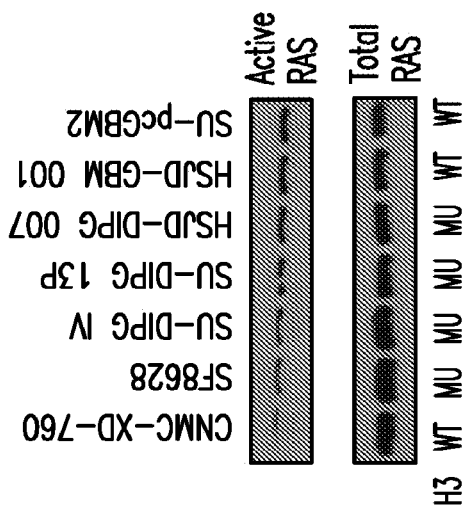
Figure 1O:
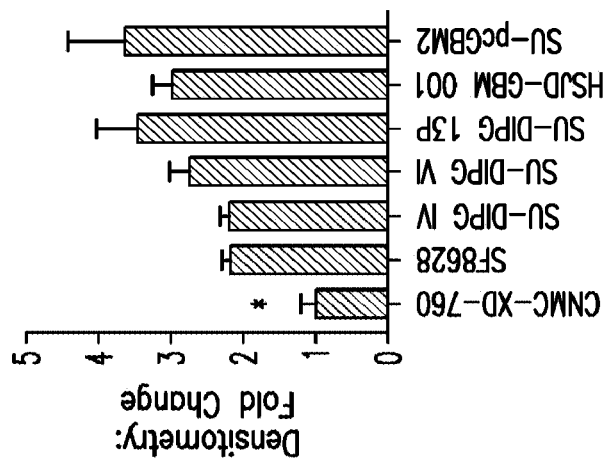

FIGS. 1A-1O provide that H3K27M increased activated RAS signaling. (1A) Direct Trypan-Blue automated cell count of control and H3K27M expressing cells over 120 h (5 days). (1B) Western blot of H9 Neural stem cells (NSC) confirming wildtype and H3K27M mutant expression, loss of H3K27Me3, and total H3. NSC control cells were transduced with empty vector. (1C) Active GTP-bound RAS immunoprecipitation (IP) in control, wildtype and H3K27M expressing cells. Whole cell lysate (W.C.L.). (1D) Densitometry ratio of active GTP-bound RAS immunoprecipitation (IP) to total RAS in NSC empty vector (EV) control and NSC H3K27M pooled clones from FIG. 1C. (1E-1G) siRNA targeting H-RAS, K-RAS, N-RAS in control (EV, IE), wildtype H3 (1F) and H3K27M NSC (1G) cells. (1H-1I). Western blot (1H) and densitometry ratio (1I) of active GTP-bound RAS immunoprecipitation (IP) to total RAS in NSC control (con), NSC H3K27M (K27M) and several DIPG cell lines. (1J-1K). Western blot (1J) and densitometry ratio (1K) of active GTP-bound RAS immunoprecipitation (IP) to total RAS in NSC control (con), NSC H3K27M (K27M), NSC PDGFRA, PDGFRA and H3K27M co-transfected (dual) and several DIPG cell lines. Western blot (1L) and densitometry ratio (1M) of active GTP-bound RAS immunoprecipitation (IP) to total RAS in NSC control (con), NSC PDGFRA, NSC H3K27M, and NSC co-transfected with PDGFRA and H3K27M (dual). Western blot (1N) and densitometry ratio (1O) of active GTP-bound RAS immunoprecipitation (IP) to total RAS in H3WT DIPG cell line, H3K27M cells and hemispheric pGBM cells. *P<0.05, ***P<0.0001.

FIGS. 2A-2L provide the results of a RAS targeted siRNA screen for identifying novel RAS effector genes that drive H3K27M growth. (2A) Quantitative Real-Time Polymerase Chain Reaction (qRT-PCR) of NSC control and NSC H3K27M cells for several RAS-GAPs. (2B) Western blot of RASAL1 and RASA3 in normal human astrocytes (NHA), two NSC lines and DIPG lines. (2C) Western blot from Whole Cell Lysate (W.C.L.) of lentiviral expression of HA-tagged RASAL1 or control vector into NSC-H3K27M or DIPG-13p cells. Active GTP-bound RAS immunoprecipitation (IP) in empty vector control and RASAL1 expressing cells was performed to assess RAS activity. (2D) Direct Trypan-Blue automated cell count of control and RASAL1 expressing cells over 7 days. (2E) Schematic of Targeted RAS siRNA screen. (2F-2G) NSC control, NSC H3K27M (2F) and DIPG-007 (2G) cells were transfected with a 294 DNA siRNA pool library. Cell viability was assessed by the Alamar blue cell viability assay 120 hours after siRNA transfection. Data were normalized using the standard z-score method. Significance of potential hits were determined using z-score cut-off values±2 (dotted line), which corresponded to a P value of <0.05 in all three biologic replicates (Rep. 1-3). (2H). Venn diagram of overlapping targets and unique targets between H3K27M NSC cells and DIPG-007 cells. (2I). Re-screen of top targets using siRNA and direct Trypan-Blue automated cell count of DIPG-007 cells over 7 days. (2J) Quantitative real-time PCR (qRT-PCR), for growth factors in control, wildtype expressing and H3K27M NSC cells. (2K) qRT-PCR for growth factors in control, wildtype expressing and H3K27M NSC cells. (2L) Western blot confirmation of EGFR and PDGFRA activity in H3K27M NSCs.

FIGS. 3A-3I provide that ERK5 was up-regulated and activated in DIPG. (3A) Schematic of the ERK5 signaling cascade. (3B) Western blot of phospho and total ERK5 in NSC cell expressing empty vector (EV), wildtype H3.3 and H3K27M. (3C) Oncoprint map of genomic alterations in H3K27M mutant DIPG patients with ERK5, NF1 and PDGFRA alterations. (3D) Western blot and densitometry of pERK5 and ERK5 in five DIPG patient samples compared to three pediatric pons from non-tumor patients. (3E) Western blot of the MAPK signing network in patient derived DIPG cultured cells compared to NSCs and NHAs. (3F) Western blot after a cellular fractionation assay for ERK5. GAPDH was used to confirm cytoplasmic purity and H3.3 for nuclear purity. (3G) Western blot of the MAPK signing network in patient derived DIPG cultured cells compared to empty vector NSCs and NSCs expressing wildtype H3 or H3K27M. (3H) Oncoprint map of genomic alterations in H3K27M mutant DIPG, H3.1 K27M, and hemispheric pGBM patient samples with ERK5 and additional MAPK signaling alterations. Dataset used was from the Paediatric High Grade Glioma dataset (ICR London, Cancer Cell 2017)(Mackay et al., Cancer cell 2017; 32(4):520-37 e5). Data was analyzed in the pediatric cBIO data-portal (https://pedcbioportal.org/, Mar. 15, 2019). (3I) ERK5 (MAPK7) RNA-seq expression (Log 2 RSEM) of all adult cancers from the TCGA pan-Cancer normalized data study. Data was accessed and analyzed in the cBIO data portal (http://www.cbioportal.org/, Mar. 15, 2019). GBM and low-grade gliomas express among the higher amounts of ERK5 expression.

FIGS. 4A-4K provide that ERK5 loss inhibited growth in DIPG cells. (4A) Western blot of control and doxycycline (Dox) treated cells (2 ug/ml) confirming ERK5 knockdown and analysis of activated ERK1/2 and AKT. Cells were treated with Dox for 5 days. (4B-4D). 5-bromo-2'-deoxyuridine (BrdU) cell proliferation assay of DIPG-13p cells (4B), DIPG-IV cells (4C) and SF8628 cells (4D). Cells were treated with no Dox or Dox starting 5 days prior to the assay. (4E). Kaplan-Meir survival curves of DIPG-13p orthotopic xenograft models (n=5 per group, p<0.05). ERK5 inducible shRNA for knockdown (ERK5 KD) was accomplished by administration of doxycycline (2 mg/mL) with 5% sucrose in drinking water. (4F) Western blot in control mice versus doxycycline mice from (4E) confirming ERK5 KD. (4G) Schematic of ERK5 rescue constructs with alterations made to the kinase domain (KD, kinase dead), transcriptional activation domain (ΔTAD, TAD deleted) or both (KD ΔTAD). (4H) Western blot in SF8628 cells confirming shRNA targeting ERK5 3'UTR inhibits ERK5 at the protein level. (4I) HA Western blot confirming ERK5 constructs expression in SF8628 cells by lentiviral transduction 72 h after infection. (4J) BrdU cell proliferation assay of DIPG-IV cells transduced with various ERK5-HA tagged constructs from (4G). (4K) Statistical analysis of (4J) compared to Dox treated cells. *p<0.05.

FIGS. 5A-5K provide that pharmacological inhibition of ERK5 triggered cell death and apoptosis in DIPG cells. 5A: EC50 dose response curves at 96 h in DIPG-007 cells using TG02. 5B: EC50 dose response curves at 96 h in DIPG-IV cells using TG02. (5C-5E). Direct Trypan-Blue automated cell count of cells treated with DMSO vehicle (control), and TG02 (100 nM) for DIPG-007 cells (5C), DIPG-IV cells (5D) and SF8628 cells (5E). (5F) Annexin-PI quantification of DIPG cells treated with TG02 at 48 h from (5G). Compared to DMSO vehicle control cells, TG02 had decreased viable cells (Annexin negative, PI negative) and increased populations in early apoptosis (Annexin positive, PI negative), late apoptosis (Annexin and PI positive) and necrosis (PI positive, Annexin negative). (5G) Representative Annexin-PI contour plots with quadrant gates showing four populations in DIPG-007 and DIPG-IV cells treated with vehicle (DMSO), and TG02. (5H-5I) Western blot confirming that TG02 inhibits the ERK5 autophosphorylation site at various doses in DIPG-007 (5H) and DIPG-IV cells (5I). (5J) EC50 dose response curves at 96 h in DIPG-007 cells using TG02. (5K) EC50 dose response curves at 96 h in DIPG-IV cells using TG02.

FIGS. 6A-6H provide that ERK5 inhibition reduced MYC protein stability. (6A) Schematic of identifying differentially expressed phospho-proteins in DIPG-IV cells expressing ERK5 and ERK5 knockdown. (6B) Ratio of phospho:total protein changes in ERK5 knockdown versus ERK5 control DIPG-IV cells. Ratios in blue were down-regulated (Z-score<2), while ratios in red were up-regulated (Z-score>2). (6C) Western blot of phospho MYC S62 in DIPG cells treated with TG02 (100 nM). (6D) Western blot of MYC in DIPG-IV cells treated with Dox and MG132 (10 uM). (6E) Immunoprecipitation of MYC and ERK5 followed by western blot of ERK5 and MYC. (6F) In vitro kinase assay of purified recombinant ERK5 and MYC in presence or absence of TG02. (6G) Western blot of DIPG cells re-transfected with constitutively active MYC S62D in presence of ERK5 loss. (6H) Cell doubling times of control and ERK5 knockdown DIPG cells and the effect of MYC S62D rescue. SF8628 cells (left) and DIPG-IV cells (right).

FIGS. 7A-7J provide that ERK5 inhibition increases in vivo survival of DIPG patient derived xenograft models. (7A) Kaplan-Meir survival curves of SF8628 orthotopic xenograft models (n=7 per treatment group). Arrows indicate period of daily treatment (2 cycles of 5 days on 2 days off). (7B) Sagittal section and hematoxylin and eosin (H&E) staining confirming tumor growth in the mid-brain. (7C) High power magnification H&E confirming high-grade glioma histology of tumors. (7D) Ki67 proliferative marker staining of xenograft models treated with vehicle, or TG02.

(7E) Ki67 quantification from (7D). Three mice per group with average of Ki67 positive cells taken from 10 high power fields of view. (7F) Sagittal section and hematoxylin and eosin (H&E) staining confirming tumor growth in the mid-brain. (7G) High power magnification H&E confirming high-grade glioma histology of tumors. (7H) Ki67 proliferative marker staining of xenograft models treated with vehicle or TG02. (7I) Kaplan-Meir survival curves of DIPG-13p orthotopic xenograft models (n=7 per treatment group). Arrows indicate period of daily treatment (2 cycles of 5 days on 2 days off). (7J) Ki67 quantification from (7H). Three mice per group with average of Ki67 positive cells taken from 10 high power fields of view. Scale bars represent 50 uM. *p<0.05.

Figure 8A:
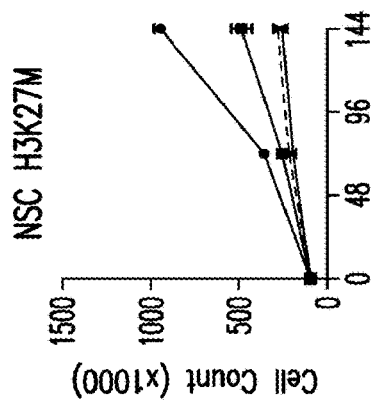
Figure 8B:
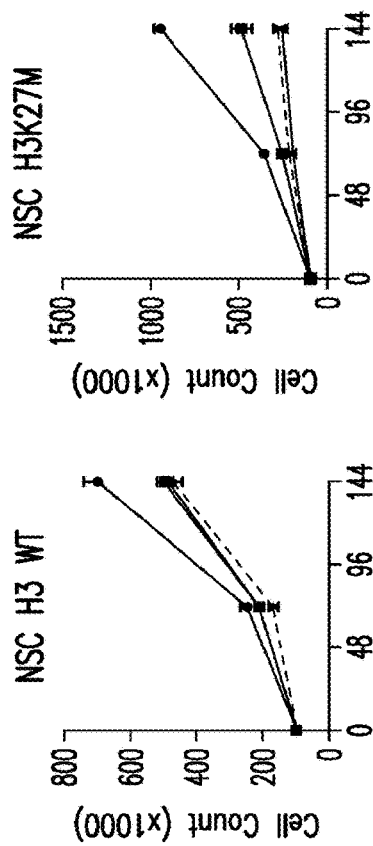
Figure 8C:
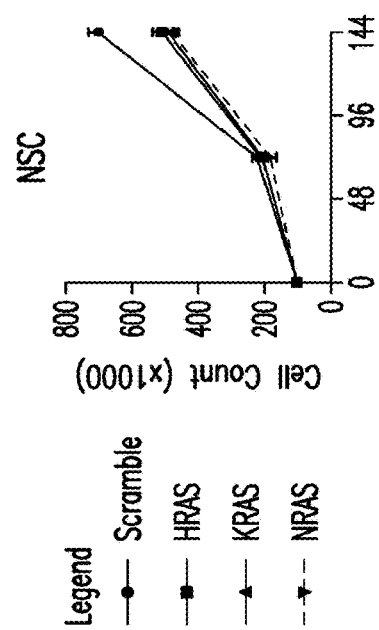

FIGS. 8A-8C provide independent siRNA targeting H-RAS, K-RAS, N-RAS in empty vector control (EV, 8A), wildtype H3F3A (8B) and H3K27M NSC (8C) cells.

Figure 8D:
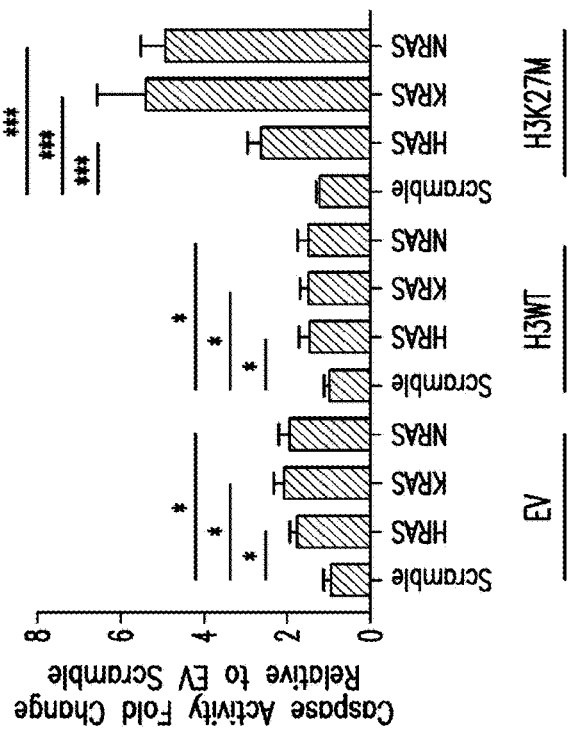

FIG. 8D provides cleaved Caspase 3 and 7 Elisa assays 72 h post transfection of cells treated with RAS siRNA.

Figure 8G:
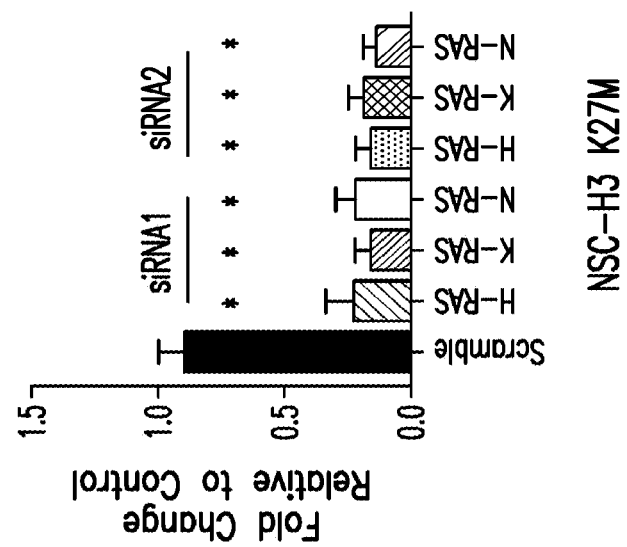
Figure 8F:
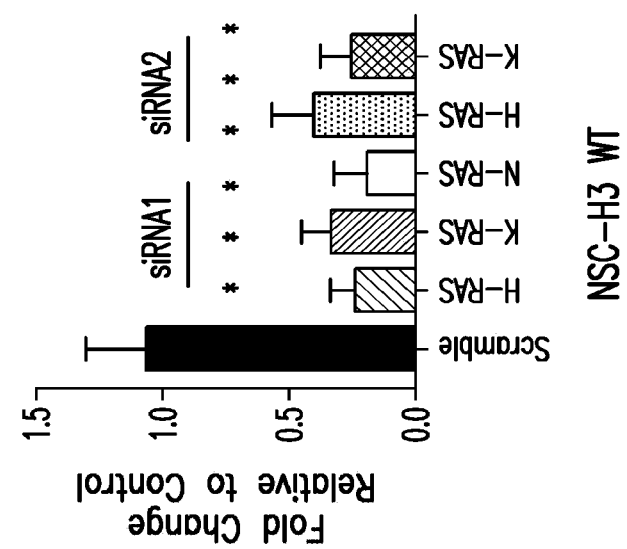
Figure 8E:
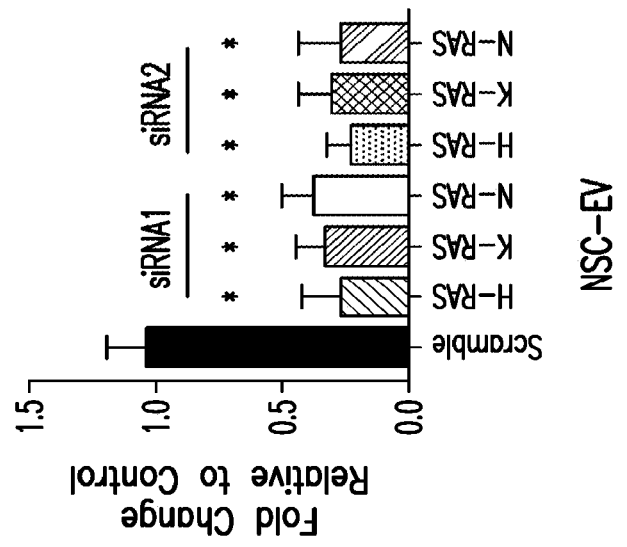

FIGS. 8E-8G provide qRT-PCR measuring fold change of H-RAS, N-RAS and K-RAS knockdown post siRNA treatment in control NSC (8E), NSCs expressing wildtype H3.3 (8F) or H3K27M (8G). *p<0.05.

Figure 9B:
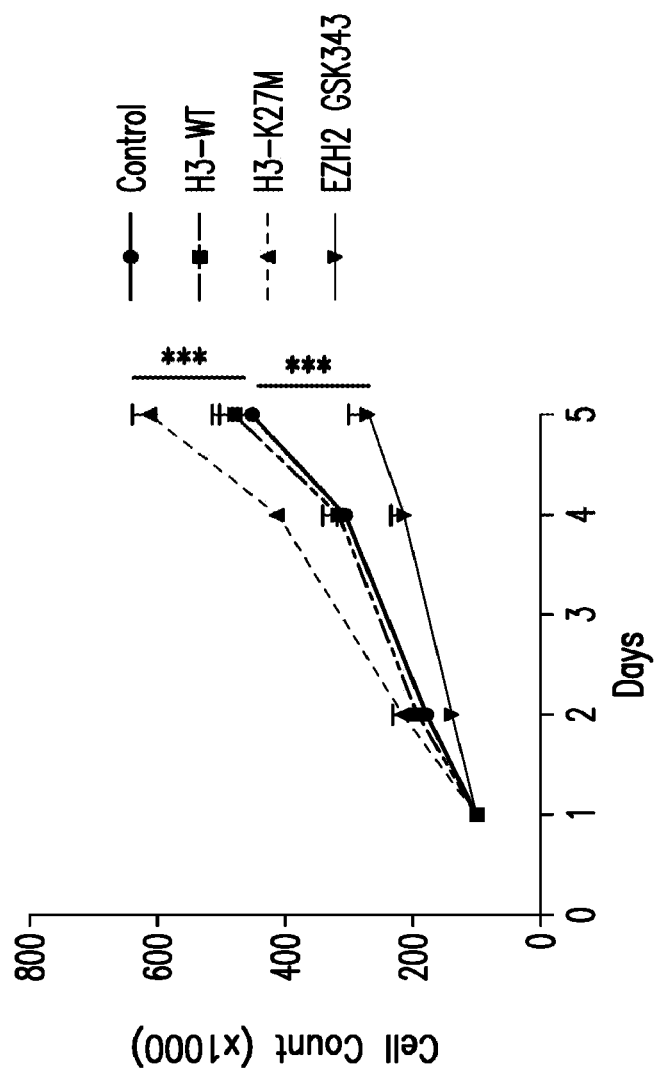
Figure 9A:
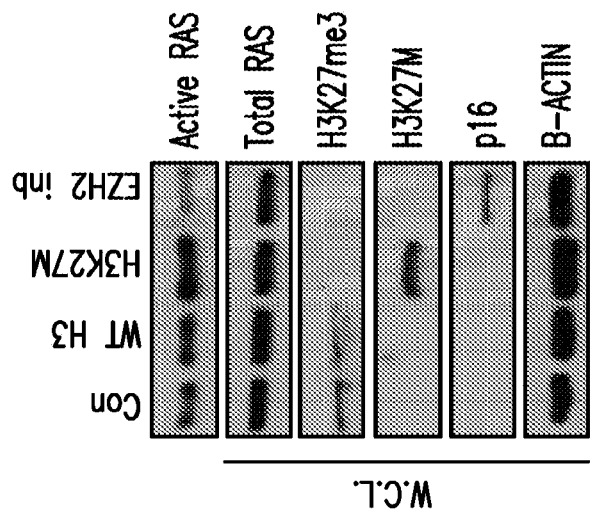

FIG. 9A provides western blot measuring RAS activation and p16 expression in NSCs expressing wildtype H3 or H3K27M or treated with the EZH2 inhibitor GSK343 (5 μM).

FIG. 9B provides direct Trypan-Blue automated cell count of NSC control cells, NSC H3K27M expressing cells, NSC H3.3 WT overexpressing cells and NSCs treated with the EZH2 inhibitor GSK343 over 5 days. *p<0.05.

Figure 9E:
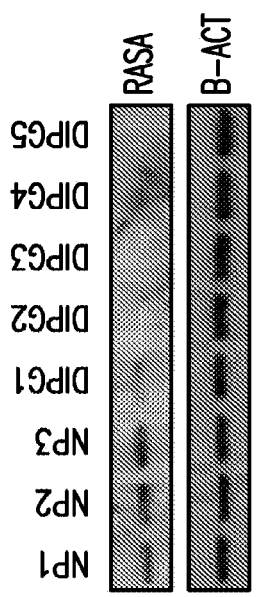
Figure 9D:
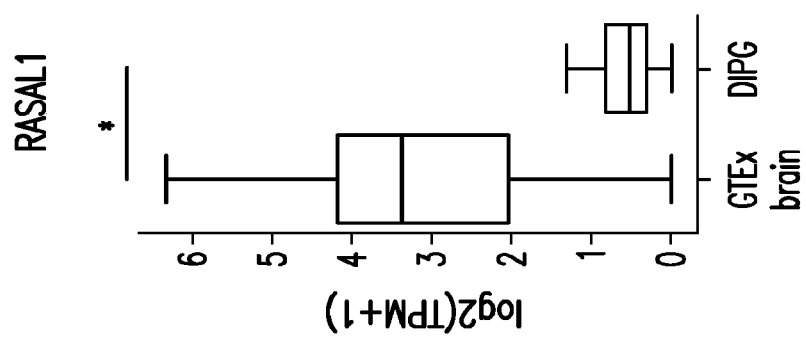
Figure 9C:
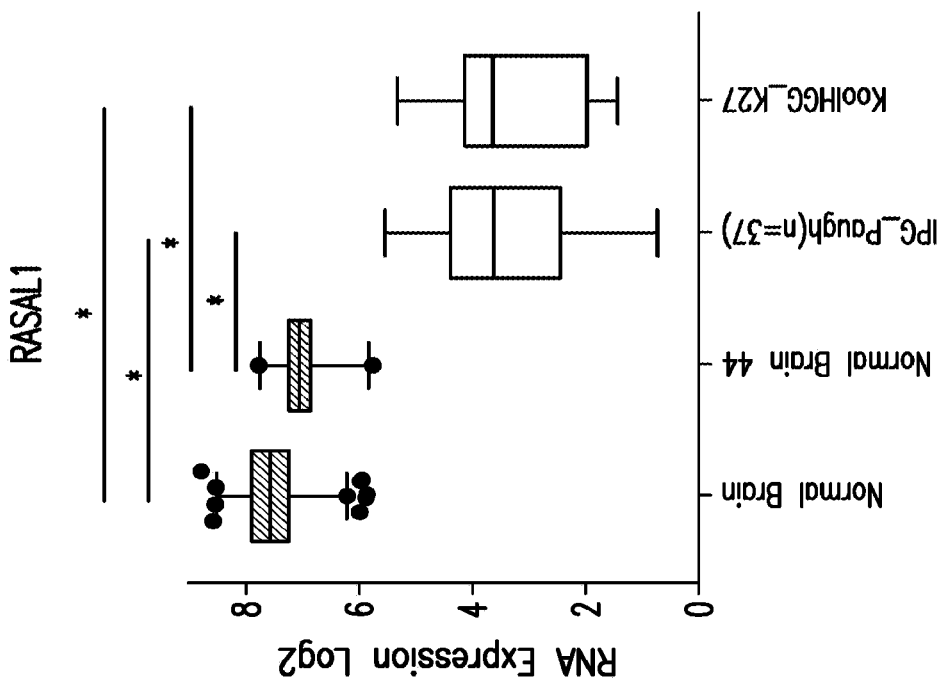

FIG. 9C provides RASAL1 microarray gene-expression in two DIPG datasets compared to two normal brain datasets.

FIG. 9D provides RNA-seq gene expression of RASAL1 comparing GTEX normal brain dataset to the Treehouse Childhood Cancer Initiative DIPG, pediatric GBM, adult GBM and adult glioma datasets.

FIG. 9E provides western blot of RASAL1 in five DIPG patient samples compared to three pediatric pons from non-tumor patients.

FIG. 9F provides western blot of stable expressing RASAL1 H3K27M NSC cells and DIPG-007 cells compared to endogenous RASAL1 in NSC and NHA.

FIG. 9G provides methylation specific PCR (MSP-PCR) of the RASAL1 promoter from methylated DNA isolated from various cells. 5mC RASAL1 refers to primers that only amplify methylated RASAL1 promoter. RASAL1 genomic DNA (bottom band) was used as a control to confirm total DNA isolation.

FIG. 9H provides western blot of RASAL1 DIPG-007 and H3K27M NSC treated five days with 1 μM decitabine (5-aza-2'-deoxycytidine) or vehicle (DMSO). *p<0.05.

Figure 2A:
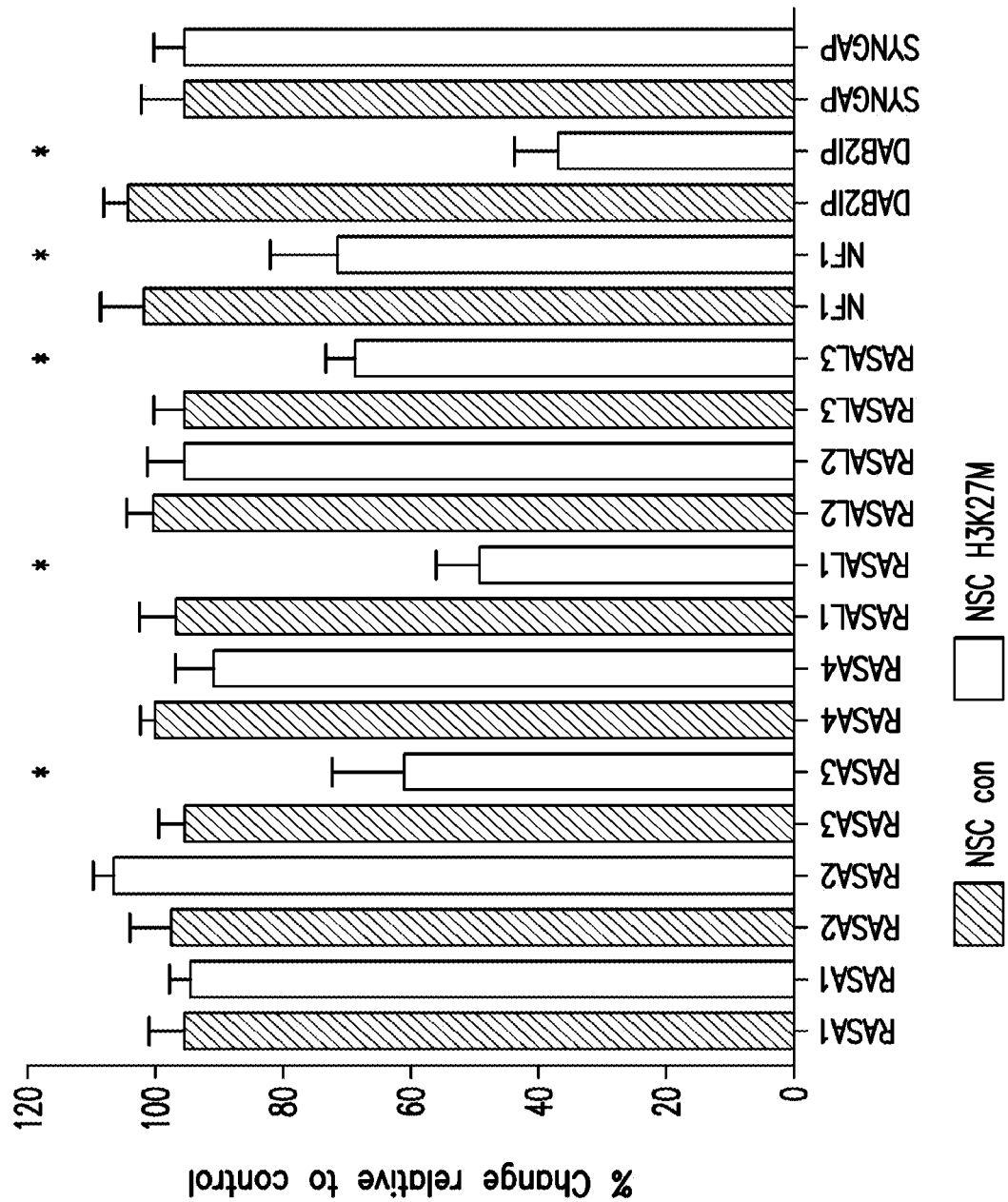
Figure 2C:
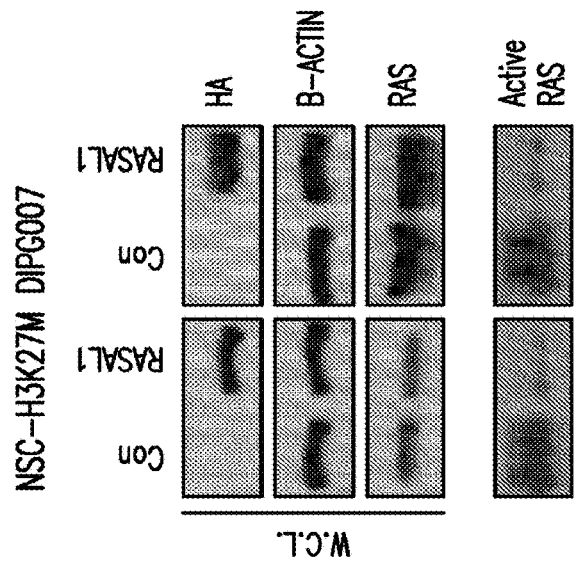
Figure 2B:
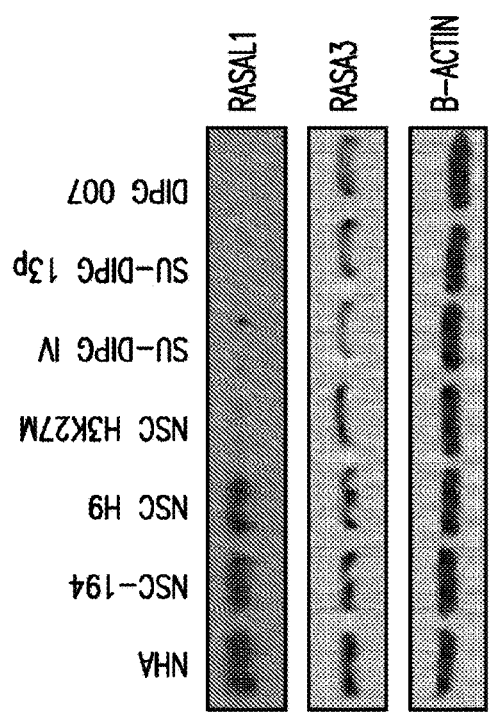
Figure 2D:
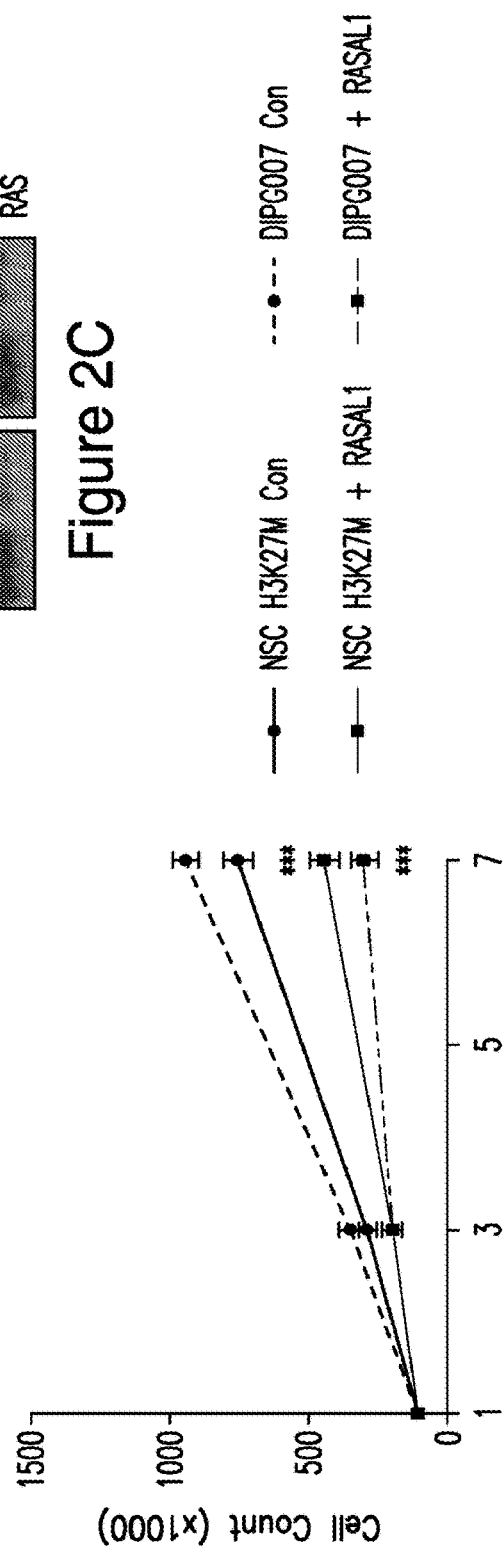
Figure 2E:
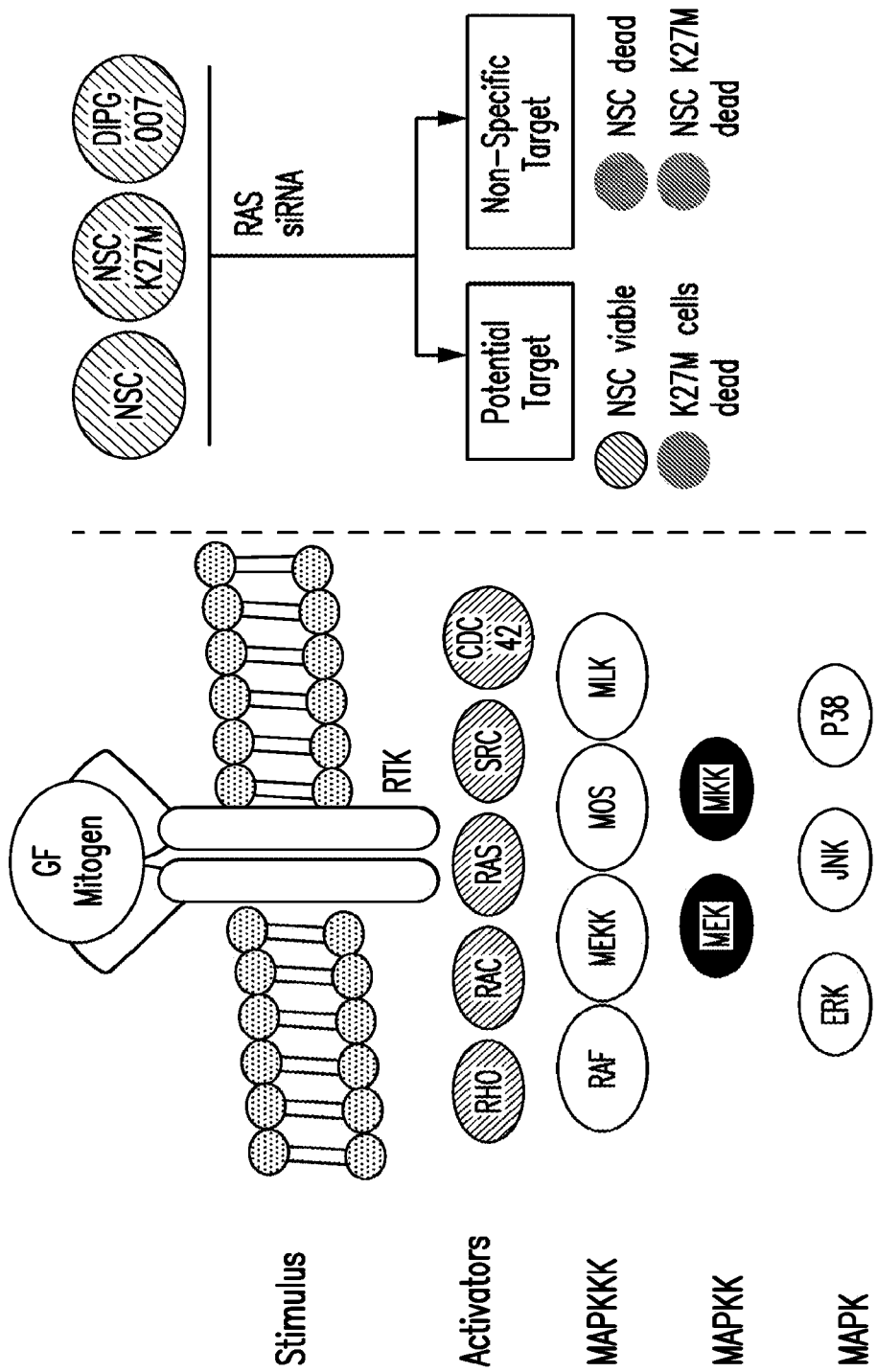
Figure 2G:
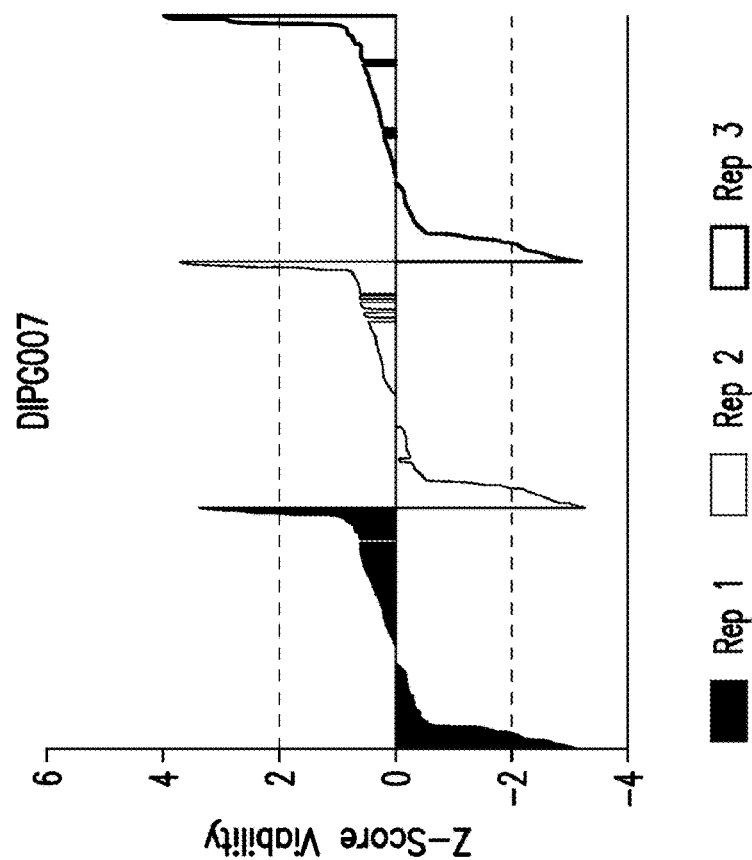
Figure 2F:
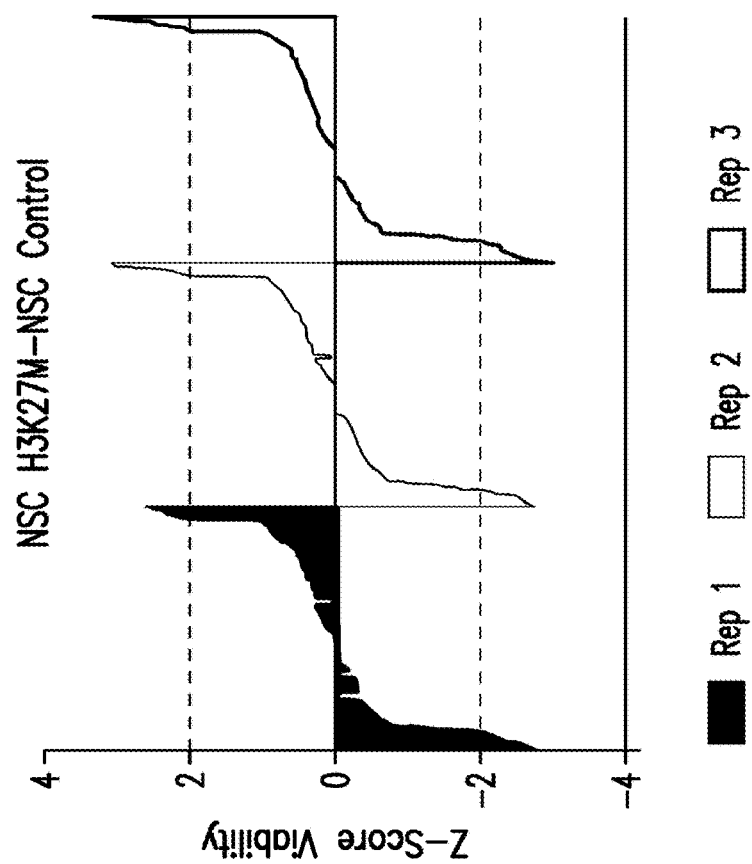
Figure 2H:
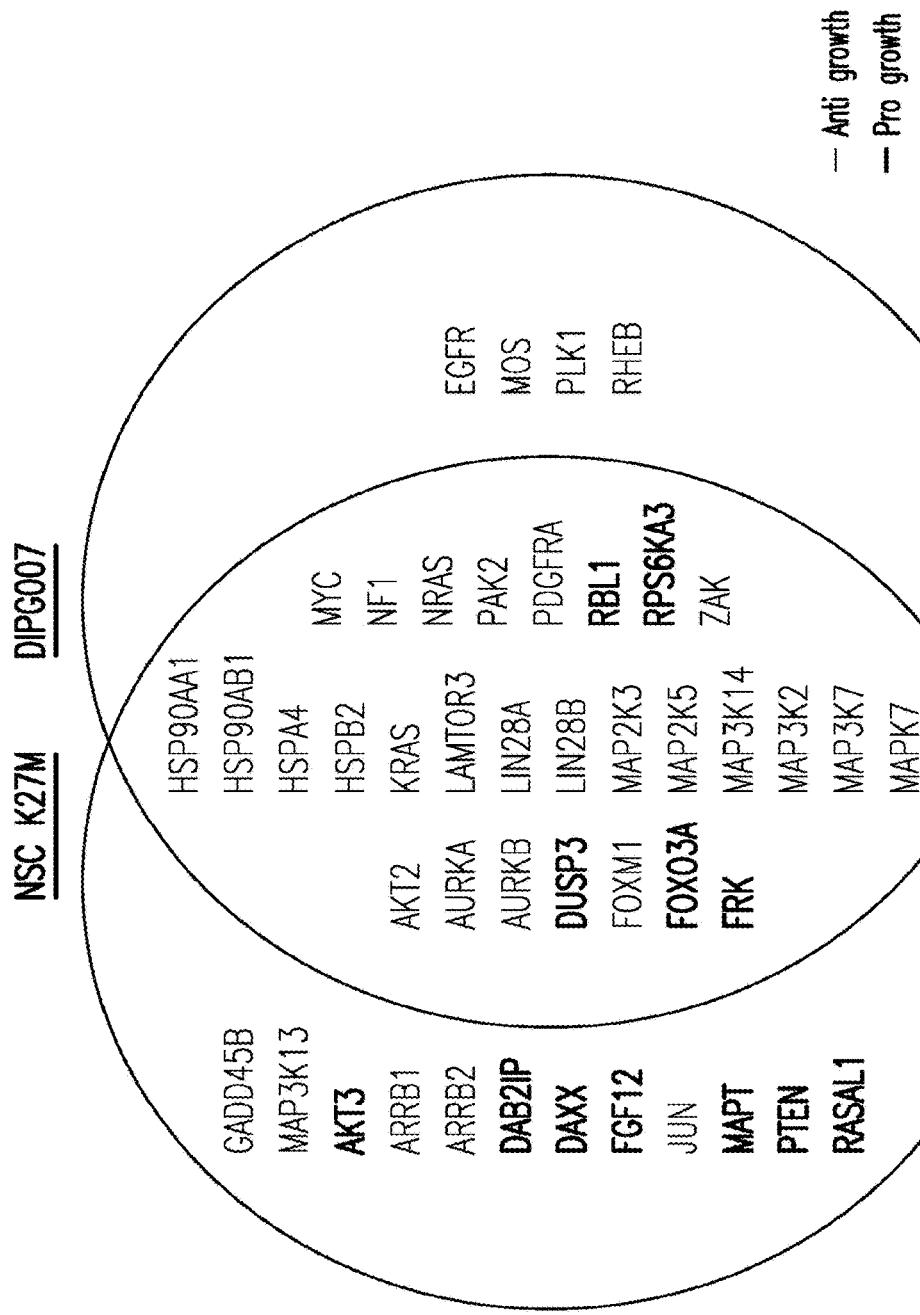
Figure 2I:
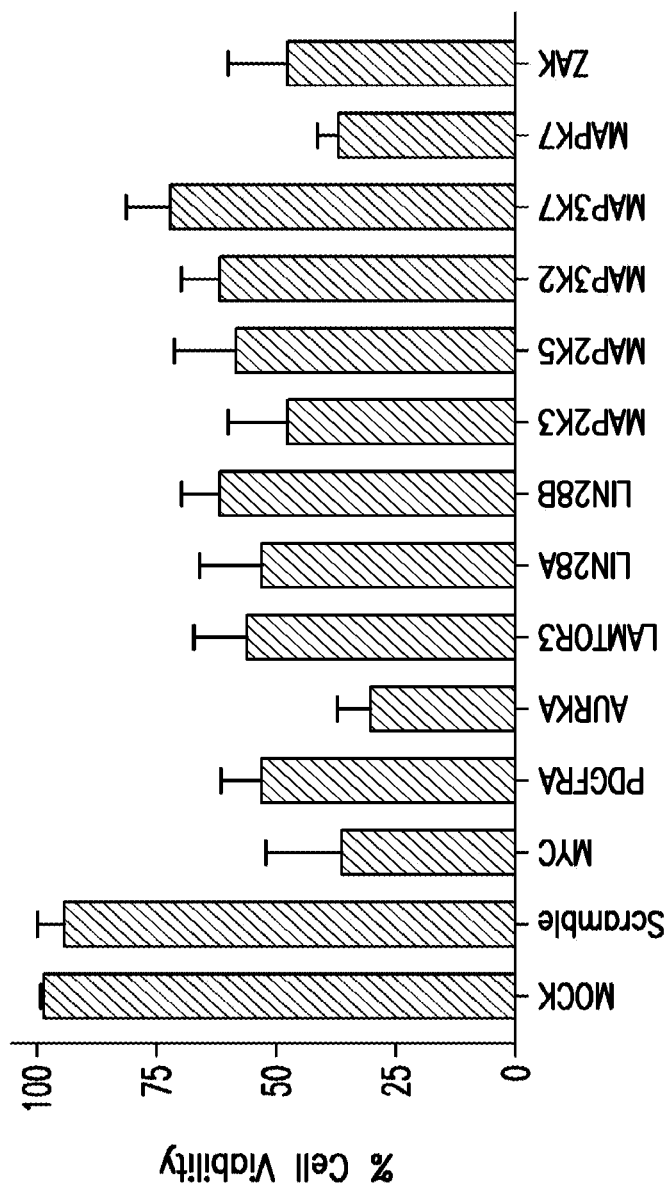
Figures 10A, 10B:
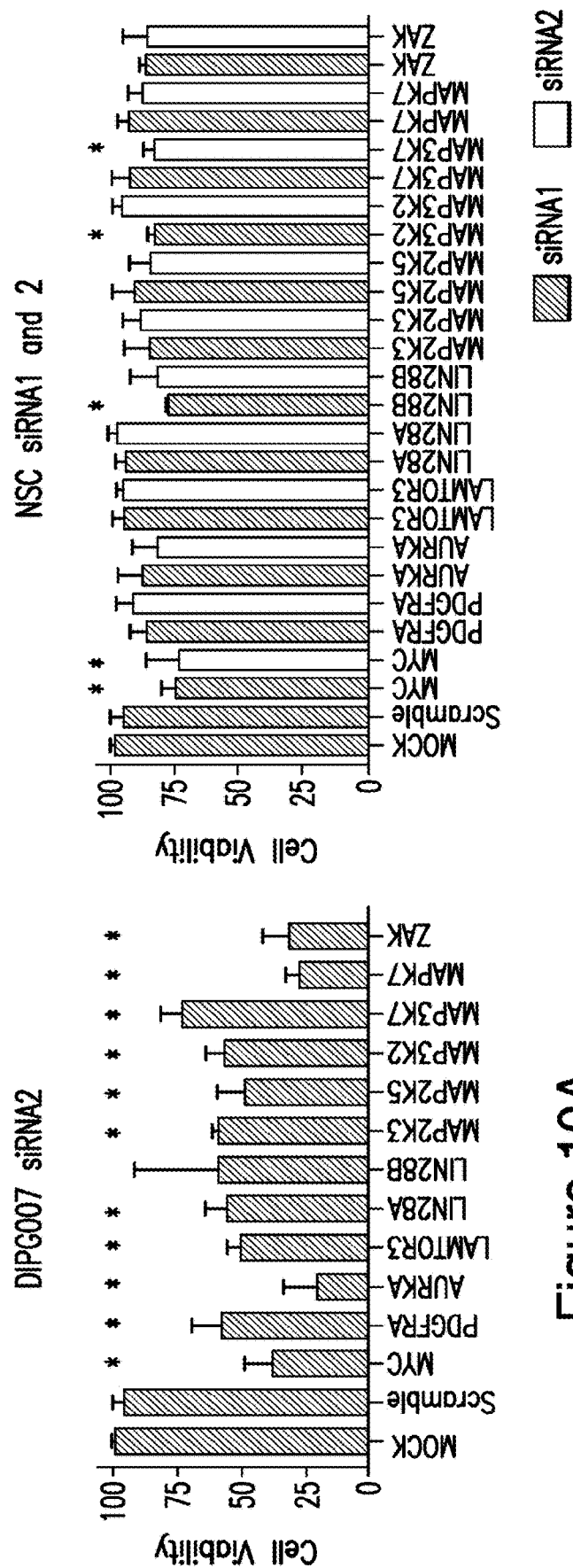

FIG. 10A provides Alamar Blue viability assay of DIPG-007 cells following transfection (96 h) with a second set of independent siRNA for top candidate genes from FIGS. 2F-2H.

Figures 10C, 10D:
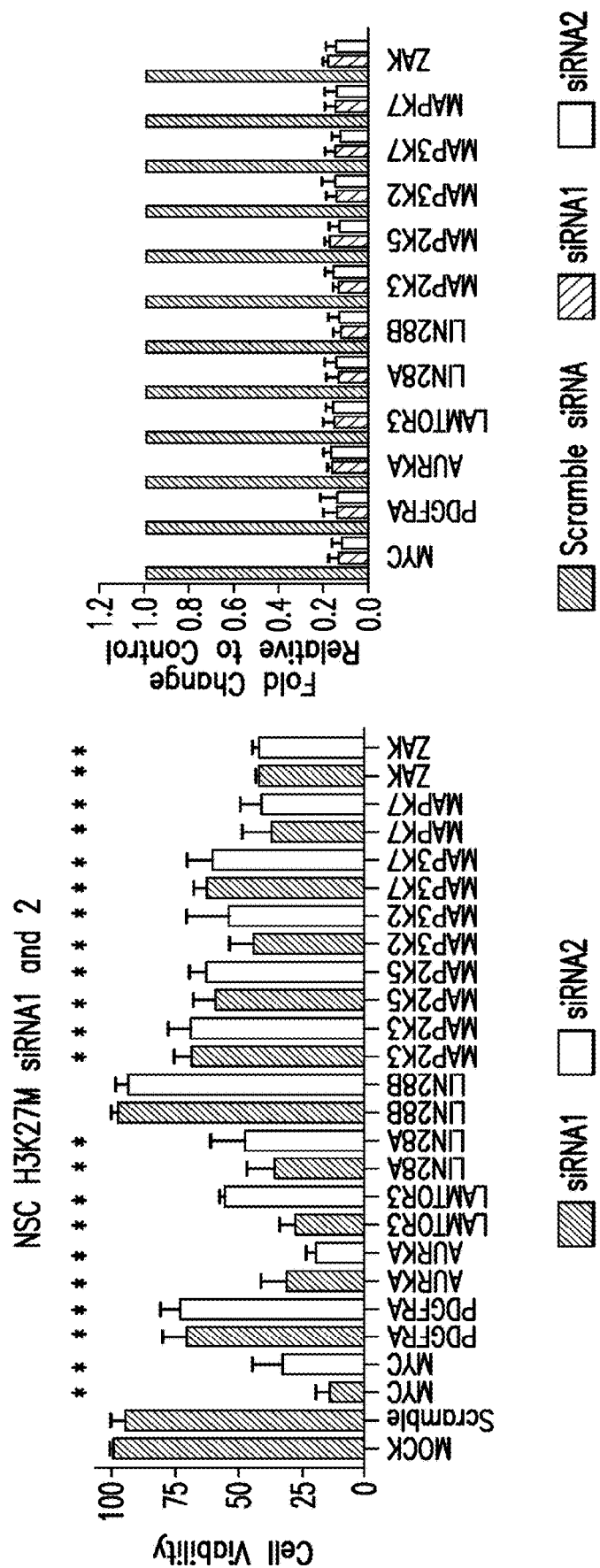

FIGS. 10B-10C provides Alamar Blue viability assay of NSCs (10B) and H3K27M NSCs (10C.) following transfection (96 h) with two independent siRNA sets for top candidate genes from FIGS. 2F-2H.

Figure 10E:
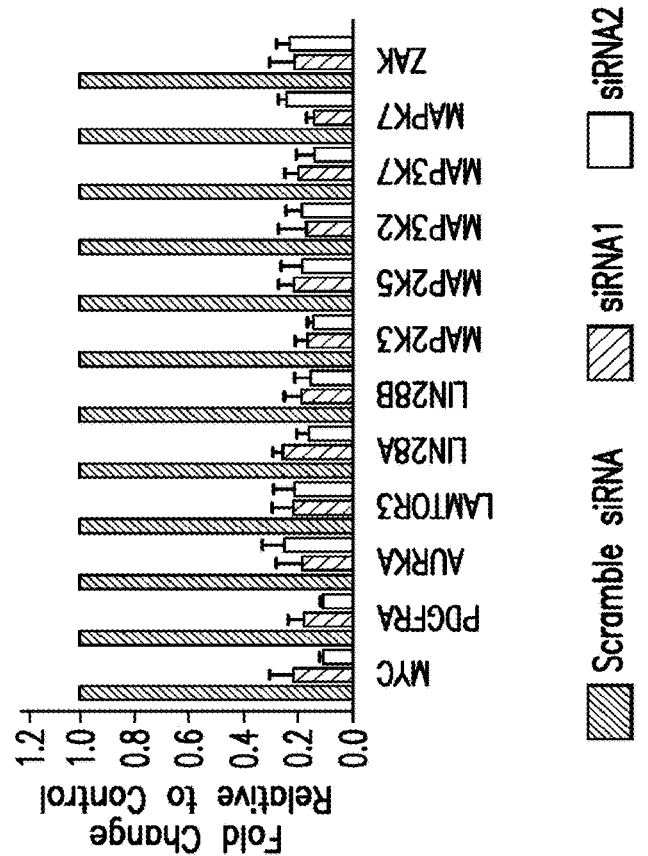
Figure 10F:
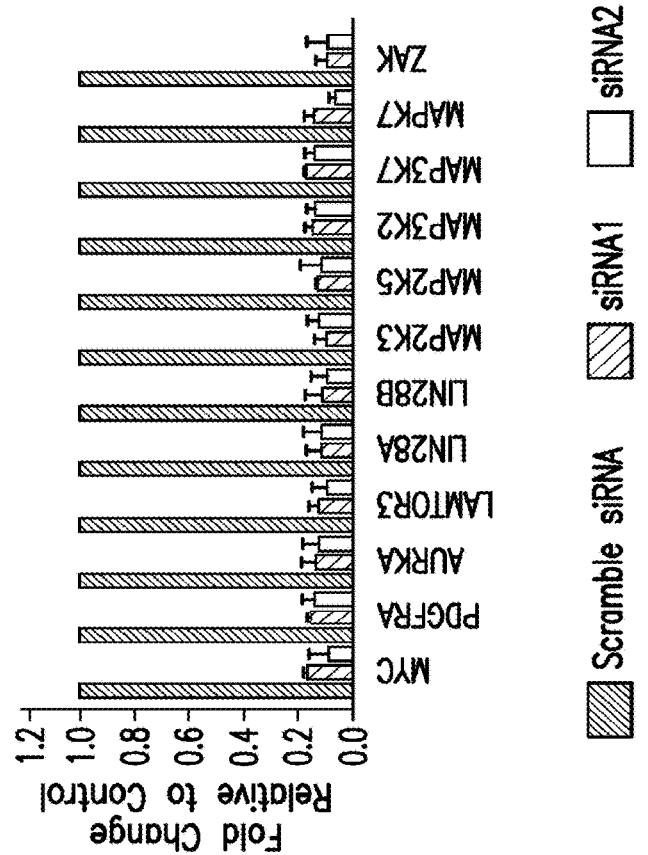

FIGS. 10D-10F provide qRT-PCR confirming effective gene knockdown by siRNA in DIPG-007 (10D), NSC-EV (10E) and NSC H3K27M (10F.). *p<0.05.

Figure 11A:
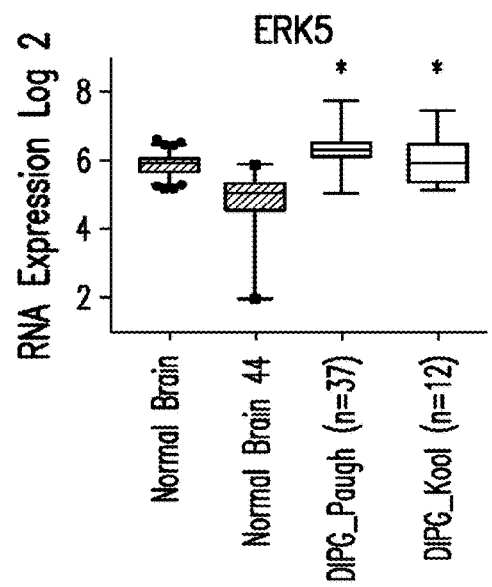

FIG. 11A provides gene-expression analysis of ERK5 in two independent DIPG datasets compared to two normal brain datasets (Berchtold et al., Proceedings of the National Academy of Sciences of the United States of America 2008; 105(40):15605-10.; Sturm et al., Cancer cell 2012; 22(4): 425-37; Paugh et al., Journal of clinical oncology: official journal of the American Society of Clinical Oncology 2010; 28(18):3061-8; Bender et al., Cancer cell 2013; 24(5):660-72).

Figure 11B:
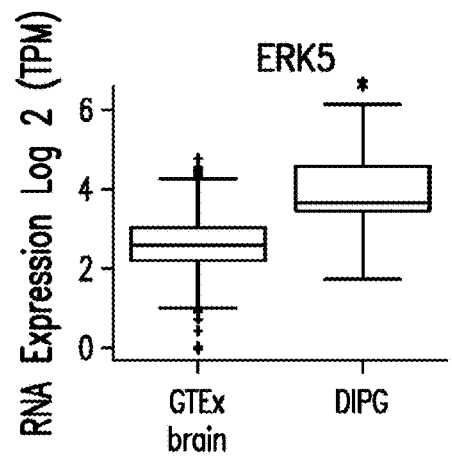

FIG. 11B provides RNA-seq gene expression of ERK5 comparing GTEX normal brain dataset to the Treehouse Childhood Cancer Initiative DIPG dataset.

Figure 11C:
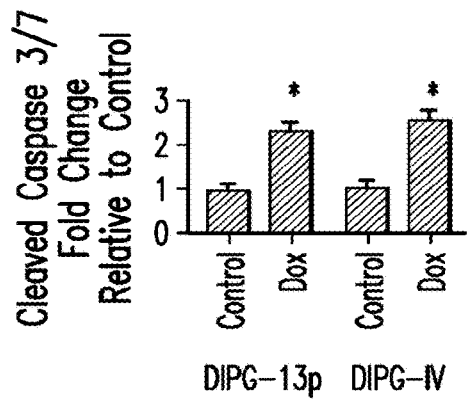

FIG. 11C provides activated cleaved Caspase 3/7 in control DIPG cell (DIPG-IV, DIPG-13p) compared ERK5 knockdown cells by doxycycline (+Dox).

Figure 11D:
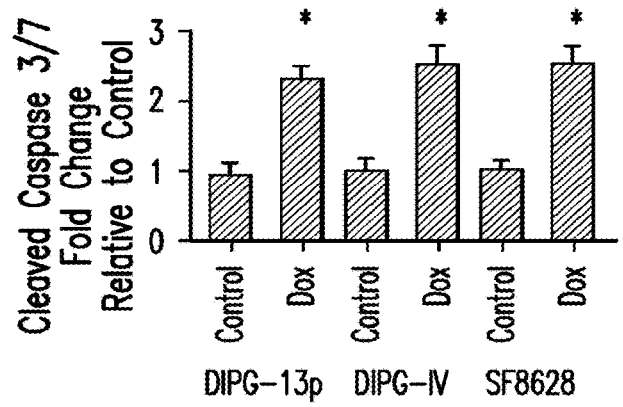

FIG. 11D provides activated cleaved Caspase 3/7 in control DIPG cells (DIPG-IV, DIPG-13p and SF8628) compared ERK5 knockdown cells by doxycycline (+Dox).

FIG. 12A provide EC50 dose response curve at 96 h in SF8628 cells using TG02.

FIG. 12B provide EC50 dose response curve at 96 h in DIPG-13p cells using TG02.

FIGS. 12C-12D provide Annexin-PI contour plots with quadrant gates showing four populations in SF8628 (12C) and DIPG-13p (12D) cells treated with vehicle (DMSO), and TG02.

FIG. 12E provides Annexin-PI quantification of DIPG cells treated in biological triplicates with ERK5 inhibitors at 48 h from (FIGS. 12C-12D). Compared to DMSO vehicle control cells, TG02 had decreased viable cells (Annexin negative, PI negative) and increased populations in early apoptosis (Annexin positive, PI negative), late apoptosis (Annexin and PI positive) and necrosis (Annexin negative PI positive). *p<0.05.

Figure 12F:
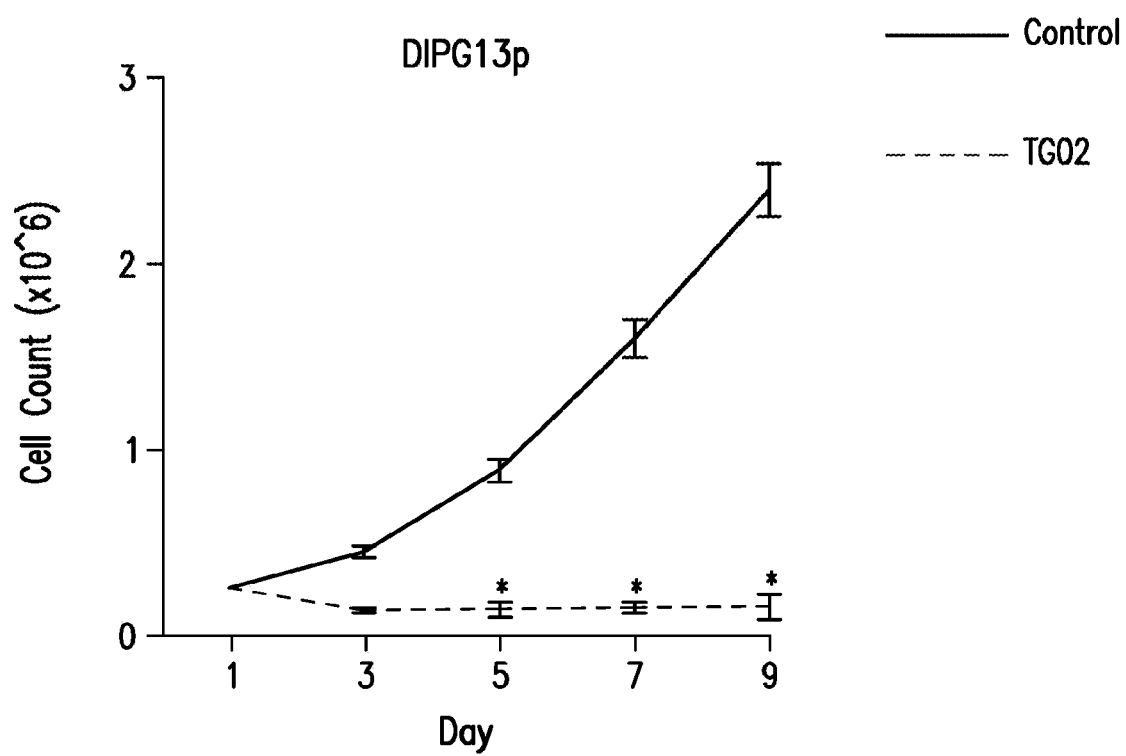

FIG. 12F provides direct Trypan-Blue automated cell count of cells treated with DMSO vehicle (control and TG02 (100 nM) for DIPG-13p cells.

FIG. 12G provides EC50 dose response curve at 96 h in SF8628 cells using TG02.

FIG. 12H provides EC50 dose response curve at 96 h in DIPG-13p cells using TG02.

FIG. 12I provides EC50 values for TG02 at 96 h in H3K27M or H3 WT cell lines.

Figure 13A:
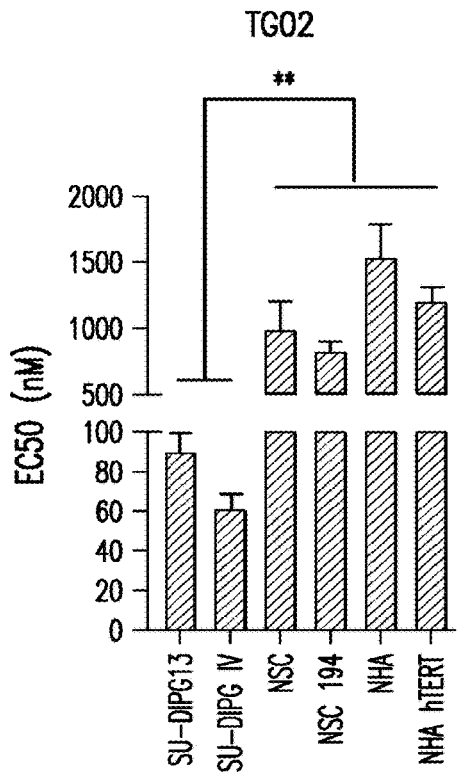

FIG. 13A provides EC50 values at 96 h in DIPG cells and several normal human stem cell (NSC) and normal human astrocyte cell lines.

Figure 13B:
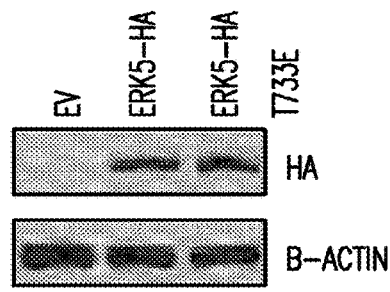

FIG. 13B provides western blot confirming expression of ERK5-HA and ERK5-HA T733E in DIPG-IV cells.

Figure 13C:
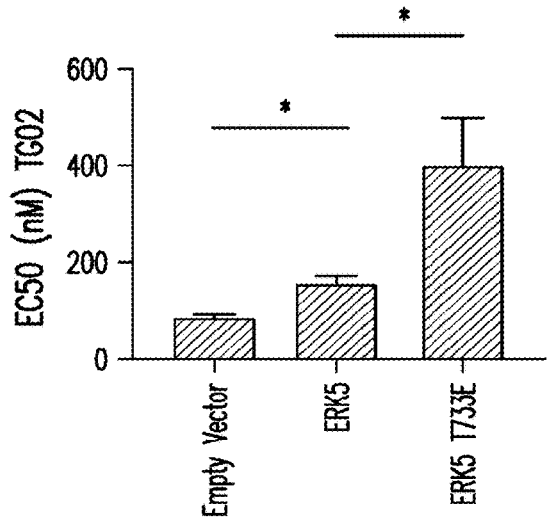

FIG. 13C provides EC50 values of TG02 treated DIPG-IV cells expressing empty vector control, ERK5-HA or ERK5-HA T733E.

Figure 13D:
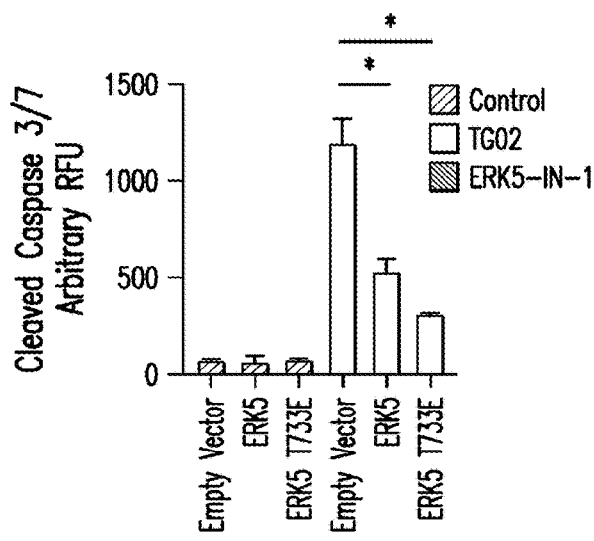

FIG. 13D provides cleaved Caspase 3/7 assay in DIPG-IV cells expressing empty vector, ERK5-HA overexpression or ERK5-HA T733E when treated with TG02 (100 nM). *p<0.05.

Figure 13F:
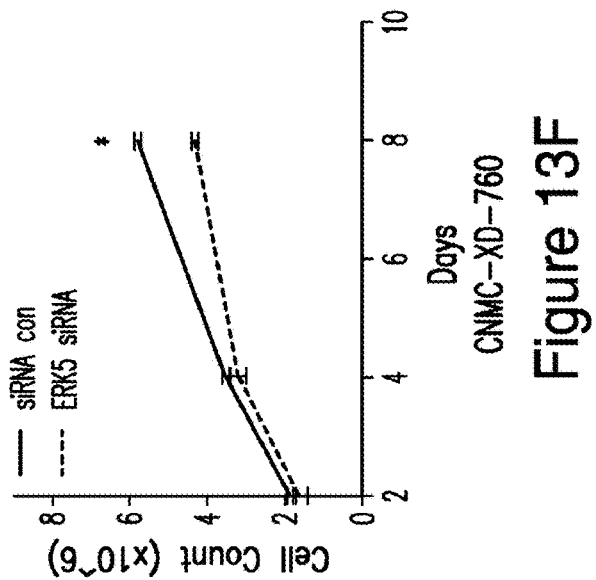
Figure 13E:
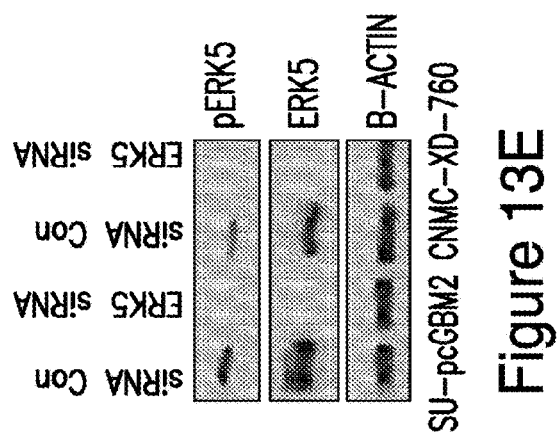

FIG. 13E provides Western blot confirming ERK5 knockdown in H3 WT DIPG cells (CNMC-XD-76) and a hemispheric pGBM line SU-pcGBM2. Pooled siRNA ERK5 lentiviral particles were delivered at an MOI of 2 using the piLenti-siRNA-GFP vector. piLenti-siRNA-GFP non-targeting shRNA was used as a control.

FIG. 13F provides cell count control and ERK5 knockdown infected cells over several days in CNMC-XD-76 cells.

Figure 13G:
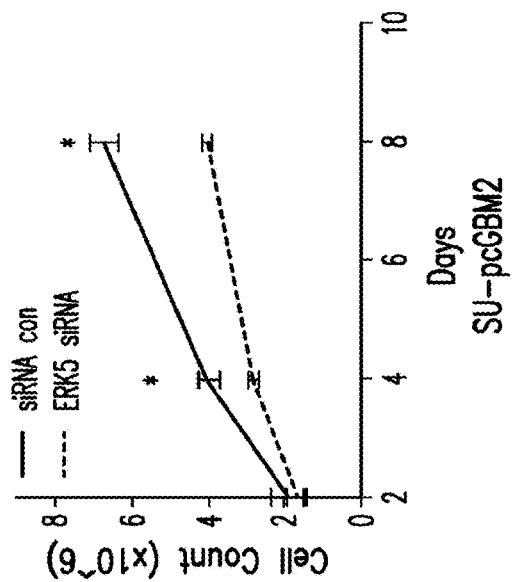

FIG. 13G provides cell count control and ERK5 knockdown infected cells over several days in SU-pcGBM2 cells.

Figure 14A:
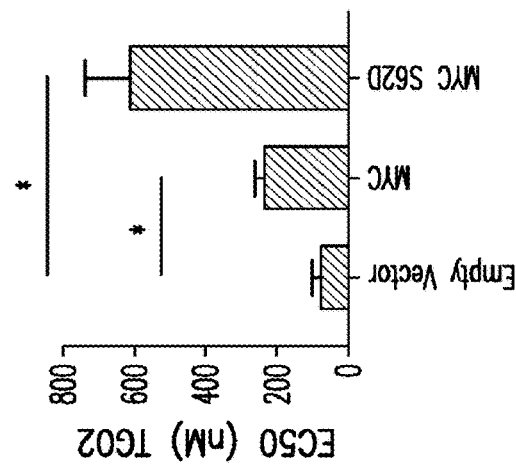

FIG. 14A provides qRT-PCR of MYC transcripts in DIPG-IV and SF8628 cells treated with vehicle, ERK5-shRNA (Dox), or TG02.

Figure 14B:
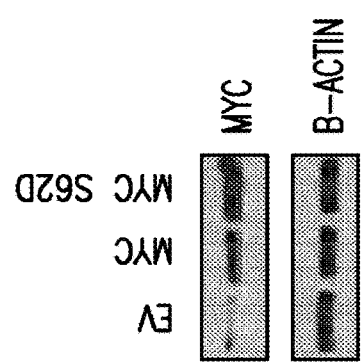

FIG. 14B provides western blot confirming expression of MYC and MYC S62D in DIPG-IV cells.

Figure 14C:
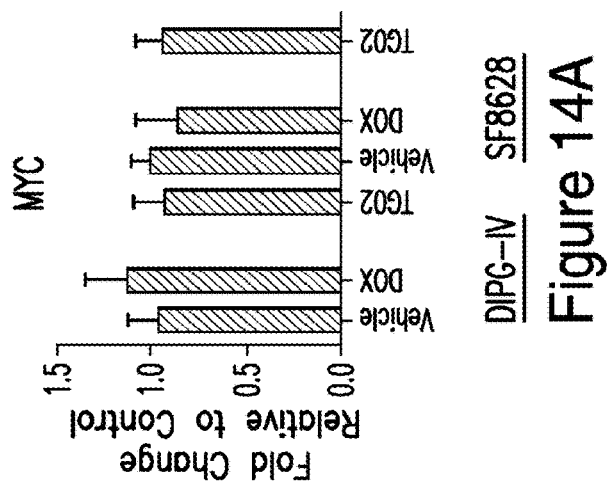

FIG. 14C provides EC50 values of TG02 for DIPG-IV cells expressing empty vector control, MYC or MYC S62D.

Figure 14D:
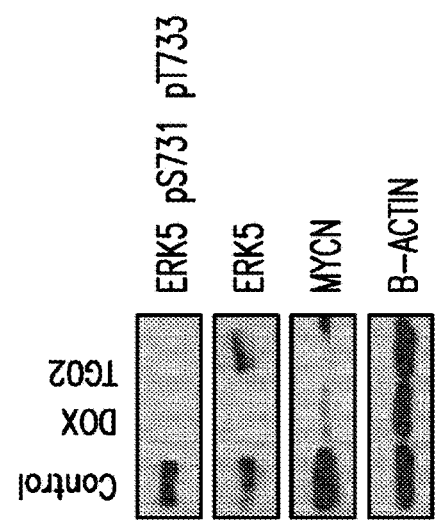

FIG. 14D provides qRT-PCR of MYCN transcript levels in DIPG-13p cells treated with vehicle, dox (ERK5 knockdown), or TG02.

Figure 14E:
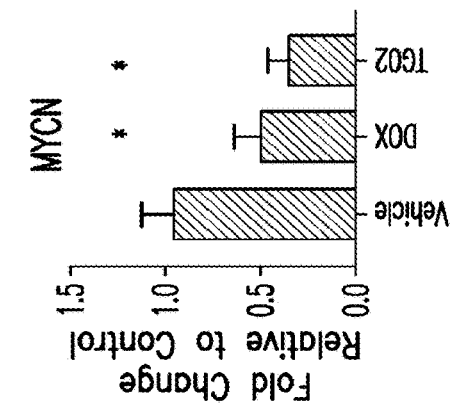

FIG. 14E provides Western blot confirming MYCN protein levels decrease in DIPG-13p cells from FIG. 14E.

FIG. 14F provides western blot of tumor lysates from mice sacrificed immediately after day 10 of vehicle treatment (n=2), TG02 treatment (n=2). pERK5 at the autophosphorylation site confirms inhibition of ERK5 with cleaved PARP used as a marker of apoptosis. Total ERK5 was used as a loading control.

FIG. 14G provides western blot of ERK5 protein on cells treated with mouse Erk5 siRNA or control siRNA. Mouse DIPG lines genotypes are as follows: H3.3WT-HA or H3.3K27M-HA with both lines expressing PDGFB and loss of p53.

FIG. 14H provides direct cell count of cells treated with ERK5 siRNA from FIG. 14H. *p<0.05.

Figure 15:
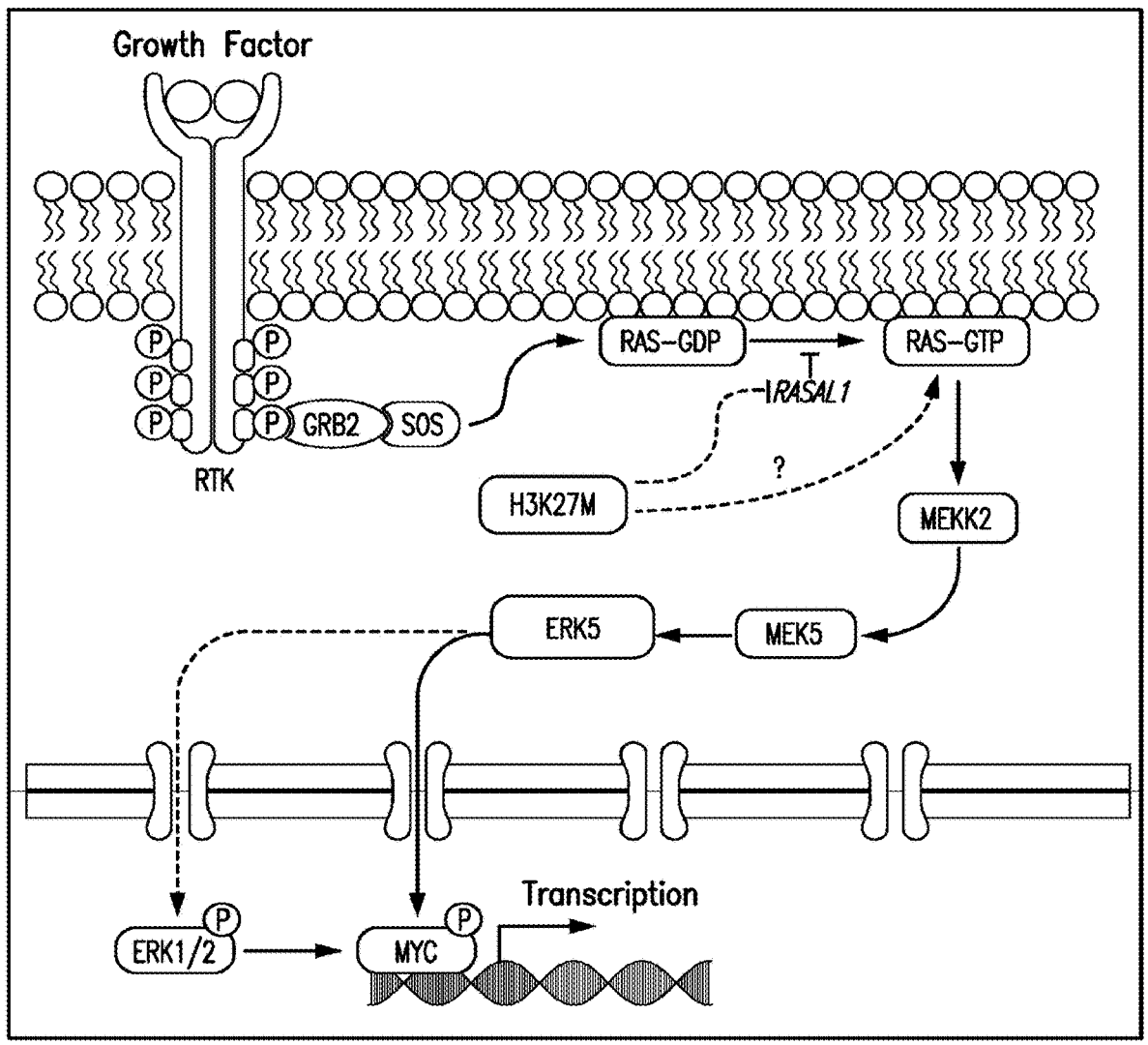

FIG. 15 provides a schematic showing how ERK5 promotes tumor growth. H3K27M mutations activate RAS partially through activation of receptor tyrosine kinases (RTKs) and growth factors. ERK5 is activated and promotes tumor growth by phosphorylating and stabilizing MYC. Additionally, H3K27M may activate RAS signaling through other direct, indirect and epigenetic mechanisms.

Figure 16:
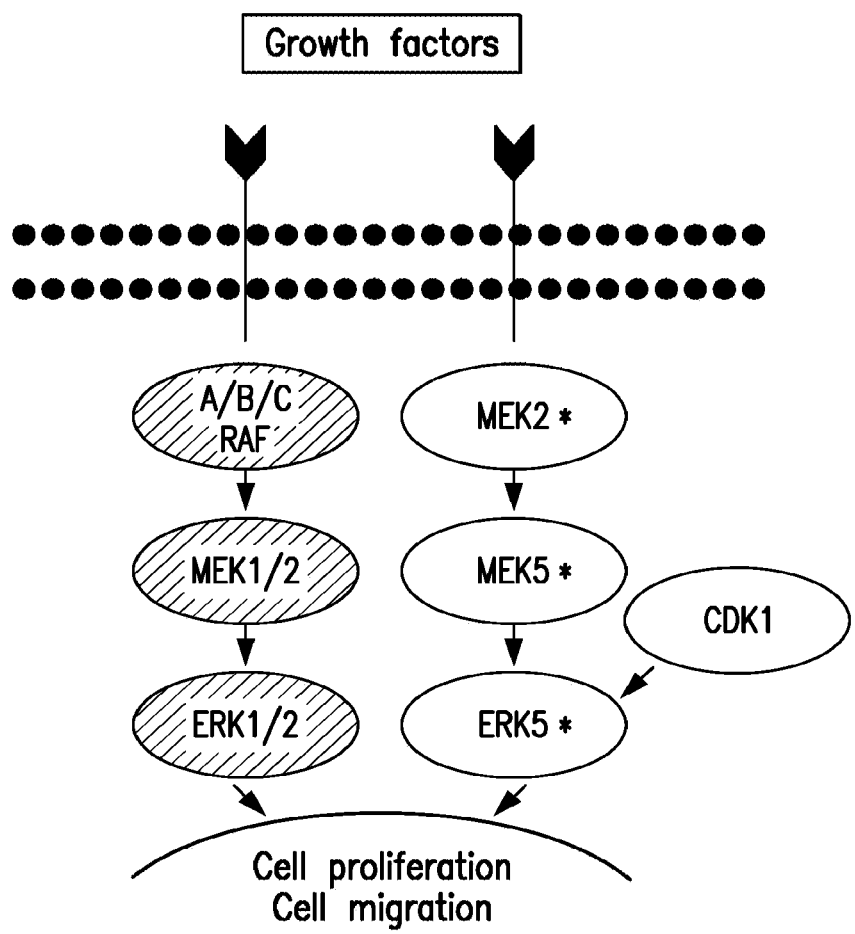

FIG. 16 provides a schematic depicting the ERK5 pathway.

Figure 17:
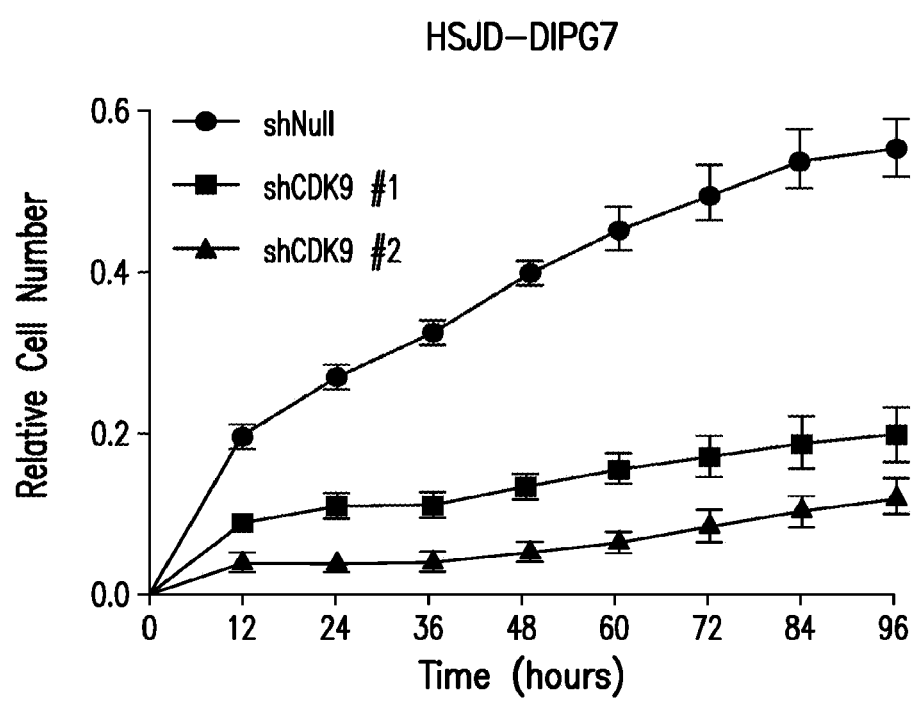

FIG. 17 provides the rate of growth of DIPG-007 cell line treated with shNull or shCDK9.

Figure 18:
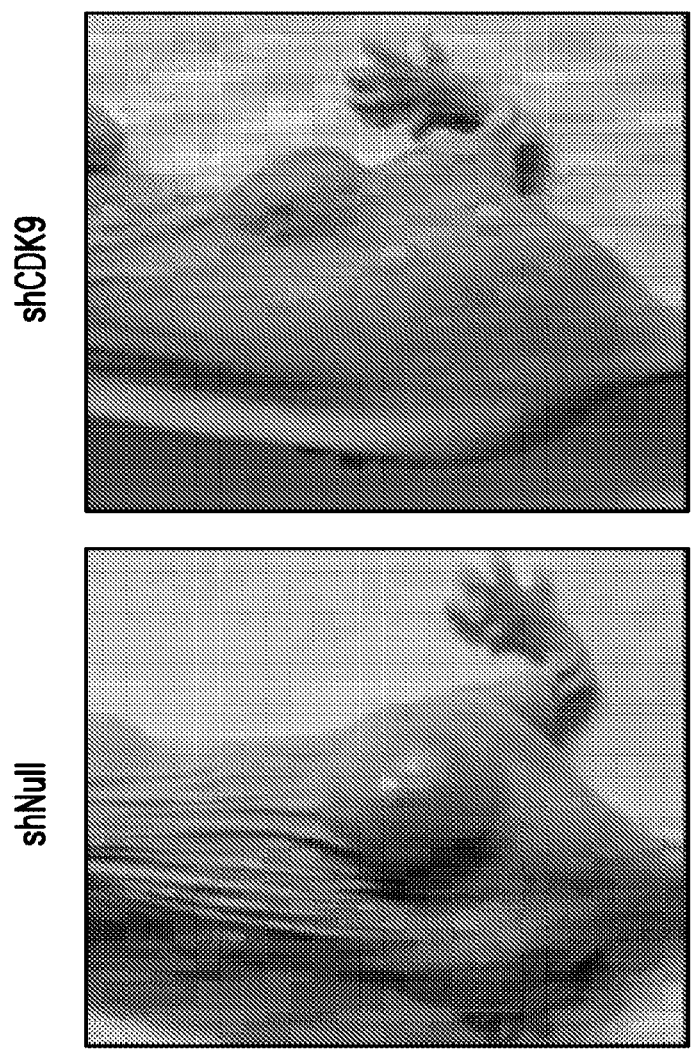

FIG. 18 provides representative images of 28 days after injection of BT 245 cell line treated with either shNull or shCDK9.

Figure 19:
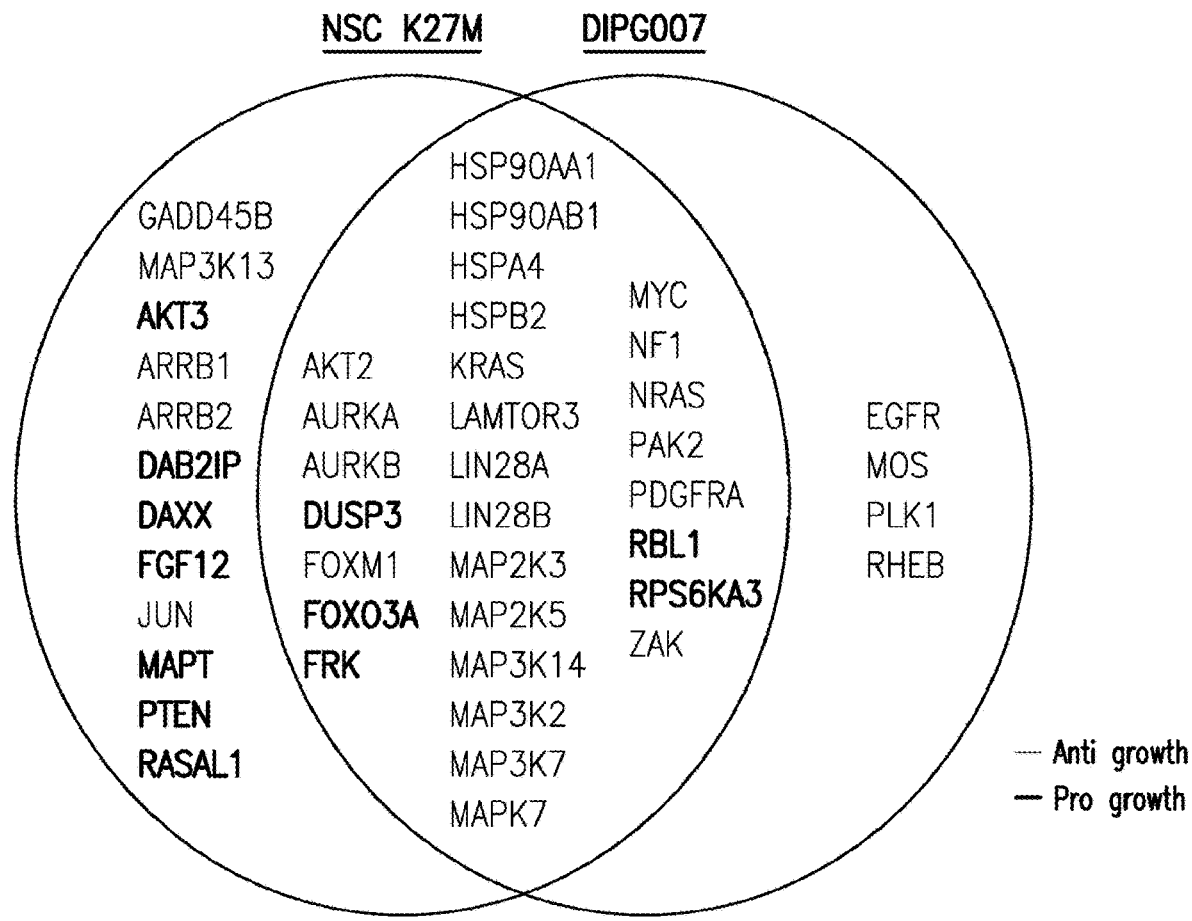

FIG. 19 provides a Venn diagram depicting overlapping and unique targets between NSC K27M and DIPG-007 cells.

Figure 20:
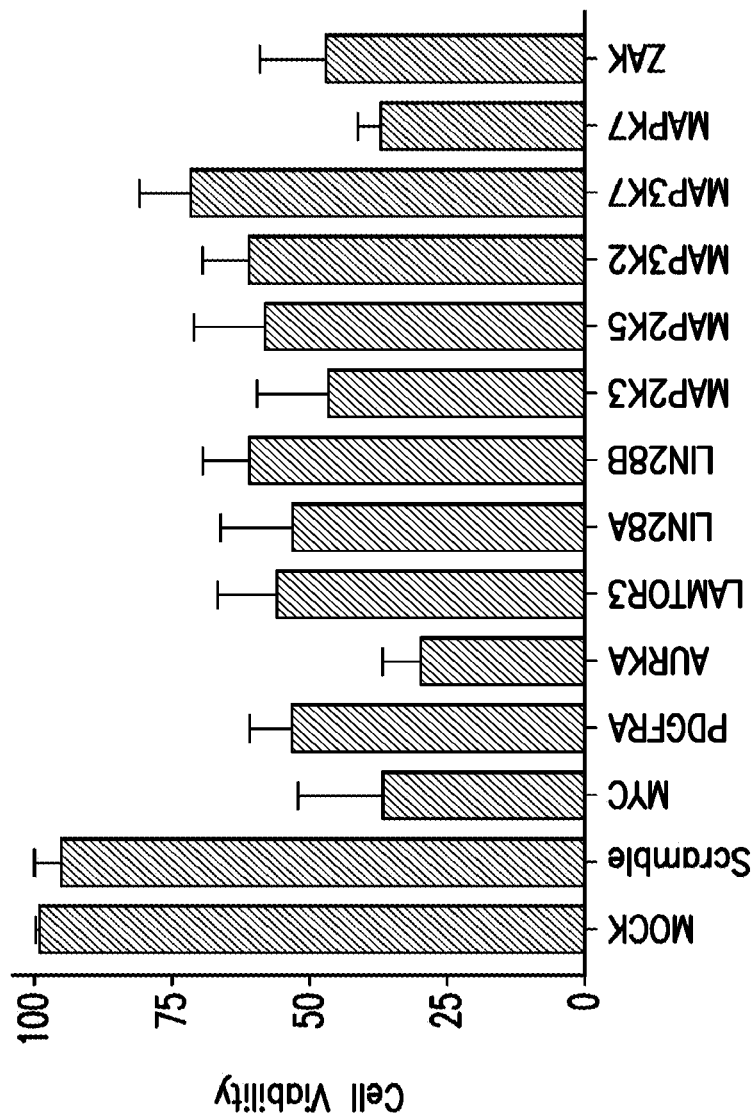

FIG. 20 provides the screening of top targets using siRNA and automated cell count of DIPG-007 cells.

Figure 21:
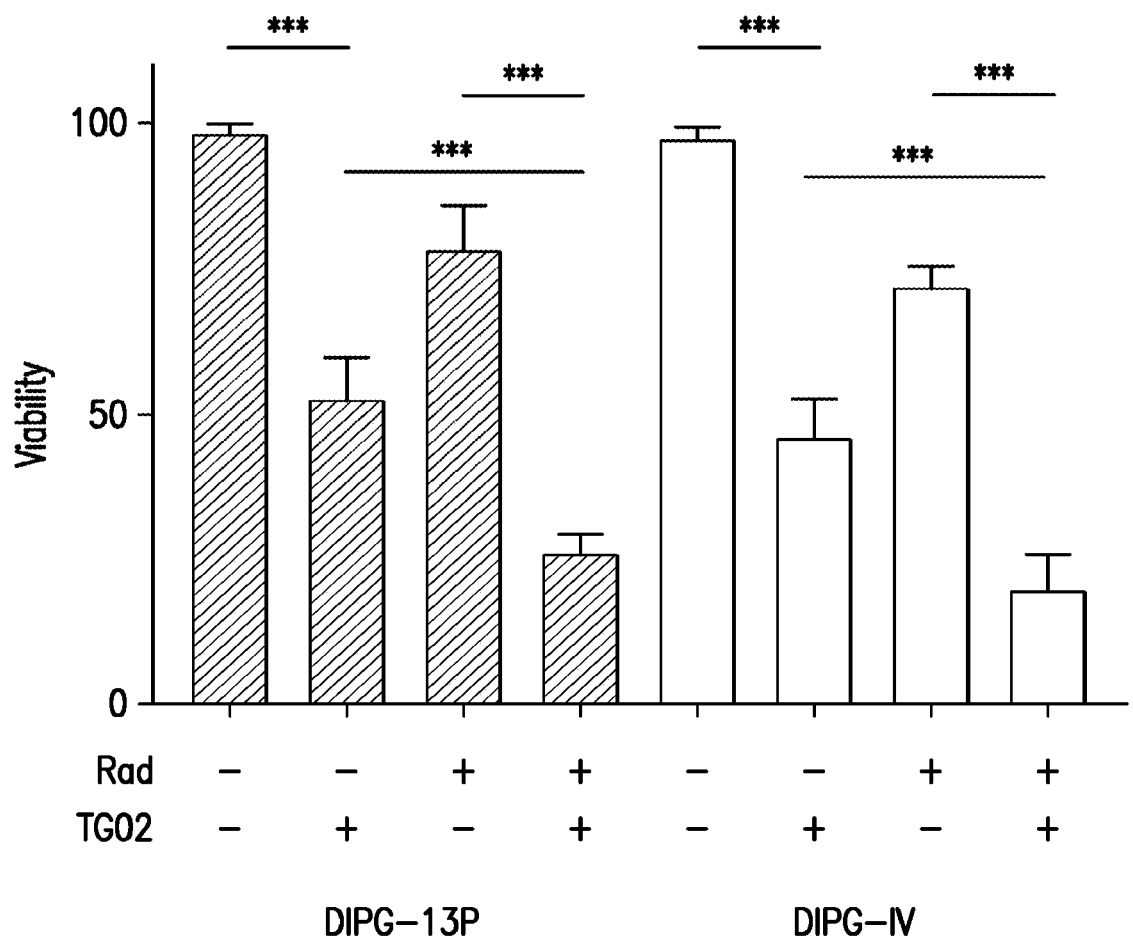

FIG. 21 provides cell line viability with TG02 and/or RT treatments.

Figure 22:
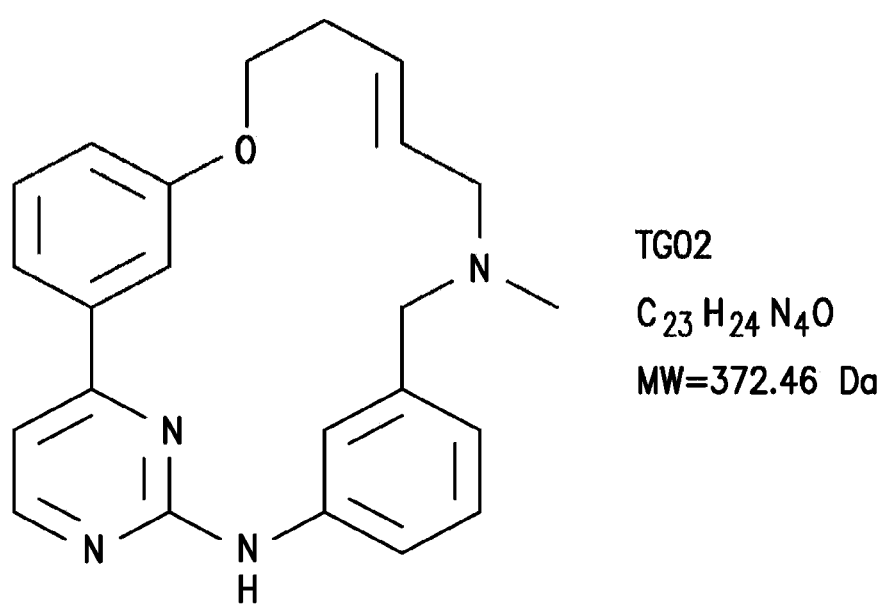

FIG. 22 provides a diagram depicting the molecular structure of TG02.

Figure 23:
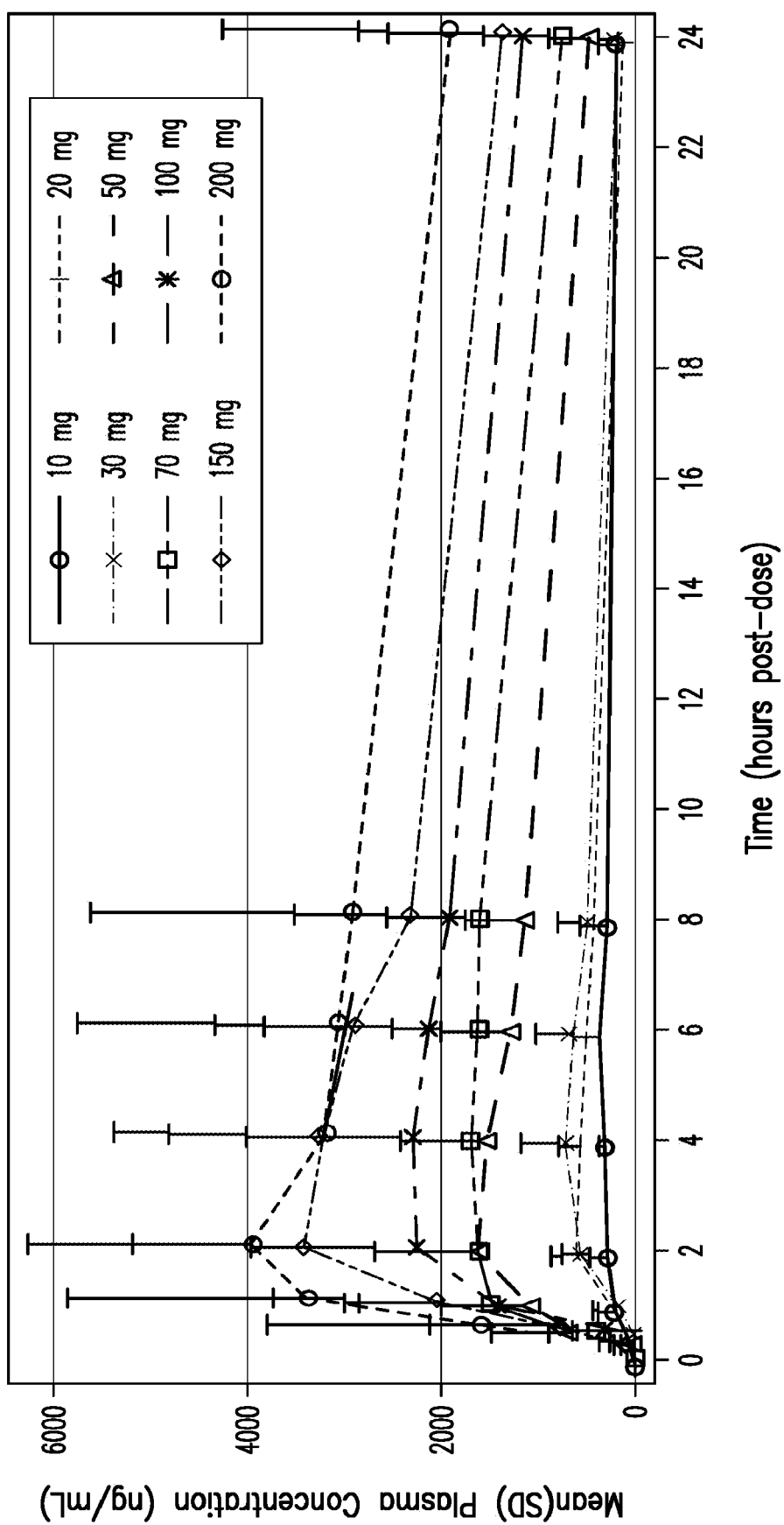

FIG. 23 provides the pharmacokinetics of TG02 after a single oral dose in adult with hematologic malignancies.

Figure 24:
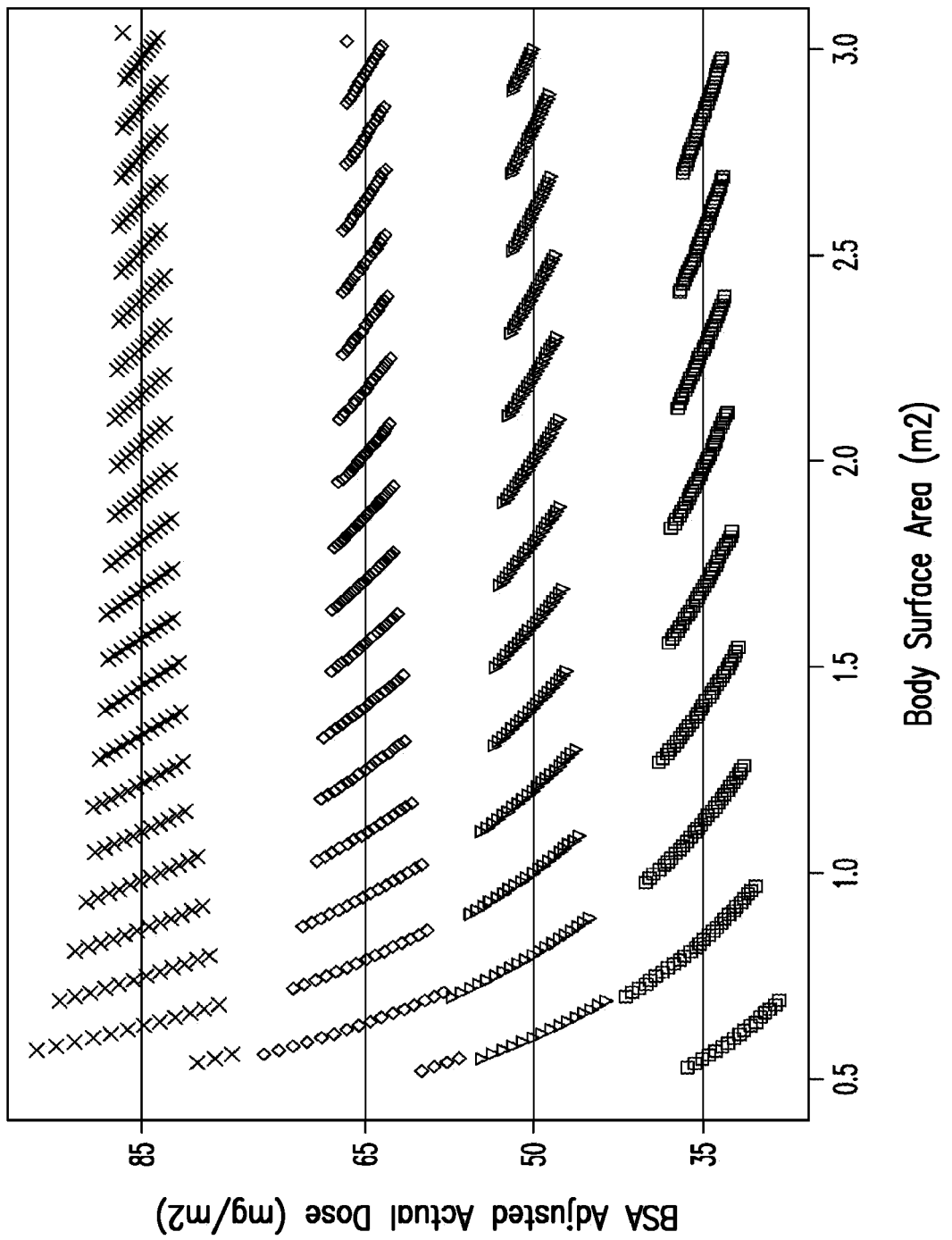

FIG. 24 provides the adjusted actual doses of TG02 based on the proposed dosage levels and patients' body surface areas.

Figure 25:
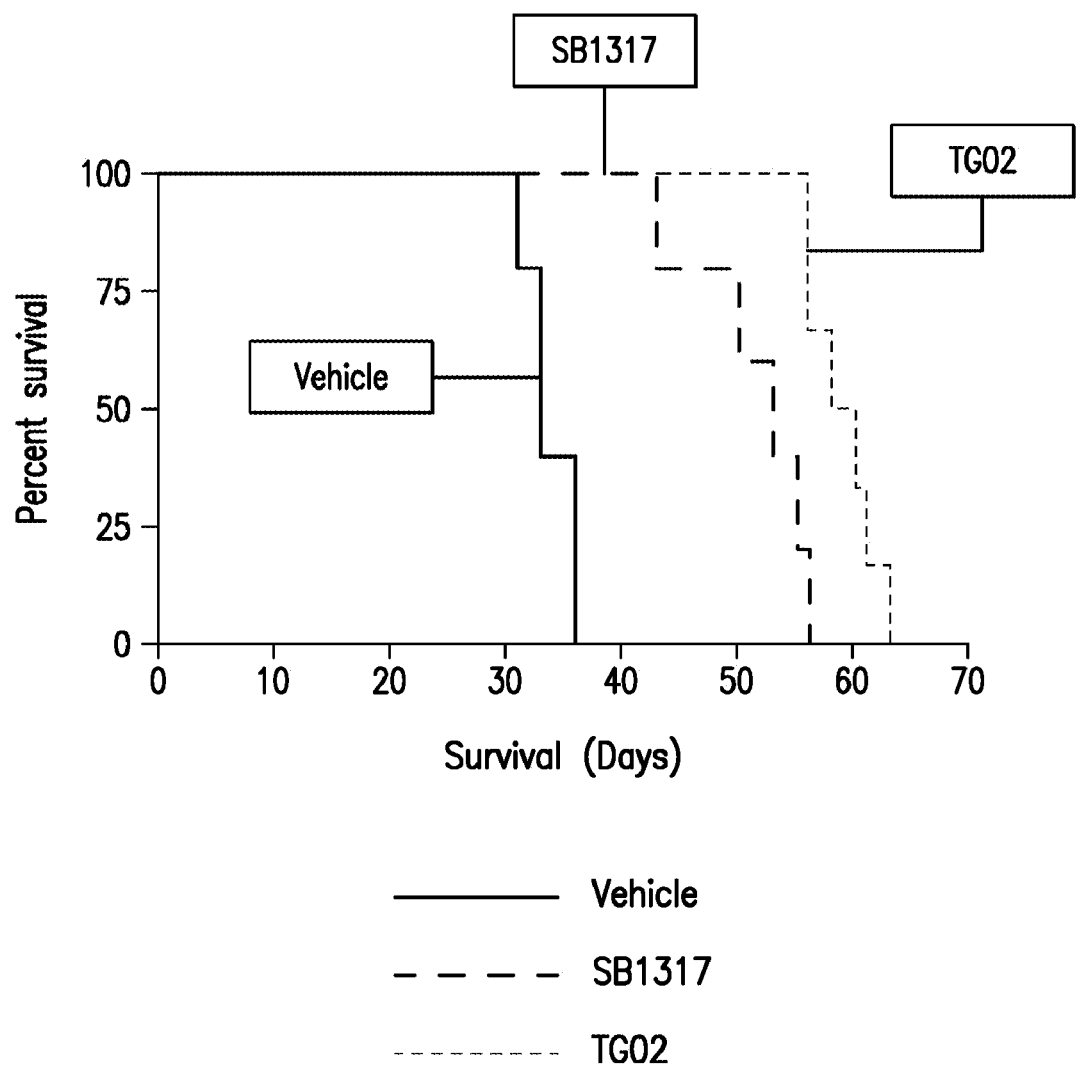

FIG. 25 provides a survival curve of SF8628 orthotopic xenograft mice treated with vehicles, TG02 purchased from commercial vendor, or TG02 obtained from Adastra Pharmaceuticals. p<0.05, vehicle vs SB1317; p<0.05, vehicle vs TG02; p<0.05, TG02 vs SB1317.

FIG. 26A provides quantification results of K167 staining. FIG. 26B provides exemplary images of H&E staining of K167. Arrows point to exemplary cells having positive staining of KI67. TG02 obtained from Adastra Pharmaceuticals significantly reduced KI67 expression. *, p<0.05.

Figure 27:
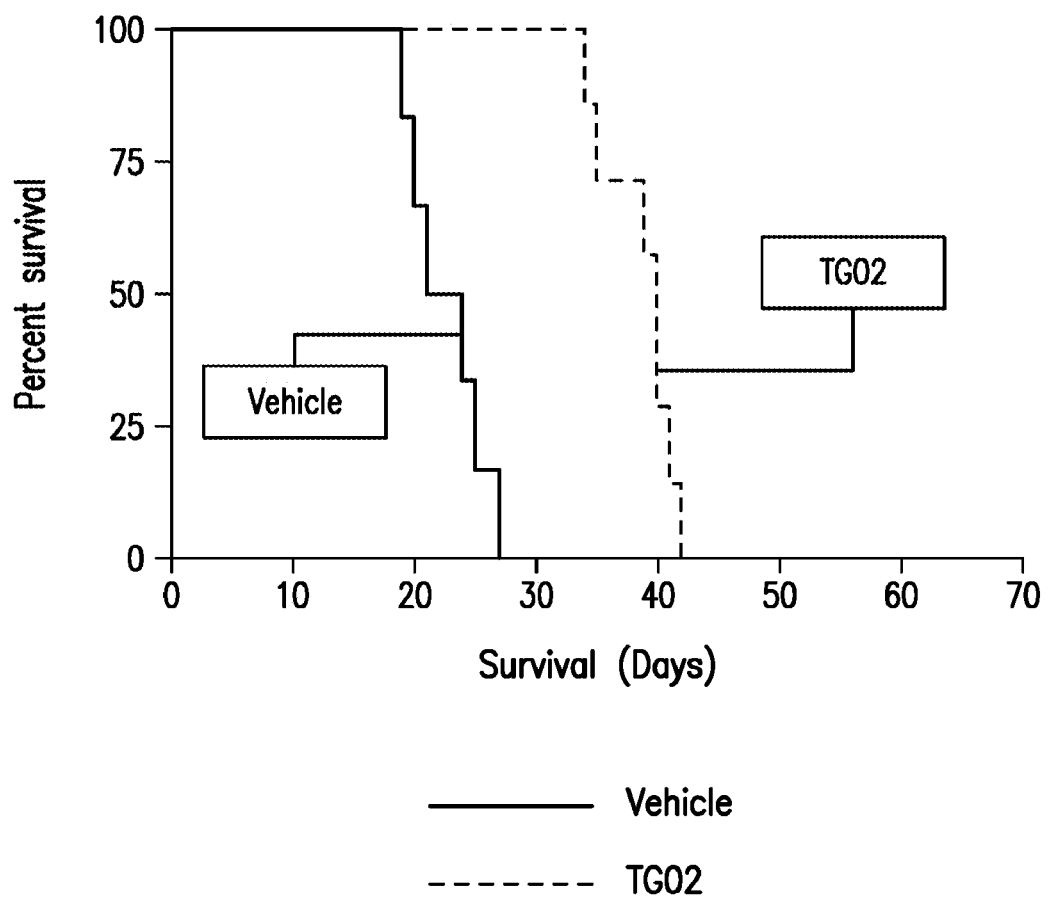

FIG. 27 provides a survival curve of DIPG13p xenograft mice treated with vehicles, or TG02 obtained from Adastra Pharmaceuticals. p<0.05, Logrank Survival Test.

Figures 28A, 28B:
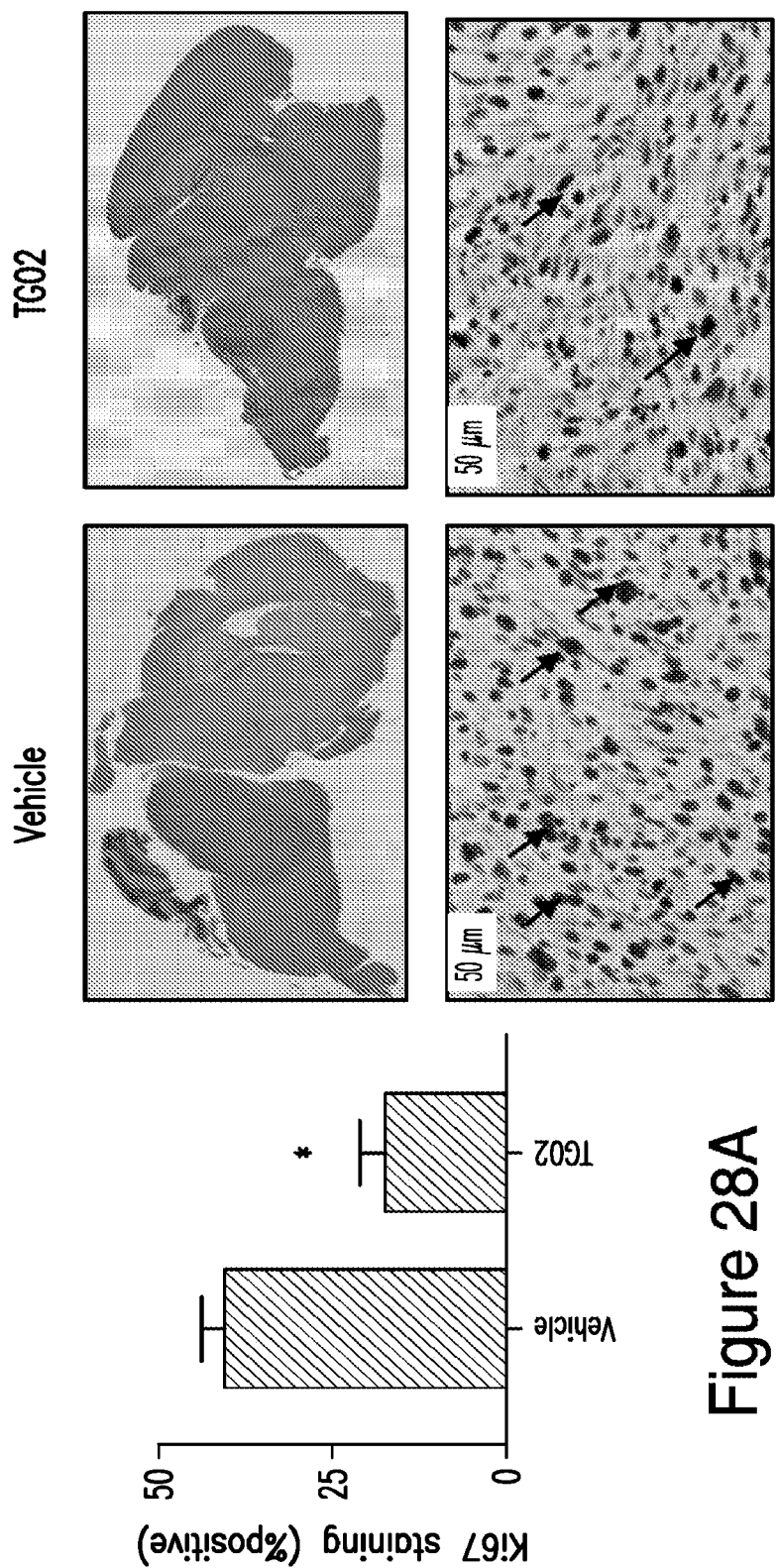

FIG. 28A provides quantification results of K167 staining. FIG. 28B provides exemplary images of H&E staining of K167. Arrows point to exemplary cells having positive staining of KI67. TG02 obtained from Adastra Pharmaceuticals significantly reduced K167 expression. *, p<0.05.

Figure 29:
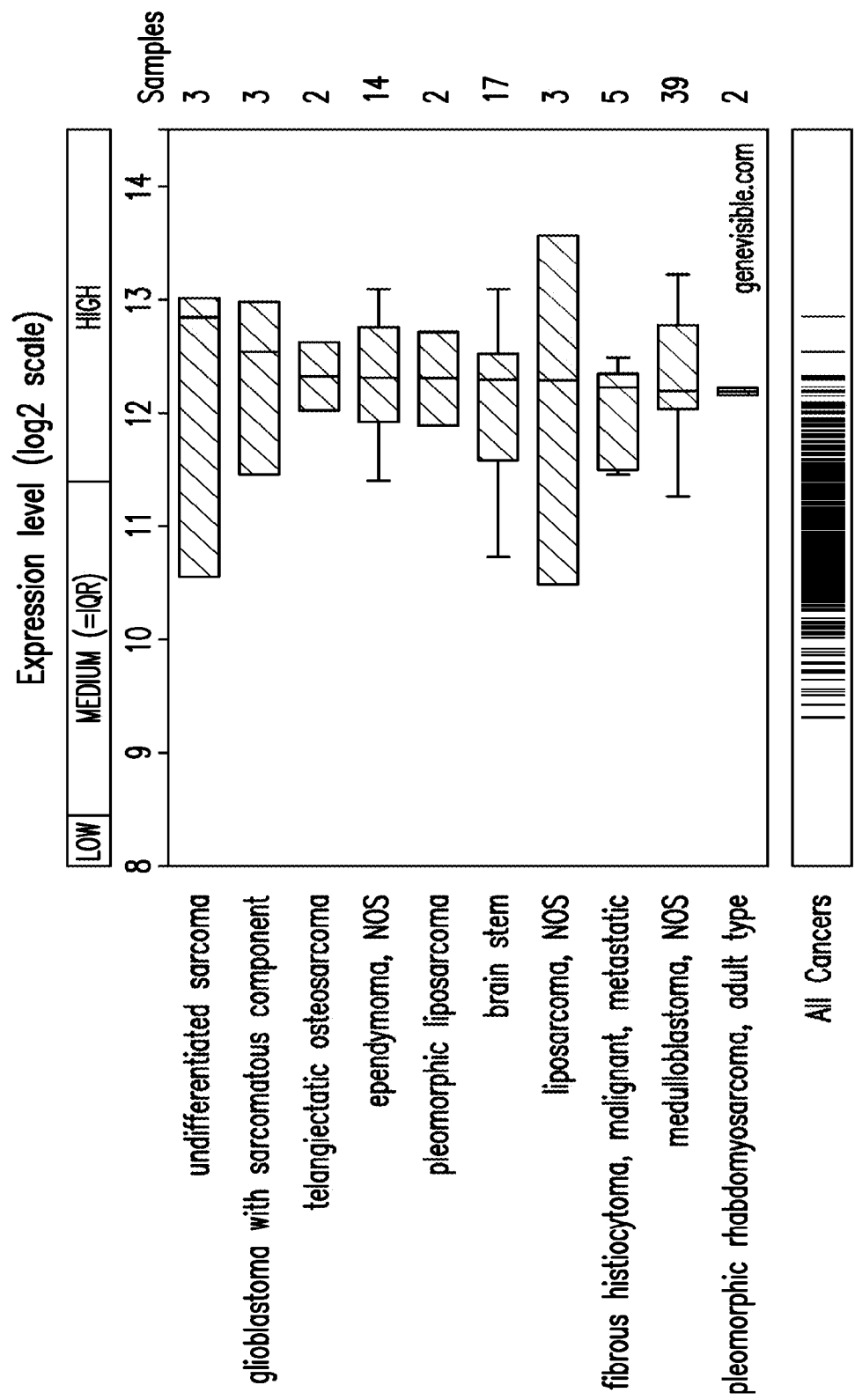

FIG. 29 provides expression levels of ERK5 in various cancer.

Figure 30A:
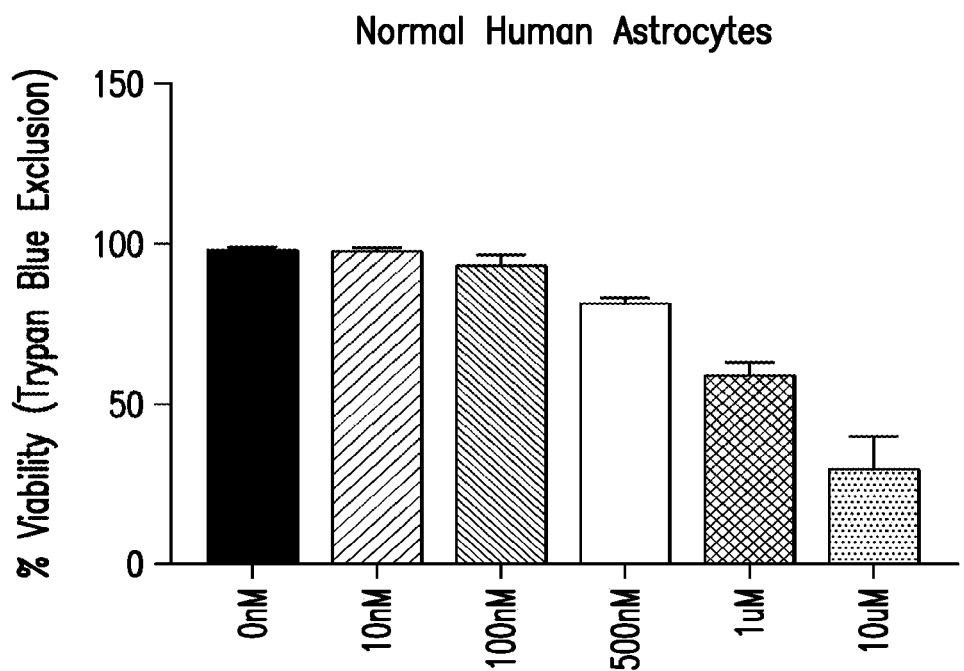
Figure 30B:
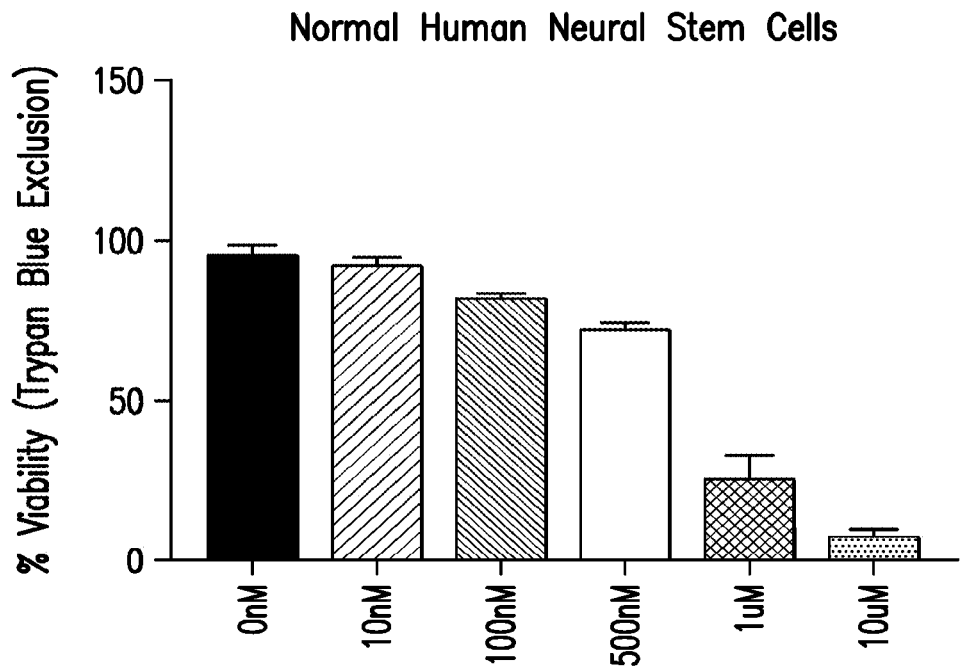

FIGS. 30A-30B provide viabilities of normal human astrocytes (30A) and normal human neural stem cells (30B) treated with various doses of TG02.

Figure 31:
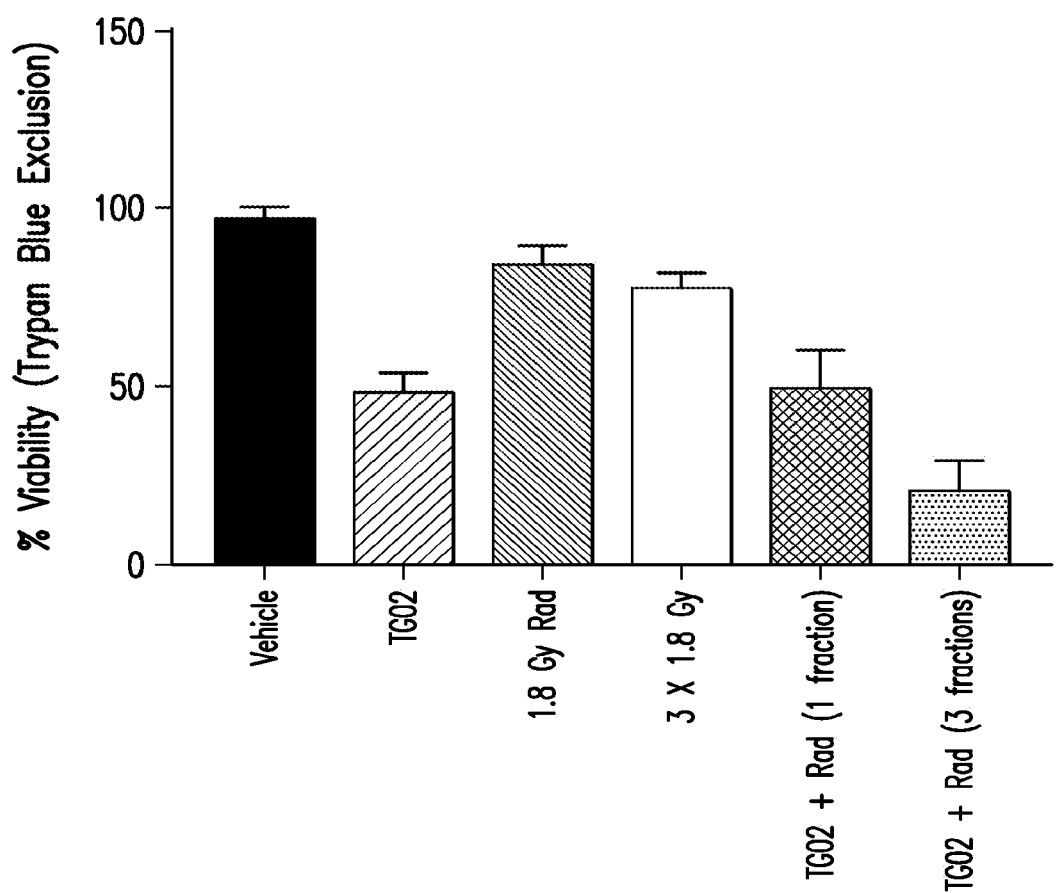

FIG. 31 provides viability of cells treated with TG02 and radiation.

FIG. 32 provides a table listing of 294 genes known to directly activate, inactivate, or cooperate with RAS pathway signaling that were used in targeted siRNA screen.

5. DETAILED DESCRIPTION

The present disclosure provides for uses of an TG02 for treating a glioma in a pediatric human subject. For example, but not by way of limitation, the glioma is a pediatric high-grade glioma (PHGG), e.g., a diffuse intrinsic pontine glioma (DIPG), and/or a H3.3-mutated glioma (e.g., a H3K27M-mutated high-grade glioma). Non-limiting embodiments of the disclosed subject matter are described by the present specification and Examples.

For purposes of clarity of disclosure and not by way of limitation, the detailed description is divided into the following subsections:

5.1 Definitions;
5.2 TG02;
5.3 Methods of treatment;
5.4 Pharmaceutical compositions; and
5.5 Kits.

5.1 Definitions

The terms used in this specification generally have their ordinary meanings in the art, within the context of the disclosed subject matter and in the specific context where each term is used. Certain terms are discussed below, or elsewhere in the specification, to provide additional guidance in describing the compositions and methods of the disclosed subject matter and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "inhibitor" refers to a compound or molecule (e.g., small molecule, peptide, peptidomimetic, natural compound, siRNA, anti-sense nucleic acid, aptamer, or antibody) that interferes with (e.g., reduces, prevents, decreases, suppresses, eliminates or blocks) the signaling function of a protein or pathway. An inhibitor can be any compound or molecule that changes any activity of a protein (signaling molecule, any molecule involved with the named signaling molecule or a named associated molecule), such as ERK5, or interferes with the interaction of a protein, e.g., ERK5, with signaling partners. Inhibitors also include molecules that indirectly regulate the biological activity of a named protein, e.g., ERK5, by intercepting upstream signaling molecules.

The terms "inhibiting," "eliminating," "decreasing," "reducing" or "preventing," or any variation of these terms, referred to herein, includes any measurable decrease or complete inhibition to achieve a desired result.

As used herein, the term "disease" refers to any condition or disorder that damages or interferes with the normal function of a cell, tissue, or organ.

A "therapeutically effective amount" of an agent, e.g., an ERK5 inhibitor, refers to an amount effective, at dosages and for periods of time necessary, to achieve the desired therapeutic or prophylactic result, e.g., treating a glioma in a pediatric subject. A therapeutically effective amount can be administered in one or more administrations.

A "subject," as referred to herein, may be a human or non-human subject, such as, but not limited to, a non-human primate, a dog, a cat, a horse, a rodent, a rabbit, etc.

An "adult human subject," as used herein, is a subject that has attained an age of at least 18 years or at least 21 years. A human subject that is not an adult is a pediatric human subject.

As used herein, "treatment" (and grammatical variations thereof such as "treat" or "treating") refers to clinical intervention in an attempt to alter the natural course of the individual being treated and can be performed either for prophylaxis or during the course of clinical pathology. Desirable effects of treatment include, but are not limited to, prolonging survival, preventing recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibodies of the presently disclosed subject matter are used to delay development of a disease or to slow the progression of a disease, e.g., pediatric gliomas, PPHG, DIPG, H3K27M-mutated high-grade gliomas, and H3K27M-mutated non-DIPG high-grade gliomas.

An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a patient diagnosed with cancer.

An "anti-cancer agent," as used herein, can be any molecule, compound, chemical or composition that has an anti-cancer effect. Anti-cancer agents include, but are not limited to, chemotherapeutic agents, radiotherapeutic agents, cytokines, anti-angiogenic agents, apoptosis-inducing agents, anti-cancer antibodies and/or agents which promote the activity of the immune system including, but not limited to, cytokines such as but not limited to interleukin 2, interferon, anti-CTLA4 antibody, anti-PD-1 antibody and/or anti-PD-L1 antibody. In certain embodiments, an anti-cancer agent can be a radiotherapeutic agent. In certain embodiments, an anti-cancer agent can be a chemotherapeutic agent, e.g., temozolomide. Other non-limiting exemplary anti-cancer agents that can be used with the presently disclosed subject matter include tumor-antigen based vaccines, and chimeric antigen receptor T-cells.

As described herein, any concentration range, percentage range, ratio range or integer range is to be understood to include the value of any integer within the recited range and, when appropriate, fractions thereof (such as one tenth and one hundredth of an integer), unless otherwise indicated.

5.2 TG02

The present disclosure provides the use of TG02 to treat a glioma in a pediatric subject (e.g., a pediatric human subject) as disclosed herein. In certain embodiments, the glioma is a PHGG or a DIPG. In certain embodiments, the glioma is a H3.3-mutated glioma, e.g., a H3K27M-mutated high-grade glioma, and/or a H3K27M-mutated non-DIPG high-grade glioma.

Extracellular signal-regulated kinase 5, also known as mitogen-activated protein kinase 7 (MAPK7), BMK1, ERK4, and PRKM7, is denoted as ERK5 herein. ERK5 is encoded by the ERK5 gene. In certain embodiments, ERK5 is a human ERK5 protein. In certain embodiments, ERK5 is a mouse ERK5 protein or a rat ERK5 protein.

In certain embodiments, ERK5 can be a human ERK5 protein having an amino acid sequence as set forth in GenBank Accession No. AAA81381.1 or an amino acid sequence at least about 95 percent or at least about 98 percent homologous thereto.

In certain embodiments, ERK5 can be a mouse ERK5 protein having an amino acid sequence as set forth in GenBank Accession No. BAA82039.1 or an amino acid sequence at least about 95 percent or at least about 98 percent homologous thereto.

In certain embodiments, ERK5 can be a rat ERK5 protein having an amino acid sequence as set forth in GenBank Accession No. NP_001178476.1 or an amino acid sequence at least about 95 percent or at least about 98 percent homologous thereto.

In certain embodiments, a nucleic acid encoding a human ERK5 protein of the present disclosed subject matter can include a nucleic acid sequence as set forth in GenBank Accession No. U25278.1 or a nucleic acid sequence at least about 95 percent or at least about 98 percent homologous thereto.

In certain embodiments, TG02 can be in a crystalline or amorphous form as a free base or as a pharmaceutically acceptable salt or solvate.

In certain embodiments, free base forms of TG02, solvate forms of TG02, pharmaceutically acceptable salt forms of TG02, derivatives of TG02, and combinations thereof can be used to treat a glioma in a pediatric subject (e.g., a pediatric human subject). Non-limiting examples of pharmaceutically acceptable salt forms include hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemi sulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, undecanoate, lactate, citrate, tartrate, gluconate, ethanedi sulfonate, benzene sulfonate, and p-toluenesulfonate salts.

In certain embodiments, TG02 is a dual CDK5 and ERK5 inhibitor. In certain embodiments, the dual CDK5 and ERK5 inhibitor is selected from the group consisting of TG02, pharmaceutically acceptable salt forms thereof, derivatives thereof, and mixtures thereof. In certain embodiments, the dual CDK5 and ERK5 inhibitor is a salt form of TG02. In certain embodiments, the ERK5 inhibitor is a citrate salt of TG02 or a hydrochloride salt of TG02. TG02 is disclosed in U.S. Pat. No. 8,143,255, which is incorporated by reference herein in its entirety. "TG02" refers to a molecule with a CAS number of 937270-47-8, a molecular formula of $C_{23}H_{24}N_4O$, and a chemical name of (16E)-14-methyl-20-oxa-5,7,14,27-tetraazatetracyclo[19.3.1.12,6.18,12]heptacosa-1(25),2(27),3,5,8(26),9,11,16,21,23-decaene, for example, see formula 5:

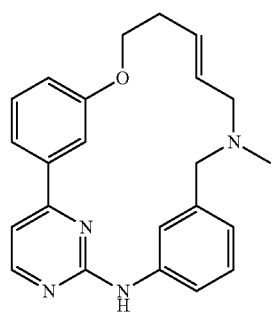

(5)

TG02 (originally designated as SB1317) is a pyrimidine-based multi-kinase inhibitor that inhibits CDK 1, 2, 7, and 9, JAK2, FLT3, and ERK5. TG02 was tested in in vitro assays against 63 kinases (Table 1). While the IC50 against CDK9 was 3 nM, the IC50 for CDK7 and ERK5 were 37 nM and 43 nM, respectively (Goh et al., Leukemia 26:236-243, 2012).

TABLE 1

Kinase activity of TG02

| Kinase | iC50 (nM) | Source |
|---|---|---|
| CDK9 | 3 | Invitrogen |
| CDK5 | 4 | Invitrogen |
| CDK2 | 5 | Invitrogen |
| CDK3 | 8 | Millipore |
| CDK1 | 9 | Invitrogen |
| Lck | 11 | Millipore |
| TYK2 | 14 | Invitrogen |
| Fyn | 15 | Millipore |
| JAK2 | 19 | Invitrogen |
| FLT3 | 19 | Invitrogen |
| FLT3$^{D835Y}$ | 21 | Millipore |
| Fms | 27 | Millipore |
| TYRO3 | 36 | Invitrogen |
| CDK7 | 37 | Millipore |
| ERK5 | 43 | CEREP |
| p386 | 56 | Invitrogen |
| JAK1 | 59 | Invitrogen |

Other kinases tested (Abl, ALK, ASK1, Aurora A, Aurora B, CaMKVI, CDK4, CDK6. Chk1, CK1α1, CK18, CK16, c-Raf, DYRKIB, EGFR, FAK, GSK3α, IGF-1R, IKK-β, InsR, IRAK4, JAK3, JNK1, KDR, Kit, MAPKAP-K2, MEK1, MKK6, Nek2, p38α, PAK2, PAK3, PDGFRβ, PDK1, Pim-3, PKA, PKBα, PKCε, PLK1, PLK3, PRAK, Src, TAK1, TLK2, TTK and ZAP-70) gave less than 50% inhibition at 100 nm. Values were determined from a 10-point titration in duplicates, done once.

5.3 Methods of Treatment

The present disclosure provides methods for treating a glioma in a pediatric subject (e.g., a pediatric human subject). In certain embodiments, the method includes administering to the subject a therapeutically effective amount of TG02, free base forms thereof, solvate forms thereof, pharmaceutically acceptable salt forms thereof, derivatives thereof, mixtures thereof, and combinations thereof.

Gliomas are divided into four grades, depending on the tumor cells' appearance under a microscope; the higher a tumor's grade number, the more severe it is. Grades 1 and 2 are considered low-grade gliomas and account for about two-thirds of all pediatric tumors. Grades 3 and 4 are considered high-grade gliomas.

In certain embodiments, the glioma is a pediatric high-grade glioma (PHGG). In certain embodiments, the glioma is a diffuse intrinsic pontine glioma (DIPG). DIPG is a particularly aggressive type of PHGG that originates primarily in the midline and pons. In certain embodiments, the glioma is a pediatric glioblastoma (GBM).

In certain embodiments, the glioma is a H3-mutant glioma. In certain embodiments, the glioma is a H3.1-mutant glioma, where the glioma has a mutation in the gene encoding histone H3.1. In certain embodiments, the glioma is a H3.3-mutant glioma, where the glioma has a mutation in the gene encoding histone H3.3. In certain embodiments, the H3.3 mutation is a H3K27M mutation or a H3G34R mutation. In certain embodiments, the glioma is a H3K27M-mutant glioma. In certain embodiments, the glioma is a H3G34R-mutant glioma. In certain embodiments, the H3.3-mutant glioma is a H3.3-mutant PHGG glioma. In certain embodiments, the H3.3-mutant glioma is a H3.3-mutant non-PHGG glioma. In certain embodiments, the H3.3-mutant glioma is a H3.3-mutant DIPG glioma. In certain embodiments, the H3.3-mutant glioma is a H3.3-mutant non-DIPG glioma. In certain embodiments, the H3K27M-mutant glioma is a H3K27M-mutant PHGG glioma. In certain embodiments, the H3K27M-mutant glioma is a H3K27M-mutant non-PHGG glioma. In certain embodiments, the H3K27M-mutant glioma is a H3K27M-mutant DIPG glioma. In certain embodiments, the H3K27M-mutant glioma is a H3K27M-mutant non-DIPG glioma. In certain embodiments, the H3G34R-mutant glioma is a H3G34R-mutant PHGG glioma. In certain embodiments, the H3G34R-mutant glioma is a H3G34R-mutant non-PHGG glioma. In certain embodiments, the H3G34R-mutant glioma is a H3G34R-mutant DIPG glioma. In certain embodiments, the H3G34R-mutant glioma is a H3G34R-mutant non-DIPG glioma.

In certain embodiments, TG02 administered to the pediatric subject prolong the survival of the pediatric subject relative to a control pediatric subject or control pediatric subject population not receiving said TG02 treatment. In certain embodiments, the period of survival is extended at least about 10 percent, at least about 25 percent, at least about 30 percent, at least about 50 percent, at least about 60 percent or at least about 70 percent. In certain embodiments, the period of survival is extended by about 1 month, about 2 months, about 4 months, about 6 months, about 8 months, about 10 months, about 12 months, about 14 months, about 18 months, about 20 months, about 2 years, about 3 years, about 5 years or more. In certain embodiments, TG02 administered to the pediatric subject prolong the remission of the glioma in the pediatric subject relative to a control pediatric subject or control pediatric subject population not receiving said TG02 treatment.

In certain embodiments, the methods disclosed herein include administering to a pediatric subject having a glioma a therapeutically effective amount of TG02 (or a pharmaceutical composition thereof) to produce an anti-cancer effect in the pediatric subject. In certain embodiments, the anti-cancer effect is selected from the group consisting of a reduction in aggregate cancer cell mass, a reduction in cancer cell growth rate, a reduction in cancer cell proliferation, a reduction in tumor mass, a reduction in tumor volume, a reduction in cancer cell proliferation, a reduction in cancer growth rate, a reduction in cancer metastasis, and combinations thereof. In certain embodiments, the anti-cancer effect is a reduction in the number of cancer cells. In certain embodiments, the anti-cancer effect is a reduction in tumor size and/or a reduction in the rate of tumor growth. In certain embodiments, the anti-cancer effect is a reduction in the aggregate cancer cell burden. In certain embodiments, the anti-cancer effect is a reduction in the rate of cell proliferation and/or an increase in the rate of cell death. In certain embodiments, the anti-cancer effect is a prolongation of survival of the pediatric subject. In certain embodiments, the anti-cancer effect is a prolongation in the interval until relapse relative to a control pediatric subject or control pediatric subject population not receiving said TG02 treatment.

5.3.1 Dosing Regimen of TG02

In certain embodiments, TG02 is administered to the pediatric subject in a single dose or divided doses in an amount of between about 20 mg/m$^2$ and 200 mg/m$^2$ body surface area (BSA) of the pediatric subject per day. In certain embodiments, TG02 is administered to the pediatric subject in a single dose or divided doses in an amount of between about 20 mg/m$^2$ and about 40 mg/m$^2$, between about 30 mg/m$^2$ and about 40 mg/m$^2$, between about 60 mg/m$^2$ and about 70 mg/m$^2$, between about 45 mg/m$^2$ and about 55 mg/m$^2$, between about 55 mg/m$^2$ and about 75 mg/m$^2$, between about 60 mg/m$^2$ and about 70 mg/m$^2$, or between about 75 mg/m$^2$ and about 95 mg/m$^2$ BSA of the pediatric subject per day. In certain embodiments, TG02 is administered to the pediatric subject in a single dose or divided doses in an amount of up to about 20 mg/m$^2$, up to about 30 mg/m$^2$, up to about 40 mg/m$^2$, up to about 50 mg/m$^2$, up to about 60 mg/m$^2$, up to about 70 mg/m$^2$, up to about 80 mg/m$^2$, up to about 90 mg/m$^2$, up to about 100 mg/m$^2$, up to about 110 mg/m$^2$, up to about 120 mg/m$^2$, up to about 130 mg/m$^2$, up to about 140 mg/m$^2$ up to about 150 mg/m$^2$, up to about 160 mg/m$^2$, up to about 170 mg/m$^2$, up to about 180 mg/m$^2$, up to about 190 mg/m$^2$, or up to about 200 mg/m$^2$ BSA of the pediatric subject per day. In certain embodiments, TG02 is administered to the pediatric subject in a single dose or divided doses in an amount of at least about 20 mg/m$^2$, at least about 30 mg/m$^2$, at least about 40 mg/m$^2$, at least about 50 mg/m$^2$, at least about 60 mg/m$^2$, at least about 70 mg/m$^2$, at least about 80 mg/m$^2$, at least about 90 mg/m$^2$, at least about 100 mg/m$^2$, at least about 110 mg/m$^2$, at least about 120 mg/m$^2$, at least about 130 mg/m$^2$, at least about 140 mg/m$^2$, at least about 150 mg/m$^2$, at least about 160 mg/m$^2$, at least about 170 mg/m$^2$, at least about 180 mg/m$^2$, at least about 190 mg/m$^2$, or at least about 200 mg/m$^2$ BSA of the pediatric subject per day. In certain embodiments, TG02 is administered to the pediatric subject in a single dose or divided doses in an amount of about 20 mg/m$^2$, about 30 mg/m$^2$, about 35 mg/m$^2$, about 45 mg/m$^2$, about 50 mg/m$^2$, about 55 mg/m$^2$, about 65 mg/m$^2$, about 75 mg/m$^2$, about 85 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, or about 200 mg/m$^2$ BSA of the pediatric subject per day. In certain embodiments, TG02 is administered to the pediatric subject in a single dose in an amount of about 35 mg/m$^2$ BSA of the pediatric subject per day. In certain embodiments, TG02 is administered to the pediatric subject in a single dose in an amount of about 50 mg/m$^2$ BSA of the pediatric subject per day. In certain embodiments, TG02 is administered to the pediatric subject in a single dose in an amount of about 65 mg/m$^2$ BSA of the pediatric subject per day. In certain embodiments, TG02 is administered to the pediatric subject in a single dose in an amount of about 85 mg/m$^2$ BSA of the pediatric subject per day.

In certain embodiments, the dosage administered varies depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. In certain embodiments, the dosage administered depends on the BSA of the pediatric subject. In certain embodiments, TG02 is administered to the pediatric subject in a single dose or divided doses in an amount of between about 20 mg/m$^2$ and 60 mg/m$^2$ BSA of the pediatric subject per day, where the pediatric subject has a BSA of at least about 55 m$^2$. In certain embodiments, TG02 is administered to the pediatric subject in a single dose or divided doses in an amount of between about 60 mg/m$^2$ and 100 mg/m$^2$ BSA of the pediatric subject per day, where the pediatric subject has a BSA of at least about 50 m$^2$. In certain embodiments, TG02 is administered to the pediatric subject in a single dose in an amount of about 35 mg/m$^2$ BSA of the pediatric subject per day, where the pediatric subject has a BSA of at least about 55 m$^2$. In certain embodiments, TG02 is administered to the pediatric subject in a single dose in an amount of about 50 mg/m$^2$ BSA of the pediatric subject per day, where the pediatric subject has a BSA of at least about 55 m$^2$. In certain embodiments, TG02 is administered to the pediatric subject in a single dose in an amount of about 65 mg/m$^2$ BSA of the pediatric subject per day, where the pediatric subject has a BSA of at least about 50 m$^2$. In certain embodiments, TG02 is administered to the pediatric subject in a single dose in an amount of about 85 mg/m$^2$ BSA of the pediatric subject per day, where the pediatric subject has a BSA of at least about 50 m$^2$.

In certain embodiments, TG02 is administered to the pediatric subject in a single dose or divided doses in an amount of between about 20 mg and 100 mg per day. In certain embodiments, TG02 is administered to the pediatric subject in a single dose or divided doses in an amount of between about 20 mg and about 30 mg, between about 30 mg and about 40 mg, between about 40 mg and about 50 mg, between about 50 mg and about 60 mg, between about 60 mg and about 70 mg, between about 70 mg and about 80 mg, between about 80 mg and about 90 mg, or between about 90 mg and about 100 mg per day. In certain embodiments, TG02 is administered to the pediatric subject in a single dose or divided doses in an amount of at least about 20 mg, at least about 30 mg, at least about 40 mg, at least about 50 mg, at least about 60 mg, at least about 70 mg, at least about 80 mg, at least about 90 mg, at least about 100 mg, up to about 20 mg, up to about 30 mg, up to about 40 mg, up to about 50 mg, up to about 60 mg, up to about 70 mg, up to about 80 mg, up to about 90 mg, or up to about 100 mg per day. In certain embodiments, TG02 is administered to the pediatric subject in a single dose or divided doses in an amount of about 20 mg, about 30 mg, about 40 mg, about 50 mg, about 60 mg, about 70 mg, about 80 mg, about 90 mg, or about 100 mg per day.

In certain embodiments, TG02 is administered to the pediatric subject in a single dose or divided doses in an amount of between about 0.4 mg/kg and about 6.6 mg/kg per day. In certain embodiments, TG02 is administered to the pediatric subject in a single dose or divided doses in an amount of at least about 0.4 mg/kg, at least about 0.6 mg/kg, at least about 1.5 mg/kg, at least about 2.5 mg/kg, at least about 3.5 mg/kg, at least about 4.5 mg/kg, at least about 5.5 mg/kg, at least about 6.6 mg/kg, up to about 0.4 mg/kg, up to about 0.6 mg/kg, up to about 1.5 mg/kg, up to about 2.5 mg/kg, up to about 3.5 mg/kg, up to about 4.5 mg/kg, up to about 5.5 mg/kg, or up to about 6.6 mg/kg per day. In certain embodiments, TG02 is administered to the pediatric subject in a single dose or divided doses in an amount of between about 0.4 mg/kg and about 1.0 mg/kg, between about 1.0 mg/kg and about 2.0 mg/kg, between about 2.0 mg/kg and about 3.0 mg/kg, between about 3.0 mg/kg and about 4.0 mg/kg, between about 4.0 mg/kg and about 5.0 mg/kg, between about 5.0 mg/kg and about 6.0 mg/kg, or between about 6.0 mg/kg and about 6.6 mg/kg per day. In certain embodiments, TG02 is administered to the pediatric subject in a single dose or divided doses in an amount of about 0.4 mg/kg, about 0.6 mg/kg, about 1.5 mg/kg, about 2.5 mg/kg, about 3.5 mg/kg, about 4.5 mg/kg, about 5.5 mg/kg, or about 6.6 mg/kg per day.

In certain embodiments, TG02 is administered to the pediatric subject in a single dose or divided doses in an amount of between about 1.3 mg/kg and about 6.6 mg/kg, wherein the pediatric subject has a body weight of about 15 kg, or at most about 15 kg. In certain embodiments, TG02 is administered to the pediatric subject in a single dose or divided doses in an amount of between about 1.3 mg/kg and about 6.6 mg/kg, wherein the pediatric subject has a body weight of about 15 kg. In certain embodiments, TG02 is administered to the pediatric subject in a single dose or divided doses in an amount of at least about 1.3 mg/kg, at least about 2.0 mg/kg, at least about 3.0 mg/kg, at least about 4.0 mg/kg, at least about 5.0 mg/kg, at least about 6.0 mg/kg, at least about 6.6 mg/kg, up to about 1.3 mg/kg, up to about 2.0 mg/kg, up to about 3.0 mg/kg, up to about 4.0 mg/kg, up to about 5.0 mg/kg, up to about 6.0 mg/kg, or up to about 6.6 mg/kg, wherein the pediatric subject has a body weight of about 15 kg, or at most about 15 kg. In certain embodiments, TG02 is administered to the pediatric subject in a single dose or divided doses in an amount of between about 1.3 mg/kg and about 2.0 mg/kg, between about 2.0 mg/kg and about 3.0 mg/kg, between about 3.0 mg/kg and about 4.0 mg/kg, between about 4.0 mg/kg and about 5.0 mg/kg, or between about 5.0 mg/kg and about 6.0 mg/kg, wherein the pediatric subject has a body weight of about 15 kg, or at most about 15 kg. In certain embodiments, TG02 is administered to the pediatric subject in a single dose or divided doses in an amount of about 1.3 mg/kg, about 2.0 mg/kg, about 3.0 mg/kg, about 4.0 mg/kg, about 5.0 mg/kg, about 6.0 mg/kg, or about 6.6 mg/kg, wherein the pediatric subject has a body weight of about 15 kg, or up to about 15 kg.

In certain embodiments, TG02 is administered to the pediatric subject in a single dose or divided doses in an amount of between about 0.4 mg/kg and about 6.6 mg/kg, wherein the pediatric subject has a body weight of about 50 kg, at least about 50 kg, or between about 15 kg and about 50 kg. In certain embodiments, TG02 is administered to the pediatric subject in a single dose or divided doses in an amount of between about 0.4 mg/kg and about 6.6 mg/kg, wherein the pediatric subject has a body weight of about 50 kg. In certain embodiments, TG02 is administered to the pediatric subject in a single dose or divided doses in an amount of at least about 0.4 mg/kg, at least about 0.6 mg/kg, at least about 1.5 mg/kg, at least about 2.5 mg/kg, at least about 3.5 mg/kg, at least about 4.5 mg/kg, at least about 5.5 mg/kg, at least about 6.6 mg/kg, up to about 0.4 mg/kg, up to about 0.6 mg/kg, up to about 1.5 mg/kg, up to about 2.5 mg/kg, up to about 3.5 mg/kg, up to about 4.5 mg/kg, up to about 5.5 mg/kg, or up to about 6.6 mg/kg per day, wherein the pediatric subject has a body weight of about 50 kg, at least about 50 kg, or between about 15 kg and about 50 kg. In certain embodiments, TG02 is administered to the pediatric subject in a single dose or divided doses in an amount of between about 0.4 mg/kg and about 1.0 mg/kg, between about 1.0 mg/kg and about 2.0 mg/kg, between about 2.0 mg/kg and about 3.0 mg/kg, between about 3.0 mg/kg and about 4.0 mg/kg, between about 4.0 mg/kg and about 5.0 mg/kg, between about 5.0 mg/kg and about 6.0 mg/kg, or between about 6.0 mg/kg and about 6.6 mg/kg per day, wherein the pediatric subject has a body weight of about 50 kg, at least about 50 kg, or between about 15 kg and about 50 kg. In certain embodiments, TG02 is administered to the pediatric subject in a single dose or divided doses in an amount of about 0.4 mg/kg, about 0.6 mg/kg, about 1.5 mg/kg, about 2.5 mg/kg, about 3.5 mg/kg, about 4.5 mg/kg, about 5.5 mg/kg, or about 6.6 mg/kg per day, wherein the pediatric subject has a body weight of about 50 kg, at least about 50 kg, or between about 15 kg and about 50 kg.

In certain embodiments, TG02 is administered to the pediatric subject in a single dose or divided doses per day, where the single dose or each divided dose is considered one unit dose. In certain embodiments, a one unit dose of TG02 includes between about 0.01 mg and about 1000 mg, e.g., between about 10 mg to about 500 mg, or between about 20 and about 100 mg of TG02. In certain embodiments, a one unit dose of TG02 includes about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg of TG02.

In certain embodiments, TG02 is administered to the pediatric subject in a single dose or divided doses per day of one day, two days, three days, four days, five days, six days, or seven days per week. In certain embodiments, TG02 is administered to the pediatric subject in a single dose per day of two days per week.

In certain embodiments, the duration of the TG02 treatment is between about one week to about two years. In certain embodiments, the duration of the TG02 treatment is at least about 1 week, at least about 2 weeks, at least about 3 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, or at least about 24 months. In certain embodiments, the duration of the TG02 treatment is up to about 1 week, up to about 2 weeks, up to about 3 weeks, up to about 1 month, up to about 2 months, up to about 3 months, up to about 4 months, up to about 5 months, up to about 6 months, up to about 7 months, up to about 8 months, up to about 9 months, up to about 10 months, up to about 11 months, up to about 12 months, up to about 13 months, up to about 14 months, up to about 15 months, up to about 16 months, up to about 17 months, up to about 18 months, up to about 19 months, up to about 20 months, up to about 21 months, up to about 22 months, up to about 23 months, or up to about 24 months. In certain embodiments, the duration of the TG02 treatment is up to about 24 months or 2 years.

In certain embodiments, TG02 is cyclically administered to a pediatric subject. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment. In certain embodiments, the treatment stops after one cycle because the subject is intolerable to the adverse effects and toxicities associated with TG02.

In certain embodiments, the number of cycles is from about one to about twenty-four cycles. In certain embodiments, the number of cycles is more than twenty-four cycles. In certain embodiments, the number of cycles is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24. In certain embodiments, the duration of a cycle is from about 21 to about 30 days. In certain embodiments, the duration of a cycle is about 21, about 22, about 23, about 24, about 25, about 26, about 27, about 28, about 29, or about 30 days. In certain embodiments, the duration of a cycle is about 27 days, about 28 days, about 29, or about 30 days. In certain embodiments, the number of cycles is about twenty-four cycles.

In certain embodiments, each cycle is followed by a rest period, where TG02 are not administered to the pediatric subject. In certain embodiments, the rest period is from about two weeks to about six weeks, from three weeks to about five weeks, from about four weeks to about six weeks. In certain embodiments, the rest period is about three weeks, about four weeks, about five weeks, or about six weeks. The present disclosure further allows the frequency, number, and length of dosing cycles and rest period to be adjusted.

5.3.2 H3 Mutations

In certain embodiments, the methods disclosed herein further includes detecting a H3 mutation. In certain embodiments, the methods disclosed herein further includes detecting a H3.3 mutation in a sample from the pediatric subject, where the H3.3 mutation is in the gene encoding histone H3.3. In certain embodiments, the sample is obtained from the glioma of the pediatric subject. In certain embodiments, the H3.3 mutation is a H3K27M mutation or a H3G34R mutation. Any suitable detecting methods known in the art can be used with the presently disclosed subject matter to detect the H3.3 mutations (e.g., H3K27M mutation or a H3G34R mutation). Non-limiting exemplary detecting methods include Polymerase chain reaction (PCR), Reverse transcriptase PCR (RT-PCR), Multiplex PCR, Nested PCR, Amplification refractory mutation system (ARMS) PCR, Real time PCR, DNA microarray, Multiplex ligation-dependent probe amplification (MLPA), and Next Generation Sequencing.

5.3.3 Second Anti-Cancer Agent and Anti-Cancer Treatment

In certain embodiments, the methods disclosed herein further include administering to the subject a second anti-cancer agent. Non-limiting exemplary anti-cancer agents include, but are not limited to chemotherapeutic agents, radiotherapeutic agents, cytokines, anti-angiogenic agents, apoptosis-inducing agents, anti-cancer antibodies, a targeted drug, agents which promote the activity of the immune system, and checkpoint inhibitors. In certain embodiments, the second anti-cancer agent is a radiotherapeutic agent. In certain embodiments, the second anti-cancer agent is a chemotherapeutic agent. In certain embodiments, the chemotherapeutic agent is temozolomide. In certain embodiments, the second anti-cancer agent is a targeted drug. In certain embodiments, the targeted drug is bevacizumab. In certain embodiments, the second anti-cancer agent is an agent that promotes the activity of the immune system, including but not limited to interleukin 2, interferon, anti-CTLA4 antibody, anti-PD-1 antibody, and/or anti-PD-L1 antibody. Other non-limiting exemplary anti-cancer agents that can be used with the presently disclosed subject matter include tumor-antigen based vaccines, and chimeric antigen receptor T-cells.

In certain embodiments, the second anti-cancer agent is an EZH2 inhibitor. Non-limiting examples of EZH2 inhibitors include compounds, molecules, chemicals, polypeptides, proteins that inhibit and/or reduce the expression and/or activity of EZH2. Additional non-limiting examples of EZH2 inhibitors include S-adenosyl-methionine-competitive small molecule inhibitors. In certain embodiments, the EZH2 inhibitor is derived from tetramethylpiperidinyl compounds. In certain embodiments, the EZH2 inhibitor is selected from the group consisting of UNC1999, 3-Deazaneplanocin A (DZNep), EI1, EPZ-5676, EPZ-6438, GSK343, EPZ005687, EPZ011989, GSK126, and combinations thereof.

Further non-limiting examples of EZH2 inhibitors are described in Garapaty-Rao et al., Chemistry and Biology, 20: pp. 1-11 (2013), PCT Patent Application Nos. WO 2013/138361, WO 2013/049770 and WO 2003/070887, and US Patent Application Nos. US 2014/0275081, US 2012/0071418, US 2014/0128393 and US 2011/0251216, the contents of which are hereby incorporated by reference herein in their entireties.

In certain embodiments, the presently disclosed methods include administering a radiotherapy and TG02 to the pediatric subject. In certain embodiments, the methods disclosed herein include first administering TG02 to the pediatric patient, then administering a radiotherapy to the pediatric patient. In certain embodiments, the methods disclosed herein include first administering the radiotherapy to the pediatric patient, then administering TG02 to the pediatric patient. In certain embodiments, the methods disclosed herein include administering the radiotherapy and TG02 to the pediatric patient substantially simultaneously, wherein the pediatric subject has received a therapeutically effective amount of TG02 while receiving the radiotherapy.

Any suitable methods known in the art for delivering a therapeutic dose of radiation to a pediatric subject can be used with the presently disclosed subject matter. Non-limiting exemplary methods for delivering radiotherapy that can be used with the presently disclosed methods include gamma-radiation, neutron beam radiotherapy, electron beam radiotherapy, proton therapy, brachytherapy, systemic radioactive isotopes, photon radiotherapy, particle beam radiation therapy, other types of radiotherapies, and combinations thereof. In certain embodiments, the radiotherapy disclosed herein is delivered to the pediatric subject using a gamma knife. In certain embodiments, the radiotherapy disclosed herein is delivered to the pediatric subject using a linear accelerator. In certain embodiments, the radiotherapy used with the presently disclosed methods uses an ionizing radiation. Non-limiting exemplary ionizing radiation relevant to the cancer treatment include X-rays, gamma rays, and particulate radiation beams.

In certain embodiments, the source of radiation used with the presently disclosed subject matter is external to the pediatric subject. In certain embodiments, the external radiation therapy includes directing a beam of high-energy radiation to a tumor site through the skin using, for instance, a linear accelerator. In certain embodiments, the source of radiation used with the presently disclosed subject matter is internal to the pediatric subject. In certain embodiments, the internal radiation therapy includes implanting a radiation-emitting source, such as beads, wires, pellets, capsules, particles, and the like, inside the body at or near the tumor site, including the use of delivery systems that specifically target cancer cells (e.g., using particles attached to cancer cell binding ligands). Non-limiting exemplary internal radiation therapies include brachytherapy, interstitial irradiation, intracavity irradiation, radioimmunotherapy, and the like.

In certain embodiments, the methods disclosed herein further includes administering at least one radiosensitizer to the pediatric subject to enhance the killing of tumor cells. Non-limiting exemplary radiosensitizers include metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, and heat (hyperthermia).

In certain embodiments, the methods disclosed herein further includes administering at least one radioprotector to the pediatric subject to protect healthy tissue from the harmful effects of radiation. Non-limiting exemplary radioprotectors include cysteamine, aminoalkyl dihydrogen phosphorothioates, amifostine (WR 2721), IL-1, and IL-6.

In certain embodiments, the methods disclosed herein includes administering a total dose of between about 0.01 Gray (Gy) and about 100 Gy radiation to the pediatric subject. In certain embodiments, the methods disclosed herein includes administering a total dose of between about 10 Gy and about 65 Gy radiation to the pediatric subject. In certain embodiments, the methods disclosed herein includes administering a total dose of at least about 10 Gy, at least about 15 Gy, at least about 20 Gy, at least about 25 Gy, at least about 30 Gy, at least about 35 Gy, at least about 40 Gy, at least about 45 Gy, at least about 50 Gy, at least about 55 Gy, at least about 60 Gy, at least about 65 Gy, up to about 10 Gy, up to about 15 Gy, up to about 20 Gy, up to about Gy, up to about 30 Gy, up to about 35 Gy, up to about 40 Gy, up to about 45 Gy, up to about 50 Gy, up to about 55 Gy, up to about 60 Gy, or up to about 65 Gy radiation to the pediatric subject. In certain embodiments, the methods disclosed herein includes administering a total dose of between about 10 Gy and about 15 Gy, between about 15 Gy and about 20 Gy, between about 20 Gy and about 25 Gy, between about 25 Gy and about 30 Gy, between about 30 Gy and about 35 Gy, between about 40 Gy and about 45 Gy, between about 45 Gy and about 50 Gy, between about 50 Gy and about 55 Gy, between about 55 Gy and about 60 Gy, or between about 60 Gy and about 65 Gy, to the pediatric subject.

In certain embodiments, the methods disclosed herein includes administering a total dose of about 10 Gy, about 15 Gy, about 20 Gy, about 25 Gy, about 30 Gy, about 35 Gy, about 40 Gy, about 45 Gy, about 50 Gy, about 55 Gy, about 60 Gy, or about 65 Gy radiation to the pediatric subject. In certain embodiments, the methods disclosed herein includes administering a total dose of about 54 Gy to the pediatric subject. In certain embodiments, the methods disclosed herein includes administering a total dose of between 54 and 59.4 Gy to the pediatric subject. In certain embodiments, the methods disclosed herein includes administering a total dose of about 54 Gy to the pediatric subject with DIPG. In certain embodiments, the methods disclosed herein includes administering a total dose of between 54 and 59.4 Gy to the pediatric subject with other non-DIPG H3.3-mutated HGGs.

In certain embodiments, the total dose of radiation is administered over the course of one day. In certain embodiments, the total dose of radiation is fractionated to maximize target cell exposure and to reduce toxicity. In certain embodiments, the total dose of radiation is fractionated and administered in between about 1 week and about 8 weeks. In certain embodiments, the total dose of radiation is fractionated and administered in at least about 2 days, at least about 3 days, at least about 4 days, at least about 5 days, at least about 6 days, at least about 7 days, at least about 10 days, at least about 14 days, at least about 17 days, at least about 21 days, at least about 24 days, at least about 28 days, at least about 31 days, at least about 35 days, at least about 38 days, at least about 42 days, at least about 45 days, at least about 49 days, at least about 52 days, or at least about 56 days.

In certain embodiments, the radiotherapy is administered to the pediatric subject in a daily dose of between about 1 Gy and about 5 Gy, between about 1 Gy and about 2 Gy, or between about 1 Gy and about 1.5 Gy. In certain embodiments, the radiotherapy is administered to the pediatric subject in a daily dose of at least about 1 Gy, at least about 1.5 Gy, at least about 1.8 Gy, at least about 2 Gy, at least about 2.5 Gy, at least about 2.8 Gy, at least about 3 Gy, at least about 3.2 Gy, at least about 3.5 Gy, at least about 3.8 Gy, at least about 4 Gy, at least about 4.2 Gy, at least about 4.5 Gy, at least about 5 Gy, up to about 1 Gy, up to about 1.5 Gy, up to about 1.8 Gy, up to about 2 Gy, up to about 2.5 Gy, up to about 2.8 Gy, up to about 3 Gy, up to about 3.2 Gy, up to about 3.5 Gy, up to about 3.8 Gy, up to about 4 Gy, up to about 4.2 Gy, up to about 4.5 Gy, or up to about 5 Gy. In certain embodiments, the radiotherapy is administered to the pediatric subject in a daily dose of about 1 Gy, about 1.5 Gy, about 1.8 Gy, about 2 Gy, about 2.5 Gy, about 2.8 Gy, about 3 Gy, about 3.2 Gy, about 3.5 Gy, about 3.8 Gy, about 4 Gy, about 4.2 Gy, about 4.5 Gy, or about 5 Gy. In certain embodiments, daily doses of radiation should be sufficient to induce destruction of the targeted DIPG cells.

In certain embodiments, the radiotherapy is administered cyclically. In certain embodiments, the number of cycles is from about one to about twenty-four cycles. In certain embodiments, the number of cycles is more than twenty-four cycles. In certain embodiments, the number of cycles is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24. In certain embodiments, the duration of each cycle is about 7 days, about 10 days, about 14 days, about 21 days, or about 28 days. In certain embodiments, the duration of a cycle is about 7 days.

In certain embodiments, each radiotherapy cycle includes a rest period, in which the radiation is not administered to the pediatric subject during the rest period. In certain embodiments, the rest period is about 21 days, about 20 days, about 19 days, about 18 days, about 17 days, about 16 days, about 15 days, about 14 days, about 13 days, about 12 days, about 11 days, about 10 days, about 9 days, about 8 days, about 7 days, about 6 days, about 5 days, about 4 days, about 3 days, about 2 days, or about 1 days.

In certain embodiments, the radiation is administered 5 days/cycle, where the duration of each cycle is 7 days, and each cycle includes a 2-day rest period. In certain embodiments, the radiation is administered on day 1, day 2, day 3, day 4, and day 5 of the 7-day cycle. In certain embodiments, the radiation is administered 1 day/cycle, 2 days/cycle, 3 days/cycle, 4 days/cycle, 5 days/cycle, 6 days/cycle, or 7 days/cycle, where the duration of each cycle is 7 days. The present disclosure further allows the frequency, number, and length of dosing cycles and rest period to be adjusted, depending on the responsiveness of the pediatric subject to the radiotherapy and the occurrence of the radiotherapy-associated side effect.

In certain embodiments, the radiotherapy can be initiated at any time during the TG02 treatment period. In certain embodiments, the radiotherapy is initiated on week 1 or week 2, and is administered for the remaining duration of TG02 treatment period. In certain embodiments, the radiotherapy is administered from week 1 to week 6, or from week 2 to week 6 of TG02 treatment period. In certain embodiments, the radiotherapy is administered from week 1 to week 5, or from week 2 to week 5, of TG02 treatment period. In certain embodiments, the methods disclosed herein include administering a radiotherapy and TG02 to the pediatric subject. In certain embodiments, the radiotherapy is administered fractionated over 6 weeks. In certain embodiments, the total dose of the radiotherapy is between about 54 and 59.5 Gy. In certain embodiments, TG02 is administered twice a week, e.g., on Mondays and Thursdays, once a day, for the duration of the radiotherapy and afterwards for a up to 2 years or until the patient experiences disease progression or clinically significant toxicity. In certain embodiments, TG02 is administered twice a week, once a day, for up to 1, 2, 3, 4, 5, 6, 7, 8, 9, 10, 11 or 12 months after the radiotherapy. In another embodiment, TG02 is administered once weekly during the radiotherapy and/or afterwards. In certain embodiments, TG02 is administered twice weekly for 3 of 4 weeks after the radiotherapy. In certain embodiments, TG02 is administered once weekly after the radiotherapy.

In certain embodiments, when TG02 is administered on the same day as the radiotherapy, TG02 is administered to the pediatric subject between about 1 hours and about 8 hours, about 1 hours and about 5 hours, between about 1 hour and about 2 hours, between about 1 hour and about 3 hours, between about 2 hours and 3 hours, or between about 2 hours and 4 hours prior to the administration of the radiotherapy. In certain embodiments, TG02 is administered to the pediatric subject about 1 hour, about 2 hours, about 3 hours, about 4 hours, about 5 hours, about 6 hours, about 7 hours, or about 8 hours prior to the administration of the radiotherapy.

These exemplary dosing protocols are not intended, however, to limit the methods provided herein.

5.3.4 Administration Methods

Any suitable methods known in the art can be used for administering TG02 to the pediatric subject. In certain embodiments, TG02 can be administered to the subject orally or parenterally. For example, and not by way of limitation, the route of administration can be intravenous, intraarterial, intrathecal, intraperitoneal, intramuscular, subcutaneous, topical, intradermal, intranasal, vaginal, rectal, route, locally to the cancer, or combinations thereof. In certain embodiments, TG02 is administered to the pediatric subject orally. In certain embodiments, TG02 is administered to the pediatric subject intravenously.

In certain embodiments, the pediatric subject has a newly diagnosed glioma, where the pediatric subject has not received any treatment for the glioma previously. In certain embodiments, the glioma is a refractory glioma. In certain embodiments, the glioma is a relapsed glioma. In certain embodiments, the glioma is a relapsed and refractory glioma.

In certain embodiments, TG02 treatment disclosed herein is administered after the subject has been treated with an additional anti-cancer treatment. In certain embodiments, TG02 treatment disclosed herein is administered simultaneously or sequentially while the subject is being treated with the additional anti-cancer treatments. Examples of the additional cancer treatments include, but are not limited to, surgery, chemotherapy, checkpoint inhibitors, radiation therapy, and combinations thereof.

5.4 Pharmaceutical Compositions

The present disclosure also provides pharmaceutical compositions including TG02 disclosed in Section 5.2 for use in treating a glioma in a pediatric human subject (e.g., a pediatric human subject). For example, but not by way of limitation, TG02 includes, free base forms thereof, solvate forms thereof, pharmaceutically acceptable salt forms thereof, derivatives thereof, mixtures thereof, and combinations thereof. In certain embodiments, the pediatric glioma is a PHGG or a DIPG. In certain embodiments, the glioma is a pediatric glioblastoma (GBM). In certain embodiments, the pediatric glioma is a H3-mutated glioma, e.g., a H3K27M-mutated high-grade glioma or a H3K27M-mutated non-DIPG high-grade glioma.

In certain embodiments, the pharmaceutical compositions further include a pharmaceutically acceptable carrier. Suitable pharmaceutically acceptable carriers that can be used with the presently disclosed subject matter have the characteristics of not interfering with the effectiveness of the biological activity of the active ingredients, e.g., TG02, and that is not toxic to the patient to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers include gels, bioabsorbable matrix materials, implantation elements containing the inhibitor and/or any other suitable vehicle, delivery or dispensing mechanism or material. Such pharmaceutically acceptable carriers can be formulated by conventional methods and can be administered to the subject. In certain embodiments, the pharmaceutical acceptable carriers can include buffers such as phosphate, citrate, and other organic acids; antioxidants including ascorbic acid and methionine; preservatives (such as, but not limited to, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). In certain embodiments, the suitable pharmaceutically acceptable carriers can include one or more of water, saline, phosphate buffered saline, dextrose, glycerol, ethanol or combinations thereof.

In certain non-limiting embodiments, the pharmaceutical compositions of the present disclosure can be formulated using pharmaceutically acceptable carriers well known in the art that are suitable for oral administration. Such carriers enable the pharmaceutical compositions to be formulated as tablets, pills, capsules, liquids, gels, syrups, slurries, suspensions and the like, for oral or nasal ingestion by a patient to be treated. In certain embodiments, the pharmaceutical composition is formulated as a capsule. In certain embodiments, the pharmaceutical composition can be a solid dosage form. In certain embodiments, the tablet can be an immediate release tablet. Alternatively or additionally, the tablet can be an extended or controlled release tablet. In certain embodiments, the solid dosage can include both an immediate release portion and an extended or controlled release portion.

In certain embodiments, the pharmaceutical compositions of the present disclosure can be formulated using pharmaceutically acceptable carriers well known in the art that are suitable for parenteral administration. The terms "parenteral administration" and "administered parenterally," as used herein, refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. For example, and not by way of limitation, pharmaceutical compositions of the present disclosure can be administered to the patient intravenously in a pharmaceutically acceptable carrier such as physiological saline. In certain embodiments, the present disclosure provides a parenteral pharmaceutical composition including TG02.

In certain embodiments, the pharmaceutical compositions suitable for use in the presently disclosed subject matter can include compositions where the active ingredients, e.g., ERK5 inhibitors, are contained in a therapeutically effective amount. The therapeutically effective amount of an active ingredient can vary depending on the active ingredient, e.g., TG02, compositions used, the cancer and its severity, and the age, weight, etc., of the subject to be treated. In certain embodiments, a pediatric human subject can receive a therapeutically effective amount of TG02 in single or multiple administrations of one or more composition, which can depend on the dosage and frequency as required and tolerated by the patient.

In certain embodiments, the pharmaceutical compositions further include a second anti-cancer agent. Non-limiting exemplary anti-cancer agents include, but are not limited to chemotherapeutic agents, radiotherapeutic agents, cytokines, anti-angiogenic agents, apoptosis-inducing agents, anti-cancer antibodies, a targeted drug, agents which promote the activity of the immune system, checkpoint inhibitors. In certain embodiments, the second anti-cancer agent is a radiotherapeutic agent. In certain embodiments, the second anti-cancer agent is a chemotherapeutic agent. In certain embodiments, the chemotherapeutic agent is temozolomide. In certain embodiment, the second anti-cancer agent is a targeted drug. In certain embodiments, the targeted drug is bevacizumab. In certain embodiments, the second anti-cancer agent is an agent that promotes the activity of the immune system, including but not limited to interleukin 2, interferon, anti-CTLA4 antibody, anti-PD-1 antibody, and/or anti-PD-L1 antibody. Other non-limiting exemplary anti-cancer agents that can be used with the presently disclosed subject matter include tumor-antigen based vaccines, and chimeric antigen receptor T-cells.

5.5 Kits

The present disclosure provides kits that can be used to practice the presently disclosed methods of treating a glioma in a pediatric subject. In certain embodiments, the kits disclosed herein include TG02 or a pharmaceutical composition thereof. In certain embodiments, the kits include a pharmaceutical composition including a therapeutically effective amount of TG02. In certain embodiments, the kits further include a second anti-cancer agent disclosed herein, e.g., within the same container as TG02 (or pharmaceutical compositions thereof) or within a second container. In certain embodiments, the second anti-cancer agent is a radiotherapeutic agent. In certain embodiments, the second anti-cancer agent is a chemotherapeutic agent. In certain embodiments, the chemotherapeutic agent is temozolomide. Other non-limiting exemplary anti-cancer agents that can be used with the presently disclosed subject matter include tumor-antigen based vaccines, and chimeric antigen receptor T-cells.

In certain embodiments, the kits further include instructions for using the kits in treating a pediatric subject. In certain embodiments, the instructions indicate that TG02 can be administered in accordance with the methods disclosed in Section 5.3. In certain embodiments, the instructions indicate TG02 can be administered orally as a single dose, twice per week. In certain embodiments, the instructions indicate TG02 can be administered for up to 2 years.

In certain non-limiting embodiments, the present disclosure provides for a kit that includes a container including TG02, e.g., a therapeutically effective amount of TG02, and/or a container including a second anti-cancer agent, e.g., a therapeutically effective amount of a second anti-cancer agent, with instructions to use any combination of the components of the one or more containers together or separately for treating cancer. For example, and not by way of limitation, the instructions can include a description of TG02 and/or a second anti-cancer agent, and, optionally, other components present in the kit. In certain embodiments, the instructions can describe methods for administration of the components of the kit, including methods for determining the proper state of the subject, the proper dosage amount and the proper administration method for administering one or more of TG02 and/or other anti-cancer agent. Instructions can also include guidance for monitoring the subject over the duration of the treatment time. In certain embodiments, the kit may further include one or more containers including other anti-cancer agents. In certain embodiments, a kit of the present disclosure includes a container that includes TG02 and an anti-cancer agent.

In certain non-limiting embodiments, the present disclosure provides for a kit of this disclosure further including one or more of the following: devices and additional reagents, and components, such as tubes, containers, cartridges, and syringes for performing the methods disclosed in Section 5.3.

In certain embodiments, the kits disclosed herein are configured to detect an H3 mutation, e.g., an H3.1 mutation and/or an H3.3 mutation, in a sample from the pediatric subject. In certain embodiments, the H3.3 mutation is in the gene encoding histone H3.3. In certain embodiments, the H3.1 mutation is in the gene encoding histone H3.1. In certain embodiments, the sample is obtained from the glioma of the pediatric subject. In certain embodiments, the H3.3 mutation is a H3K27M mutation or a H3G34R mutation. Any suitable detecting means known in the art can be used with the presently disclosed subject matter to detect the H3.3 mutations (e.g., H3K27M mutation, H3G34R mutation). Non-limiting exemplary configurations for detecting an H3 mutation include a processor linked to one or more non-transitory memories storing instructions for performing polymerase chain reaction (PCR), Reverse transcriptase PCR (RT-PCR), Multiplex PCR, Nested PCR, Amplification refractory mutation system (ARMS) PCR, Real time PCR, DNA microarray, Multiplex ligation-dependent probe amplification (MLPA), and Next Generation Sequencing.

6. EXAMPLES

The presently disclosed subject matter will be better understood by reference to the following Example, which is provided as exemplary of the presently disclosed subject matter, and not by way of limitation.

Example 1: Identification of Novel Therapeutic Vulnerabilities in RAS Signaling for Diffuse Intrinsic Pontine Gliomas The RAS-MAPK signaling pathway, which stimulates cell proliferation and survival, is included of clinically actionable targets, with several inhibitors that target specific pathway signaling mediators already in clinical use (Bhullar et al., Molecular cancer 2018; 17:48). RAS, though infrequently mutated, is often hyperactive in DIPG due to a variety of mechanisms including: recurrent growth factor activation, mutations in receptor tyrosine kinases such as platelet derived growth factor receptor alpha (PDGFRA), and genetic inactivation of RAS regulatory proteins such as Neurofibromin 1 (NF1) (Mackay et al., Cancer cell 2017; 32:520-37 e5; Sturm et al., Cancer cell 2012; 22:425-37; Schwartzentruber et al., Nature 2012; 482:226-31). However, the relationship between the H3K27M mutations and RAS pathway has yet to be explored.

Here, the present disclosure shows that H3K27M mutations contribute to RAS pathway signaling, which is augmented by additional RAS activators including PDGFRA. The present disclosure observed that the H3K27M mutations lead to increased expression of receptor tyrosine kinases (RTKs). From a RAS pathway functional screen, ERK5, but not ERK1/2, was identified in accordance with the present disclosure as a RAS pathway effector important for DIPG growth. Suppression of ERK5, which is highly expressed in DIPG, decreased DIPG cell proliferation and induced apoptosis both in vitro and in vivo. Additionally, ERK5 knockdown or treatment with an ERK5 inhibitor (e.g., TG02) significantly increased survival of mice intracranially engrafted with DIPG cells. Mechanistically, the present disclosure shows that ERK5 directly activates and stabilizes the proto-oncogene MYC. ERK5 overexpression fully rescued ERK5-depleted cells and partial rescue was achieved by expression of ERK5 mutants lacking kinase activity or the transactivation domain ($\Delta$TAD). However, no rescue was achieved with kinase-dead, $\Delta$TAD double mutants. Additionally, ERK5 knockdown or treatment with an ERK5 inhibitor (e.g., TG02) significantly increased survival of mice intracranially engrafted with DIPG cells. TG02 was a very effective treatment and extended the median survival time nearly two-fold. Without being limited to a particular theory, TG02 destabilizes MYC at the protein level. Collectively, this data demonstrates a role of H3K27M contributing to RAS activation, and in so doing reveals a novel therapeutic target for treating these tumors.

Materials and Methods

Cell Culture

Human Neural Stem Cells (H9 hESC-Derived) were purchased from Invitrogen and grown in DMEM/F12 containing penicillin/streptomycin/amphotericin B (1% vol/vol) supplemented with N2 (2% vol/vol; Invitrogen), EGF (20 ng/ml; Invitrogen), and FGF-2 (20 ng/ml; Invitrogen). DIPG cell lines (all with the H3K27M mutation) SU-DIPG-IV (DIPG-IV), SU-DIPG-13p (DIPG-13p), and HSJD-DIPG-007 (DIPG-007) were grown and passaged in DIPG medium as previously reported (Grasso et al., Nature medicine 2015; 21:555-9; Nagaraja et al., Cancer cell 2017; 31:635-52 e6; Vinci et al., Nature medicine 2018). SF8628 and immortalized NHAs were grown in DMEM (Invitrogen) supplemented with 10% FBS (Invitrogen). All cell lines were confirmed by STR profiling and tested mycoplasma negative by PCR. All tumor-derived cell lines used are described in Table 2.

TABLE 2

Description of tumor-derived cell lines

| Cell line | Tumor of origin | Histone 3 status | |
|---|---|---|---|
| SF8628 | DIPG | H3.3 K27M | |
| DIPG-IV | DIPG | H3.1 K27M | ACVR1 G328V; MDM4, NTRK1 gain |
| DIPG-VI | DIPG | H3.3 K27M | TP53 mutant |
| DIPG-007 | DIPG | H3.3 K27M | |
| DIPG-XIII | DIPG | H3.3 K27M | |
| CNMC-XD-760 | DIPG | H3 Wild-type | |
| HSJD-GBM-001 | Ped. GBM | H3 Wild-type | PDGFRA mutant |
| SU-pcGBM2 | Ped. GBM | H3 Wild-type | TP53 mutant; EGFR amplified |

Generation of Inducible ERK5 Knockdown Cells.

To produce lentivirus, 400 µl of Opti-MEM I (Gibco) containing 2.4 µg pCMV-dR8.2 dvpr, 1.8 µg pCMV-VSV-G, 3 µg piSMART mCMV/TurboGFP shRNA plasmid (Dharmacon), and 20 µl FuGENE HD (Fugent LLC) was added to a 10 cm plate of HEK293T cells grown in complete media+ 10% FBS. Media was collected from the HEK293T cells 48 hours after transfection, spun at 2000×g, and the virus-containing supernatant was either used directly for lentiviral transduction or concentrated with Lenti-X lentiviral concentrator (Takara). Cells were transduced by overnight incubation with lentivirus in appropriate growth media containing 5-8 µg/ml Polybrene (EMD Millipore). Beginning two days after transduction, cells were cultured with 0.5-1 µg/ml puromycin (Gibco) for 5-7 days.

Plasmids and Plasmid Construction

Wildtype human H3F3A cDNA was ligated with a puromycin selection marker and a self-cleaving T2A sequence using Gibson Assembly Cloning and cloned into pLV with an EF1a promoter. HA-RASAL1 (NM_001193520.1) with an N-terminal HA tag, MYC (NM_002467.4), or MAPK7 (ERK5, NM_139033) were ligated with T2A mCherry and cloned into pLV under the control of the EF1a promoter. Cloning and plasmid sequence validation were performed by VectorBuilder Services (Santa Clara, Calif. 95050). Site-directed mutagenesis was performed to generate H3F3A K27M, H3F3A G34R, MYC S62D, and ERK5 mutant constructs using the QuikChange II Site-Directed Mutagenesis Kit and manufacturer's protocol (Agilent, Cat #200523, Santa Clara, Calif. 95051). Lentiviral ERK5 GIPZ shRNA plasmids were purchased from Dharmacon (Lafayette, Colo. 80026, Cat #RHS4531-EG5598 glycerol set: V2LHS_202701, V3LHS_366737, V3LHS_366738, V3LHS_366740, V3LHS_640828, V3LHS_640830).

Cell Proliferation Assays, Viability Assays, and Drug EC50 Analysis

Direct cell counts were performed using the Countess II FL Automated Cell Counter (ThermoFisher Scientific). Alamar blue viability (ThermoFisher Scientific) and the 5-bromo-2'-deoxyuridine (BrdU) incorporated cell proliferation assay (Cell Signaling Technology Cat #6813) were performed using the manufacturer's standard protocol. EC50 curve analysis was performed using raw fluorescent Alamar blue values that were inputted into PRISM 7.0. Drug concentrations were log 10 transformed and values normalized to percent viability with respect to vehicle treated cells. EC50 values were interpolated from a log inhibitor vs. normalized response with variable slope using a least square fit model.

Small Molecule Inhibitors

TG02 was obtained from Tragara Pharmaceutical.

Apoptosis Assay

Apoptosis was quantified using the Pacific Blue Annexin V Apoptosis Detection Kit with propidium iodide (BioLegend, San Diego, Calif. Cat #640926). Analysis was performed at the Flow Cytometry Core, Rangos Research Center, UPMC Children's Hospital of Pittsburgh.

RAS Activity Assay

RAS activity was measured using the RAS activation assay (Cell Signaling Technology, Cat #8814). Briefly, active Ras Detection GST-RAF1-RBD fusion protein was used to bind the activated form of GTP-bound RAS, which was then immunoprecipitated from 500 µg of total cell lysate with glutathione resin. RAS activation levels were then determined by western blot using a RAS Mouse mAb. Activated RAS immune-precipitate was normalized to total RAS from whole cell lysate.

RAS siRNA Screen

5000 NSC control, NSC H3K27M, and DIPG-007 cells were plated in black 96 well plates. 12 h post plating, cells were transfected with a custom Endoribonuclease-prepared siRNA library (esiRNA) (Sigma, St. Louis Mo.). 20 ng of esiRNA were used per target with X-tremeGENE HP DNA Transfection Reagent (Sigma, St. Louis Mo.). Cell viability was assessed 96 h later by the Alamar blue cell viability assay (Invitrogen, Cat #DAL1025). Data were normalized using the standard z-score using the percent viability difference of NSC control vs NSC H3K27M for each siRNA target and control siRNA DIPG-007 vs DIPG-007 siRNA target gene. For significance, z-score cut off values were +/−2 (p-value <0.05) in three biological replicates. Validation of esiRNA screen was performed using two individual Dicer-Substrate siRNA (DsiRNA) per gene-target (Integrated DNA Technologies, Iowa, USA).

Western Blotting and Immuno-Precipitation

Cell pellets were lysed in PLC lysis buffer containing protease and phosphatase inhibitors (Roche Inc.). Protein lysates were quantified using the bicinchoninic acid (BCA) assay (Pierce Chemical Co., Rockford, Ill.). 30 µg of total protein lysate was loaded in 10% SDS-PAGE gels and electrophoresed. Proteins were transferred to PVDF membranes using a semi-dry transfer apparatus (Bio-Rad). Membranes were blocked for one hour and probed for various proteins overnight in 5% non-fat milk or 5% BSA in Tris Buffered Saline Solution, 0.5% Tween-20 (TBST) or Phosphate Buffered Saline Solution with 0.5% Tween-20 (PBST). Membranes were washed for 5 mins in TBST (3×) and incubated with horseradish peroxidase-conjugated antibodies specific for the primary antibody (BioRad Laboratories, Inc., CA, USA). Binding was detected using Chemiluminescence Reagent Plus (PerkinElmer Inc., MA, USA). Antibodies were used at the following dilutions:

H3K27M (1:1000, Abcam cat #190631), H3K27Me3 (1:1000, Cell Signaling cat #9733), H3K27Ac (1:1000, Cell Signaling cat #4353), B-actin (1:10000, Cell Signaling cat #3700), p-ERK1/2 (1:1000, Cell Signaling cat #8544), ERK1/2 (1:1000, Cell Signaling cat #4695), RASAL1 (1:1000, ThermoFisher Scientific cat #PA5-22031), RASA3 (1:3000, Invitrogen cat #PA5-30445), HA (1:1000, Cell Signaling cat #3724), RAS (1:1000, Cell Signaling cat #3965), p-ERK5 (T218/Y220) (1:1000, Cell Signaling cat #3371), p-ERK5 (S731/T733) (ThermoFisher Scientific cat #PAB15919), ERK5 (1:1000, ThermoFisher cat #PA5-17689), MEKK3 (1:1000, Cell Signaling cat #5727), p-MEK5 (S311/T315) (1:1000, ThermoFisher Scientific cat #480024), MEK5 (ThermoFisher Scientific cat #PA5-15083), MEKK2 (Cell Signaling cat #19607), GAPDH (Cell Signaling cat #5174), H3.3 (1:500, Biolegend cat #601901), pAKT ser473 (1:2000, Cell Signaling cat #4060), AKT (1:1000, Cell Signaling cat #4691), MYC S62 (1:1000, ThermoFisher cat #PA5-36671), MYC (1:1000, BioLegend cat #626802). Immuno-precipitations and co-immuno-precipitations (co-IP) were performed using 500 µg total lysate using manufacturer specific dilutions. Denaturing IPs were performed as previously described (Smith et al., Journal of cell science 2013; 126:1366-80; Agnihotri et al., J Exp Med 2011; 208:689-702; Amanchy et al., Nature biotechnology 2007; 25:285-6).

In Vitro Kinase Assays

Purified active recombinant ERK5 protein was purchased from ThermoFisher Scientific (Cat #A32872) and purified recombinant MYC was purchased from Abcam (Cat #ab84132). Purified ERK5 and MYC were resuspended in 40 µl of 1× kinase buffer supplemented with 200NM ATP, 0.25 µg substrate, and 1.0 µg purified recombinant and active kinase. Samples were incubated in the presence or absence of an ERK5 inhibitor for 30 minutes at 30° C. The reaction was terminated with 20 µl 3×SDS sample buffer. Samples were then boiled at 100° C. for 5 minutes and then evaluated by western blotting using a phospho MYC ser62 antibody (1:1000). 1× Kinase Buffer recipe: 25 mM Tris (pH 7.5), 5 mM O-glycerophosphate, 2 mM DTT, 0.1 mM $Na_3VO_4$, 10 mM $MgCl_2$.

Cancer Signaling Antibody Array

The Cancer Signaling Antibody Array was purchased from Full Moon Biosystems and is an ELISA based Antibody Array platform including of 269 antibodies targeting proteins involved in cancer signaling (Table 3).

TABLE 3

Ratio Analysis for Paired Antibodies

| Antibody List | | Signal Ratio | | Fold Change |
| --- | --- | --- | --- | --- |
| | | 4000022475 (Con) | 4000022476 (KD) | KD/Con |
| cdc25A (Phospho-Ser75) | cdc25A (Ab-75) | 1.376757469 | 0.596004827 | 0.43 |
| Myc (Phospho-Ser62) | Myc (Ab-62) | 1.803310929 | 0.831335536 | 0.46 |
| MEK1 (Phospho-Ser217) | MEK1 (Ab-217) | 2.350363289 | 1.112725451 | 0.47 |
| p44/42 MAP Kinase (Phospho-Thr202) | p44/42 MAP Kinase (Ab-202) | 1.318134439 | 0.634102259 | 0.48 |
| ERK8 (Phospho-Thr175/Tyr177) | ERK8 (Ab-175/177) | 1.18010269 | 0.615210176 | 0.52 |
| eIF4E (Phospho-Ser209) | eIF4E (Ab-209) | 1.355683152 | 0.716018174 | 0.53 |
| MEK1 (Phospho-Ser221) | MEK1 (Ab-221) | 1.920467644 | 1.016486405 | 0.53 |
| MEK1 (Phospho-Thr291) | MEK1 (Ab-291) | 1.507179012 | 0.806152272 | 0.53 |
| PDGF Receptor beta (Phospho-Tyr751) | PDGF Receptor beta (Ab-751) | 0.753164942 | 0.416551697 | 0.55 |
| HSP27 (Phospho-Ser78) | HSP27 (Ab-78) | 1.82431827 | 1.026803182 | 0.56 |
| p44/42 MAP Kinase (Phospho-Tyr204) | p44/42 MAP Kinase (Ab-204) | 1.682729805 | 0.960610964 | 0.57 |
| HSF1 (Phospho-Ser303) | HSF1 (Ab-303) | 1.449795263 | 0.838215851 | 0.58 |
| Src (Phospho-Tyr529) | Src (Ab-529) | 1.881542074 | 1.199719368 | 0.64 |
| MSK1 (Phospho-Ser376) | MSK1 (Ab-376) | 1.804486272 | 1.246143228 | 0.69 |
| Caspase 9 (Phospho-Ser196) | Caspase 9 (Ab-196) | 0.689699508 | 0.496113572 | 0.72 |
| Trk B (Phospho-Tyr515) | Trk B (Ab-515) | 0.838735746 | 0.607967043 | 0.72 |
| BRCA1 (Phospho-Ser1423) | BRCA1 (Ab-1423) | 0.262969712 | 0.193269039 | 0.73 |
| eEF2K (Phospho-Ser366) | eEF2K (Ab-366) | 0.739526602 | 0.547743348 | 0.74 |
| Caspase 9 (Phospho-Thr125) | Caspase 9 (Ab-125) | 0.785479804 | 0.587419736 | 0.75 |
| Histone H2A.X (Phospho-Ser139) | Histone H2A.X (Ab-139) | 1.318689415 | 0.998934064 | 0.76 |
| PI3-kinase p85-subunit alpha/gamma (Phospho-Tyr467/Tyr199) | PI3-kinase p85-subunit alpha/gamma (Ab-467/199) | 1.446615825 | 1.101611825 | 0.76 |
| FGF Receptor 1 (Phospho-Tyr154) | FGF Receptor 1 (Ab-154) | 0.998088891 | 0.760098522 | 0.76 |
| c-Kit (Phospho-Tyr721) | c-Kit (Ab-721) | 0.806198509 | 0.624713886 | 0.77 |
| IKK alpha (Phospho-Thr23) | IKK alpha (Ab-23) | 0.933442525 | 0.723912684 | 0.78 |
| ERK3 (Phospho-Ser189) | ERK3 (Ab-189) | 1.400147384 | 1.092449083 | 0.78 |
| HSP27 (Phospho-Ser15) | HSP27 (Ab-15) | 1.985330878 | 1.574279672 | 0.79 |
| PI3-kinase p85-alpha (Phospho-Tyr607) | PI3-kinase p85-alpha (Ab-607) | 1.208067341 | 0.971288943 | 0.80 |
| SAPK/JNK (Phospho-Thr183) | SAPK/JNK (Ab-183) | 1.100005046 | 0.897738616 | 0.82 |
| Chk1 (Phospho-Ser345) | Chk1 (Ab-345) | 0.960990033 | 0.78487433 | 0.82 |
| Caspase 9 (Phospho-Tyr153) | Caspase 9 (Ab-153) | 0.460222918 | 0.377224911 | 0.82 |
| FAK (Phospho-Tyr397) | FAK (Ab-397) | 1.271555556 | 1.047234336 | 0.82 |
| mTOR (Phospho-Ser2448) | mTOR (Ab-2448) | 1.574956438 | 1.321486633 | 0.84 |
| HSP90B (Phospho-Ser254) | HSP90B (Ab-254) | 0.966808799 | 0.812033111 | 0.84 |
| Rac1/cdc42 (Phospho-Ser71) | Rac1/cdc42 (Ab-71) | 1.674215913 | 1.407425461 | 0.84 |
| NFkB-p65 (Phospho-Ser529) | NFkB-p65 (Ab-529) | 1.320496385 | 1.113783426 | 0.84 |
| 4E-BP1 (Phospho-Thr36) | 4E-BP1 (Ab-36) | 1.412538281 | 1.192029955 | 0.84 |
| CrkII (Phospho-Tyr221) | CrkII (Ab-221) | 0.578369689 | 0.488760149 | 0.85 |
| Met (Phospho-Tyr1349) | Met (Ab-1349) | 0.903855563 | 0.764628512 | 0.85 |
| IkB-alpha (Phospho-Ser32/Ser36) | IkB-alpha (Ab-32/36) | 2.971654921 | 2.514295117 | 0.85 |
| EGFR (Phospho-Tyr1110) | EGFR (Ab-1110) | 1.103170163 | 0.952400111 | 0.86 |
| IkB-epsilon (Phospho-Ser22) | IkB-epsilon (Ab-22) | 0.548142031 | 0.481385115 | 0.88 |
| Pyk2 (Phospho-Tyr402) | Pyk2 (Ab-402) | 1.445392604 | 1.276802764 | 0.88 |
| p70 S6 Kinase (Phospho-Ser424) | p70 S6 Kinase (Ab-424) | 1.662963754 | 1.472030546 | 0.89 |
| p53 (Phospho-Ser315) | p53 (Ab-315) | 1.379283315 | 1.222080504 | 0.89 |
| p53 (Phospho-Ser6) | p53 (Ab-6) | 1.288802083 | 1.143859498 | 0.89 |
| MDM2 (Phospho-Ser166) | MDM2 (Ab-166) | 0.156484647 | 0.139536548 | 0.89 |
| GSK3 alpha (Phospho-Ser21) | GSK3 alpha (Ab-21) | 1.078328643 | 0.961613217 | 0.89 |
| 14-3-3 zeta (Phospho-Ser58) | 14-3-3 zeta (Ab-58) | 1.529842073 | 1.367067513 | 0.89 |
| Caspase 9 (Phospho-Ser144) | Caspase 9 (Ab-144) | 0.903882144 | 0.822593395 | 0.91 |
| Rel (Phospho-Ser503) | Rel (Ab-503) | 1.260667287 | 1.151651086 | 0.91 |
| eIF2a (Phospho-Ser51) | eIF2a (Ab-51) | 1.068809695 | 0.979140436 | 0.92 |
| Caspase 3 (Phospho-Ser150) | Caspase 3 (Ab-150) | 1.027794016 | 0.943169254 | 0.92 |
| Tau (Phospho-Ser404) | Tau (Ab-404) | 1.563963964 | 1.455132053 | 0.93 |
| Elk-1 (Phospho-Ser383) | Elk-1 (Ab-383) | 1.282727961 | 1.202650469 | 0.94 |
| JAK1 (Phospho-Tyr1022) | JAK1 (Ab-1022) | 0.975779967 | 0.920816075 | 0.94 |
| IkB-alpha (Phospho-Tyr42) | IkB-alpha (Ab-42) | 1.744873596 | 1.687409025 | 0.97 |
| c-Jun (Phospho-Thr239) | c-Jun (Ab-239) | 1.012094006 | 0.982871355 | 0.97 |

TABLE 3-continued

Ratio Analysis for Paired Antibodies

| Antibody List | | Signal Ratio | | Fold Change |
| --- | --- | --- | --- | --- |
| | | 4000022475 (Con) | 4000022476 (KD) | KD/Con |
| BAD (Phospho-Ser155) | BAD (Ab-155) | 1.196148024 | 1.16475916 | 0.97 |
| CDC2 (Phospho-Tyr15) | CDC2 (Ab-15) | 0.874823125 | 0.856182134 | 0.98 |
| CaMKII (Phospho-Thr286) | CaMKII (Ab-286) | 1.112145558 | 1.093010896 | 0.98 |
| FAK (Phospho-Tyr925) | FAK (Ab-925) | 1.087976395 | 1.069581097 | 0.98 |
| p27Kip1 (Phospho-Thr187) | p27Kip1 (Ab-187) | 1.279626026 | 1.263319266 | 0.99 |
| MKK3 (Phospho-Ser189) | MKK3 (Ab-189) | 0.938914994 | 0.927140442 | 0.99 |
| IGF-1R (Phospho-Tyr1161) | IGF-1R (Ab-1161) | 1.373625731 | 1.366458719 | 0.99 |
| Integrin beta-3 (Phospho-Tyr773) | Integrin beta-3 (Ab-773) | 0.982494339 | 0.979691639 | 1.00 |
| Keratin 18 (Phospho-Ser33) | Keratin 18 (Ab-33) | 1.544149178 | 1.541974046 | 1.00 |
| GSK3 beta (Phospho-Ser9) | GSK3 beta (Ab-9) | 1.229211415 | 1.231616635 | 1.00 |
| FAK (Phospho-Tyr861) | FAK (Ab-861) | 1.246727301 | 1.265083413 | 1.01 |
| HDAC8 (Phospho-Ser39) | HDAC8 (Ab-39) | 1.276072195 | 1.29572945 | 1.02 |
| c-Jun (Phospho-Ser243) | c-Jun (Ab-243) | 0.801891185 | 0.817173221 | 1.02 |
| Integrin beta-3 (Phospho-Tyr785) | Integrin beta-3 (Ab-785) | 0.995267072 | 1.015035732 | 1.02 |
| BAD (Phospho-Ser112) | BAD (Ab-112) | 1.124370087 | 1.15468039 | 1.03 |
| Chk1 (Phospho-Ser317) | Chk1 (Ab-317) | 1.042771278 | 1.073853458 | 1.03 |
| BAD (Phospho-Ser136) | BAD (Ab-136) | 1.652586265 | 1.721881712 | 1.04 |
| NFkB-p105/p50 (Phospho-Ser907) | NFkB-p105/p50 (Ab-907) | 1.124008228 | 1.175752184 | 1.05 |
| Chk2 (Phospho-Ser516) | Chk2 (Ab-516) | 0.882912318 | 0.924708425 | 1.05 |
| p21Cip1 (Phospho-Thr145) | p21Cip1 (Ab-145) | 1.128235231 | 1.184705353 | 1.05 |
| p27Kip1 (Phospho-Ser10) | p27Kip1 (Ab-10) | 1.576096491 | 1.657796258 | 1.05 |
| Shc (Phospho-Tyr349) | Shc (Ab-349) | 0.90905601 | 0.956398979 | 1.05 |
| P38 MAPK (Phospho-Tyr182) | P38 MAPK (Ab-182) | 0.272999551 | 0.289213363 | 1.06 |
| MEK2 (Phospho-Thr394) | MEK2 (Ab-394) | 1.207165039 | 1.280730526 | 1.06 |
| STAT1 (Phospho-Ser727) | STAT1 (Ab-727) | 1.527911018 | 1.621537642 | 1.06 |
| Rb (Phospho-Ser780) | Rb (Ab-780) | 0.749743035 | 0.796436258 | 1.06 |
| Akt2 (Phospho-Ser474) | Akt2 (Ab-474) | 1.327540754 | 1.419641264 | 1.07 |
| NFkB-p100/p52 (Phospho-Ser865) | NFkB-p100/p52 (Ab-865) | 0.583876789 | 0.627895188 | 1.08 |
| SHP-2 (Phospho-Tyr580) | SHP-2 (Ab-580) | 1.42393987 | 1.53969381 | 1.08 |
| AMPK1 (Phospho-Thr174) | AMPK1 (Ab-174) | 1.557669903 | 1.694690482 | 1.09 |
| CDK2 (Phospho-Thr160) | CDK2 (Ab-160) | 1.138415003 | 1.243811816 | 1.09 |
| Raf1 (Phospho-Ser259) | Raf1 (Ab-259) | 0.77915804 | 0.853179475 | 1.10 |
| Chk2 (Phospho-Thr68) | Chk2 (Ab-68) | 0.859213553 | 0.943780333 | 1.10 |
| FKHR (Phospho-Ser256) | FKHR (Ab-256) | 0.818106015 | 0.908482618 | 1.11 |
| TYK2 (Phospho-Tyr1054) | TYK2 (Ab-1054) | 1.208315044 | 1.342495518 | 1.11 |
| Chk1 (Phospho-Ser280) | Chk1 (Ab-280) | 1.405465572 | 1.566394915 | 1.11 |
| c-Jun (Phospho-Ser73) | c-Jun (Ab-73) | 0.208381165 | 0.233043575 | 1.12 |
| Beta-Catenin (Phospho-Thr41/Ser45) | Beta-Catenin (Ab-41/45) | 1.561393152 | 1.758002937 | 1.13 |
| BCL-2 (Phospho-Ser70) | BCL-2 (Ab-70) | 1.093494351 | 1.23242779 | 1.13 |
| PDK1 (Phospho-Ser241) | PDK1 (Ab-241) | 0.77286827 | 0.886700202 | 1.15 |
| NFkB-p100/p52 (Phospho-Ser869) | NFkB-p100/p52 (Ab-869) | 0.962211277 | 1.117210682 | 1.16 |
| Beta-Catenin (Phospho-Ser37) | Beta-Catenin (Ab-37) | 0.772923099 | 0.902213269 | 1.17 |
| Caveolin-1 (Phospho-Tyr14) | Caveolin-1 (Ab-14) | 1.727489605 | 2.025217672 | 1.17 |
| VEGFR2 (Phospho-Tyr951) | VEGFR2 (Ab-951) | 0.165231286 | 0.19373722 | 1.17 |
| NFkB-p105/p50 (Phospho-Ser893) | NFkB-p105/p50 (Ab-893) | 0.912569966 | 1.077296462 | 1.18 |
| Estrogen Receptor-alpha (Phospho-Ser167) | Estrogen Receptor-alpha (Ab-167) | 1.397783319 | 1.67556349 | 1.20 |
| Myc (Phospho-Thr58) | Myc (Ab-58) | 1.038891439 | 1.248259939 | 1.20 |
| HER2 (Phospho-Tyr877) | HER2 (Ab-877) | 1.410503597 | 1.71645869 | 1.22 |
| ICAM-1 (Phospho-Tyr512) | ICAM-1 (Ab-512) | 2.086383987 | 2.555767095 | 1.22 |
| Akt (Phospho-Ser473) | Akt (Ab-473) | 0.787936476 | 0.968590517 | 1.23 |
| BCL-XL (Phospho-Ser62) | BCL-XL (Ab-62) | 0.141542421 | 0.17480476 | 1.23 |
| BRCA1 (Phospho-Ser1524) | BRCA1 (Ab-1524) | 0.603557988 | 0.748725965 | 1.24 |
| PTEN (Phospho-Ser380/Thr382/Thr383) | PTEN (Ab-380/382/383) | 0.644335784 | 0.801502933 | 1.24 |
| Akt (Phospho-Thr308) | Akt (Ab-308) | 0.739653601 | 0.937721701 | 1.27 |
| Src (Phospho-Tyr418) | Sty (Ab-418) | 0.228090157 | 0.290208117 | 1.27 |
| JunB (Phospho-Ser79) | JunB (Ab-79) | 1.26164446 | 1.611336032 | 1.28 |
| BCL-2 (Phospho-Thr56) | BCL-2 (Ab-56) | 1.015364419 | 1.30853697 | 1.29 |
| CREB (Phospho-Ser133) | CREB (Ab-133) | 0.750202904 | 0.999545909 | 1.33 |
| NFkB-p65 (Phospho-Thr254) | NFkB-p65 (Ab-254) | 0.863913306 | 1.156196348 | 1.34 |
| STAT6 (Phospho-Tyr641) | STAT6 (Ab-641) | 1.319833119 | 1.796965517 | 1.36 |
| cdc25C (Phospho-Ser216) | cdc25C (Ab-216) | 0.175394901 | 0.239431313 | 1.37 |
| JunD (Phospho-Ser255) | JunD (Ab-255) | 1.27640738 | 1.772525337 | 1.39 |
| STAT6 (Phospho-Thr645) | STAT6 (Ab-645) | 0.391640547 | 0.561082695 | 1.43 |
| JAK2 (Phospho-Tyr221) | JAK2 (Ab-221) | 0.869563011 | 1.276100781 | 1.47 |
| JunB (Phospho-Ser259) | JunB (Ab-259) | 1.211644149 | 1.841459559 | 1.52 |

TABLE 3-continued

Ratio Analysis for Paired Antibodies

| Antibody List | | Signal Ratio | | Fold Change |
| --- | --- | --- | --- | --- |
| | | 4000022475 (Con) | 4000022476 (KD) | KD/Con |
| STAT3 (Phospho-Ser727) | STAT3 (Ab-727) | 1.010848023 | 1.573108445 | 1.56 |
| STAT1 (Phospho-Tyr701) | STAT1 (Ab-701) | 1.280646735 | 2.065109643 | 1.61 |
| STAT5A (Phospho-Ser780) | STAT5A (Ab-780) | 0.194376876 | 0.316362771 | 1.63 |
| STAT5A (Phospho-Tyr694) | STAT5A (Ab-694) | 1.146375693 | 1.91655525 | 1.67 |
| Myc (Phospho-Thr358) | Myc (Ab-358) | 0.300234217 | 0.542465691 | 1.81 |
| STAT3 (Phospho-Tyr705) | STAT3 (Ab-705) | 0.988335041 | 1.88976234 | 1.91 |
| JAK2 (Phospho-Tyr1007) | JAK2 (Ab-1007) | 0.761005787 | 1.457101371 | 1.91 |
| STAT4 (Phospho-Tyr693) activating | STAT4 (Ab-693) | 0.933033764 | 1.897658458 | 2.03 |
| Myc (Phospho-Ser373) | Myc (Ab-373) | 0.809399042 | 1.683082156 | 2.08 |

The array involves: 1) Protein extraction with non-denaturing lysis buffer; 2) Biotinylation of protein samples; 3) Incubation of labeled samples with antibody array; and 4) Detection by dye conjugated streptavidin. Biological triplicates of FERK5 knockdown or control SU-DIPG IV cells were pooled and assayed on two independent arrays. The array was performed as per the manufacturer's protocol with image quantification and analysis performed by Full Moon Biosystems data service.

Immunohistochemistry

Paraffin embedded blocks were cut in 5 µm sections. Slides were processed as follows: de-waxed in xylene followed by rehydration in a standard alcohol series. Antigen retrieval was by pressure cooking for 20 minutes in citrate buffer (pH 6.0), followed by blocking of endogenous peroxidase in 3% $H_2O_2$. The antibodies were added and incubated overnight at 4° C. Antibodies were detected using a secondary-HRP labeled mouse or rabbit antibody detection system (Dako EnVision+ System-HRP cat #k4401, cat #k4403) followed by addition 3,3'-Diaminobenzidine (DAB) chromagen (Vector Labs) for visualization. Sections were counter-stained with hematoxylin (Fisher Scientific Inc., Canada) and slides dehydrated in 70, 80, and 100% ethanol and xylene. Slides were cover slipped and mounted in Permount (Fisher Scientific Inc.). Antibodies and concentrations for IHC are as follows: Ki67 (1:100, Dako, cat #F7268). All images were captured on a Leica DM 100 microscope using Leica Application Suite Software (Switzerland, Version 3.8.0).

Gene-Expression and Copy Number Analysis

Copy number analysis of ERK5, PDGFRA, and NF1 was performed using the Mackay et al. dataset (Mackay et al., Cancer cell 2017; 32:520-37 e5) using the pediatric cBioPortal website (https://pedcbioportal.org/). Using the R2 software (http://r2.amc.nl), the present disclosure analyzed gene expression levels in normal brain and two independent, non-overlapping patient cohorts (Paugh et al., Journal of clinical oncology: official journal of the American Society of Clinical Oncology 2010; 28:3061-8; Berchtold et al., Proceedings of the National Academy of Sciences of the United States of America 2008; 105:15605-10).

RASAL1 Promoter Methylation Assay.

Methylated DNA immunoprecipitation was performed as previously described (Paugh et al., Journal of clinical oncology: official journal of the American Society of Clinical Oncology 2010; 28:3061-8; Berchtold et al., Proceedings of the National Academy of Sciences of the United States of America 2008; 105:15605-10). Briefly, methylated DNA was captured using the Methylamp MethylatedDNA capture Kit (Epigentek). Methylation specific PCR and electrophoresis of PCR products were performed.

Real Time Quantitative Polymerase Chain Reaction

Total RNA isolation was performed using an RNA extraction kit according to the manufacturer's instructions (RNeasy kit, Qiagen). cDNA was synthesized from 100 ng of total RNA using the Quantitect RT kit which included DNAse treatment (Qiagen). Quantitative real-time PCR was performed on 10 ng of cDNA template in a final volume of 20 µl using the Chromo4 Real Time PCR detector (MJ Research, a Division of Bio-Rad Laboratories Ltd) using SYBR green fluorescence. RT-PCR data was analyzed using Opticon Monitor 3.1.3 analysis software. Data analysis was done using the delta CT method with HPRT1 as a reference/control gene. Specific Primers are available in Table 4.

TABLE 4

Primer Sequence

| GENE | FWD Primer 5'-->3' | REV Primer 5'-->3' | FWD start | REV end | Amplicon Size (bp) |
| --- | --- | --- | --- | --- | --- |
| RASA1 | GGGACATCC AATAAACGC CTTCG | TTTGCTACT TGGACACTA TTCAGG | 1949 | 2079 | 130 |
| RASA2 | CTCACCTAC CACAAACAG CCAG | CCTGGACAT AGAGTGGTT TCTCC | 1949 | 2099 | 150 |
| RASA3 | TTCCACGCC ATCACTGAG TCTG | GGCGCAAAG AACCTCAGG AAGA | 1912 | 2066 | 154 |
| RASA4 | GCTGAAGGA CTTCATCAC CAAGC | TTGCCCTTG GTCCTGTGG ATGA | 1683 | 1811 | 128 |
| RASAL1 | CTCCAGCAG AAGCCACCT AAAG | TCCATGAG AGGCTGGT AGCACT | 965 | 1116 | 151 |
| RASAL2 | CCAAATGTC AGTGGAAGC CTCTC | CTGTGTTG TCCTGGCT TGGAGA | 2031 | 2133 | 102 |
| RASAL3 | CCTCACACT GATTGCCAA GGTC | TACCTGGT CCAGGAAG CATTGC | 148 | 302 | 154 |

TABLE 4-continued

Primer Sequence

| GENE | FWD Primer 5'-->3' | REV Primer 5'-->3' | FWD start | REV end | Amplicon Size (bp) |
|---|---|---|---|---|---|
| NF1 | GCCTTGAGGAAAACCAGCGGAA | TCCTACTGCACCGATGCTGTTC | 4375 | 4538 | 163 |
| DAB2IP | TCATCGCCAAGGTCACCCAGAA | CGCTGCATGTTGGTCCACTCAT | 1661 | 1772 | 111 |
| SYNGAP | CAACCTGCGAATGTGCTGTGAG | CGCTGATAAGCCTGTCTGCGAT | 1818 | 1966 | 148 |
| HRAS | ATGACGGAATATAAGCTGGTGGT | GGCACGTCTCCCCATCAATG | 206 | 359 | 153 |
| ERAS | CAGTAGACACAAAACAGGCTCAG | TGTCGGATCTCCCTCACCAATG | 563 | 686 | 123 |
| NRAS | GAAACCTCAGCCAAGACCAGAC | GGCAATCCCATACAACCTGAG | 681 | 808 | 127 |
| AURKA | GGAGAGCTTAAAATTGCAGATTTTG | GCTCCAGAGATCCACCTTCTCAT | 1312 | 1452 | 140 |
| LAMTOR3 | GTGGTGAGTTTCATAGCCAGCAG | AGAAACTTCCACAACTTGTCTCAG | 493 | 600 | 107 |
| LIN28A | CCAGTGGATGTCTTTGTGCACC | GTGACACGGATGGATTCCAGAC | 338 | 453 | 115 |
| LIN28B | CCTGTTTAGGAAGTGAAAGAAGAC | CACTTCTTTGGCTGAGGAGGTAG | 520 | 655 | 135 |
| MAP2K3 | CTACATGCCCCTGAGAGGAT | TCCAGACGTCGGACTTGACA | 1077 | 1147 | 70 |
| MAP2K5 | CCTTCCAGTTGGAGAGTTCTCG | CGGCATTTCCATCATTGAACTGC | 1215 | 1351 | 136 |
| MAP3K2 | TACACCCGTCAGATTCTGAGG | ATGGTCTGAAGCCGTTTGCTGG | 1534 | 1679 | 145 |
| MAP3K7 | CAGAGCAACTCTGCCACCAGTA | CATTTGTGGCAGGAACTTGCTCC | 1343 | 1445 | 102 |
| MAPK7 | GCTGATGGGCCACAGGAT | TGGAGGTCAGGCAGGTCAG | 2453 | 2616 | 163 |
| MYC | CGTCTCCACACATCAGCACA | CACTGTCCAACTTGACCCT | 2105 | 2190 | 85 |
| PDGFRA | GGCATTCTTTGCAATACTGCTTAA | CATCTGCCGATAGCACAGTGA | 5303 | 5391 | 88 |
| ZAK | GCAGTCCAACTTGCCATTCAGAC | CCTCAGAGTATCTAACCACTGGC | 1832 | 1934 | 102 |

Animal Xenograft Studies

All animal procedures were carried out ethically according to animal user protocols approved by Institutional Animal Care Committee (IACUC). 4-6 week-old non-obese diabetic severe combined immune deficiency male or female mice (NOD-SCID-Prkdc$^{scid}$) were injected with $1 \times 10^5$ SU-DIPG-13p cells or $1 \times 10^5$ SF8628 DIPG cells. Cells were re-suspended in 2 μl of PBS and injected into the pons/midbrain using a stereotactic frame (Stoelting) and automated cell injector (Stoelting) with cells delivered over 4 minutes. Coordinates were as follows from the Lambda suture (x=0.8 mm, y=−0.8 mm, z=−5.0 mm). Ten days post injection mice were randomized into two groups: vehicle, and TG02 (20 mg/kg). Mice were treated for two cycles (5 days on, with two days off per cycle). Mice were sacrificed at sign of neurological duress and brains were extracted and fixed in 4% PFA.

Statistical Analysis

Statistical analysis was performed in GraphPad Prism 7.0 (La Jolla, Calif.). All in vitro experiments were performed in biological triplicates unless otherwise stated. Values reported are the mean and standard error of the mean. Analysis of variance (ANOVA) was conducted for multi-group comparisons followed by a post-hoc Tukey's test or post-hoc Dunnett's test to identify differences within groups. Z-score analysis was performed to identify significant genes from the siRNA screen and from the cancer phospho proteomic array. Survival analysis was performed using the Log-Rank Survival test. For direct pairwise comparisons where appropriate, an unpaired two-tailed Student's t-test was used. Significance was established as $*p<0.05$, $p<0.01$, $*p<0.001$.

Results

H3K27M Activates RAS in Neural Stem Cells

H9 derived neural stem cells (NSC) were stably transfected with lentivirus expressing the mutant H3F3A K27M (H3K27M) and a selectable puromycin marker. Introduction of H3K27M promoted increased proliferation from 96 h onwards, as compared to NSC expressing wildtype H3F3A or empty vector controls (FIG. 1A). H3K27M mutant protein expression was confirmed by immunoblotting (FIG. 1B). Expression of H3K27M in NSCs leads to the reduction of H3 trimethylated Lysine 27 (H3K27Me3, FIG. 1B).

Given the relevance of activated RAS in cell growth, the present disclosure hypothesised that H3K27M may promote proliferation through activation of RAS. A pan-RAS activity pulls down assay confirmed that H3K27M mutant NSC lines harbored activated RAS as well as activated downstream signaling mediator phospho ERK1/2 (FIG. 1C). Increased active RAS was confirmed by densitometry (FIG. 1D). Stable expression of H3 WT did not increase activated RAS (FIGS. 1C-1D).

The present disclosure next performed siRNA knockdown of three major RAS isoforms (NRAS, KRAS, and HRAS) in NSCs expressing empty vector control, H3 WT, or H3K27M. Compared to scrambled control siRNA, loss of HRAS, KRAS, and NRAS had modest effects on cell proliferation in NSCs expressing empty vector control or wildtype H3 but had a significant effect on proliferation in H3K27M NSCs (FIGS. 1E-1G; FIGS. 8A-8C). Compared to control or H3 WT, H3K27M expressing NSCs treated with RAS siRNA had the greatest degree of apoptosis as evaluated by activated cleaved Caspase 3/7 (FIG. 8D). Reduced RAS expression was confirmed by quantitative reverse transcriptase real-time PCR (qRT-PCR, FIGS. 1E-1G). The present disclosure compared the H3K27M NSCs to patient derived H3K27M expressing DIPG cell lines: SU-DIPG-IV (DIPG-IV), HSJD-DIPG-007 (DIPG-007), and HSJD- DIPG-13p (DIPG-13p). Compared to NSC H3K27M, DIPG lines harbored significantly more active RAS (FIGS. 1H-1I, ***p<0.001).

DIPG cells harbor amplification of PDGFRA and loss of NF1, both of which result in RAS activation. The present disclosure hypothesized that H3K27M expression would be additive with known drivers of RAS signaling. Interestingly, overexpression of PDGFRA in NSCs increased activated RAS comparably to that of H3K27M, and combined PDGFRA+H3K27M expression was additive with respect to effect on activated RAS levels (FIGS. 1J-1M, *p<0.05). Active RAS pull downs in DIPG lines harbouring H3K27M mutations have comparable active RAS to hemispheric high-grade gliomas (FIGS. 1N-1O). Interestingly, CNMC-XD-760, an H3 wildtype DIPG cell line, had the least active RAS (FIGS. 1N-1O).

The Polycomb repressive complex 2 (PRC2) has histone methyltransferase activity and trimethylates H3K27 via EZH2 subunit activity. H3K27M inhibits EZH2 function with respect to H3K27 trimethylation (H3K27Me3). The present disclosure investigated whether pharmacologic inhibition of EZH2 would have similar effects on H3K27 methylation as ectopic H3K27M expression. EZH2 inhibition by GSK343 (5 µM) resulted in loss of H3K27Me3 and reduced cell proliferation (FIGS. 9A-9B). In addition, EZH2 inhibition but not H3K27M resulted in activation of the CDKN2A locus as indicated by p16 protein immunoblot results (FIGS. 9A-9B). Also, EZH2 inhibition did not result in RAS activation as observed with H3K27M, but rather in reduced activated RAS (FIG. 9A).

Deregulation of RTKs in H3K27M Neural Stem Cells and DIPGs

RAS has weak intrinsic guanosine triphosphatase (GTPase) activity and the conversion of active RAS to its inactive state is highly dependent on RAS GTPase-activating proteins. At least ten different RAS-GAPs have been identified with only NF1 being reported as mutated or inactive in DIPG. The present disclosure hypothesized that H3K27M expressing NSC and DIPG cells may suppress the expression and/or activity of additional RAS-GAP genes. The present disclosure performed qRT-PCR for ten RAS-GAP proteins comparing NSC empty vector cells to H3K27M expressing NSCs and identified five RAS-GAPs (RASA3, RASAL1, RASA3, DAB2IP, and NF1) as significantly down-regulated in H3K27M NSCs compared to control cells (FIG. 2A, *p<0.05). Two of these, DAB2IP and RASAL1, were indicated as significantly down-regulated in independent DIPG datasets, as compared to normal brain (FIGS. 9C-9D, *p<0.05). In a limited patient cohort, the present disclosure confirmed loss of RASAL1 protein in DIPG tissue from three patients compared to three samples of normal pediatric pons tissue (FIG. 9E). Immunoblotting confirmed down-regulation of RASAL1 in NSC H3K27M cells and DIPG primary cell lines, as compared to NSC and normal human astrocytes (NHA) (FIG. 2B, *p<0.05). RASA3, although down-regulated at the transcript level, was not altered at the protein level (FIG. 2B, *p<0.05). Ectopic expression of hemagglutinin (HA) tagged RASAL1 reduced activated RAS in H3K27M NSC and DIPG-007 cells and reduced cell proliferation (FIGS. 2C-2D, *p<0.05). Ectopic expression of RASAL1 in cells was comparable to protein levels observed in NHAs and NSCs (FIG. 9F).

The present disclosure hypothesized that H3K27M results in loss of RASAL1 by promoter methylation, given this mutation results in epigenetic reorganization by loss of H3K27Me3 and altered DNA methylation (Fangusaro et al., Journal of child neurology 2009; 24:1409-17). Moreover, RASAL1 promoter methylation has been observed in cardiac fibrosis, gastric cancer, and liver cancer (Berchtold et al., Proceedings of the National Academy of Sciences of the United States of America 2008; 105:15605-10; Khuong-Quang et al., Acta neuropathologica 2012; 124:439-47; Hashizume et al., Nature medicine 2014; 20:1394-6). The present disclosure observed significantly increased RASAL1 promoter methylation in DIPG-007, DIPG-13p, and H3K27M-expressing NSC cells compared to NSC control cells as evaluated by methylation specific PCR analysis (MSP) (FIG. 9G, *p<0.05). Strikingly, treatment of DIPG-007 and NSC H3K27M cells with decitabine for 5 days restored expression of RASAL1 protein (FIG. 9H).

Figure 2J:
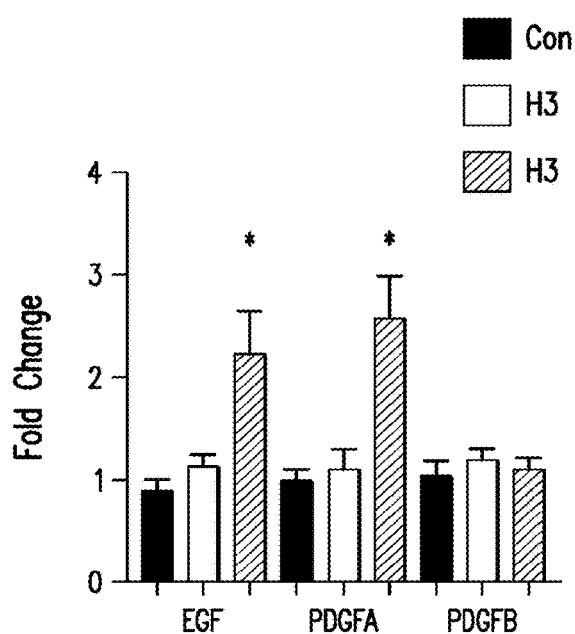
Figure 2K:
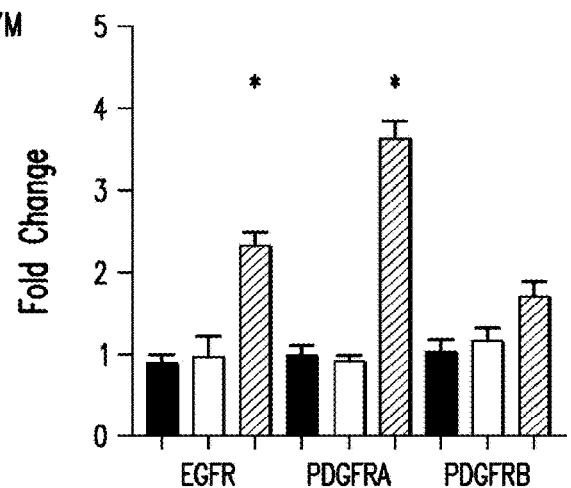
Figure 2L:
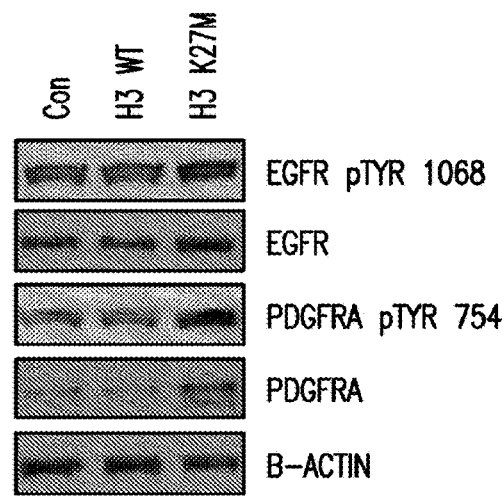

H3K27M mutations may de-regulate receptor tyrosine kinases (RTKs) involved in gliomagenesis as a potential source of RAS activation. qRT-PCR confirmed up-regulation of RTK growth factors EGF, PDGFA but not PDGFB (FIG. 2J, *p<0.05). An increased RNA expression of major glioma RTKs PDGFRA and EGFR was also observed (FIG. 2K, *p<0.05). It was confirmed that H3K27M NSCs but not control or H3 wildtype expressing NSC had increased total and activated PDGFRA (FIG. 2L).

siRNA Screening Identifies Novel Effectors of RASsignaling Important to DIPG Cells The RAS pathway is critical for tumor cell conversion of external signals from mitogens into signal transduction events that promote cell growth and proliferation (FIG. 2E). Given the importance of H3K27M in activating RAS signaling and promoting cell proliferation, the present disclosure set out to identify effectors of RAS signaling that are critical for its proliferative effect. To accomplish this, the present disclosure performed a targeted siRNA screen focused on 294 genes known to directly activate, inactivate, or cooperate with RAS pathway signaling (FIG. 2E, FIG. 32).

The viability of NSC control, NSC H3K27M, and DIPG-007 cells was assessed at 96 h post siRNA transfection. The present disclosure next performed Z-score analysis of three individual experiments to identify gene suppressions that selectively target NSCs-H3K27M cells (FIG. 2F). Twenty-six genes were identified that when silenced led to inhibition of NSC-H3K27M growth (viability change >−40%, Z-score <−2, *p<0.05), and 15 genes were identified for which inhibition accelerated growth (viability change >40%, Z-score >2, *p<0.05) (FIG. 2F, FIG. 32). To complement the NSC data, the present disclosure performed a validation siRNA screen in DIPG-007 cells and identified 27 genes that when silenced led to inhibition of NSC-H3K27M growth (viability change >−50%, Z-score <−2, *p<0.05) and 6 genes where inhibition accelerated growth viability change >30%, Z-score >2, *p<0.05) (FIG. 2G, FIG. 32). Twenty-six genes were identified in both screens (FIG. 2H). Interestingly, AKT2, AURKA, AURKB, MYC, and PDGFRA, previously identified as important oncogenes in DIPG, were identified by this approach. The present disclosure next rescreened and validated the top 10 candidates based on greatest viability decline at day 5 treatment, using two independent siRNAs per gene target to reduce the potential of off target effects that can be caused by pooled siRNA, with MYC and PDGFRA used as positive controls in DIPG-007 cells (FIG. 2I and FIGS. 10A-10F). siRNA knockdown efficiency was validated by qRT-PCR and reduced cell viability was confirmed for all 10 genes using a second set of siRNAs and in NSC and NSC H3K27M cells (FIGS. 10A-10F).

ERK5 is Active and Expressed in DIPG

Figure 3C:
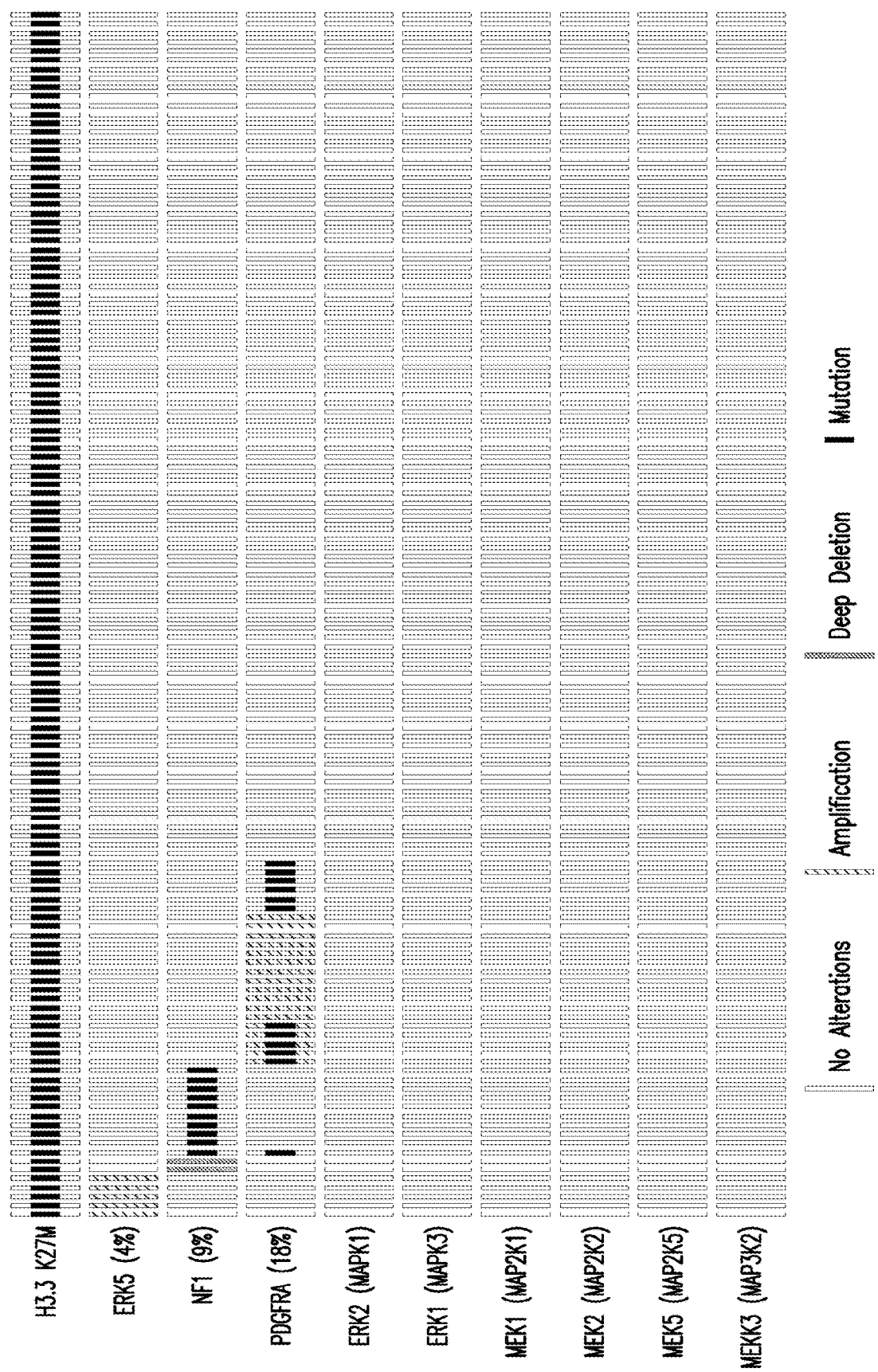
Figure 3D:
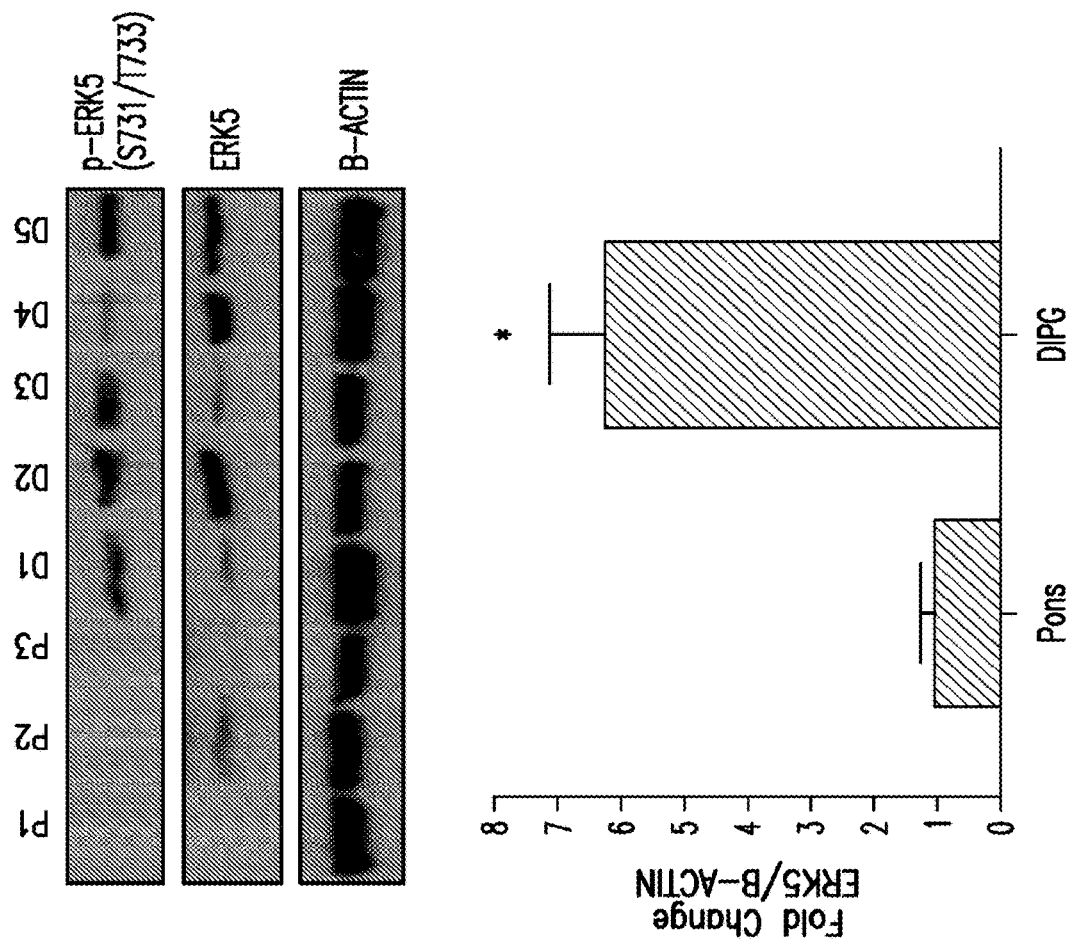
Figures 3E, 3F:
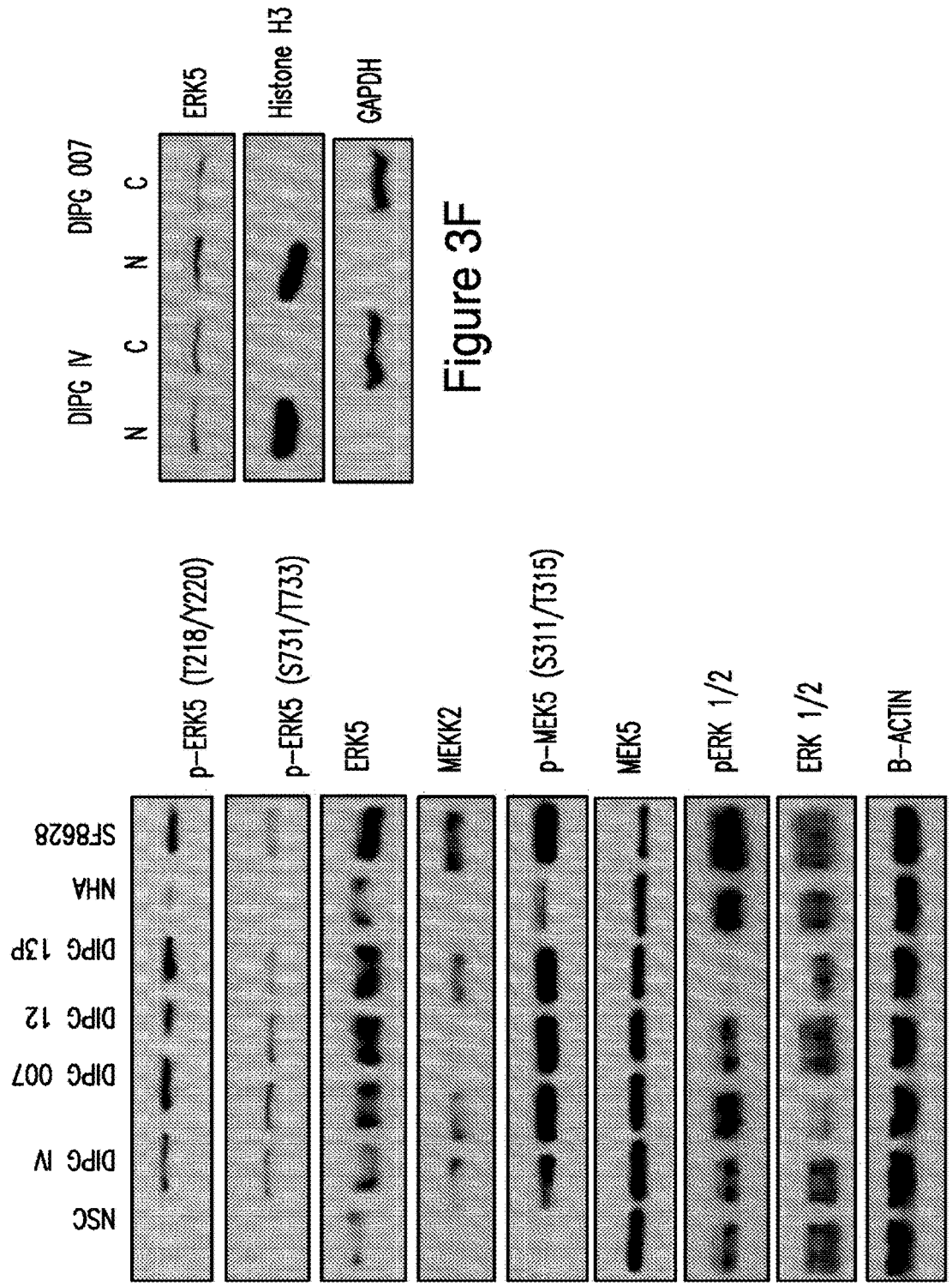
Figure 3G:
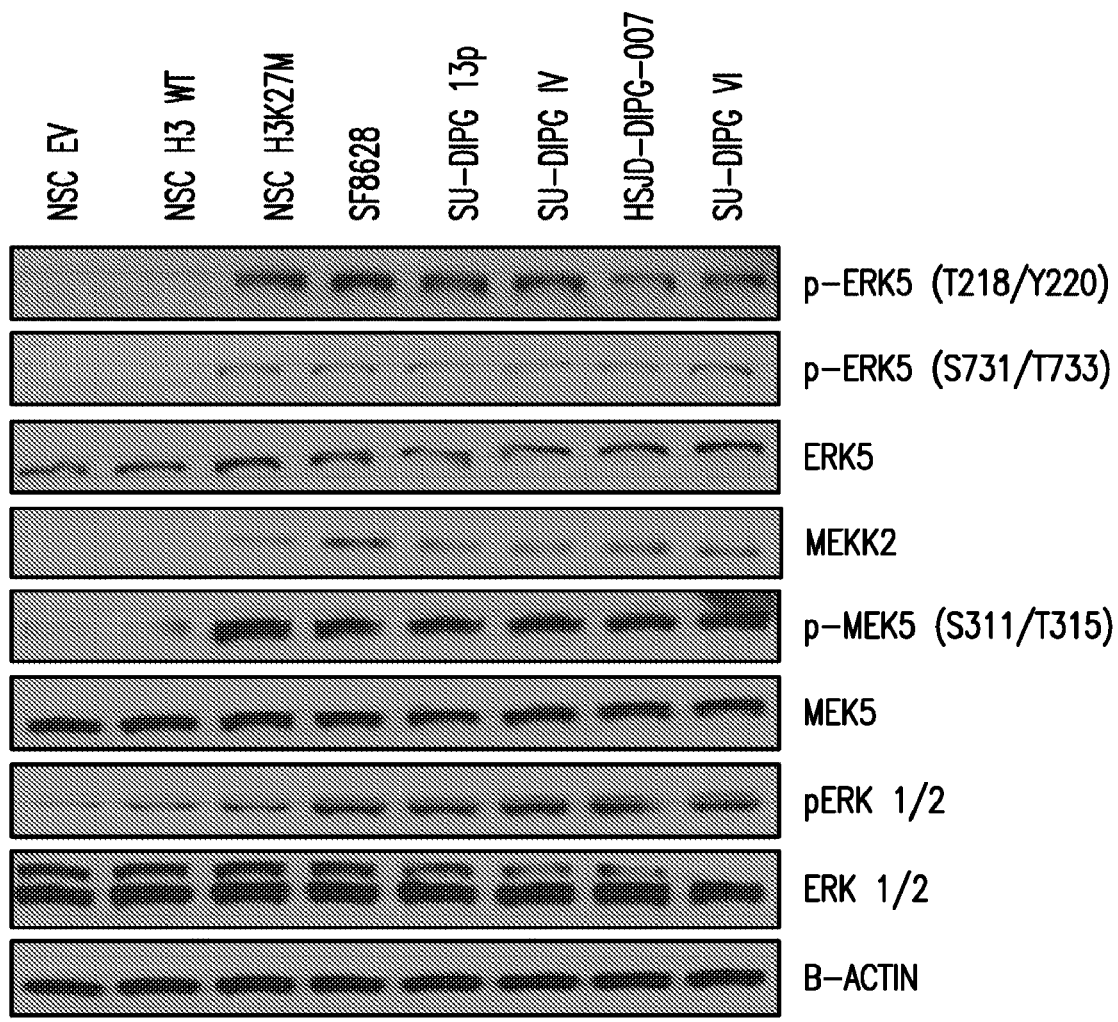
Figure 3H:
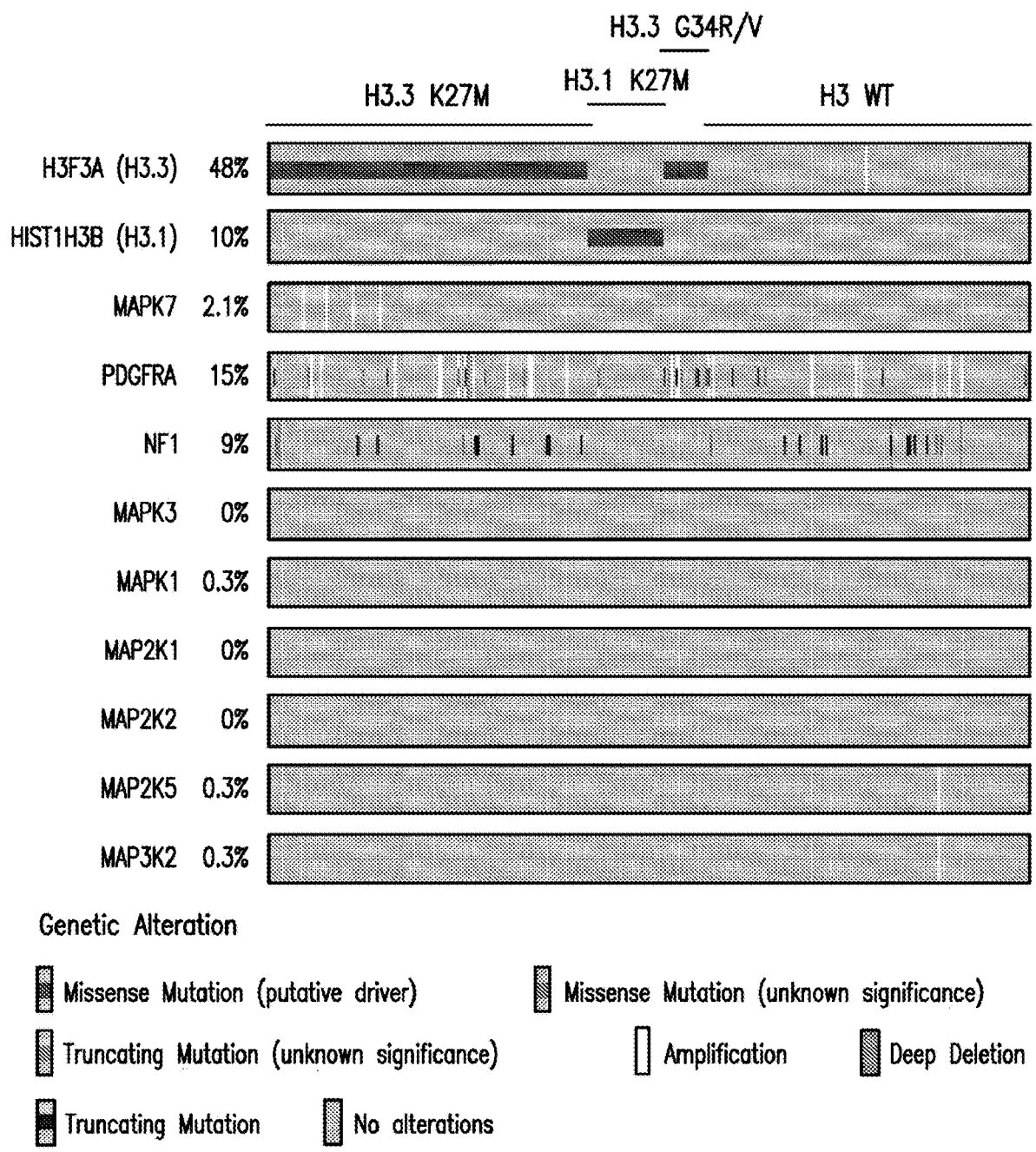
Figure 3I:
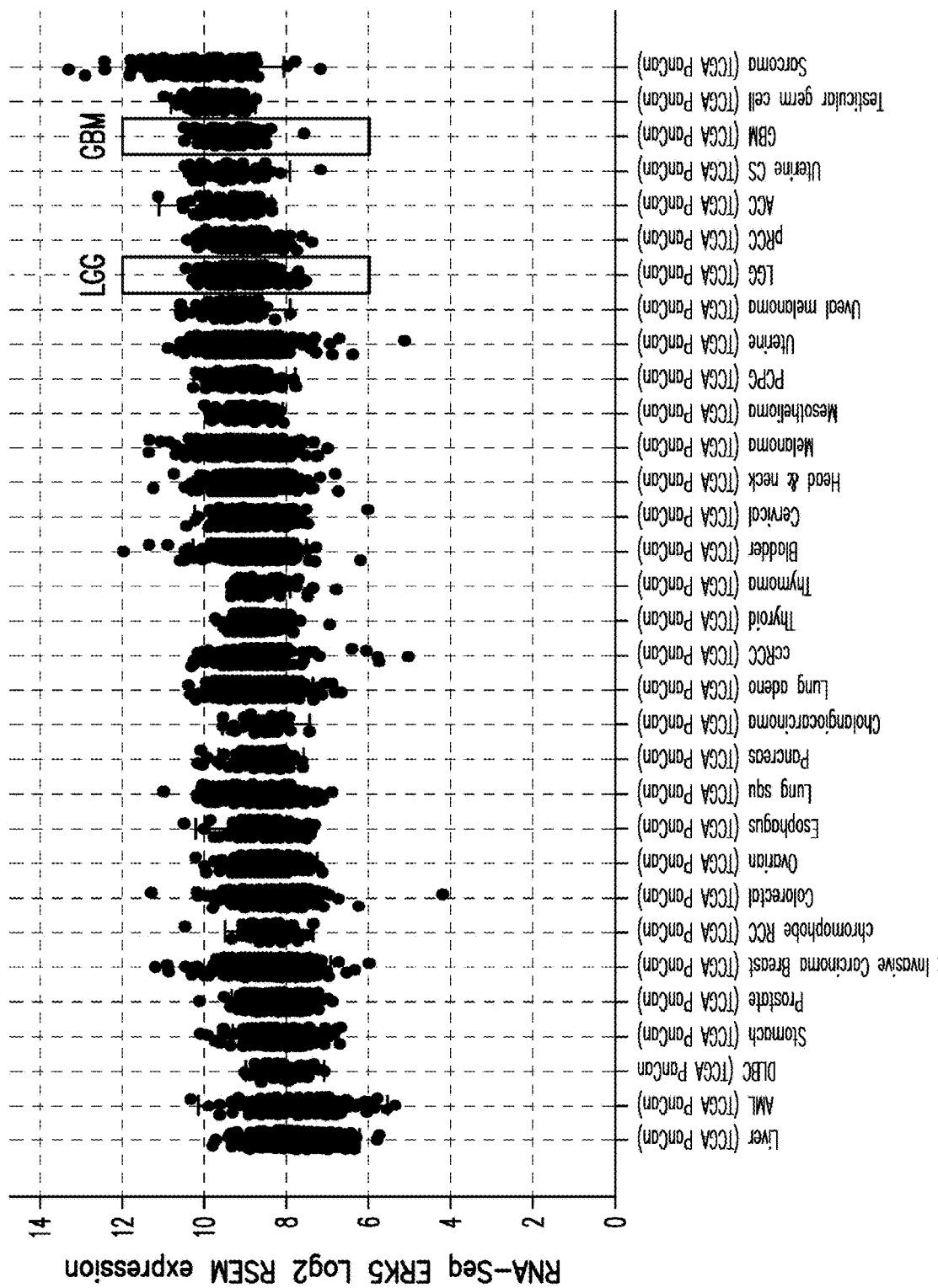

Strikingly, three of the validated targets MAP3K2 (MEKK2), MAP2K5 (MEK5), and MAPK7 (ERK5) are interconnected and form the MEKK2-MEK5-ERK5 signaling cascade that signals in parallel with the more commonly studied RAF-MEK1/2-ERK1/2 signaling cascade (FIG. 3A). The present disclosure confirmed that the H3K27M NSCs expressed elevated phospho ERK5 compared to empty vector control NSCs (FIG. 3B). Although low in frequency, the present disclosure observed 4% of DIPG tumors have high-level amplification of the ERK5 gene. Interestingly, ERK5 gene amplification was mutually exclusive with PDGFRA mutation or amplification and also exclusive with NF1 mutation or deletion, as indicated in a dataset of H3.3 K27M mutant PHGGs for which mutation and copy number information are available (FIG. 3C). The present disclosure observed no amplification or mutations in this dataset for ERK1, ERK2, ERK3, ERK4, MEKK1, or activators of ERK5, namely MEK5, MEKK2, and MEKK3. Moreover, the present disclosure found increased total and phospho ERK5 in five DIPG patient samples compared to three normal pediatric pons (FIG. 3D, *p<0.05). Immunoblotting confirmed increased total MEKK2, activated MEK5 (Phospho Ser311, Thr315), total ERK5, and activated ERK5 (Phospho Thr218, Tyr220 and Phospho Ser731 and Thr733) in DIPG cell cultures compared to NSCs and normal human astrocytes (NHAs) (FIG. 3E), or compared to NSCs empty vector and NSC H3 WT over-expressing controls (FIG. 3G). Furthermore, the present disclosure observed robust nuclear ERK5 protein expression in the cytoplasm and nucleus of DIPG-IV and DIPG-007 cells (FIG. 3F). Significant increased ERK5 transcription was observed in DIPG compared to normal brain (FIGS. 11A-11B, *p<0.05). Expanding the analysis into all pediatric high-grade glioma (PHGG) subgroups revealed two additional amplification events of ERK5 in H3WT PHGG and no amplifications of ERK or ERK2 (FIG. 3H). Given the importance of ERKs in glioma and cancer, the analysis performed in accordance with the present disclosure was expanded, and it was observed that GBM had one of the highest ERK5 RNA expression levels of all adult cancers from TCGA RNA seq data (FIG. 3I).

Loss of ERK5 Inhibits Growth of DIPG

To assess the long-term effect of ERK5 knockdown, the present disclosure generated doxycycline (Dox) inducible shRNA stable DIPG cell lines (SF8628, DIPG-IV, and DIPG-13p). For all three lines Dox treatment (2 μg/ml) resulted in complete ERK5 knockdown at the protein level (FIG. 4A) and reduced cell proliferation, as measured by Alamar blue viability assay and 5-bromo-2'-deoxyuridine (Brdu) incorporation (FIGS. 4B-4D, *p<0.05). A significant increase in Caspase 3/7 cleavage, which is indicative of apoptosis, was observed on day 5 in ERK5 knockdown cells compared to control cells (FIGS. 11C-11D, *p<0.05). Interestingly, loss of ERK5 resulted in reduction of phosphorylation of ERK1/2 but not phosphorylation of AKT (Ser473 and Thr308), both of which are key signaling mediators of major glioma proliferation and survival pathways, including for DIPG (FIG. 4A). To validate the ERK5 knockdown phenotype in vivo, the present disclosure generated an orthotopic DIPG xenograft by injection of DIPG-13p cells into the midbrain of NOD-SCID mice. Mice were randomized into two groups, a control group and one receiving doxycycline administered through drinking water (2 μg/ml) to induce sustained ERK5 knockdown. Mice receiving doxycycline had significantly longer overall survival compared to the control group (FIG. 4E, *p<0.05). Immunoblotting confirmed absence of ERK5 in the doxycycline group compared to the control group (FIG. 4F).

Figure 4G:
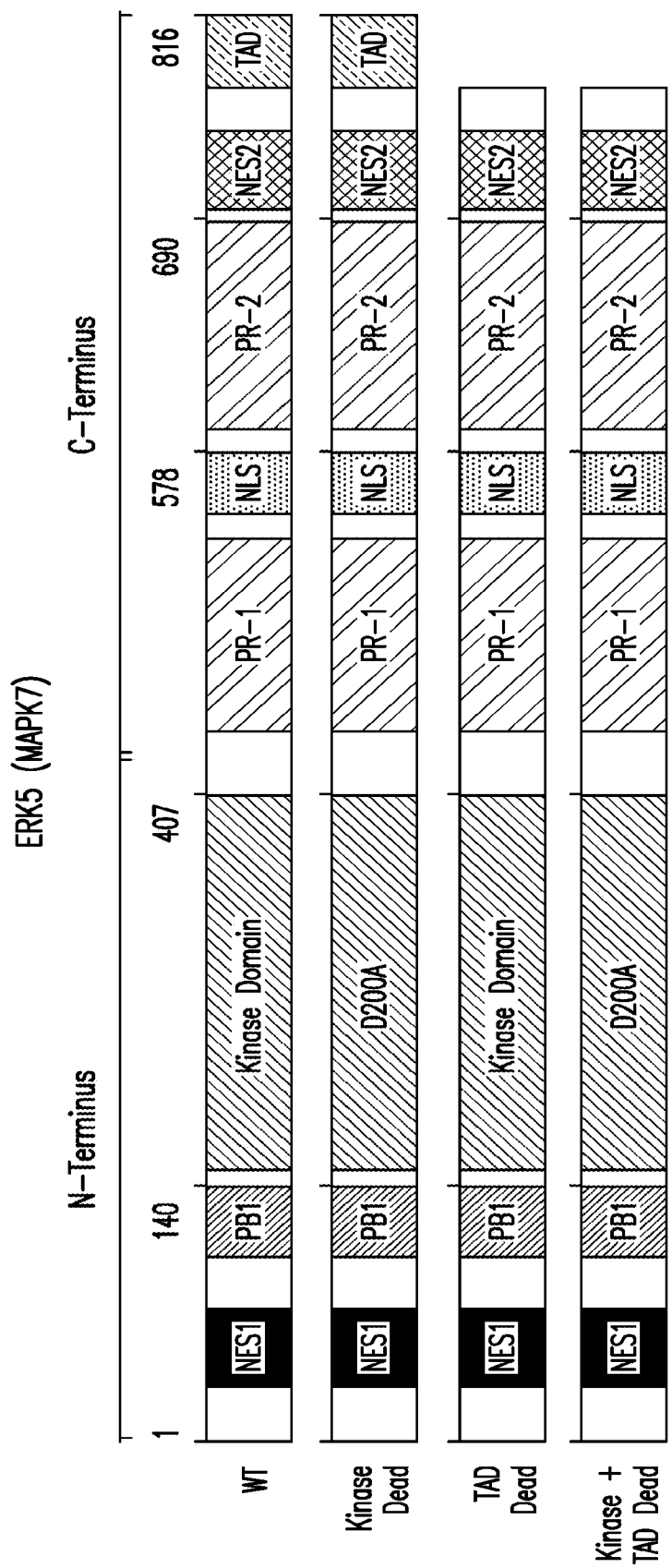

Unlike ERK1/2, ERK5 contains both a kinase domain and a transactivation domain. To ascertain which domain or domains are responsible for ERK5 function the present disclosure generated lentiviral constructs containing HA-tagged complete or partial ERK5 coding sequence: wild-type, kinase dead (D200A), transactivation domain deleted (delta TAD), and kinase dead with delta TAD (FIG. 4G). The present disclosure also generated another inducible ERK5 shRNA stable cell line in SF8628 cells, in which the shRNA targets the 3'UTR of ERK5 to prevent gene-silencing of transduced ERK5 constructs (FIG. 4H). Re-introduction of ERK5 in knockdown cells was confirmed post infection with HA immunoblotting in SF8628 cells (FIG. 4I). Full length ERK5 was able to rescue the proliferation defect caused by shRNA-mediated suppression, with the kinase dead and delta TAD constructs partially rescuing growth defects as evaluated by Brdu incorporation (FIGS. 4J-4K, *p<0.05). Expression of double dead (kinase dead, delta TAD) ERK5 had no pro-proliferative effect (FIGS. 4J-4K).

Pharmacological Inhibition of ERK5 Inhibits DIPG Tumor Growth and Promotes Apoptosis The present disclosure tested an ERK5 inhibitor that is specific for its effects on H3K27M cells: TG02 (CDK9 and ERK5 inhibitor). The present disclosure generated EC50 curves for DIPG-007 (FIGS. 5A, 5J), DIPG-IV (FIGS. 5B, 5K), SF8628 (FIGS. 12A-12C, 12G), and DIPG-13p cells (FIGS. 12B, 12H).

Next, the EC50 value of TG02 was evaluated in a DIPG histone wildtype H3 cell line, CNMC-XD-760 and hemispheric glioblastoma. CNMC-XD-760 had the highest EC50 values for TG02 compared to H3 mutant DIPG cells and hemispheric pGBM cells SU-pcGBM2 and HSJD-GBM-001 (FIG. 12I). NSCs and NSCs over expressing wildtype H3 also had higher TG02 EC50 values compared to H3K27M DIPG and hemispheric pGBM lines, but EC50 values were significantly lower in NSCs expressing H3K27M (FIG. 12I).

Figure 5G:
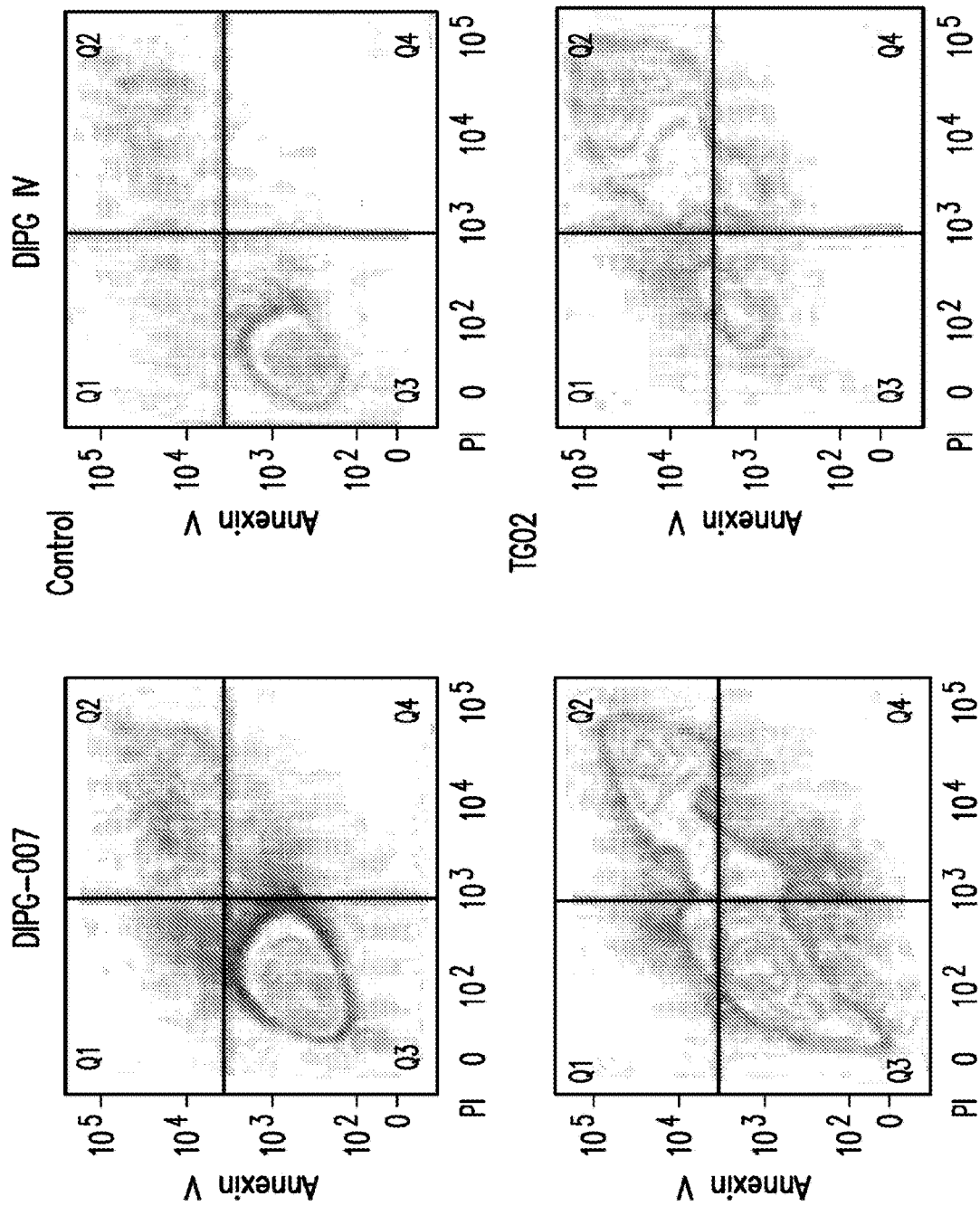
Figures 5H, 5I:
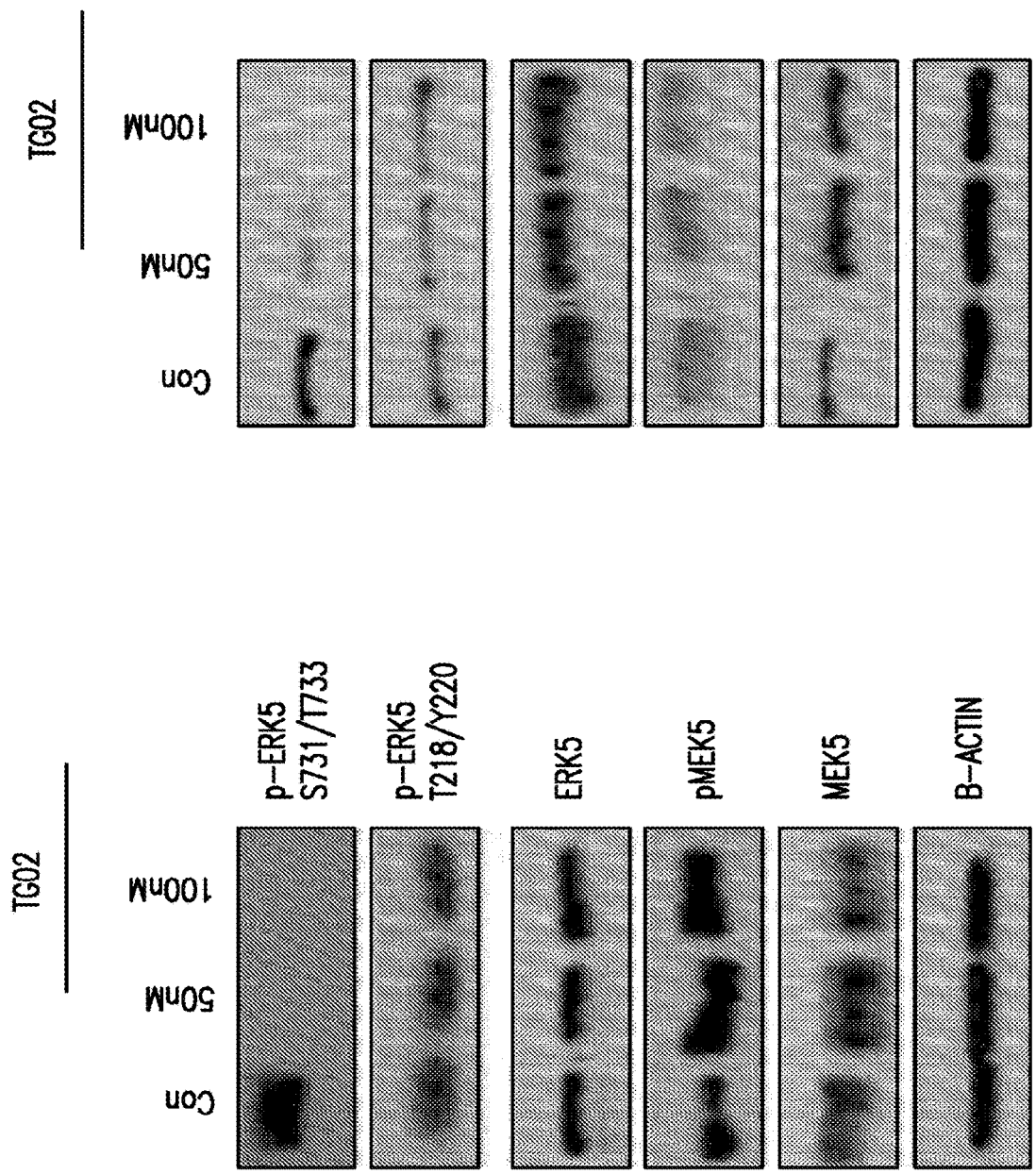
Figures 5J, 5K:
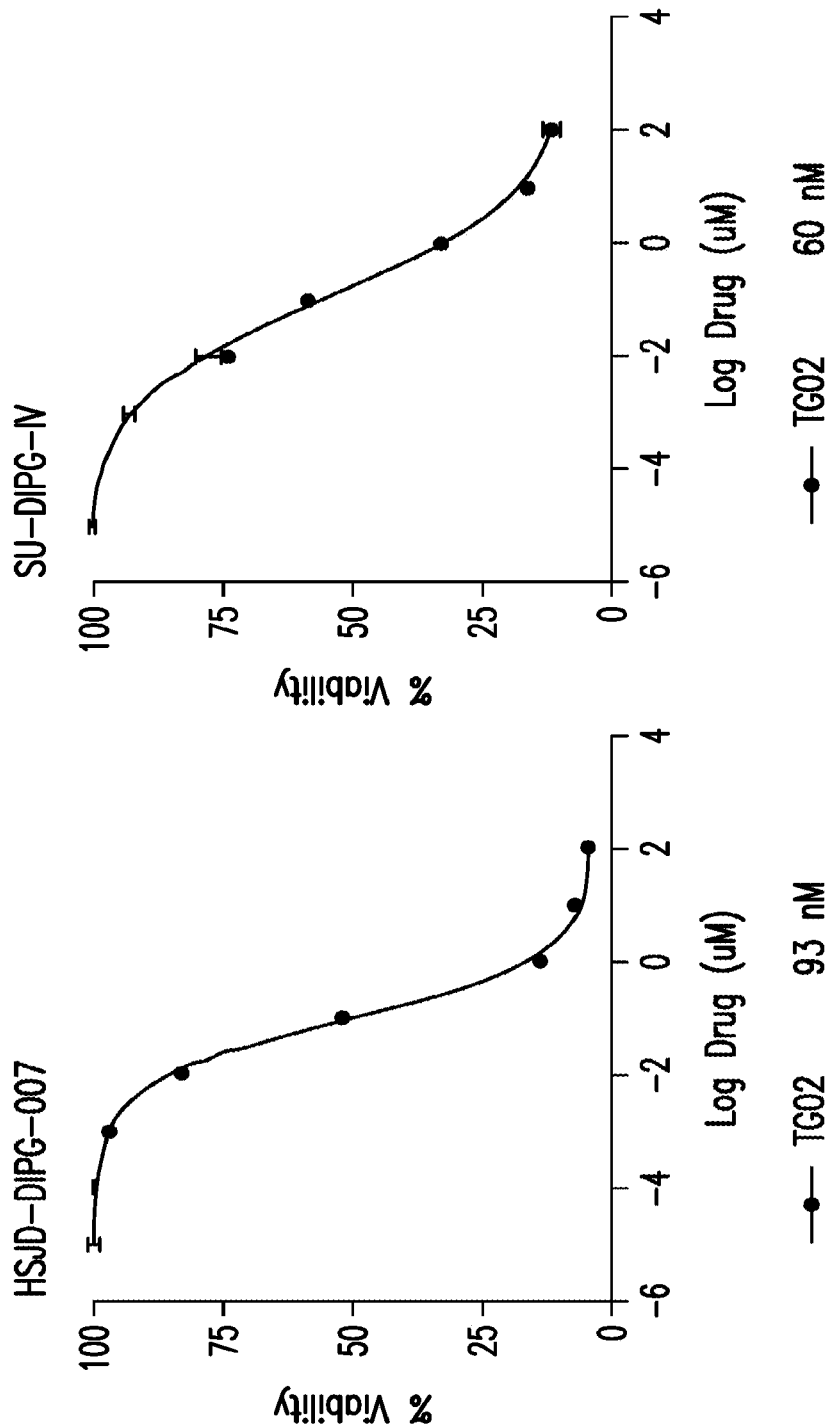

Cell counting following 9 days of treatment for DIPG-007, DIPG-IV, and SF8628 cells showed significant decreases in cell number with 50 nM of TG02, as compared to cells treated with vehicle (FIGS. 5C-5E, *p<0.05). Annexin-PI flow cytometry confirmed DIPG-007 and DIPG-IV cells treated with TG02 were undergoing significantly higher rates of apoptosis lines compared to controls (FIGS. 5F-5G, *p<0.05). TG02 was confirmed to inhibit ERK5 auto-phosphorylation and ERK5 activity sites (Ser731 and Thr733) at 50 nM, but did not inhibit ERK5 Thr218/Tyr220, which is regulated by MEK5 (FIGS. 5H-5I). The present disclosure also observed diminished cell growth and induction of apoptosis in DIPG-13p and SF8628 cells treated with TG02 (FIGS. 12C-12E). Loss of ERK5 by siRNA or pharmacological inhibitors in a DIPG histone wildtype H3 cell line, CNMC-XD-760, also had a significant reduction in viability although the effect was not as pronounced in mutant histone DIPG cells (FIGS. 13A, 13E, 13F). Loss of ERK5 in a hemispheric pediatric GBM (SU-pcGBM2 EGFR amplified), displayed similar growth inhibition as the mutant H3K27M cells (FIG. 13G). Expression of wild-type HA-tagged ERK5 and constitutively active ERK5 (ERK5 T733E) promoted resistance to TG02 as indicated by increased EC50 values (FIG. 13B-13C) and reduced cleaved Caspase 3/7 levels, with the greatest resistance occurring in cells expressing the ERK5 T733E constitutively active mutant (FIG. 13D).

MYC is a Direct Target of ERK5

Figures 6A, 6B:
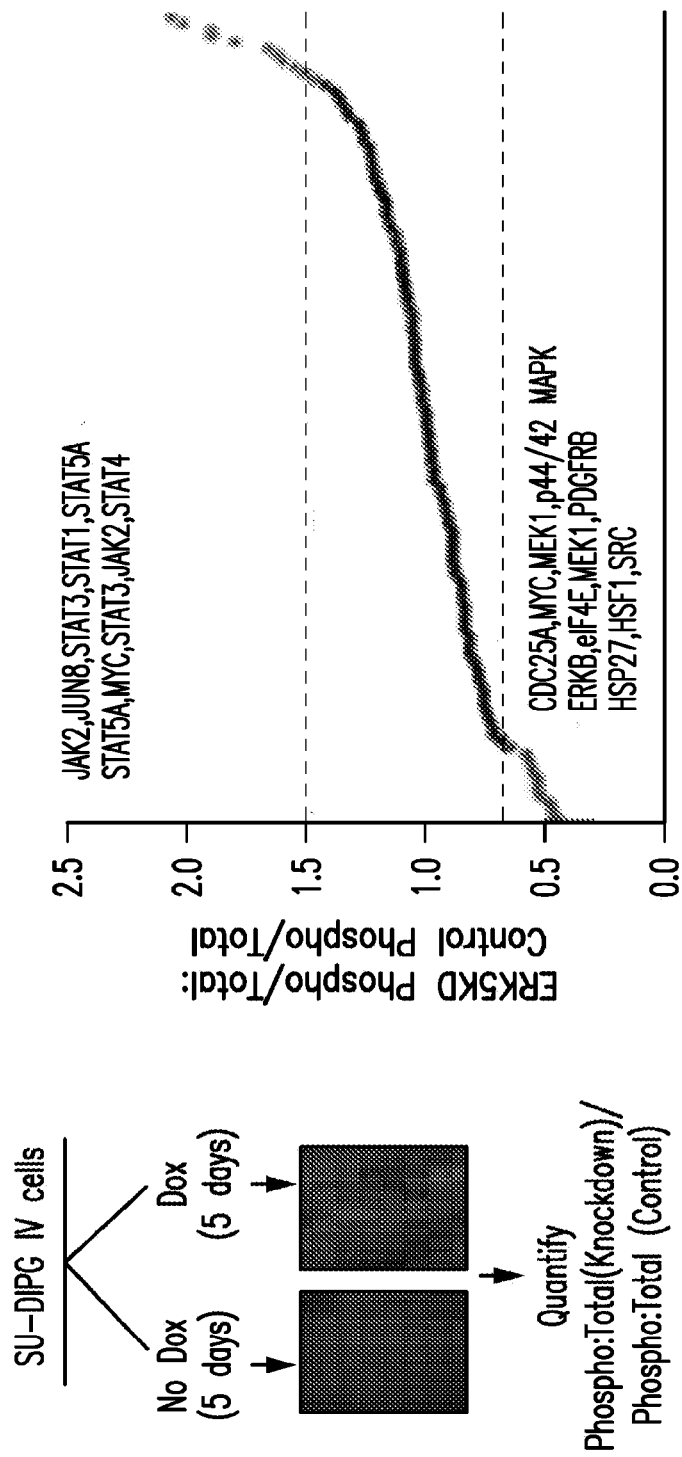
Figure 6C:
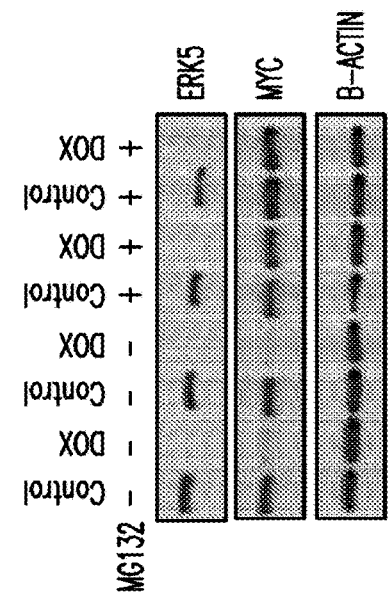
Figure 6D:
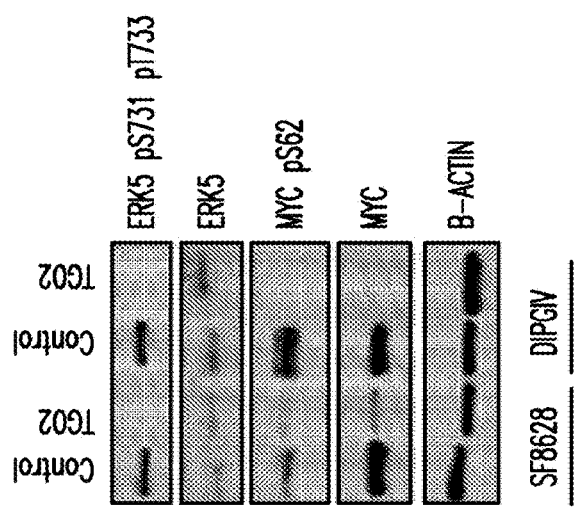

The present disclosure performed a high-throughput ELISA-based antibody array for quantitative protein phosphorylation profiling using 269 phospho antibodies (94 known cancer proteins in total) to identify ERK5 signaling mediators. The initial screen was performed using DIPG-IV cells with or without ERK5 knockdown. The present disclosure identified 24 differentially phosphorylated peptides associated with 15 proteins in ERK5 knockdown DIPG-IV cells compared to controls (FIGS. 6A-6B). Strikingly, the present disclosure observed significant reduction of phosphorylation at MYC serine residue 62 (S62), a critical phosphorylation site for MYC stability. The present disclosure confirmed down-regulation of total MYC and phospho MYC (S62) in ERK5 knockdown cells compared to control (FIG. 6C). Moreover, ERK5 inhibition by TG02 leads to reduced phospho and total MYC (FIG. 6C) in DIPG-IV and SF8628 cells. MG132, a proteasome inhibitor, restored protein expression of total MYC in DIPG-IV cells, indicating that loss of ERK5 results in proteasomal degradation of MYC (FIG. 6D). The present disclosure observed no transcriptional changes of MYC at the RNA level (FIG. 14A).

Figure 6F:
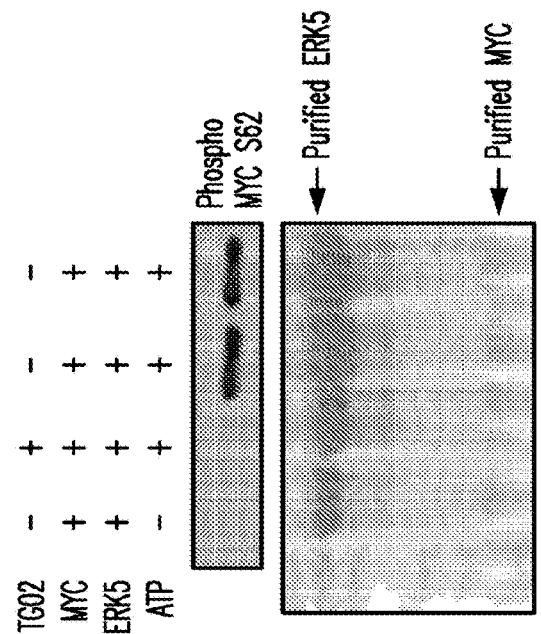
Figure 6E:
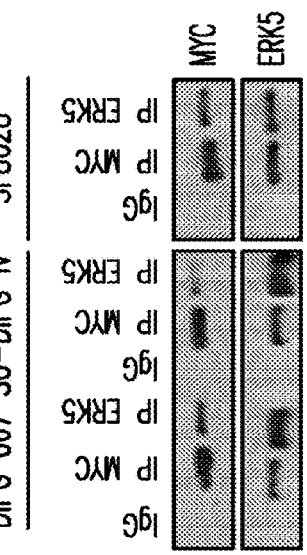
Figure 6H:
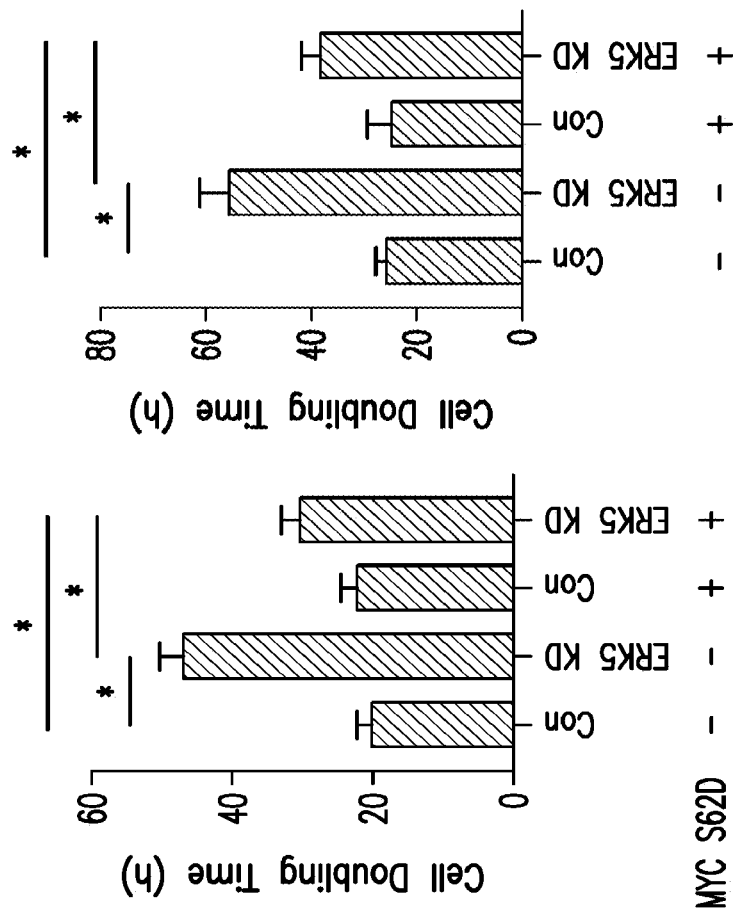
Figure 6G:
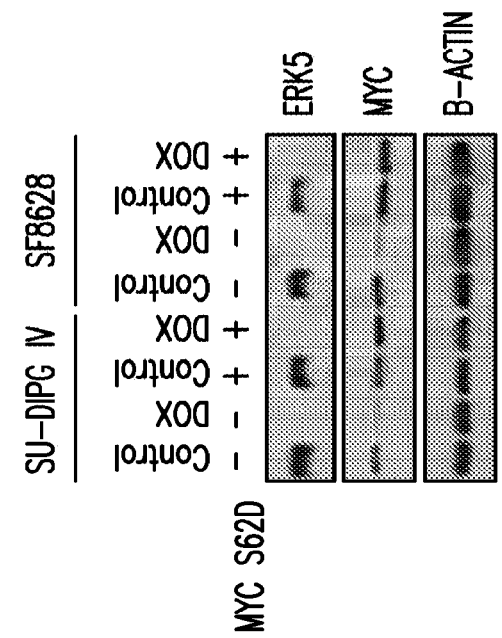

Several kinases including CDK1, ERK1, and ERK2 have been reported to stabilize MYC at (S62). The results suggest ERK5 may play a role in MYC S62 phosphorylation. Immunoprecipitations (IPs) of ERK5 from DIPG-007, DIPG-IV, and SF8628 cells co-precipitated MYC, and reverse IPs of MYC co-precipitated ERK5 (FIG. 6E). The present disclosure performed an in vitro kinase assay with purified MYC and ERK5 and observed direct phosphorylation on MYC(S62) in the presence of ERK5 and ATP (FIG. 6F). Phosphorylation of MYC(S62) was inhibited in the presence of TG02 (FIG. 6F). Introduction of non-degradable MYC (S62D) in DIPG cells significantly rescued proliferation defects of ERK5 knockdown (FIGS. 6G-6H, *p<0.01). Also, MYC S62D promoted resistance to TG02 (FIGS. 14B-14D, *p<0.05). DIPG-13p cells harbor MYCN amplification and, interestingly, the present disclosure observed that ERK5 loss or inhibition by TG02 resulted in MYCN protein and transcriptional down-regulation (FIG. 14E, *p<0.05).

ERK5 Inhibitors Increase Survival of Mice Bearing DIPG Xenografts and for Mice Bearing Syngeneic DIPG.

Figure 7A:
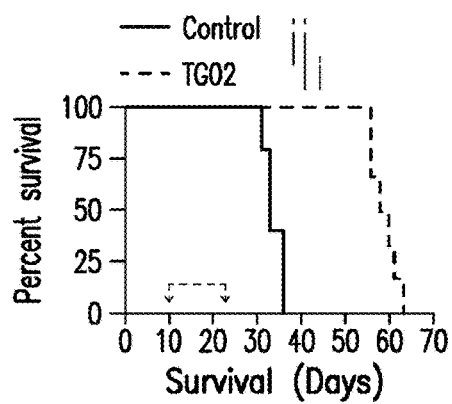
Figure 7B:
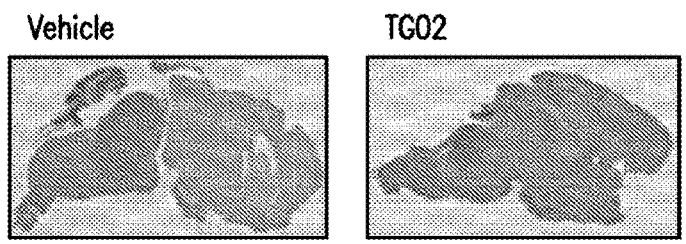
Figure 7C:
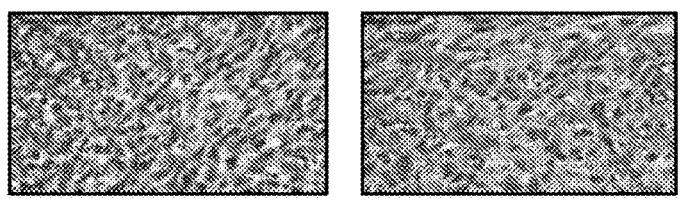
Figure 7D:
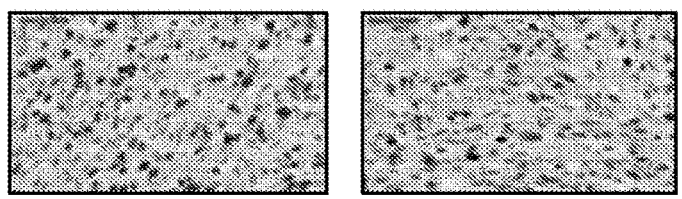
Figure 7E:
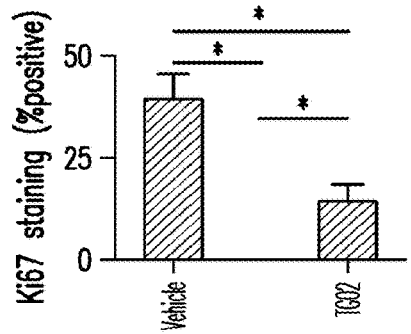
Figure 7I:
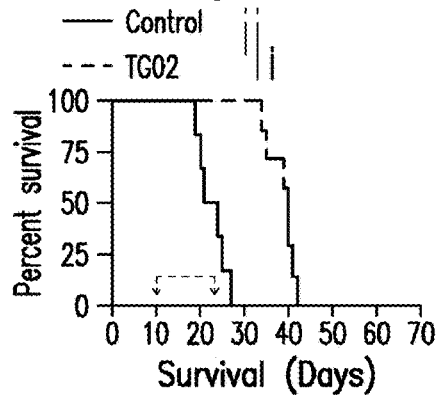
Figure 7F:
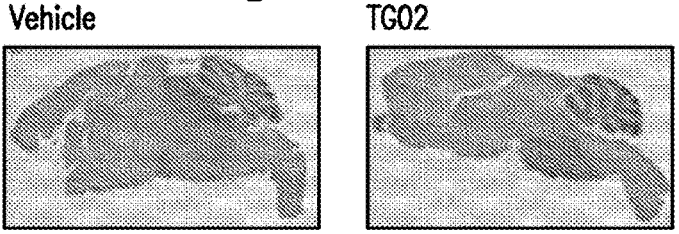
Figure 7G:
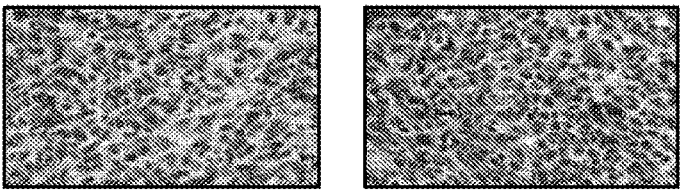
Figure 7H:
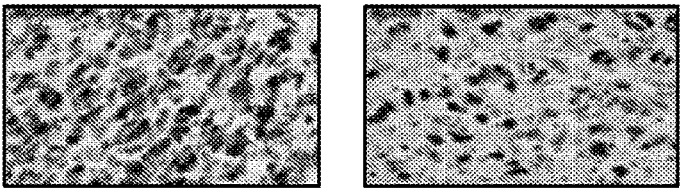
Figure 7J:
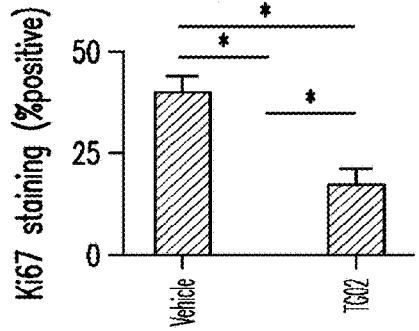

The present disclosure next examined whether TG02 could extend survival in an orthotopic DIPG xenograft model. Mice bearing SF8628 intracranial xenografts were treated with vehicle or TG02 (20 mg/kg) for 2 weeks. Vehicle treated mice had median survival of 33 days Mice treated with TG02 showed a substantial increase in median survival: 59 days (FIG. 7A, *p<0.05). Hematoxylin and eosin (H&E) staining confirmed high-grade tumor histology and no gross histology differences between treatment arms, but mice treated with TG02 showed reduced KI-67 staining, a marker of cell proliferation (FIGS. 7B-7E, *p<0.05). Similar results were obtained in a second xenograft model using DIPG-13p cells, with TG02 treated mice showing a median survival of 40 days. The median survival of TG02 treated mice were significantly greater than vehicle control mice whose median survival was 22.5 days (FIGS. 7F-7J, *p<0.05). The present disclosure confirmed in vivo inhibition of ERK5 auto-phosphorylation and induction of apoptosis by cleaved PARP on mice sacrificed after 5 days of treatment with TG02 (FIG. 14G). Also, the present disclosure used two established cell lines derived from transgenic mouse models of DIPG. Both lines are p53 null and express PDGFB, differing only in their H3.3 mutation status. Strikingly, H3K27M cells were more sensitive than H3 wildtype cells to ERK5 knockdown (FIGS. 14H-14H).

Discussion

There are currently no sufficiently effective treatment options for DIPG patients (Mohammad et al., Nature medicine 2017; 23:483-92). Certain recent large-scale genomic analyses of DIPG patient samples have redirected the course of treatment development toward targeted therapies. Importantly, genomic analyses revealed that a majority of DIPG cases have the H3K27M mutation (Mackay et al., Cancer cell 2017; 32:520-37 e5; Schwartzentruber et al., Nature 2012; 482:226-31; Khuong-Quang et al., Acta neuropathologica 2012; 124:439-47). The high frequency and predictability of H3K27M mutation in DIPG render it and its consequences attractive therapeutic targets.

H3K27M can result in inhibition of the PRC2 complex, specifically the catalytic subunit of the complex, EZH2. EZH2 inhibition results in global reduction of H3K27 trimethylation and attendant alterations in cell transcriptomes (Lewis et al., Science (New York, N.Y.) 2013; 340:857-61). Several studies have demonstrated therapeutic possibilities associated with targeting histone modifiers and transcriptional regulators in DIPG models. Notably, certain DIPG growth has proven vulnerable to the: (1) inhibition of histone demethylases (Hashizume et al., Nature medicine 2014; 20:1394-6); (2) inhibition of residual EZH2 function (Mohammad et al., Nature medicine 2017; 23:483-92); (3) inhibition of histone deacetylases (HDAC) by panobinostat, a drug that is currently being evaluated in a DIPG clinical trial (NCT02717455) (Grasso et al., Nature medicine 2015; 21:555-9); and (4) disruption of transcription by bromodomain inhibitors and CDK7 inhibitors (Nagaraja et al., Cancer cell 2017; 31:635-52 e6). The efficacy indicated by the results of preclinical success for certain therapies suggests that disrupting epigenetic and transcriptional effects of H3K27M may be an effective strategy for DIPG treatment. Moreover, a study characterizing the transcriptional dependencies of DIPG identified several DIPG-specific transcripts and super enhancers of gene targets of the MAPK pathway (Nagaraja et al., Cancer cell 2017; 31:635-52 e6). Notable were MAP3K2, an upstream activator of ERK5, and MEF2A/MEF2C transcription factors, both direct targets of ERK5 (Hayashi et al., The Journal of clinical investigation 2004; 113:1138-48; Wang et al., Brain research 2009; 1255: 32-41).

Since H3K27M causes global epigenetic and transcriptional changes in DIPG cells, the present disclosure hypothesized that it is likely activating the transcription of known oncogenic pathways to sustain tumor growth and survival. To address this hypothesis, the present disclosure investigated the impact of H3K27M mutations on RAS-MAPK/ERK5 signaling. It has been shown by others that RAS-MAPK/ERK activation in DIPG can result from: (1) PDGFRA amplification, (2) the loss of RAS-GAP NF1, and rarely, (3) point mutations in K-RAS and N-RAS (Mackay et al., Cancer cell 2017; 32:520-37 e5; Recurrent et al., Nature medicine 2016; 22:1314-20). However, transcriptional effects that would connect H3K27M with RAS activation have not been previously explored. While the primary oncogenic function of H3K27M can be PRC2 inhibition and loss of H3K27 trimethylation, it was observed that while either H3K27M expression or treatment with an EZH2 inhibitor reduced H3K27 trimethylation, EZH2 inhibition resulted in decreased active RAS (FIG. 9H). The present observation supports that EZH2 inhibition and H3K27M mutation may not be synonymous. EZH2 inhibitors can ablate focal H3K27 trimethylation that persists in H3K27M DIPG (Harutyunyan et al., Nature communications 2019; 10:1262; Mohammad et al., Nature medicine 2017; 23:483-92). Additionally, EZH2 inhibition causes loss of H3K27 dimethylation and trimethylation while H3K27M disproportionately affects trimethylation (Harutyunyan et al., Nature communications 2019; 10:1262). Such differences between H3 mutation and EZH2 inhibition can be important, given their opposing effects on RAS activity, and worthy of further investigation.

RAS protein activity is known to be important in multiple cancers, yet despite sustained efforts RAS has remained largely undruggable. Targeting key effectors of RAS signaling may prove more feasible than, and perhaps as effective, as targeting RAS itself. The RAS-MAPK signaling pathway is included of a highly diverse family of proteins with interactions that are extensively networked. To identify potential therapeutic vulnerabilities within this network the present disclosure used a targeted siRNA screen that revealed less-studied signaling arms of the RAS pathway as being important to DIPG growth. Among these, ERK5 was of particular interest as a treatment target because, unlike ERK1/2, it has two distinct functional domains. Interestingly, the present disclosure uncovered an unreported feedback between ERK5 and ERK1/2, whereby loss of ERK5 inhibits activation of ERK1/2. H3K27M is not necessarily the sole driver of RAS activation and active ERK5 is not exclusive to DIPG. Other tumors may also be sensitive to ERK5 inhibition as ERK5 has been shown to have oncogenic activity in other cancers and is known to promote proliferation as well as angiogenesis (Umapathy et al., Science signaling 2014; 7:ra102; Tusa et al., Oncogene 2018; 37:2601-14; Pavan et al., Oncogene 2018; 37:4197-213). Notable H3K27M DIPG and H3 WT pediatric hemispheric GBM cell lines tested had similar active RAS levels, which were higher than that observed in the H3 WT DIPG cell line. The lower relative active RAS supports H3K27M having a function in RAS activation. The H3 WT DIPG cell line was also the least sensitive to ERK5 inhibition, while the H3 WT pediatric GBM and H3K27M DIPG cell lines were similarly responsive. While H3K27M mutation results in sensitivity to ERK5 loss or inhibition, targeting ERK5 in pediatric GBM also warrants consideration.

ERK5 suppression through inducible shRNA or pharmacological inhibition attenuated DIPG growth through destabilization of MYC protein. The presently disclosed working model posits that MYC and activation of ERK1/2, in association with RAS activation, are critical to tumor growth (FIG. 15). ERK5 has been shown to promote phosphorylation of MYC as a compensatory response to ERK1/2 inhibition, and direct targeting of ERK5 inhibits MYC stability and activity of ERK1/2 have been identified (English et al., The Journal of biological chemistry 1998; 273:3854-60; Vaseva et al., Cancer cell 2018; 34:807-22 e7). Moreover, the present disclosure shows that ERK5-mediated MYC regulation can be important in DIPG pathobiology. However, a non-degradable version of MYC was not fully able to rescue anti-tumor effects of ERK5 suppression, thereby suggesting that additional ERK5 targets may contribute to its pro-proliferative activity.

Both RAS and MYC can be undruggable, whereas small molecule inhibitors of ERK5 are available and could be rationally combined with therapies in DIPG, such as radiation. ERK5 inhibition by gene silencing or small molecule inhibition also led to reduction of MYCN RNA and protein in DIPG-13p cells, suggesting that ERK5 has importance in MYCN transcription. This relationship between ERK5 and MYCN has been observed in neuroblastoma (Umapathy et al., Science signaling 2014; 7:ra102).

The presently disclosed ERK5 inhibitor tests included the use of in vivo models that yielded results showing that treatment with inhibitors TG02 increased survival of mice bearing patient-derived xenograft (PDX) tumors. In association with the inhibitor experiments the present disclosure determined that constitutively active ERK5 or MYC confers some, but not complete, resistance to TG02, indicating that this drug works in part through its effect on ERK5 and MYC. Importantly, TG02 is blood-brain barrier penetrant and in clinical trials for several adult cancers (NCT03224104, NCT02942264, and NCT01204164). Interestingly, the present disclosure observed reduced KI-67, a marker of proliferation, in tumors collected from mice weeks after treatment of TG02 had ceased. This may reflect a potential treatment escape known as cancer cell dormancy, where tumor cells recovering from minimal residual disease (MRD) have been shown to have a less proliferative state. Moreover, this phenomenon is known to occur when targeting the RAS-MAPK or PI3K-AKT signaling pathways (Townson et al., Cell cycle (Georgetown, Ill.) 2006; 5:1744-50; Yeh et al., Cancer research 2015; 75:5014-22; Gupta et al., Cell 2011; 146:633-44). However, the present disclosure treated mice 5 days each week for two weeks and this potential resistance mechanism may possibly be negated by either treatment regimen optimization or combination therapies. Targeting CDKs in DIPG has been considered as a therapeutic strategy, and the presently disclosed data supports dual CDK and ERK5 inhibition as a strategy that merits consideration.

The presently disclosed phospho-proteomic array revealed activation of the JAK/STAT pathway in response to ERK5 knockdown. In addition to ERK5, TG02 also inhibits JAKs, which may contribute to the apoptotic phenotype in response to TG02 treatment. Interestingly, STAT3 is a transcriptional regulator of MEK5, the activator of ERK5 (Song et al., Oncogene 2004; 23:8301-9). Activation of the JAK/STAT pathway may be a compensation mechanism to elicit additional ERK5 activation. Elucidating the relative importance of JAK/STAT activation in the context of ERK5 inhibition requires further investigation, as it may have translational relevance.

Although the impact of the H3K27M mutation is well characterized for its ability to activate and alter both transcription and epigenetics, its role in cell signaling has not been well-characterized. Here, the role of H3K27M in cell signaling was investigated and the present disclosure determined that this mutation engages multiple unreported effectors of RAS signaling that are essential for promoting DIPG tumor growth. Certain effectors are therapeutically accessible, and their discovery as key contributors to the tumor biology of DIPG could motivate clinical trials to assess potential patient benefit from their targeted inhibition.

Example 2: Phase 1 Clinical Trial of TG02 in Pediatric Patients with Diffuse Intrinsic Pontine Gliomas and Other H3.3 K27M-Mutated High-Grade Gliomas New agents that target the cell-cycle-related cyclin-dependent kinase (CDK)4/6 or the mitogen-activated protein kinase (MAPK)/extracellular signal-regulated kinase (ERK) 1/2 pathways, which are critical in driving growth of cancer, are now considered standard care for certain adults with breast cancer and melanoma, respectively (Grimaldi et al., Am J Clin Dermatol 18:745-754, 2017; Wander et al., J Clin Oncol 35:2866-2870, 2017). Such medications have already shown promising activity against some pediatric central nervous system (CNS) cancers (Banerjee et al., Neuro Oncol 19:1135-1144, 2017; Geoerger et al., Clin Cancer Res 23:2433-2441, 2017). The present disclosure relates to the use of TG02, a potent oral inhibitor of multiple non-cell-cycle-related CDKs and ERK5 in patients with diffuse intrinsic pontine glioma (DIPG) and other histone H3.3 K27M-mutated high-grade gliomas (HGGs).

CDKs, protein kinases characterized by the need of a separate unit (cyclin) for their enzymatic activity, integrate extracellular and intracellular signals to modulate protein transcription and cell-cycle progression (Malumbres et al., Nat Rev Cancer 9:153-166, 2009). They are functionally divided into two major partially overlapping subgroups: cell-cycle-related (CDK1, 4, 6, and 7) and transcriptional (CDK7, 8, 9, 11, and 20). Since the cell-cycle-related CDK4/6 have a well-recognized role in cancer (Klein et al., Cell 34:9-20, 2018; Malumbres et al., Nat Rev Cancer 9:153166, 2009), three inhibitors (i.e., palbociclib, ribociclib, and abemaciclib) of this pathway, which specifically target CDK4/6 ($IC_{50}$ mostly above 250 nM for all other CDKs), have already been approved for care in adults with cancer (Klein et al., Cell 34:9-20, 2018). All three agents have already been tested in children with cancer.

Of the transcriptional CDKs, the constitutively active CDK7 is a component of the 10-unit transcription initiation factor II-H (TFIIH) complex which phosphorylates the carboxy-terminal domain (CTD) of the RNA polymerase II at gene promoters thereby leading to initiation of transcription (Malumbres et al., Nat Rev Cancer 9:153166, 2009). CDK7 is also able to phosphorylate and activate other CDKs, including CDK9. Both CDK8 and CDK9 can phosphorylate and activate RNA polymerase II as well (Malumbres et al., Nat Rev Cancer 9:153166, 2009). CDK7 and CDK9 phosphorylate different aminoacid residues in the CTD of the RNA polymerase II affecting the initiation, pausing, and elongation phases of transcription. CDK8 phosphorylates multiple targets, including CDK7, and serves as a link between several intracellular pathways and RNA polymerase II (Malumbres et al., Nat Rev Cancer 9:153166, 2009). The transcription factor TFIIH, which contains CDK7, is also involved in nucleotide-excision repair, a pathway involved in removal of large DNA adducts, including those caused by some chemotherapeutic agents (e.g., cisplatin) (Malumbres et al., Nat Rev Cancer 9:153166, 2009). CDK9 was shown to be essential for maintaining epigenetic silencing of tumor suppressor genes at heterochromatic loci in pre-clinical models of adult cancers, particularly carcinomas (Zhang et al., Cell 175:1244-1258, 2018). Specific inhibition of CDK9 in such models led to restored tumor suppressor gene expression, cell differentiation, and a cellular immune response that may sensitize to checkpoint inhibitors (Zhang et al., Cell 175:1244-1258, 2018). These investigators showed that CDK9 inhibition reactivated genes by spatially remodeling chromatin but without affecting DNA methylation (Zhang et al., Cell 175:1244-1258, 2018).

Super enhancers are large clusters of regulatory elements within the DNA characterized by activations marks (e.g., H3K27 acetylation) and binding of complex transcriptional regulatory elements/factors (e.g., RNA polymerase II and BRD4) (Sengupta et al., Trends Cancer 3:269-281, 2017). Super enhancers have been shown to be enriched for oncogenes that drive growth and normal regulators of cell identity in multiple cancers, including DIPG (Nagaraja et al., Cancer Cell 31:635-652, 2017). The use of THZ1, a specific CDK7 inhibitor, led to preferential downregulation of the transcription of genes associated with super enhancers and produced significant anticancer activity in cell lines of several cancers, including DIPG (Nagaraja et al., Cancer Cell 31:635-652, 2017; Sharifnia et al., Nat Med 25:292-300, 2019).

Little is known about the role of this pathway in cancer, particularly in CNS cancers (Hoang et al., Cancer Lett 392:51-59, 2017). The ERK5 pathways (FIG. 16) can be activated by environmental stress, growth factors, and cytokines and it has been implicated in important characteristics in cancer such as resistance to therapy, cell proliferation, and development of metastatic disease (Hoang et al., Cancer Lett 392:51-59, 2017).

Pre-Clinical Data Regarding the Use of TG02, a Transcriptional CDK and ERK5 Inhibitor Since DIPGs display significant transcriptional dysregulation, Nagaraja et al. analyzed the impact of BET or CDK7 inhibition in this tumor (Nagaraja et al., Cancer Cell 31:635-652, 2017). Treatment of seven patient-derived histone-mutant DIPG cell lines (H3.3 [n=6] and H3.1 [n=1]) and one wildtype (MYCN amplified) with THZ1 caused a dose-dependent reduction in cell viability, decreased proliferation, and increased apoptosis with a median $IC_{50}$ of 56 nM (range; 28-533 nM) (Nagaraja et al., Cancer Cell 31:635-652, 2017). The DIPG cell line with wildtype histone had an $IC_{50}$ less than 100 nM. One non-DIPG histone-wildtype glioblastoma cell line that harbored a TP53 mutation and EGFR amplification had an $IC_{50}$ of 640 nM. Loss of phosphorylation of the CTD site of RNA polymerase II was observed 24 hrs after therapy with THZ1 to confirm adequate CDK7 inhibition (Nagaraja et al., Cancer Cell 31:635-652, 2017). THZ1 does not have a robust CNS penetration. Treatment of an aggressive DIPG orthotopic xenograft with intraperitoneal THZ1 led to a modest increase (approximately 4.5 days) in survival compared to control animals. Combination of THZ1 and panabinostat produced synergistic decreased cell viability, and more effective inhibition of proliferation and induction of apoptosis in DIPG cell lines. THZ1 retained submicromolar activity against DIPG cell lines induced to be resistant to panobinostat (Nagaraja et al., Cancer Cell 31:635-652, 2017). RNA sequencing of DIPG cell lines treated with THZ1 showed global downregulation of active transcripts (Nagaraja et al., Cancer Cell 31:635-652, 2017). On the other hand, treatment of these cell lines with a BET inhibitor or panobinostat yielded an overlapping downregulation of a specific subset of genes that clustered separately from those affected by THZ1.

The effects of transcription inhibition on pre-clinical models of pediatric HGGs were evaluated. Treatment of the DIPG-007 cell line with two non-overlapping shRNA lentivirus targeting CDK9 led to decreased protein expression and decreased cell growth in vitro (FIG. 17). Furthermore, BT 245 cell lines, which are derived from a pediatric H3.3 K27M-mutated supratentorial glioblastoma, were treated with either shNull or shCDK9 and then injected in the flanks of athymic nude mice. Representative images of these mice 28 days after tumor injection is shown in FIG. 18.

The role of RAS signaling in DIPG was evaluated. A screening using 295 siRNAs against genes known to modulate the function of RAS signaling was performed in neural stem cells (NSC) transfected with empty vector (control) or H3F3A K27M plasmids (NSC K27M), and in patient-derived DIPG-007 cell line. The inhibition of 26 and 15 genes caused decreased or increased growth of NSC K27M, respectively. Likewise, the inhibition of 27 and 6 genes led to decreased or increased growth of DIPG-007 cell lines, respectively. Twenty-six genes were identified in both screens, several of which belong to the MAPK pathway (FIG. 19). Re-screening of the ten top candidates with two independent siRNAs per gene target confirmed the specificity of these genes to decreased cell viability (FIG. 20). Several components of the ERK5 pathway, including ERK5 (MAPK7) itself were included among the top genes to modulate growth of NSC K27M and DIPG-007 cells. Total and phosphorylated ERK5 were overexpressed in NSC K27M compared to controls. Increased total ERK and phosphorylated ERK5 were seen in other patient-derived DIPG cell lines. Robust nuclear and cytoplasmic expression of ERK5 protein occurred in DIPG-IV and DIPG-007 cells. Similarly, another study recently corroborated these findings by showing significant ERK5 RNA overexpression in 38 human DIPG samples (Berlow et al., PLoS One 13:e0193565, 2018).

Doxycycline-induced shRNA knockdown of ERK5 in patient-derived DIPG cell lines resulted in decreased growth and reduction of ERK1/2 phosphorylation. Treatment of four DIPG cell lines in vitro with TG02, an oral multi-kinase inhibitor of CDK 1, 2, 5, 7, and 9, and ERK5 produced significant dose-proportional decreased viability (median $EC_{50}$ of 75 nM; range: 60 to 93) and increased apoptosis. Overexpression of ERK5 and constitutively active ERK in DIPG-IV cells led to increased $EC_{50}$ to treatment with TG02 (above 1000 nM).

Treatment of mice bearing orthotopic SF8628 (FIG. 7A) or DIPG13p DIPG xenografts (FIG. 71) with TG02 at a dose of 20 mg/Kg for 5 consecutive days for 2 weeks showed a statistically significant increased median survival compared to controls.

In vitro testing of six adult patient-derived glioblastoma cell lines (e.g., BT228, BT286, BT145) showed mostly a synergistic effect when combining radiation therapy (RT) and TG02 at concentration between 100 and 250 nM. Two cell lines, DIPG-13p and DIPG-IV cells were treated in vitro with DMSO, 50 nM of TG02, 10 Gy of RT (2-Gy fractions over 5 days in a row) or 50 nM TG02 and 10 Gy of RT. Cell viability was assessed on Day 5. Compared to control, TG02 and RT alone significantly reduced cell viability (p<0.001). RT and TG02 led to statistically significant reduction in cell viability compared to RT or TG02 only (p<0.001) (FIG. 21).

Drug Information

TG02 (originally designated as SB1317) is a new pyrimidine-based multi-kinase inhibitor that inhibits CDK 1, 2, 7, and 9, JAK2, FLT3, and ERK5. TG02 was tested in in vitro assays against 63 kinases (Table 1). While the IC50 against CDK9 was 3 nM, the IC50 for CDK7 and ERK5 were 37 nM and 43 nM, respectively (Goh et al., Leukemia 26:236-243, 2012). Since TG02 is a substrate of CYP3A4 and CYP1A2, inducers/inhibitors of these liver enzymes need to be avoided during therapy.

Tissue and plasma distribution of TG02 was analyzed after a single PO dose of 75 mg/kg in female nude mice. Three mice were sacrificed at a time 10 min, 30 min, 1, 2, 4, 8, and 24 hrs after dosing and pharmacokinetic levels were assessed. $C_{max}$ and exposure ($AUC_{0-last}$) to TG02 were at least twice as high in the brain compared to plasma. TG02 is available in 10- (size 2), 50- (size 2), and 150-mg (size 0) capsules. The molecular structure of TG02 is shown in FIG. 22.

Clinical Trial in Adults

Escalating doses of TG02 alone or in combination with carfilzomib were tested in 115 adults with hematologic malignancies. The maximum tolerated dose (MTD) of TG02 administered as a single agent in one of these studies was not determined due to poor patient accrual. In another Phase 1 study, escalating doses of intermittent TG02 (starting at 150 mg per dose) and fixed doses of arfilzomib (varying between 20 mg and 27 mg/m$^2$) were administered twice a week for 21 of 28 days. The MTD of TG02 was 250 mg per dose. The most common toxicities associated with TG02 (≥20%) in adults with acute leukemia were nausea, vomiting, fatigue, abdominal pain, diarrhea, constipation, and hypophosphatemia. Serious adverse events consisted of nausea and vomiting (grades 2 and 3), fatigue (grade 3), altered mental status (grade 2), rash (grade 3), thrombocytopenia (grade 4), and neutropenic fever with sepsis (grade 3).

A phase 1 clinical trial evaluated TG02 administered along with temozolomide at a dose-dense (DD; 125 m/m$^2$ per day 7 days on/7 days off) or metronomic (MN; 50 mg/m$^2$) regimen in adults with recurrent high-grade astrocytomas (Wu et al., Neuro Oncol 19 (Suppl 6):vi15 (ACTR abstract 69), 2017). The dose of TG02 was increased starting from 200 mg a day administered 4 times every 28 days on days −3, 1, 12, 15, and 26 of cycle 1, and days 1, 12, 15, and 26 from cycle 2 afterwards. The MTD of TG02 was 250 mg and 200 mg in the DD and MN regimens, respectively. The dose-limiting toxicities (DLTs) in the DD regimen consisted of grade 3 diarrhea (n=1) at 200 mg of TG02, and grade 4 neutropenia and grade 3 increase in ALT (n=1) at 250 mg of TG02. The DLTs in the MN regimen were grade 4 lymphopenia (n=2) and increase in ALT (n=1) at 250 mg of TG02. A phase 2 study using the same combination in adults with recurrent anaplastic astrocytoma or glioblastoma is ongoing (NCT02942264).

A second clinical trial is using TG02 as single agent or in combination with RT or temozolomide (NCT03224104) in adult patients with anaplastic astrocytoma or glioblastoma. Newly diagnosed elderly patients with non-IDH mutated MGMT-promoter-methylated tumors receive the combination of TG02 and temozolomide. Patients with unmethylated tumors receive TG02 and RT. Adult patients in first recurrence after receiving RT and temozolomide followed by adjuvant temozolomide receive TG02 only at a dose of 250 mg in an intermittent schedule.

The MTD of TG02 as single-agent administered twice a week in older adults is probably 150 mg per dose. Significant drug-related toxicities have been increased liver function tests and grade 3 neutropenia. When TG02 is combined with RT, the most clinically significant toxicities have been grade 2 nausea and vomiting and grade 3 neutropenia.

Human pharmacokinetic data are available for patients treated with TG02 as a single agent. The median $T_{max}$ of TG02 at doses between 10 and 200 mg was between 1 and 8 hrs. There was a dose-proportional increase in $C_{max}$ and $AUC_{0-t}$ of TG02 within this dose range. Accumulation ratios after 15 days of daily dosing of TG02 varied between 1.4 and 5.6 across dosage levels. The $t_{1/2}$ of TG02 is approximately 18 hrs. FIG. 23 depicts $C_{max}$ and exposure after a single dose of TG02 in adults with hematologic malignancies.

Clinical Trial in Pediatric Patients

Patients with newly diagnosed non-metastatic DIPG and other H3.3 K27M-mutated HGGs are eligible for this study. A tumor biopsy of patients with DIPG is strongly encouraged but confirmation of histone mutation status is not a requisite for protocol enrollment for such cases.

Once enrolled on study, patients start standard fractionated RT (54 Gy for patients with DIPG and between 54 and 59.4 Gy for those with other non-DIPG H3.3-mutated HGGs) along with treatment with TG02. The DLT-evaluation period consists of the first 6 weeks of treatment.

Treatment with TG02 is administered twice a week (preferentially on Mondays and Thursdays), once a day for the duration of RT and afterwards for a maximum of 2 years unless patients experience disease progression or clinically significant toxicities.

Correlative studies, consisting of plasma and cerebrospinal fluid (CSF) pharmacokinetics (the latter is optional for patients with Ommaya reservoirs), pharmacodynamics of TG02 targets in peripheral blood mononuclear cells (PBMC), molecular analyses of tumor and circulating tumor DNA (ctDNA; liquid biopsy) in plasma and CSF samples (if available), and serial evaluation of long-term memory of patients are included in this clinical trial.

Pharmacokinetic Studies

Plasma samples for pharmacokinetic studies of TG02 are obtained before and after 1, 2, 4 (±2), 8 (±4), 24 (±6), and 48 (±6) hrs from first dose on day 1 of therapy; before dose on day 4; before and at 1, 2, 4 (±2), 8 (±4), and 24 (±6) hrs on day 15 of therapy; and before dose on day 1 cycle 2 and 4 of therapy following standard methods.

Pharmacodynamic Studies

The effect of TG02 on the activity of CDK9 in peripheral blood mononuclear cells (PBMCs) is studied by using a CDK9 activity assay from Bioscience (Catalog #: 79628). An immunoblot of the CTD of RNA polymerase II is performed to assess phosphorylation of Ser5, a direct target of CDK9. These highly sensitive assays require a very small amount of input material (<10 ug/sample). Samples for pharmacodynamic studies are collected concurrently with pharmacokinetic studies before and 2 hrs after dosing of TG02 on days 1 and 15 of therapy.

Molecular Analyses

Targeted molecular analyses of available tumor samples are performed to be able to correlate to similar analyses of ctDNA in plasma and CSF (if available), akin to multiple other PBTC clinical trials. Immunohistochemical evaluation of ERK5 and MYC in tumor samples is also performed. No molecular markers that predict tumor response to CDK7, CDK9, or ERK5 inhibitors have been reported to date in cancer. The present study also includes such analyses.

Long-Term Memory Evaluation

Transcription of immediate early genes in neurons is critical for long-term memory (Tischmeyer et al., Cell Mol Life Sci 55:564-574, 1999). One study showed that the use of THZ1 in vitro produced changes associated with decreased long-term memory, including decreased expression of immediate early genes, which encode specific memories in mice neurons, along with decreased phosphorylation of the CTD of the RNA polymerase II (He et al., Fron Mol Neurosci in press). These authors showed some evidence in vivo that THZ1 could affect long-term memory (approximately 24 hrs after drug administration) in mice compared to control. Patients are administered the California Verbal Learning Test-Children Edition (CVLT-C) or CVLT Third Edition (CVLT-III) depending on age. This task evaluates immediate and delayed rote verbal learning and memory in patients older than 5 years. Assessments are performed at baseline (before or up to 1 week after start of therapy), and at 3 and 6 months after start of therapy.

The presently disclosed subject matter treats a population of patients where no standard medical therapies are available, except for local RT. The present presently disclosed subject matter establishes a safe, biological effective dose of TG02 in children based on plasma pharmacokinetic levels that far exceeds its $IC_{50}$ in patient-derived cell lines in vitro. The present disclosure also has the benefit of avoiding toxicity associated with short and long-term use of TG02 and the use of TG02 in combination with other medications, such as diarrhea, neutropenia, and lymphoenia.

TG02 is best suited to be tested in newly diagnosed patients since the poor overall wellbeing and rapid pace of progression in patients with recurrent DIPG and other H3.3 K27M-mutated HGGs commonly precludes adequate evaluation of new medical therapies. such as diarrhea, neutropenia, and lymphoenia. The present disclosure provides compelling in vitro data for using a combination of local RT and TG02. There is lack of significant overlapping toxicities between TG02 and local RT except for nausea and vomiting. The combination of local RY an TG02 also provides convenience of conducting the DLT-evaluation during the 6-week interval of local RT.

Results

A safe, tolerable and biological effective dose (as assessed by pharmacodynamic studies in PBMC) of TG02 is determined in children with newly diagnosed DIPG and other H3.3-mutated non-DIPG HGGs. The detailed pharmacokinetic studies in children show a similar pattern as adults where TG02 displayed a long half-life and reached plasma concentrations that far exceeded the necessary in vitro IC50 in human-derived DIPG cell lines. Of note, while the peak concentration of TG02 reached in the plasma of adults after a single dose of 200 mg (4,000 ng/mL; FIG. 23) was equivalent to 11,000 nM, the IC50 of TG02 in vitro against DIPG cell lines was approximately 100 nM.

Pharmacokinetic studies and pharmacodynamic analyses of TG02 target inhibition in PBMCs are critical to establish biologic relevant doses (and potentially lower than the MTD or phase 2 recommended dose) assuming a good CNS penetration of this agent. Pharmacokinetic and pharmacodynamic studies are not performed in real time, but are performed with batch samples and proceed with analyses once the MTD or phase 2 dose are established.

The present disclosure evaluates the safety and toxicity profile and establishes the Phase 2 recommended dose and/or biological effective dose of TG02 administered during and after local RT in children with newly diagnosed DIPG and other H3.3 K27M non-DIPG HGGs.

The present disclosure evaluates the pharmacokinetics of TG02 administered during and after local RT in children with newly diagnosed DIPG and other H3.3 K27M non-DIPG HGGs.

The present disclosure evaluates the pharmacodynamic effects of TG02 by assessing inhibition of phosphorylation at the CTD of RNA polymerase II in PBMC of children with newly diagnosed DIPG and other H3.3 K27M non-DIPG HGGs.

The present disclosure also assesses the potential impact of transcriptional CDK inhibition in cognitive function, particularly long-term memory, in children with newly diagnosed DIPG and other H3.3 K27M non-DIPG HGGs.

The present disclosure performs targeted molecular analyses of available tumor and ctDNA in plasma and CSF (if available) and potentially correlate with tumor response in children with newly diagnosed DIPG and other H3.3 K27M non-DIPG HGGs.

The present disclosure further describes progression-free and overall survival of children with newly diagnosed non-metastatic DIPG and other H3.3 K27M non-DIPG HGGs treated with local TG02 during and after RT in the context of a Phase 1 study.

Inclusion criteria for the enrolled patients of the presently disclosed clinical trial are as follows:

Patients younger than 22 years of age;

Newly diagnosed DIPG or other H3.3 K27M non-DIPG HGGs;

Diagnosis of either a DIPG, based on history and MRI findings including a pontine-based tumor involving more than 2/3 of this segment, or other H3.3 K27M non-DIPG HGGs irrespective of the primary location;

For patients with DIPG who undergo tumor biopsy, patients diagnosed with H3.3 or any of the other histone mutations, or those with anaplastic astrocytoma (WHO grade III) or diffuse astrocytoma (WHO grade II) are eligible for this study. Patients with DIPG without any detectable histone mutation are also eligible for this study;

No previous anticancer therapy, except for dexamethasone;

Patients need to be able to swallow capsules (based on this criterion, it is expected that children as young as 5 years are candidates for this study);

A minimal body surface area (BSA) is required for each dosage level of TG02 based on available capsules strengths;

Performance score (Lansky for those <16 years and Karnofsky for those ≥16 years)≥50;

Patients must have adequate organ and bone marrow function as described below:

Absolute neutrophil count 1000/μL;

Platelets ≥100,000/μL (unsupported, defined as no platelet transfusion within 7 days);

Hemoglobin ≥8 g/dL (may be transfusion dependent);

Total bilirubin ≤1.5 times institutional upper limit of normal (ULN);

ALT (SGPT)≤3 times ULN;

Albumin ≥2 g/dL;

Serum creatinine based on age/gender as noted in Table 6. Patients who do not meet the criteria below but have a 24-hr creatinine clearance or GFR (radioisotope or iothalamate)≥70 mL/min/1.73 m² are eligible; and Negative pregnancy test for females of child-bearing potential according to institutional guidelines.

TABLE 6

Creatinine values according to age and gender
Serum Creatinine for Age/Gender

| Age (years) | Maximum Serum Concentration (mg/dL) | |
|---|---|---|
| | Male | Female |
| 1 to <2 | 0.6 | 0.6 |
| 2 to <6 | 0.8 | 0.8 |
| 6 to <10 | 1 | 1 |
| 10 to <13 | 1.2 | 1.2 |
| 13 to <16 | 1.5 | 1.4 |
| ≥16 | 1.7 | 1.4 |

The threshold creatinine values in this table were derived from the Schwartz formula for estimating GFR (Schwartz et al. J Pediatr 106: 522-6) utilizing child length and stature published by the CDC Exclusion criteria for the enrolled patients of the presently disclosed clinical trial are as follows:

Pregnant or lactating female patients;

Concurrent diagnosis of other medical and/or psychiatric conditions severe enough to affect tolerance to current therapy or able to cause more severe toxicities in patients;

Patients of child-bearing or child-fathering potential who refuse to practice safe and effective contraception;

Patients receiving any other investigational therapies;

Presence of metastatic disease; and

Concomitant use of CYP3A4 or CYP1A2 inducers or inhibitors.

Study Design

The presently disclosed Phase 1 clinical trial uses TG02 as a single agent in the treatment of children with DIPG and other H3.3 K27M non-DIPG HGGs. TG02 is administered in an intermittent schedule once daily, twice a week (preferentially on Mondays and Thursdays). The rolling-6 design is used to define the MTD and/or pediatric Phase 2 recommended dose. Each cycle of chemotherapy lasts 28 days. Treatment lasts for up to 2 years unless there is disease progression, unacceptable toxicities, or withdrawal of therapy consent. The DLT-evaluation period includes the first 6 weeks of therapy. Once an MTD/Phase 2 recommended dose and biological effective doses are established, a small expansion cohort of 6 patients is performed using the later dose of the study agent (biologic effective dose) to further assess treatment tolerability and correlative studies. Of note, compliance with therapy is assessed by having parents/legal guardians fill out drug diaries to document the administration of TG02.

Treatment Plan

Table 7 shows the proposed escalation scheme for this Phase 1 study. Since the $C_{max}$ of TG02 in adults exceeded its in vitro $IC_{50}$ in patient-derived DIPG cell lines by almost 2 logs, the instant Example does not intend to necessarily reach or surpass the adult MTD of this agent in children. Therefore, a limited dose escalation is adopted. The starting dosage level (dosage level 1) will be 50 mg/m² per dose twice a week, which is equivalent to approximately 85 mg per dose in adults. The dose of TG02 will be escalated to a maximum of 85 mg/m² which is equivalent to approximately 150 mg per dose in adults. The instant Example establishes potentially effective biologic doses that are able to inhibit RNA transcription in PBMCs.

TABLE 7

Schema for dose escalation of TG02

| | Dose of TG02 | Minimal BSA |
|---|---|---|
| Dosage level 0 | 35 mg/m² | ≥55 m² |
| * Dosage level 1 | 50 mg/m² | ≥55 m² |
| Dosage level 2 | 65 mg/m² | ≥50 m² |
| Dosage level 3 | 85 mg/m² | ≥50 m² |

* Starting dosage level

The following events are considered a DLT:

Non-Hematologic Toxicities:

Any grade 4 non-hematologic toxicity

Any grade 3 non-hematologic toxicity except for:
  Grade 3 nausea and vomiting of <5 days
  Grade 3 diarrhea <3 days without proper use of antidiarrheal agents
  Grade 3 elevation of transaminases that returns to levels meeting eligibility criteria within 7 days of study drug interruption and does not recur upon restarting drug.
  Grade 3 fever or infection of fewer than 5 days in duration
  Grade 3 hypophosphatemia, hypokalemia, hypocalcemia or hypomagnesemia responsive to oral supplementation Any grade 2 non-hematologic toxicity that persists for >7 days and is considered medically significant or sufficiently intolerable by the patient that the toxicity requires treatment interruption.

Hematologic Toxicities:

Any grade 4 neutropenia, anemia, or thrombocytopenia
Grade 3 neutropenia with fever
Grade 3 thrombocytopenia on two separate days or requiring a platelet transfusion on 2 separate days within a 7-day period.

In addition, any adverse events associated with the use of TG02 during the first course of therapy that lead to a dose reduction, a delay of treatment >7 days, or result in the permanent cessation of therapy are considered a DLT.

FIG. 24 shows that the presently disclosed dosage escalation can be properly conducted with minimal overlap of actual doses between different dosage levels and BSAs.

Local RT is delivered at 1.8-Gy fractions five days a week for a total dose of 54 Gy (30 sessions; DIPG) and between 54 and 59.4 Gy (between 30 and 33 sessions; other H3.3 K27M non-DIPG HGGs). The clinical target volume (CTV) includes the gross tumor volume (GTV) as determined by the extent of hyperintense signal abnormalities in T2-weighted and/or FLAIR images, with an additional extension of 2 cm in all directions respecting anatomic boundaries through which contiguous tumor dissemination cannot occur. The planning target volume (PTV) contains a 0.3-cm extension in all directions to account for variations inpatients' position.

Endpoints/Statistical Considerations:

Between two to six patients are accrued to each dosage level following the rolling-6 design. Decisions as to which dose level to enroll a patient is based on the number of patients currently enrolled and evaluable, the number of patients experiencing DLTs, and the number of patients still at risk of developing a DLT at the time of new patient entry. The MTD is empirically defined as the highest dosage level at which six patients have been treated with at most one patient experiencing a DLT and the next higher dose level has been determined to be too toxic (two or more DLTs out of two to six patients enrolled).

Example 3: TG02 Extended Survival in Mouse Models of DIPG

Malignant gliomas are a leading cause of childhood related cancer deaths. About 10-15% of malignant gliomas grow in the midline of the brain (DMG/DIPG), and 80% have hot spot mutations in the H3.3 and H3.1 genes (H3.3K27M or H3.1K27M mutations), in heterozygous forms. Other recurrent mutations or copy number variations (CNV) of malignant gliomas include TP53, PDGFRA, ACVR1, PIK3CA, CDKN2A, and PTEN/LOH 10q.

TG02 purchased from commercial vendor (SB1317) and obtained from Adastra Pharmaceuticals were tested in several DIPG cell lines in vitro, and in two mouse models of DIPG in vivo. Experimental results from DIPG cells lines are shown in Table 8.

TABLE 8

IC$_{50}$ values of two forms of TG02 in four tested DIPG cell lines

| Cell lines | IC$_{50}$ of SB1317 (nM) | IC50 of TG02 obtained from Adastra Pharmaceuticals (nM) |
| --- | --- | --- |
| DIPG007 | 170 | 93 |
| DIPG4 | 102 | 60 |

TABLE 8-continued

IC$_{50}$ values of two forms of TG02 in four tested DIPG cell lines

| Cell lines | IC$_{50}$ of SB1317 (nM) | IC50 of TG02 obtained from Adastra Pharmaceuticals (nM) |
| --- | --- | --- |
| SF8628 | 90 | 70 |
| DIPG13p | 100 | 80 |

In a first DIPG mouse model, NOD-SCID gamma mice were injected with $2 \times 10^5$ SF8628 cells in the midbrain. On Day 0, mice were randomized into three groups:

Vehicle: receiving no drug
SB1317: receiving commercially available form of TG02
TG02: receiving TG02 obtained from Adastra Pharmaceuticals For each cycle, the compounds were administered 20 mg/kg/day for 5 days, followed with 2 days of rest period. Each mice received 2 cycles of treatment. Both forms of TG02 extended survival in the first xenograft model of DIPG (FIG. 25). Compared to vehicles, TG02 obtained from Adastra Pharmaceuticals significantly reduced K167 expression, which is a biomarker for proliferation (FIG. 26).

In a second DIPG mouse model, mice were injected with $1 \times 10^5$ DIPG13p cells in the midbrain of NOD-SCID gamma mice. On Day 0, mice were randomized into two groups:

Vehicle: receiving no drug
TG02: receiving TG02 obtained from Adastra

For each cycle, the compounds were administered 20 mg/kg/day for 5 days, followed with 2 days of rest period. Each mice received 2 cycles of treatment. TG02 obtained from Adastra Pharmaceuticals extended survival in the second xenograft model of DIPG (FIG. 27). Compared to vehicles, TG02 obtained from Adastra Pharmaceuticals significantly reduced K167 expression, which is a marker for proliferation (FIG. 28).

Molecular signature of the two DIPG cell lines used in the present example is show in Table 9.

TABLE 9

Molecular signature of two DIPG cell lines

| DIPG SF8628 | DIPG 13p |
| --- | --- |
| H3 K27M mutant | H3 K27M mutant |
| P53 mutant | P53 mutant |
| MYC overexpressed | MYCN overexpressed |

Example 4 Synergistic Effects of TG02 and Radiotherapy

Brain gliomas express high levels of ERK5 (FIG. 29). TG02 was not toxic to normal astrocytes or neural stem cells in nM ranges (FIGS. 30A-30B).

Cells were plated on day 1 ($1 \times 10^6$). On day 2, vehicle, TG02 or 1.8 Gy radiation was delivered to cells. On day 5, cell viability were measured by cell count/trypan blue assay on thermo cell countess machines. For fractionated rad, additional 1.8 Gy doses were given on days 3 and 4. FIG. 31 shows that cells treated with radiation alone had almost no difference in tumor cell viability (about 90%) as compared to cells treated with vehicle control (about 100%). Cells treated with TG02 alone had much reduced tumor cell viability (50%) as compared to vehicle control. Unexpectedly, cells treated with TG02 and radiation (3 fractions) together had significantly lower tumor cell viability (about 25%). Therefore, the combination of TG02 and radiation can provide significant, synergistic benefits for treating DIPG as compared to when TG02 and radiation are administered alone.

Although the presently disclosed subject matter and its advantages have been described in detail, it should be understood that various changes, substitutions and alterations can be made herein without departing from the spirit and scope of the disclosed subject matter. Moreover, the scope of the present application is not intended to be limited to the particular embodiments of the process, machine, manufacture, and composition of matter, methods and processes described in the specification. As one of ordinary skill in the art will readily appreciate from the disclosed subject matter of the presently disclosed subject matter, processes, machines, manufacture, compositions of matter, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, methods, or steps.

Various patents, patent applications, publications, product descriptions, protocols, and sequence accession numbers are cited throughout this application, the inventions of which are incorporated herein by reference in their entireties for all purposes.

What is claimed is:

1. A method for treating diffuse intrinsic pontine glioma (DIPG) in a pediatric human subject, comprising administering to the subject a therapeutically effective amount of (16E)-14-methyl-20-oxa-5,7,14,26-tetraazatetracyclo [19.3.1.1(2,6).1(8,12)]-heptacosa-1(25),2(26),3,5,8(27),9, 11,16,21,23-decaene (TG02), or a pharmaceutically acceptable salt thereof, in combination with radiation therapy, wherein the DIPG is a H3K27M-mutant DIPG.

2. The method of claim 1, wherein the TG02 is a citric salt of TG02.

3. The method of claim 2, wherein the citric salt of TG02 has a powder x-ray diffraction pattern with peaks at 15.2, 15.5, 21.7, 22.1, 23.0, 26.2, and 29.9 degrees 2θ.

4. The method of claim 1, wherein the pediatric human subject is between about 4 years old and about 11 years old.

5. The method of claim 1, wherein the TG02 is administered orally in an amount of between about 20 mg and about 100 mg per day.

6. The method of claim 1, wherein the TG02 is administered intermittently to the pediatric human subject.

7. The method of claim 1, wherein the radiation is administered to the pediatric human subject in fractionated doses.

8. The method of claim 7, wherein a total dose of between about 54 Gy and about 60 Gy of the radiation is administered to the pediatric human subject over a period of between about 1 week and about 8 weeks.

9. The method of claim 1, wherein when the TG02 is administered on the same day as the radiation, and the TG02 is administered between about 1 hour and about 8 hours prior to the administration of the radiation.

* * * * *

SEQUENCE LISTING

```
<160> NUMBER OF SEQ ID NOS: 50

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggacatcca ataaacgcct tcg                                            23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcacctacc acaaacagcc ag                                             22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttccacgcca tcactgagtc tg                                             22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctgaaggac ttcatcacca agc                                            23

<210> SEQ ID NO 5
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 5
ctccagcaga agccacctaa ag                                              22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccaaatgtca gtggaagcct ctc                                             23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctcacactg attgccaagg tc                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccttgagga aaaccagcgg aa                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcatcgccaa ggtcacccag aa                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caacctgcga atgtgctgtg ag                                              22

<210> SEQ ID NO 11
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 11
atgacggaat ataagctggt ggt                                           23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagtagacac aaaacaggct cag                                           23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaaacctcag ccaagaccag ac                                            22

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggagagctta aaattgcaga ttttg                                         25

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtggtgagtt tcatagccag cag                                           23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccagtggatg tctttgtgca cc                                            22

<210> SEQ ID NO 17
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 17
cctgtttagg aagtgaaaga agac                                          24

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctacatggcc cctgagagga t                                             21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccttccagtt ggagagttct cg                                            22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tacacccgtc agattctgga gg                                            22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagagcaact ctgccaccag ta                                            22

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctgatgggc cacaggat                                                 18

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 23
cgtctccaca catcagcaca a                                              21

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcattcttt gcaatactgc ttaa                                           24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcagtccaac ttgccattca gac                                            23

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tttgctactt ggacactatt cagg                                           24

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctggacata gagtggtttc tcc                                            23

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggcgcaaaga acctcaggaa ga                                             22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttgcccttgg tcctgtggat ga                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tccatgagag gctggtagca ct                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctgtgttgtc ctggcttgga ga                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tacctggtcc aggaagcatt gc                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcctactgca ccgatgctgt tc                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgctgcatgt tggtccactc at                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 35
cgctgataag cctgtctgcg at                                              22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggcacgtctc cccatcaatg                                                 20

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgtcggatct ccctcaccaa tg                                              22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggcaatccca tacaaccctg ag                                              22

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gctccagaga tccaccttct cat                                             23

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agaaacttcc acaacttgtc tcag                                            24

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
```
gtgacacgga tggattccag ac                                              22

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cacttctttg gctgaggagg tag                                             23

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tccagacgtc ggacttgaca                                                 20

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cggcatttcc atcattgaac tgc                                             23

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atggtctgaa gccgtttgct gg                                              22

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
catttgtggc aggaacttgc tcc                                             23

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
tggaggtcag gcaggtcag                                                    19

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cactgtccaa cttgaccctc t                                                 21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
catctgccga tagcacagtg a                                                 21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cctcagagta tctaaccact ggc                                               23
```